US012729234B2

(12) United States Patent
Kurella et al.

(10) Patent No.: US 12,729,234 B2
(45) Date of Patent: Sep. 8, 2026

(54) TAU BINDING COMPOUNDS

(71) Applicant: Voyager Therapeutics, Inc., Cambridge, MA (US)

(72) Inventors: Vinodhbabu Kurella, Cambridge, MA (US); Li Liu, Cambridge, MA (US); Dillon Kavanagh, Cambridge, MA (US); Allan D. Capili, Somerville, MA (US); Jinzhao Hou, Lexington, MA (US); Todd Carter, Cambridge, MA (US); Wencheng Liu, Cambridge, MA (US)

(73) Assignee: Voyager Therapeutics, Inc., Lexington, MA (US)

( * ) Notice: Subject to any disclaimer, the term of this patent is extended or adjusted under 35 U.S.C. 154(b) by 607 days.

(21) Appl. No.: 18/267,711

(22) PCT Filed: Dec. 15, 2021

(86) PCT No.: PCT/US2021/063551

§ 371 (c)(1), (2) Date: Jun. 15, 2023

(87) PCT Pub. No.: WO2022/132923

PCT Pub. Date: Jun. 23, 2022

(65) Prior Publication Data

US 2024/0059766 A1 Feb. 22, 2024

Related U.S. Application Data

(60) Provisional application No. 63/126,024, filed on Dec. 16, 2020.

(51) Int. Cl.

| | |
|---|---|
| ***C07K 16/18*** | (2006.01) |
| ***A61P 25/28*** | (2006.01) |
| ***C12N 15/63*** | (2006.01) |

(52) U.S. Cl.

CPC .............. *C07K 16/18* (2013.01); *A61P 25/28* (2018.01); *C12N 15/63* (2013.01); *C07K 2317/14* (2013.01); *C07K 2317/31* (2013.01); *C07K 2317/565* (2013.01); *C07K 2317/92* (2013.01)

(58) Field of Classification Search

None

See application file for complete search history.

(56) References Cited

FOREIGN PATENT DOCUMENTS

| | | | |
|---|---|---|---|
| WO | 2012/045882 | A2 | 4/2012 |
| WO | 2013/050567 | A1 | 4/2013 |
| WO | 2014/100600 | A2 | 6/2014 |
| WO | 2019/118906 | A2 | 6/2019 |
| WO | 2019/186276 | A2 | 10/2019 |

OTHER PUBLICATIONS

Augustinack et al., Specific tau phosphorylation sites correlate with severity of neuronal cytopathology in Alzheimer's disease. Acta Neuropathol. Jan. 2002; 103(1):26-35.

Ercan et al., A validated antibody panel for the characterization of tau post-translational modifications. Mol Neurodegener. Nov. 21, 2017;12(1):87, 19 pages.

Goedert et al., Epitope mapping of monoclonal antibodies to the paired helical filaments of Alzheimer's disease: identification of phosphorylation sites in tau protein. Biochem J. Aug. 1, 1994;301 ( Pt 3)(Pt 3):871-7.

Goedert et al., Monoclonal antibody AT8 recognises tau protein phosphorylated at both serine 202 and threonine 205. Neurosci Lett. Apr. 21, 1995; 189(3):167-9.

Strang et al., Generation and characterization of new monoclonal antibodies targeting the PHF1 and AT8 epitopes on human tau. Acta Neuropathol Commun. Jul. 31, 2017;5(1):58, 11 pages.

Van Ameijde et al., Enhancement of therapeutic potential of a naturally occurring human antibody targeting a phosphorylated Ser422 containing epitope on pathological tau. Acta Neuropathol Commun. Jul. 12, 2018;6(1):59, 14 pages.

International Search Report and Written Opinion for Application No. PCT/US2021/063551, dated May 30, 2022, 23 pages.

*Primary Examiner* — Nelson B Moseley, II

*Assistant Examiner* — James Ryland Melchior

(74) *Attorney, Agent, or Firm* — McCarter & English, LLP; Yu Lu

(57) ABSTRACT

The present disclosure provides anti-tau antibodies. Also provided are methods of using anti-tau antibodies for treatment and diagnosis of neurological indications.

17 Claims, 5 Drawing Sheets

Specification includes a Sequence Listing.

SEQUENCE LISTING

```
<160> NUMBER OF SEQ ID NOS: 301

<210> SEQ ID NO 1
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Met Val Glu Ser Gly Gly Gly Leu Val Gln Pro Gly Gly
1               5                   10                  15

Ser Leu Thr Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Tyr Ile Ser Ser Ser Arg Ser Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Thr Leu Gly Ile Gly Tyr Trp Gly Gln Gly Thr Leu Val Thr Val
            100                 105                 110

Ser Ser


<210> SEQ ID NO 2
<211> LENGTH: 114
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Arg Ser Gly Ser Thr Ile Tyr Tyr Ala Asp Ser Val
    50                  55                  60

Glu Gly Arg Phe Thr Ile Ser Arg Asp Asn Ala Tyr Asn Ser Leu Tyr
65                  70                  75                  80

Leu Gln Met Ile Ser Leu Arg Asp Asp Asp Thr Ala Val Tyr Tyr Cys
                85                  90                  95

Ala Arg Gly Asn Trp Ala Tyr Trp Gly Gln Gly Ile Leu Val Thr Val
            100                 105                 110

Ser Ser


<210> SEQ ID NO 3
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Thr Phe Ser Asn Tyr
            20                  25                  30

Asn Met Asn Trp Val Arg Gln Ala Pro Gly Lys Gly Leu Glu Trp Ile
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Asp Glu Asp Thr Ala Val Tyr Tyr Cys
                85                  90                  95

Ala Ser Leu Gly Arg Gly Tyr Trp Gly Gln Gly Thr Leu Val Thr Val
            100                 105                 110

Ser Ser


<210> SEQ ID NO 4
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Val Gln Leu Val Glu Ser Gly Gly Gly Leu Val Gln Ala Gly Gly
1               5                   10                  15
```

```
Ser Leu Arg Leu Ser Cys Ala Ala Ser Gly Phe Thr Phe Ser Asp Tyr
            20                  25                  30

Ser Met Asn Trp Val Arg Gln Ala Pro Gly Lys Gly Leu Glu Trp Val
        35                  40                  45

Ser Tyr Ile Arg Ser Ser Ser Ser Ile Ile Tyr Tyr Ala Asp Ser Val
    50                  55                  60

Lys Gly Arg Phe Thr Ile Ser Arg Asp Asn Ala Lys Asn Ser Leu His
65                  70                  75                  80

Leu Gln Met Asn Ser Leu Arg Asp Glu Asp Thr Ala Val Tyr Tyr Cys
                85                  90                  95

Ala Arg Arg Gly His Phe Asp Tyr Trp Gly Gln Gly Thr Leu Val Thr
            100                 105                 110

Val Ser Ser
        115


<210> SEQ ID NO 5
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Arg Ser Ser Ser Ser Thr Ile Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Asp Glu Asp Thr Ala Val Tyr Tyr Cys
                85                  90                  95

Ala Arg Arg Ser Ile Ala Asp Tyr Trp Gly Gln Gly Thr Leu Val Thr
            100                 105                 110

Val Ser Ser
        115


<210> SEQ ID NO 6
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45
```

```
Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Ser Leu Gly Arg Gly Asp Cys Trp Gly Gln Gly Thr Leu Val Thr
            100                 105                 110

Val Ser Ser
        115


<210> SEQ ID NO 7
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Thr Trp Ile Arg Gln Pro Ala Gly Lys Gly Leu Glu Trp Ile
        35                  40                  45

Gly Arg Val Tyr Thr Ser Gly Ser Ala Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Thr Leu Ser Ser Val Thr Ala Ala Asp Thr Ala Val Tyr Tyr Cys Ala
                85                  90                  95

Arg Asp Arg Gly Leu Tyr Tyr Trp Gly Gln Gly Thr Leu Val Thr Val
            100                 105                 110

Ser Ser


<210> SEQ ID NO 8
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Tyr Ser Ser Tyr
            20                  25                  30

Ala Met Ser Trp Val Arg Arg Ala Pro Gly Lys Gly Leu Glu Trp Ile
        35                  40                  45

Ser Ile Ile Ser Gly Ser Ser Ser Ile Thr Tyr Tyr Ala Asp Ser Met
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

```
Ala Lys Gly Gly Arg Tyr Gly Tyr Phe Gln His Trp Gly Gln Gly Thr
            100                 105                 110

Leu Val Thr Val Ser Ser
        115


<210> SEQ ID NO 9
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Ile Thr Leu Lys Glu Ser Gly Pro Thr Leu Val Lys Pro Thr Gln
1               5                   10                  15

Thr Leu Thr Leu Thr Cys Thr Leu Ser Gly Phe Ser Leu Ser Thr Ser
            20                  25                  30

Glu Val Gly Val Gly Trp Ile Arg Gln Pro Pro Gly Lys Ala Leu Glu
        35                  40                  45

Trp Leu Ala Ile Ile Tyr Trp Asn Asp His Lys Arg Tyr Ser Pro Ser
    50                  55                  60

Leu Lys Asn Arg Leu Thr Phe Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Val Thr Gly Glu Gly Phe Asp Pro Trp Gly Gln Gly
            100                 105                 110

Thr Leu Val Thr Val Ser Ser
        115


<210> SEQ ID NO 10
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Gly Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Val Thr Thr His Phe His His Trp Gly Gln Gly Thr Leu Val Thr
            100                 105                 110

Val Ser Ser
        115
```

<210> SEQ ID NO 11
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Asp Thr Tyr Tyr Asn Pro Ser Leu Gln
    50                  55                  60

Ser Arg Val Thr Met Ser Val Asp Thr Ser Lys Asn Gln Phe Ser Leu
65                  70                  75                  80

Lys Leu Ser Ala Val Thr Ala Ala Asp Thr Ala Val Tyr Tyr Cys Ala
                85                  90                  95

Arg Ala Gly Ile Val Gly Thr Pro Gly Leu Gly Met Asp Val Trp Gly
            100                 105                 110

Gln Gly Thr Thr Val Thr Val Ser Ser
        115                 120

<210> SEQ ID NO 12
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Ile
        35                  40                  45

Ser Tyr Ile Ser Ser Ser Ser Asn Thr Ile Tyr Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Thr Leu Gly Arg Gly Tyr Trp Gly Gln Gly Thr Leu Val Ile Ala
            100                 105                 110

Ser Ser

<210> SEQ ID NO 13
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Asp Thr Ser Gly Ser Thr Asn Tyr Asn Pro Ser Leu Lys
    50                  55                  60

Ser Arg Val Thr Met Ser Ile Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Asp Gly Tyr Arg Tyr Trp Gly Gln Gly Thr Leu Val Thr
            100                 105                 110

Val Ser Ser
        115

<210> SEQ ID NO 14
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Ile
        35                  40                  45

Ser Tyr Ile Ser Ser Ser Asn Ser Thr Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Arg Ser Leu Gly Asp Tyr Trp Gly Gln Gly Thr Leu Val Ile
            100                 105                 110

Val Ser Ser
        115

<210> SEQ ID NO 15
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 15

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Phe
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Thr Asp Tyr Pro Lys Asp Val Trp Gly Gln Gly Thr Thr
            100                 105                 110

Val Thr Val Ser Ser
        115


<210> SEQ ID NO 16
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Asp Met His Trp Val Arg Gln Ala Ala Gly Lys Gly Leu Glu Trp Val
        35                  40                  45

Ser Thr Ile Gly Ala Ala Gly Asp Thr Tyr Tyr Pro Gly Ser Val Lys
    50                  55                  60

Gly Arg Phe Ile Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Gly Glu Thr Leu Glu Gly Ala Thr Ile Gly Tyr Tyr Tyr Gly
            100                 105                 110

Met Asp Val Trp Gly Gln Gly Thr Thr Val Thr Val Ser Ser
        115                 120                 125


<210> SEQ ID NO 17
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
```

```
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Gly Asp Ala Phe Asp Ile Trp Gly Gln Gly Thr Met Val Thr Val
            100                 105                 110

Ser Ser


<210> SEQ ID NO 18
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ile Asn Ala
            20                  25                  30

Arg Met Ala Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Ile Met Thr Asn Met Asp Pro Val Asp Thr Ala Thr Tyr Tyr
                85                  90                  95

Cys Ala Arg Ile Arg Gly Tyr Ser Tyr Asn Tyr Gly Met Asp Val Trp
            100                 105                 110

Gly Gln Gly Thr Thr Val Thr Val Ser Ser
        115                 120


<210> SEQ ID NO 19
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Thr Arg Val Glu Ala Glu Asp Val Gly Ile Tyr Tyr Cys Met Gln Val
                85                  90                  95
```

```
Thr Gln Phe Pro Arg Thr Phe Gly Gln Gly Thr Lys Val Glu Ile Arg
            100                 105                 110


<210> SEQ ID NO 20
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Phe Tyr Cys Gln Ser Tyr Asp Ser Ser
                85                  90                  95

Leu Ser Gly Ser Val Phe Gly Gly Gly Thr Lys Leu Thr Val Leu
            100                 105                 110


<210> SEQ ID NO 21
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Arg Thr Phe Gly Gln Gly Ser Lys Leu Glu Ile Lys
            100                 105                 110


<210> SEQ ID NO 22
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Tyr
            20                  25                  30

Leu Ala Trp Tyr Gln Gln Lys Pro Gly Gln Ala Pro Arg Leu Phe Ile
        35                  40                  45

Tyr Asp Val Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 23
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Glu Ile Val Leu Thr Gln Ser Pro Ala Thr Leu Ser Ser Ser Pro Gly
1               5                   10                  15

Glu Arg Ala Thr Leu Ser Cys Arg Ala Ser Gln Ser Val Thr Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Leu Tyr Tyr Cys Gln Gln Arg Ser Asn Trp Pro Tyr
                85                  90                  95

Thr Phe Gly Gln Gly Thr Lys Leu Glu Ile Lys
            100                 105
```

<210> SEQ ID NO 24
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Lys Arg Phe Ser Gly Val Pro
    50                  55                  60
```

```
Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Arg Thr Phe Gly Gln Gly Thr Arg Leu Glu Ile Lys
            100                 105                 110
```

<210> SEQ ID NO 25
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Asp Ile Val Met Thr Gln Thr Pro Leu Ser Ser Leu Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Lys Arg Phe Phe Gly Val Pro
    50                  55                  60

Asp Arg Phe Ser Gly Ser Gly Ala Gly Thr Asp Phe Thr Leu Lys Ile
65                  70                  75                  80

Asn Arg Val Glu Ala Glu Asp Val Gly Ile Tyr Tyr Cys Met Gln Ala
                85                  90                  95

Thr Gln Phe Pro Leu Thr Phe Gly Gly Gly Thr Lys Val Glu Ile Lys
            100                 105                 110
```

<210> SEQ ID NO 26
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Pro
                85                  90                  95

Val Val Phe Gly Gly Gly Thr Met Leu Thr Val Leu
            100                 105
```

<210> SEQ ID NO 27
<211> LENGTH: 107

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Gln Tyr Ala
20 25 30

Tyr Trp Tyr Gln Gln Lys Pro Gly Gln Ala Pro Val Leu Val Ile Phe
35 40 45

Lys Asp Thr Glu Arg Pro Ser Gly Ile Pro Glu Arg Phe Ser Gly Ser
50 55 60

Ser Ser Gly Thr Thr Val Thr Leu Thr Ile Ser Gly Val Gln Ala Glu
65 70 75 80

Asp Glu Ala Asp Tyr Tyr Cys Gln Ser Ala Asp Ser Ser Gly Ser Tyr
85 90 95

Val Phe Gly Thr Gly Thr Lys Val Thr Val Leu
100 105

<210> SEQ ID NO 28
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Leu Thr Phe Gly Gln Gly Thr Arg Leu Glu Ile Lys
100 105 110

<210> SEQ ID NO 29
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

Gln Ala Val Leu Thr Gln Pro Ser Ser Leu Ser Ala Ser Pro Gly Ala
1 5 10 15

Ser Ala Arg Leu Thr Cys Thr Leu Arg Ser Gly Ile Asn Val Gly Ala

```
            20                  25                  30

Tyr Arg Leu Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Trp Val Phe Gly Gly Gly Thr Lys Leu
            100                 105                 110

Thr Val Leu
        115


<210> SEQ ID NO 30
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ser Tyr Glu Leu Thr Gln Pro Pro Ser Val Ser Val Ser Pro Gly Gln
1               5                   10                  15

Thr Ala Arg Ile Thr Cys Ser Gly Glu Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Arg Val Phe Gly Gly Gly Thr Lys Leu Thr Val Leu
            100                 105


<210> SEQ ID NO 31
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Val Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Thr Gln Phe Pro Arg Thr Phe Gly Gln Gly Thr Lys Leu Glu Ile Lys
            100                 105                 110


<210> SEQ ID NO 32
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Cys Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Thr Gly Val Gln Ala Glu
65                  70                  75                  80

Asp Glu Ala Asp Tyr Tyr Cys Gln Ser Thr Asp Ser Ser Gly Ser Trp
                85                  90                  95

Val Phe Gly Gly Gly Thr Lys Leu Thr Val Leu
            100                 105


<210> SEQ ID NO 33
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Leu Gln Lys Pro Gly Gln Ala Pro Arg Leu Leu Ile
        35                  40                  45

Tyr Asp Val Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Arg Asn Trp Pro Tyr
                85                  90                  95

Thr Phe Gly Gln Gly Thr Lys Leu Glu Ile Lys
            100                 105


<210> SEQ ID NO 34
<211> LENGTH: 107
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 34

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Cys Ser
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105
```

<210> SEQ ID NO 35
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Lys Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Ala
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Thr Phe Gly Gln Gly Thr Lys Leu Glu Ile
            100                 105                 110

Lys
```

<210> SEQ ID NO 36
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Asp Ile Leu Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Phe
65                  70                  75                  80

Ser Arg Val Glu Ala Glu Asp Val Gly Leu Tyr Tyr Cys Met Gln Ala
                85                  90                  95

Leu Gln Ile Pro Leu Thr Phe Gly Gly Gly Thr Lys Val Glu Ile Lys
            100                 105                 110


<210> SEQ ID NO 37
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys


<210> SEQ ID NO 38
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Val Met Thr Gln Ser Pro Leu Ser Leu Pro Val Ile Pro Gly
1               5                   10                  15

Glu Pro Ala Ser Ile Ser Cys Arg Ser Ser Gln Ser Leu Leu His Ser
            20                  25                  30

Asn Gly Tyr Ile Tyr Leu Asp Trp Tyr Leu Gln Lys Pro Gly Gln Ser
        35                  40                  45

Pro Gln Leu Leu Ile Tyr Val Gly Ser Asn Arg Ala Ser Gly Val Pro
    50                  55                  60

Asp Arg Phe Ser Gly Ser Gly Ser Gly Thr Asp Phe Lys Leu Lys Ile
65                  70                  75                  80

Ser Arg Val Glu Ala Glu Asp Val Gly Val Tyr Tyr Cys Met Gln Thr
```

-continued 85 90 95

Leu Gln Ile Pro Arg Thr Phe Gly Gly Gly Thr Lys Val Glu Ile Lys
100 105 110

<210> SEQ ID NO 39
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39
gaggtgcaga tggtggagtc tgggggaggc ttggtacagc ctggggggtc cctgacactc 60
tcctgtgcag cctctggatt caccttcagt agctatagaa tgaactgggt ccgccaggct 120
ccagggaagg ggctggagtg ggtttcatac attagcagta gtagaagtgc catatactac 180
gcagactctg tgaagggccg attcaccatc tccagagaca atgccaagaa ctcactgtat 240
ctgcaaatga acagcctgag agacgaggac acggctgtgt attactgtgc gaccctgggg 300
ataggctact ggggccaggg aaccctggtc accgtctcct ca 342

<210> SEQ ID NO 40
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 40
caggtcacct tgaaggagtc tggtcctgtg ctggtgaaac ccacagagac cctcacgctg 60
acctgcaccg tctctgggtt ctcactcatc aatgctagaa tggctgtgag ctggatccgt 120
cagcccccag ggaaggccct ggagtggctt gcacacattt tttcgaatga cgaaaaatcc 180
tacagcacat ctctgaagag cagactcacc atctccaagg acacctccaa aagccaggtg 240
gtccttatca tgaccaacat ggaccctgtg gacacagcca catattactg tgcacggatc 300
cgtggataca gctataacta cggtatggac gtctggggcc aagggaccac ggtcaccgtc 360
tcctca 366

<210> SEQ ID NO 41
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41
gaggtgcagt tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcatac attaggagta gtagtagtac catatactac 180
gcagactctg tgaagggccg attcaccatc tccagagaca atgccaagaa atcattgtat 240
ctgcaaatga atagtctgag agacgaggac acggctgtgt attactgtgc gagaaggagt 300
atagctgact actggggcca gggaaccctg gtcaccgtct cctca 345

<210> SEQ ID NO 42
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42
gaggtgcagc tggtggagtc tgggggaggc ttggtacagc ctgggggtc cctgagactc 60 tcctgtgcag cctctggatt caccttcaat aactacgaca tgcactgggt ccgccaagct 120
gcaggaaaag gtctggagtg ggtctcaact attggtgctg ctggtgacac atattatcca 180
ggctccgtga agggccgatt catcatctcc agagaaaatg ccaagaactc cttgtatctt 240
caaatgaaca gcctgagagc cggggacacg gctgtgtatt actgtgcaag agccggagag 300
accttagagg gagctactat cggctactac tacggtatgg acgtctgggg ccaggggacc 360
acggtcaccg tctcctca 378

<210> SEQ ID NO 43
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43
gaggtgcagc tggtggagtc tgggggaggc ttggtaaagc ctgggggtc ccttagactc 60 tcctgtgcag cctctggatt cactttcagt aacgcctgga tgagctgggt ccgccaggct 120
ccagggaagg ggctggagtg gtttggccgt attaaaagca aaactgatgg tgggacaaca 180
gactacgctg cacccgtgaa aggcagattc accatctcaa gagatgactc aaaaaacacg 240
ctgtatctgc aaatgaacag cctgaaaacc gaggacacag ccgtgtatta ctgtgtcaca 300
gattacccga aggacgtctg gggccaaggg accacggtca ccgtctcctc a 351

<210> SEQ ID NO 44
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 44
gaggtgcagc tggtggagtc tgggggaggc ttggtacagc ctgggggtc cctgagactc 60 tcctgtgcag cctctggatt caccttcagt agctatagca tgaactgggt ccgccaggct 120
ccagggaagg ggctggagtg gatttcatac attagtagta gtaatagtac cataaagtac 180
gcagactctg tgaagggccg attcaccatc tccagagaca atgccaagaa ctcactgtat 240
ctgcaaatga acagcctgag agacgaggac acggctgtgt attactgtgc gagaaggagt 300
ctaggtgact actggggcca gggaaccctg gtcatcgtct cctca 345

<210> SEQ ID NO 45
<211> LENGTH: 345
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 45

caggtgcagc tgcaggagtc gggcccagga ctggtgaagc cttcggagac cctgtccctc     60

acctgcactg tctctggtgg ctccatcagt agttactact ggacctggat ccggcagccc    120

gccgggaagg gactggagtg gattgggcgt atcgatacca gtgggagcac caactacaac    180

ccctccctca agagtcgagt caccatgtca atagacacgt ccaagaaaca gttctccctg    240

aagctgagct ctgtgaccgc cgcggacacg gccgtgtatt actgtgcgag agggggagat    300

ggctaccgct actggggcca gggaaccctg gtcaccgtct cctca                    345


<210> SEQ ID NO 46
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

gaggtgcaac tggtggagtc tgggggaggc ttggtacagc ctggggggtc cctgagactc     60

tcctgtgcag cctctggatt caccttcagt agctataaca tgaactgggt tcgccaggct    120

ccagggaagg ggctggagtg gatttcatac attagtagta gtagtaatac catatactac    180

gcagactctg tgaagggccg attcaccgtc tccagggaca atgccaagaa ctcactgtat    240

ctgcaaatga acagcctgag agacgaggac acggctgtgt attactgtgc gactctgggg    300

aggggctact ggggccaggg aaccctggtc atcgcctcct ca                       342


<210> SEQ ID NO 47
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

caggtgcagc tgcaggagtc gggcccagga ctggtgaagc cttcggagac cctgtccctc     60

acctgcactg tctctggtgg ctccatcagt aattactact ggagttggat ccggcagccc    120

gccgggaagg gtctggagtg gattgggcgt atctatacca gtggggacac ctactacaac    180

ccctccctcc agagtcgagt caccatgtca gtagacacgt ccaagaacca gttctccctg    240

aagctgagcg ctgtgaccgc cgcggacacg gccgtctatt actgtgcgag agcgggtata    300

gtgggaactc cgggactcgg tatggacgtc tggggccaag ggaccacggt caccgtctcc    360

tca                                                                  363


<210> SEQ ID NO 48
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 48
gaggtgcagc tggtggagtc tgggggaggc ctggtcaagc ctggggggtc cctgagactc 60
tcctgtgcag cctctggatt caccttcagt acctatagca tgaactgggt ccgccaggct 120
ccagggaagg ggctggagtg ggtctcatcc attagtagtg gtagtagtta catatactac 180
gcagactcag tgaagggccg attcaccatc tccagagaca acgccaagaa ctcactgtat 240
ctgcaaatga acagcctgag agccgaggac acggctgtgt attactgtac agtaactaca 300
cacttccacc actggggcca gggcaccctg gtcaccgtct cctca 345

<210> SEQ ID NO 49
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49
cagatcacct taaaggagtc tggtcctacg ctggtgaaac ccacacagac cctcacgctg 60
acctgcaccc tctctgggtt ctcactcagc actagtgaag tgggtgtggg ctggatccgt 120
cagcccccag gaaaggccct ggagtggctt gcaatcattt attggaatga tcataagcgc 180
tacagcccat ctctgaagaa caggctcacc ttcaccaagg acacctccaa aaaccaggtg 240
gtccttacaa tgaccaacat ggaccctgtg gacacagcca catattattg tgcacgcaga 300
gtaactgggg aggggttcga cccctggggc cagggaaccc tggtcaccgt ctcctca 357

<210> SEQ ID NO 50
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50
gaggtgcagc tgttggagtc tgggggaggc ttggtacagc cggggggtc cctgagactc 60 tcctgtgcag cctcgggatt cacctatagc agctatgcca tgagctgggt ccgccgggct 120
ccagggaagg ggctggagtg gatctcaatt attagtggta gtagtagtat cacatactac 180
gcagactcca tgaagggccg gttcactatc tctagagaca attccaagaa cacgcttttt 240
ctgcaaatga atagcctgag agccgaggac acggccgttt attactgtgc gaaggggggg 300
aggtacgggt acttccaaca ctggggccag ggcaccctgg tcaccgtctc ctca 354

<210> SEQ ID NO 51
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51
caggtgcagc tgcaggagtc gggcccagga ctggtgaagc cttcggagac cctgtccctc 60
acctgcactg tctctggtgg ctccatcagt aattactact ggacctggat ccggcagccc 120
gccgggaagg gactggagtg gattgggcgt gtctatacca gtgggagcgc caactacaac 180

```
ccctccctca agagtcgagt taccatgtca gtagacacgt ccaagaacca gttctccctg    240

acgctgagct ctgtgaccgc cgcggacacg gccgtgtatt actgtgcgag agatagagga    300

ctctactact ggggccaggg aaccctggtc accgtctcct ca                       342


<210> SEQ ID NO 52
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

gaggtgcagc tggtggagtc tgggggaggc ttggtacagc ctggggggtc cctgagactc     60

tcctgtgcag cctctggatt caccttcagt agttatacca tgaactgggt ccgccaggct    120

ccagggaagg ggctggagtg ggtttcatac attagtagta gtagtagtac catatactac    180

gcagactctg tgaagggccg attcaccatc tccagagaca atgccaagaa ctcactgtat    240

ctgcaaatga acagcctgag agacgaggac acggctgtgt attactgtgc gagtctgggg    300

agaggggact gctggggcca gggaaccctg gtcaccgtct cctca                    345


<210> SEQ ID NO 53
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53

caggtgcagc tggtgcagtc tggggctgag gtgaagaagc ctggggcctc agtgaaggtc     60

tcctgcaagg cttctggata caccttcacc ggctactata tgcactgggt gcgacaggcc    120

cctggacaag ggcttgagtg gatgggatgg atcaacccta acagtggtgg cacaaactat    180

gcacagaagt ttcagggcag ggtcaccatg accagggaca cgtccatcag cacagcctac    240

atggagctga gcaggctgag atctgacgac acggccgtgt attactgtgc tggggatgct    300

tttgatatct ggggccaagg gacaatggtc accgtctctt ca                       342


<210> SEQ ID NO 54
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54

gaggtgcagc tggtggagtc tgggggaggc ttggtacagg ctggggggtc cctgagactc     60

tcctgtgcag cctctggatt caccttcagt gactatagca tgaactgggt ccgccaggct    120

ccagggaagg ggctggagtg ggtttcatat attaggagta gtagtagtat catatactac    180

gcagactctg tgaagggccg attcaccatc tccagagaca atgccaagaa ctcactgcat    240

ttgcaaatga acagcctgag agacgaggac acggctgtgt attactgtgc gagacggggt    300

cactttgact actggggcca gggaaccctg gtcaccgtct cctca                    345
```

<210> SEQ ID NO 55
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55
gaggtgcagc tggtggagtc tgggggaggc ttggtacagc ctgggggtc cctgagactc 60 tcctgtgcag cctctagatt caccttcagt aactataaca tgaactgggt ccgccaggct 120
ccagggaagg ggctggagtg gatttcatac attagtagta gtagtagtac catatactac 180
gcagactctg tgaagggccg attcaccatc tccagagaca atgccaagaa ctcactgtct 240
ctgcaaatga acagcctgag agacgaggac acggctgtgt attactgtgc gagtctgggg 300
aggggctact ggggccaggg aaccctggtc accgtctcct ca 342

<210> SEQ ID NO 56
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56
gaggtgcagc tggtggagtc tgggggaggc ttggtacagc ctgggggtc cctgagactc 60 tcctgtgcag cctctggatt caccttcagt agctatagca tgaactgggt ccgccaggct 120
ccagggaagg ggctggagtg ggtttcatac attagtcgta gtggtagtac catatactac 180
gcagactctg tggagggccg attcaccatc tccagagaca atgcctacaa ctcactgtat 240
ctgcaaatga tcagcctgag agacgatgac acggctgtgt attactgtgc gagagggaac 300
tgggcctact ggggccaggg aatcctggtc accgtctcct ca 342

<210> SEQ ID NO 57
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57
gatattgtga tgacccagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taaccggttc 180
tctggggtcc cagacagatt cagtggcagt ggggcaggga cagatttcac actgaaaatc 240
accagggtgg aggctgagga tgtcgggatt tattactgca tgcaagttac acaatttcct 300
cggacgttcg gccaagggac caaggtggaa atcaga 336

<210> SEQ ID NO 58
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

```
gatattgtga tgactcagtc tccactctcc ctgcccgtca tccctggaga gccggcctcc     60

atctcctgca ggtctagtca gagcctcctg catagtaatg gatacatcta tttggattgg    120

tacctgcaga agccagggca gtctccacag ctcctgatct atgtgggttc taatcgggcc    180

tccggggtcc ctgacaggtt cagtggcagt ggatcaggca cagatttcaa actgaaaatc    240

agcagagtgg aggctgagga tgttggggtt tattactgca tgcaaactct acaaattccg    300

cgcactttcg gcggagggac caaggtggag atcaaa                              336
```

<210> SEQ ID NO 59
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
gaaattgtgt tgacacagtc tccagccacc ctgtcttcgt ctccagggga aagagccacc     60

ctctcctgca gggccagtca gagtgttacc agctacttaa actggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctcgagcct    240

gaagattttg cactttatta ctgtcagcag cgtagcaact ggccgtacac ttttggccag    300

gggaccaaac tggagatcaa a                                              321
```

<210> SEQ ID NO 60
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60

```
gatattctga tgactcagtc tccactctcc ctgcccgtca cccctggaga gccggcctcc     60

atctcctgca ggtctagtca gagcctcctg catagtaatg gatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaattc    240

agcagagtgg aggctgagga tgttggactt tattactgca tgcaagctct acaaattccg    300

ctcactttcg gcggagggac caaggtggag atcaaa                              336
```

<210> SEQ ID NO 61
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

```
gacatcgtga tgacccagtc tccagactcc ctggctgtgt ctctgggcga gagggccacc     60
```

-continued

```
atcaactgca agtccagcca gagtgtttta tacagctcca aaaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcgcc    240

atcagcagcc tgcaggctga agatgtggca gtttattact gtcagcaata ttatagtagt    300

ccgtacactt ttggccaggg gaccaagctg gagatcaaa                           339


<210> SEQ ID NO 62
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62

gaaattgtgt tgacacagtc tccagccacc ctgtctttgt ctccagggga aagagccacc     60

ctctcctgca gggccagtca gagtgttagc agctacttag cctggtacct acagaaacct    120

ggccaggctc ccaggctcct catctatgat gtgtccaaca gggccactgg catcccagcc    180

aggttcagtg gcagtgggtc tgggacagac ttcactctca ccatcagcag actagagcct    240

gaagattttg cagtttatta ctgtcagcag cgtcgcaact ggccgtacac ttttggccag    300

gggaccaagc tggagatcaa a                                              321


<210> SEQ ID NO 63
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63

gacatccagt tgacccagtc tccatccttc ctgtctgcat ctgtaggaga cagagtcacc     60

atcacttgcc gggccagtca gggcattagc tgttctttag cctggtatca gcaaaaacca    120

gggaaagccc ctaagctcct gatctatgct gcatccactt tgcaaagtgg ggtcccatca    180

aggttcagcg gcagtggatc tgggacagaa ttcactctca caatcagcag cctgcagcct    240

gaagattttg caacttatta ctgtcaacag tttaatagtt acccattcac tttcggccct    300

gggaccaaag tggatatcaa a                                              321


<210> SEQ ID NO 64
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64

tcctatgagc tgacacagcc accctcggtg tcagtgtccc caggacagac ggccaggatc     60

acctgctctg gagatgcatt gccaaagcaa tatgcttgtt ggtaccagca gaagccaggc    120

caggcccctg tgctggtgat atataaagac agtgagaggc cctcagggat ccctgagcga    180

ttctctggct ccagctcagg gacaacagtc acgttgacca tcactggagt ccaggcagaa    240

gatgaggctg actattactg tcaatccaca gacagcagtg gttcttgggt gttcggcgga    300
```

gggaccaagc tgaccgtcct a 321

<210> SEQ ID NO 65
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65
gatgttgtga tgacccagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagctac acaatttcct 300
cgcacttttg gccaggggac caagctggag atcaaa 336

<210> SEQ ID NO 66
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66
tcctatgagc tgacacagcc accctcggtg tcagtgtccc caggacagac ggccaggatc 60
acctgctctg gagaagcatt gccaaagcaa tatgcttatt ggtaccagca gaagccaggc 120
caggcccctg tgctggtgat atataaagac agtgagaggc cctcagggat ccctgagcga 180
ttctctggct ccagctcagg gacaacagtc acgttgacca tcagtggagt ccaggcagaa 240
gatgaggctg actattactg tcaatcagca gacagcagtg gtacttatcg ggtgttcggc 300
ggagggacca agctgaccgt ccta 324

<210> SEQ ID NO 67
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actaaaaatc 240
agcagggtgg aggctgagga tgttggggtt tattactgca tgcaaggtac acactggcct 300
ctcaccttcg gccaagggac acgactggag attaaa 336

<210> SEQ ID NO 68
<211> LENGTH: 345
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

caggctgtgc tgactcagcc gtcttccctc tctgcatctc ctggagcatc agccagactc     60

acctgcacct tgcgcagtgg catcaatgtt ggtgcctaca ggctatactg gtaccagcag    120

aagccaggaa gtcctcccca gtatctcctg aggtacaaat cagactcaga taagcagcag    180

ggctctggag tccccagccg cttctctgga tccaaagatg cttcggccaa tgcagggatt    240

ttactcatct ctgggctcca gtctgaggat gaggctgact attactgtat gatttggcac    300

agcagcgctt gggtgttcgg cggagggacc aagctgaccg tccta                    345


<210> SEQ ID NO 69
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69

tcctatgagc tgacacagcc accctcggtg tcagtgtccc caggacagac ggccaggatc     60

acctgctctg gagatgcatt gccaaagcaa tatgcttatt ggtaccagca gaagccaggc    120

caggcccctg tgctggtgat atttaaagac actgagaggc cctcagggat ccctgagcga    180

ttctctggct ccagctcagg gacaacagtc acgttgacca tcagtggagt ccaggcagaa    240

gatgaggctg actattactg tcaatcagca gacagcagtg gttcttatgt cttcggaact    300

gggaccaagg tcaccgtcct a                                              321


<210> SEQ ID NO 70
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

tcctatgtgc tgactcagcc accctcggtg tcagtggccc caggacagac ggccaggatt     60

acctgtgggg gaaacaacat tggaagtaaa agtgtgcact ggtaccagca gaagccaggc    120

caggcccctg tgctggtcgt ctatgatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcctgt ggtattcggc    300

ggagggacca tgctgaccgt ccta                                           324


<210> SEQ ID NO 71
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
```

gatattgtga tgacccagac tccactctcc tcacttgtca cccttggaca gccggcctcc 60
atctcctgca ggtctagtca aagcctcgta cacagtgatg gaaacaccta tttgagttgg 120
cttcagcaga ggccaggcca gcctccaaga ctcctaattt ataagatttc taagcggttc 180
tttggggtcc cagacagatt cagtggcagt ggggcaggga cagatttcac actgaaaatc 240
aacagggtgg aagctgagga tgtcgggatt tattactgca tgcaagctac acaatttccg 300
ctcactttcg gcggagggac caaggtggag atcaaa 336

<210> SEQ ID NO 72
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 72
gatattgtga tgacccagac tccactctcc tcacctgtca cccttggaca gccggcctcc 60
atctcctgca ggtctagtca aagcctcgta cacagtgatg gaaacaccta cttgagttgg 120
cttcagcaga ggccaggcca gcctccaaga ctcctaattt ataagatttc taaacggttc 180
tctggggtcc cagacagatt cagtggcagt ggggcaggga cagatttcac actgaaaatc 240
agcagggtgg aagctgagga tgtcggggtt tattactgca tgcaagctac acaatttcct 300
cggaccttcg gccaagggac acgactggag attaaa 336

<210> SEQ ID NO 73
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 73
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
ccgctcactt tcggcggagg gaccaaggtg gagatcaaa 339

<210> SEQ ID NO 74
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 74
gaaattgtgt tgacacagtc tccagccacc ctgtctttgt ctccagggga aagagccacc 60
ctctcctgca gggccagtca gagtgttagc gactacttag cctggtacca acagaaacct 120
ggccaggctc ccaggctctt catctatgat gtatccaaga gggccactgg catcccagcc 180

```
aggttcagtg gcagtgggtc tgggacagac ttcactctca ccatcagcag cctagagcct    240

gaagattttg cagtttatta ctgtcagcag cgtagcaact ggccgctcac tttcggcgga    300

gggaccaagg tggagatcaa a                                              321
```

<210> SEQ ID NO 75
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
gatattgtga tgacccagac tccactctcc tcacctgtca cccttggaca gccggcctcc     60

atctcctgca ggtctagtca aagcctcgta cacagtgatg gaaacaccta cttgagttgg    120

cttcagcaga ggccaggcca gcctccaaga ctcctaattt ataagatttc taaccggttc    180

tctggggtcc cagacagatt cagtggcagt ggggcaggga cagatttcac actgaaaatc    240

agcagggtgg aagctgagga tgtcggggtt tattattgta tgcaagctac tcaatttcct    300

cgcacttttg gccaggggtc caagctggag atcaaa                              336
```

<210> SEQ ID NO 76
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 76

```
cagtctgtgc tgacgcagcc gccctcagtg tctggggccc cagggcagag ggtcaccatc     60

tcctgcactg ggagcagctc caacatcggg gcaggttatg atgtacactg gtaccagcag    120

cttccaggaa cagcccccaa actcctcatc tatggtaaca gcaatcggcc ctcaggggtc    180

cctgaccgat tctctggctc caagtctggc acctcagcct ccctggccat cactgggctc    240

caggctgagg atgagactga tttttactgc cagtcctatg acagcagcct gagtggttcg    300

gttttcggcg gagggaccaa gctgaccgtc ctg                                 333
```

<210> SEQ ID NO 77
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 77

```
Gly Phe Thr Phe Ser Ser Tyr Arg
1               5
```

<210> SEQ ID NO 78
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

Gly Phe Thr Phe Ser Ser Tyr Ser
1 5

<210> SEQ ID NO 79
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

Arg Phe Thr Phe Ser Asn Tyr Asn
1 5

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

Gly Phe Thr Phe Ser Asp Tyr Ser
1 5

<210> SEQ ID NO 81
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

Gly Phe Thr Phe Ser Ser Tyr Thr
1 5

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Gly Gly Ser Ile Ser Asn Tyr Tyr
1 5

<210> SEQ ID NO 83
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

Gly Phe Thr Tyr Ser Ser Tyr Ala
1 5

<210> SEQ ID NO 84
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

Gly Phe Ser Leu Ser Thr Ser Glu Val Gly
1 5 10

<210> SEQ ID NO 85
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 85

Gly Phe Thr Phe Ser Thr Tyr Ser
1 5

<210> SEQ ID NO 86
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

Gly Phe Thr Phe Ser Ser Tyr Asn
1 5

<210> SEQ ID NO 87
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 87

Gly Gly Ser Ile Ser Ser Tyr Tyr
1 5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 88

Gly Phe Thr Phe Ser Asn Ala Trp
1 5

<210> SEQ ID NO 89
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Phe Thr Phe Asn Asn Tyr Asp
1               5


<210> SEQ ID NO 90
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gly Tyr Thr Phe Thr Gly Tyr Tyr
1               5


<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Phe Ser Leu Ile Asn Ala Arg Met Ala
1               5                   10


<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ile Ser Ser Ser Arg Ser Ala Ile
1               5


<210> SEQ ID NO 93
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Ile Ser Arg Ser Gly Ser Thr Ile
1               5


<210> SEQ ID NO 94
<211> LENGTH: 8
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic peptide"

<400> SEQUENCE: 94

Ile Ser Ser Ser Ser Ser Thr Ile
1               5

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ile Arg Ser Ser Ser Ser Ile Ile
1               5

<210> SEQ ID NO 96
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ile Arg Ser Ser Ser Ser Thr Ile
1               5

<210> SEQ ID NO 97
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Val Tyr Thr Ser Gly Ser Ala
1               5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Ile Ser Gly Ser Ser Ser Ile Thr
1               5

<210> SEQ ID NO 99
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Ile Tyr Trp Asn Asp His Lys
1 5

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 100

Ile Ser Ser Gly Ser Ser Tyr Ile
1 5

<210> SEQ ID NO 101
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 101

Ile Tyr Thr Ser Gly Asp Thr
1 5

<210> SEQ ID NO 102
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 102

Ile Ser Ser Ser Ser Asn Thr Ile
1 5

<210> SEQ ID NO 103
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 103

Ile Asp Thr Ser Gly Ser Thr
1 5

<210> SEQ ID NO 104
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 104

Ile Ser Ser Ser Asn Ser Thr Ile
1 5

<210> SEQ ID NO 105
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 105

Ile Lys Ser Lys Thr Asp Gly Gly Thr Thr
1 5 10

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 106

Ile Gly Ala Ala Gly Asp Thr
1 5

<210> SEQ ID NO 107
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 107

Ile Asn Pro Asn Ser Gly Gly Thr
1 5

<210> SEQ ID NO 108
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 108

Ile Phe Ser Asn Asp Glu Lys
1 5

<210> SEQ ID NO 109
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 109

Ala Thr Leu Gly Ile Gly Tyr
1 5

<210> SEQ ID NO 110
<211> LENGTH: 7
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 110

Ala Arg Gly Asn Trp Ala Tyr
1 5

<210> SEQ ID NO 111
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 111

Ala Ser Leu Gly Arg Gly Tyr
1 5

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 112

Ala Arg Arg Gly His Phe Asp Tyr
1 5

<210> SEQ ID NO 113
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 113

Ala Arg Arg Ser Ile Ala Asp Tyr
1 5

<210> SEQ ID NO 114
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 114

Ala Ser Leu Gly Arg Gly Asp Cys
1 5

<210> SEQ ID NO 115
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 115

Ala Arg Asp Arg Gly Leu Tyr Tyr
1 5

<210> SEQ ID NO 116
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 116

Ala Lys Gly Gly Arg Tyr Gly Tyr Phe Gln His
1 5 10

<210> SEQ ID NO 117
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 117

Ala Arg Arg Val Thr Gly Glu Gly Phe Asp Pro
1 5 10

<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 118

Thr Val Thr Thr His Phe His His
1 5

<210> SEQ ID NO 119
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 119

Ala Arg Ala Gly Ile Val Gly Thr Pro Gly Leu Gly Met Asp Val
1 5 10 15

<210> SEQ ID NO 120
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 120

```
Ala Thr Leu Gly Arg Gly Tyr
1               5


<210> SEQ ID NO 121
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ala Arg Gly Gly Asp Gly Tyr Arg Tyr
1               5


<210> SEQ ID NO 122
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Ala Arg Arg Ser Leu Gly Asp Tyr
1               5


<210> SEQ ID NO 123
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Val Thr Asp Tyr Pro Lys Asp Val
1               5


<210> SEQ ID NO 124
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Ala Arg Ala Gly Glu Thr Leu Glu Gly Ala Thr Ile Gly Tyr Tyr Tyr
1               5                   10                  15

Gly Met Asp Val
            20


<210> SEQ ID NO 125
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Ala Gly Asp Ala Phe Asp Ile
```

-continued 1 5

<210> SEQ ID NO 126
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Ala Arg Ile Arg Gly Tyr Ser Tyr Asn Tyr Gly Met Asp Val
1 5 10

<210> SEQ ID NO 127
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 127

Gln Ser Leu Val His Ser Asp Gly Asn Thr Tyr
1 5 10

<210> SEQ ID NO 128
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 128

Ser Ser Asn Ile Gly Ala Gly Tyr Asp
1 5

<210> SEQ ID NO 129
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 129

Gln Ser Val Ser Asp Tyr
1 5

<210> SEQ ID NO 130
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 130

Gln Ser Val Thr Ser Tyr
1 5

<210> SEQ ID NO 131

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Asn Ile Gly Ser Lys Ser
1               5


<210> SEQ ID NO 132
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Ala Leu Pro Lys Gln Tyr
1               5


<210> SEQ ID NO 133
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Gln Ser Leu Val Tyr Ser Asp Gly Asn Thr Tyr
1               5                   10


<210> SEQ ID NO 134
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Ser Gly Ile Asn Val Gly Ala Tyr Arg
1               5


<210> SEQ ID NO 135
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Gln Ser Val Ser Ser Tyr
1               5


<210> SEQ ID NO 136
<211> LENGTH: 6
<212> TYPE: PRT
<213> ORGANISM: Artificial Sequence
<220> FEATURE:
```

<221> NAME/KEY: source
<223> OTHER INFORMATION: /note="Description of Artificial Sequence:
Synthetic peptide"

<400> SEQUENCE: 136

Gln Gly Ile Ser Cys Ser
1 5

<210> SEQ ID NO 137
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 137

Gln Ser Val Leu Tyr Ser Ser Lys Asn Lys Asn Tyr
1 5 10

<210> SEQ ID NO 138
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 138

Gln Ser Leu Leu His Ser Asn Gly Tyr Asn Tyr
1 5 10

<210> SEQ ID NO 139
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 139

Gln Ser Val Leu Tyr Ser Ser Asn Asn Lys Asn Tyr
1 5 10

<210> SEQ ID NO 140
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 140

Gln Ser Leu Leu His Ser Asn Gly Tyr Ile Tyr
1 5 10

<210> SEQ ID NO 141
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 141

Lys Ile Ser
1

<210> SEQ ID NO 142
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 142

Gly Asn Ser
1

<210> SEQ ID NO 143
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 143

Asp Val Ser
1

<210> SEQ ID NO 144
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 144

Asp Ala Ser
1

<210> SEQ ID NO 145
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 145

Asp Asp Ser
1

<210> SEQ ID NO 146
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 146

Lys Asp Thr
1

-continued

<210> SEQ ID NO 147
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Lys Val Ser
1

<210> SEQ ID NO 148
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Tyr Lys Ser Asp Ser Asp Lys
1               5

<210> SEQ ID NO 149
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 149

Lys Asp Ser
1

<210> SEQ ID NO 150
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 150

Ala Ala Ser
1

<210> SEQ ID NO 151
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 151

Trp Ala Ser
1

<210> SEQ ID NO 152
<211> LENGTH: 3

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 152

Leu Gly Ser
1

<210> SEQ ID NO 153
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 153

Val Gly Ser
1

<210> SEQ ID NO 154
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 154

Met Gln Val Thr Gln Phe Pro Arg Thr
1 5

<210> SEQ ID NO 155
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 155

Gln Ser Tyr Asp Ser Ser Leu Ser Gly Ser Val
1 5 10

<210> SEQ ID NO 156
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 156

Met Gln Ala Thr Gln Phe Pro Arg Thr
1 5

<210> SEQ ID NO 157
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Gln Gln Arg Ser Asn Trp Pro Leu Thr
1               5

<210> SEQ ID NO 158
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Gln Gln Arg Ser Asn Trp Pro Tyr Thr
1               5

<210> SEQ ID NO 159
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Met Gln Ala Thr Gln Phe Pro Leu Thr
1               5

<210> SEQ ID NO 160
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Gln Val Trp Asp Ser Ser Ser Asp Pro Val Val
1               5                   10

<210> SEQ ID NO 161
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Gln Ser Ala Asp Ser Ser Gly Ser Tyr Val
1               5                   10

<210> SEQ ID NO 162
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

-continued

Met Gln Gly Thr His Trp Pro Leu Thr
1               5

<210> SEQ ID NO 163
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Met Ile Trp His Ser Ser Ala Trp Val
1               5

<210> SEQ ID NO 164
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Gln Ser Ala Asp Ser Ser Gly Thr Tyr Arg Val
1               5                   10

<210> SEQ ID NO 165
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gln Ser Thr Asp Ser Ser Gly Ser Trp Val
1               5                   10

<210> SEQ ID NO 166
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gln Gln Arg Arg Asn Trp Pro Tyr Thr
1               5

<210> SEQ ID NO 167
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Gln Gln Phe Asn Ser Tyr Pro Phe Thr
1               5

<210> SEQ ID NO 168
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 168

Gln Gln Tyr Tyr Ser Ser Pro Tyr Thr
1 5

<210> SEQ ID NO 169
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 169

Met Gln Ala Leu Gln Ile Pro Leu Thr
1 5

<210> SEQ ID NO 170
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 170

Gln Gln Tyr Tyr Ser Thr Pro Leu Thr
1 5

<210> SEQ ID NO 171
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 171

Met Gln Thr Leu Gln Ile Pro Arg Thr
1 5

<210> SEQ ID NO 172
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 172

Glu Val Gln Met Val Glu Ser Gly Gly Gly Leu Val Gln Pro Gly Gly
1 5 10 15

Ser Leu Thr Leu Ser Cys Ala Ala Ser
20 25

```
<210> SEQ ID NO 173
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25


<210> SEQ ID NO 174
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25


<210> SEQ ID NO 175
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25


<210> SEQ ID NO 176
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25


<210> SEQ ID NO 177
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 177

Gln Ile Thr Leu Lys Glu Ser Gly Pro Thr Leu Val Lys Pro Thr Gln
1 5 10 15

Thr Leu Thr Leu Thr Cys Thr Leu Ser
20 25

<210> SEQ ID NO 178
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 178

Glu Val Gln Leu Val Glu Ser Gly Gly Gly Leu Val Lys Pro Gly Gly
1 5 10 15

Ser Leu Arg Leu Ser Cys Ala Ala Ser
20 25

<210> SEQ ID NO 179
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 179

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 180
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 180

Gln Val Thr Leu Lys Glu Ser Gly Pro Val Leu Val Lys Pro Thr Glu
1 5 10 15

Thr Leu Thr Leu Thr Cys Thr Val Ser
20 25

<210> SEQ ID NO 181
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 181

Met Asn Trp Val Arg Gln Ala Pro Gly Lys Gly Leu Glu Trp Val Ser
1 5 10 15

Tyr

<210> SEQ ID NO 182
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 182

Met Asn Trp Val Arg Gln Ala Pro Gly Lys Gly Leu Glu Trp Ile Ser
1 5 10 15

Tyr

<210> SEQ ID NO 183
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 183

Trp Thr Trp Ile Arg Gln Pro Ala Gly Lys Gly Leu Glu Trp Ile Gly
1 5 10 15

Arg

<210> SEQ ID NO 184
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 184

Met Ser Trp Val Arg Arg Ala Pro Gly Lys Gly Leu Glu Trp Ile Ser
1 5 10 15

Ile

<210> SEQ ID NO 185
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 185

Val Gly Trp Ile Arg Gln Pro Pro Gly Lys Ala Leu Glu Trp Leu Ala
1 5 10 15

Ile

<210> SEQ ID NO 186
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 186

Met Asn Trp Val Arg Gln Ala Pro Gly Lys Gly Leu Glu Trp Val Ser
1 5 10 15

Ser

<210> SEQ ID NO 187
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 187

Trp Ser Trp Ile Arg Gln Pro Ala Gly Lys Gly Leu Glu Trp Ile Gly
1 5 10 15

Arg

<210> SEQ ID NO 188
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

Met Ser Trp Val Arg Gln Ala Pro Gly Lys Gly Leu Glu Trp Phe Gly
1 5 10 15

Arg

<210> SEQ ID NO 189
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

Met His Trp Val Arg Gln Ala Ala Gly Lys Gly Leu Glu Trp Val Ser
1 5 10 15

Thr

<210> SEQ ID NO 190
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Met His Trp Val Arg Gln Ala Pro Gly Gln Gly Leu Glu Trp Met Gly
1 5 10 15

Trp

<210> SEQ ID NO 191
<211> LENGTH: 17

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Val Ser Trp Ile Arg Gln Pro Pro Gly Lys Ala Leu Glu Trp Leu Ala
1 5 10 15

His

<210> SEQ ID NO 192
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

Tyr Tyr Ala Asp Ser Val Lys Gly Arg Phe Thr Ile Ser Arg Asp Asn
1 5 10 15

Ala Lys Asn Ser Leu Tyr Leu Gln Met Asn Ser Leu Arg Asp Glu Asp
20 25 30

Thr Ala Val Tyr Tyr Cys
35

<210> SEQ ID NO 193
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 193

Tyr Tyr Ala Asp Ser Val Glu Gly Arg Phe Thr Ile Ser Arg Asp Asn
1 5 10 15

Ala Tyr Asn Ser Leu Tyr Leu Gln Met Ile Ser Leu Arg Asp Asp Asp
20 25 30

Thr Ala Val Tyr Tyr Cys
35

<210> SEQ ID NO 194
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 194

Tyr Tyr Ala Asp Ser Val Lys Gly Arg Phe Thr Ile Ser Arg Asp Asn
1 5 10 15

Ala Lys Asn Ser Leu Ser Leu Gln Met Asn Ser Leu Arg Asp Glu Asp
20 25 30

Thr Ala Val Tyr Tyr Cys
35

<210> SEQ ID NO 195

<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 195

```
Tyr Tyr Ala Asp Ser Val Lys Gly Arg Phe Thr Ile Ser Arg Asp Asn
1               5                   10                  15

Ala Lys Asn Ser Leu His Leu Gln Met Asn Ser Leu Arg Asp Glu Asp
            20                  25                  30

Thr Ala Val Tyr Tyr Cys
        35
```

<210> SEQ ID NO 196
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 196

```
Tyr Tyr Ala Asp Ser Val Lys Gly Arg Phe Thr Ile Ser Arg Asp Asn
1               5                   10                  15

Ala Lys Lys Ser Leu Tyr Leu Gln Met Asn Ser Leu Arg Asp Glu Asp
            20                  25                  30

Thr Ala Val Tyr Tyr Cys
        35
```

<210> SEQ ID NO 197
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 197

```
Asn Tyr Asn Pro Ser Leu Lys Ser Arg Val Thr Met Ser Val Asp Thr
1               5                   10                  15

Ser Lys Asn Gln Phe Ser Leu Thr Leu Ser Ser Val Thr Ala Ala Asp
            20                  25                  30

Thr Ala Val Tyr Tyr Cys
        35
```

<210> SEQ ID NO 198
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 198

```
Tyr Tyr Ala Asp Ser Met Lys Gly Arg Phe Thr Ile Ser Arg Asp Asn
1               5                   10                  15

Ser Lys Asn Thr Leu Phe Leu Gln Met Asn Ser Leu Arg Ala Glu Asp
            20                  25                  30
```

```
Thr Ala Val Tyr Tyr Cys
        35


<210> SEQ ID NO 199
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Arg Tyr Ser Pro Ser Leu Lys Asn Arg Leu Thr Phe Thr Lys Asp Thr
1               5                   10                  15

Ser Lys Asn Gln Val Val Leu Thr Met Thr Asn Met Asp Pro Val Asp
            20                  25                  30

Thr Ala Thr Tyr Tyr Cys
        35


<210> SEQ ID NO 200
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35


<210> SEQ ID NO 201
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Tyr Tyr Asn Pro Ser Leu Gln Ser Arg Val Thr Met Ser Val Asp Thr
1               5                   10                  15

Ser Lys Asn Gln Phe Ser Leu Lys Leu Ser Ala Val Thr Ala Ala Asp
            20                  25                  30

Thr Ala Val Tyr Tyr Cys
        35


<210> SEQ ID NO 202
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Tyr Tyr Ala Asp Ser Val Lys Gly Arg Phe Thr Val Ser Arg Asp Asn
```

```
1               5                   10                  15

Ala Lys Asn Ser Leu Tyr Leu Gln Met Asn Ser Leu Arg Asp Glu Asp
            20                  25                  30

Thr Ala Val Tyr Tyr Cys
        35


<210> SEQ ID NO 203
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Asn Tyr Asn Pro Ser Leu Lys Ser Arg Val Thr Met Ser Ile Asp Thr
1               5                   10                  15

Ser Lys Lys Gln Phe Ser Leu Lys Leu Ser Ser Val Thr Ala Ala Asp
            20                  25                  30

Thr Ala Val Tyr Tyr Cys
        35


<210> SEQ ID NO 204
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Lys Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Asp Glu Asp
            20                  25                  30

Thr Ala Val Tyr Tyr Cys
        35


<210> SEQ ID NO 205
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Asp Tyr Ala Ala Pro Val Lys Gly Arg Phe Thr Ile Ser Arg Asp Asp
1               5                   10                  15

Ser Lys Asn Thr Leu Tyr Leu Gln Met Asn Ser Leu Lys Thr Glu Asp
            20                  25                  30

Thr Ala Val Tyr Tyr Cys
        35


<210> SEQ ID NO 206
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 206

Tyr Tyr Pro Gly Ser Val Lys Gly Arg Phe Ile Ile Ser Arg Glu Asn
1 5 10 15

Ala Lys Asn Ser Leu Tyr Leu Gln Met Asn Ser Leu Arg Ala Gly Asp
20 25 30

Thr Ala Val Tyr Tyr Cys
35

<210> SEQ ID NO 207
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 207

Asn Tyr Ala Gln Lys Phe Gln Gly Arg Val Thr Met Thr Arg Asp Thr
1 5 10 15

Ser Ile Ser Thr Ala Tyr Met Glu Leu Ser Arg Leu Arg Ser Asp Asp
20 25 30

Thr Ala Val Tyr Tyr Cys
35

<210> SEQ ID NO 208
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 208

Ser Tyr Ser Thr Ser Leu Lys Ser Arg Leu Thr Ile Ser Lys Asp Thr
1 5 10 15

Ser Lys Ser Gln Val Val Leu Ile Met Thr Asn Met Asp Pro Val Asp
20 25 30

Thr Ala Thr Tyr Tyr Cys
35

<210> SEQ ID NO 209
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 209

Trp Gly Gln Gly Thr Leu Val Thr Val Ser Ser
1 5 10

<210> SEQ ID NO 210
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 210

Trp Gly Gln Gly Ile Leu Val Thr Val Ser Ser
1 5 10

<210> SEQ ID NO 211
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Trp Gly Gln Gly Thr Thr Val Thr Val Ser Ser
1 5 10

<210> SEQ ID NO 212
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Trp Gly Gln Gly Thr Leu Val Ile Ala Ser Ser
1 5 10

<210> SEQ ID NO 213
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 213

Trp Gly Gln Gly Thr Leu Val Ile Val Ser Ser
1 5 10

<210> SEQ ID NO 214
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 214

Trp Gly Gln Gly Thr Met Val Thr Val Ser Ser
1 5 10

<210> SEQ ID NO 215
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 215

Asp Ile Val Met Thr Gln Thr Pro Leu Ser Ser Pro Val Thr Leu Gly

```
1               5                   10                  15

Gln Pro Ala Ser Ile Ser Cys Arg Ser Ser
            20                  25


<210> SEQ ID NO 216
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Gln Ser Val Leu Thr Gln Pro Pro Ser Val Ser Gly Ala Pro Gly Gln
1               5                   10                  15

Arg Val Thr Ile Ser Cys Thr Gly Ser
            20                  25


<210> SEQ ID NO 217
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25


<210> SEQ ID NO 218
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Glu Ile Val Leu Thr Gln Ser Pro Ala Thr Leu Ser Ser Ser Pro Gly
1               5                   10                  15

Glu Arg Ala Thr Leu Ser Cys Arg Ala Ser
            20                  25


<210> SEQ ID NO 219
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Asp Ile Val Met Thr Gln Thr Pro Leu Ser Ser Leu Val Thr Leu Gly
1               5                   10                  15

Gln Pro Ala Ser Ile Ser Cys Arg Ser Ser
            20                  25


<210> SEQ ID NO 220
```

```
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Ser Tyr Val Leu Thr Gln Pro Pro Ser Val Ser Val Ala Pro Gly Gln
1               5                   10                  15

Thr Ala Arg Ile Thr Cys Gly Gly Asn
            20                  25


<210> SEQ ID NO 221
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Ser Tyr Glu Leu Thr Gln Pro Pro Ser Val Ser Val Ser Pro Gly Gln
1               5                   10                  15

Thr Ala Arg Ile Thr Cys Ser Gly Asp
            20                  25


<210> SEQ ID NO 222
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Asp Val Val Met Thr Gln Ser Pro Leu Ser Leu Pro Val Thr Leu Gly
1               5                   10                  15

Gln Pro Ala Ser Ile Ser Cys Arg Ser Ser
            20                  25


<210> SEQ ID NO 223
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gln Ala Val Leu Thr Gln Pro Ser Ser Leu Ser Ala Ser Pro Gly Ala
1               5                   10                  15

Ser Ala Arg Leu Thr Cys Thr Leu Arg
            20                  25


<210> SEQ ID NO 224
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 224

Ser Tyr Glu Leu Thr Gln Pro Pro Ser Val Ser Val Ser Pro Gly Gln
1 5 10 15

Thr Ala Arg Ile Thr Cys Ser Gly Glu
20 25

<210> SEQ ID NO 225
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 225

Asp Val Val Met Thr Gln Thr Pro Leu Ser Ser Pro Val Thr Leu Gly
1 5 10 15

Gln Pro Ala Ser Ile Ser Cys Arg Ser Ser
20 25

<210> SEQ ID NO 226
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 226

Asp Ile Gln Leu Thr Gln Ser Pro Ser Phe Leu Ser Ala Ser Val Gly
1 5 10 15

Asp Arg Val Thr Ile Thr Cys Arg Ala Ser
20 25

<210> SEQ ID NO 227
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 227

Asp Ile Val Met Thr Gln Ser Pro Asp Ser Leu Ala Val Ser Leu Gly
1 5 10 15

Glu Arg Ala Thr Ile Asn Cys Lys Ser Ser
20 25

<210> SEQ ID NO 228
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 228

Asp Ile Leu Met Thr Gln Ser Pro Leu Ser Leu Pro Val Thr Pro Gly
1 5 10 15

Glu Pro Ala Ser Ile Ser Cys Arg Ser Ser

```
            20                  25


<210> SEQ ID NO 229
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Asp Ile Val Met Thr Gln Ser Pro Leu Ser Leu Pro Val Ile Pro Gly
1               5                   10                  15

Glu Pro Ala Ser Ile Ser Cys Arg Ser Ser
            20                  25


<210> SEQ ID NO 230
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Leu Ser Trp Leu Gln Gln Arg Pro Gly Gln Pro Pro Arg Leu Leu Ile
1               5                   10                  15

Tyr


<210> SEQ ID NO 231
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Val His Trp Tyr Gln Gln Leu Pro Gly Thr Ala Pro Lys Leu Leu Ile
1               5                   10                  15

Tyr


<210> SEQ ID NO 232
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Leu Ala Trp Tyr Gln Gln Lys Pro Gly Gln Ala Pro Arg Leu Phe Ile
1               5                   10                  15

Tyr


<210> SEQ ID NO 233
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide”

<400> SEQUENCE: 233

Leu Asn Trp Tyr Gln Gln Lys Pro Gly Gln Ala Pro Arg Leu Leu Ile
1 5 10 15

Tyr

<210> SEQ ID NO 234
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide”

<400> SEQUENCE: 234

Val His Trp Tyr Gln Gln Lys Pro Gly Gln Ala Pro Val Leu Val Val
1 5 10 15

Tyr

<210> SEQ ID NO 235
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide”

<400> SEQUENCE: 235

Ala Tyr Trp Tyr Gln Gln Lys Pro Gly Gln Ala Pro Val Leu Val Ile
1 5 10 15

Phe

<210> SEQ ID NO 236
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide”

<400> SEQUENCE: 236

Leu Asn Trp Phe Gln Gln Arg Pro Gly Gln Ser Pro Arg Arg Leu Ile
1 5 10 15

Tyr

<210> SEQ ID NO 237
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide”

<400> SEQUENCE: 237

Leu Tyr Trp Tyr Gln Gln Lys Pro Gly Ser Pro Pro Gln Tyr Leu Leu
1 5 10 15

Arg

<210> SEQ ID NO 238

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Ala Tyr Trp Tyr Gln Gln Lys Pro Gly Gln Ala Pro Val Leu Val Ile
1               5                   10                  15

Tyr


<210> SEQ ID NO 239
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Ala Cys Trp Tyr Gln Gln Lys Pro Gly Gln Ala Pro Val Leu Val Ile
1               5                   10                  15

Tyr


<210> SEQ ID NO 240
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Leu Ala Trp Tyr Leu Gln Lys Pro Gly Gln Ala Pro Arg Leu Leu Ile
1               5                   10                  15

Tyr


<210> SEQ ID NO 241
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Leu Ala Trp Tyr Gln Gln Lys Pro Gly Lys Ala Pro Lys Leu Leu Ile
1               5                   10                  15

Tyr


<210> SEQ ID NO 242
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Leu Ala Trp Tyr Gln Gln Lys Pro Gly Gln Pro Pro Lys Leu Leu Ile
```

```
1               5                   10                  15

Tyr


<210> SEQ ID NO 243
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Leu Asp Trp Tyr Leu Gln Lys Pro Gly Gln Ser Pro Gln Leu Leu Ile
1               5                   10                  15

Tyr


<210> SEQ ID NO 244
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Asn Arg Phe Ser Gly Val Pro Asp Arg Phe Ser Gly Ser Gly Ala Gly
1               5                   10                  15

Thr Asp Phe Thr Leu Lys Ile Thr Arg Val Glu Ala Glu Asp Val Gly
            20                  25                  30

Ile Tyr Tyr Cys
        35


<210> SEQ ID NO 245
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Thr
            20                  25                  30

Asp Phe Tyr Cys
        35


<210> SEQ ID NO 246
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

Asn Arg Phe Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
```

```
            20                  25                  30

Val Tyr Tyr Cys
        35


<210> SEQ ID NO 247
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247

Lys Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35


<210> SEQ ID NO 248
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Leu Tyr Tyr Cys
        35


<210> SEQ ID NO 249
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

Lys Arg Phe Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
            20                  25                  30

Val Tyr Tyr Cys
        35


<210> SEQ ID NO 250
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 250
```

```
Lys Arg Phe Phe Gly Val Pro Asp Arg Phe Ser Gly Ser Gly Ala Gly
1               5                   10                  15

Thr Asp Phe Thr Leu Lys Ile Asn Arg Val Glu Ala Glu Asp Val Gly
            20                  25                  30

Ile Tyr Tyr Cys
        35


<210> SEQ ID NO 251
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

Asp Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
        35


<210> SEQ ID NO 252
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Glu Arg Pro Ser Gly Ile Pro Glu Arg Phe Ser Gly Ser Ser Ser Gly
1               5                   10                  15

Thr Thr Val Thr Leu Thr Ile Ser Gly Val Gln Ala Glu Asp Glu Ala
            20                  25                  30

Asp Tyr Tyr Cys
        35


<210> SEQ ID NO 253
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Asn Arg Asp Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35


<210> SEQ ID NO 254
<211> LENGTH: 38
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 254

Gln Gln Gly Ser Gly Val Pro Ser Arg Phe Ser Gly Ser Lys Asp Ala
1               5                   10                  15

Ser Ala Asn Ala Gly Ile Leu Leu Ile Ser Gly Leu Gln Ser Glu Asp
            20                  25                  30

Glu Ala Asp Tyr Tyr Cys
        35


<210> SEQ ID NO 255
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 255

Glu Arg Pro Ser Gly Ile Pro Glu Arg Phe Ser Gly Ser Ser Ser Gly
1               5                   10                  15

Thr Thr Val Thr Leu Thr Ile Thr Gly Val Gln Ala Glu Asp Glu Ala
            20                  25                  30

Asp Tyr Tyr Cys
        35


<210> SEQ ID NO 256
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Asn Arg Ala Thr Gly Ile Pro Ala Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35


<210> SEQ ID NO 257
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

Thr Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35
```

<210> SEQ ID NO 258
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 258

```
Thr Arg Glu Ser Gly Val Pro Asp Arg Phe Ser Gly Ser Gly Ser Gly
1               5                   10                  15

Thr Asp Phe Thr Leu Ala Ile Ser Ser Leu Gln Ala Glu Asp Val Ala
            20                  25                  30

Val Tyr Tyr Cys
        35
```

<210> SEQ ID NO 259
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 259

```
Asn Arg Ala Ser Gly Val Pro Asp Arg Phe Ser Gly Ser Gly Ser Gly
1               5                   10                  15

Thr Asp Phe Thr Leu Lys Phe Ser Arg Val Glu Ala Glu Asp Val Gly
            20                  25                  30

Leu Tyr Tyr Cys
        35
```

<210> SEQ ID NO 260
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 260

```
Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35
```

<210> SEQ ID NO 261
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 261

```
Asn Arg Ala Ser Gly Val Pro Asp Arg Phe Ser Gly Ser Gly Ser Gly
1               5                   10                  15

Thr Asp Phe Lys Leu Lys Ile Ser Arg Val Glu Ala Glu Asp Val Gly
            20                  25                  30
```

```
Val Tyr Tyr Cys
        35


<210> SEQ ID NO 262
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Phe Gly Gln Gly Thr Lys Val Glu Ile Arg
1               5                   10


<210> SEQ ID NO 263
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Phe Gly Gly Gly Thr Lys Leu Thr Val Leu
1               5                   10


<210> SEQ ID NO 264
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Phe Gly Gln Gly Ser Lys Leu Glu Ile Lys
1               5                   10


<210> SEQ ID NO 265
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Phe Gly Gly Gly Thr Lys Val Glu Ile Lys
1               5                   10


<210> SEQ ID NO 266
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Phe Gly Gln Gly Thr Lys Leu Glu Ile Lys
1               5                   10
```

<210> SEQ ID NO 267
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 267

Phe Gly Gln Gly Thr Arg Leu Glu Ile Lys
1 5 10

<210> SEQ ID NO 268
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 268

Phe Gly Gly Gly Thr Met Leu Thr Val Leu
1 5 10

<210> SEQ ID NO 269
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 269

Phe Gly Thr Gly Thr Lys Val Thr Val Leu
1 5 10

<210> SEQ ID NO 270
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 270

Phe Gly Pro Gly Thr Lys Val Asp Ile Lys
1 5 10

<210> SEQ ID NO 271
<211> LENGTH: 329
<212> TYPE: PRT
<213> ORGANISM: Homo sapiens

<400> SEQUENCE: 271

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

-continued

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 272
<211> LENGTH: 106
<212> TYPE: PRT
<213> ORGANISM: Homo sapiens

<400> SEQUENCE: 272

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
```

100 105

<210> SEQ ID NO 273
<211> LENGTH: 107
<212> TYPE: PRT
<213> ORGANISM: Homo sapiens

<400> SEQUENCE: 273

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 274
<211> LENGTH: 441
<212> TYPE: PRT
<213> ORGANISM: Homo sapiens

<400> SEQUENCE: 274

Met Ala Glu Pro Arg Gln Glu Phe Glu Val Met Glu Asp His Ala Gly
1 5 10 15

Thr Tyr Gly Leu Gly Asp Arg Lys Asp Gln Gly Gly Tyr Thr Met His
20 25 30

Gln Asp Gln Glu Gly Asp Thr Asp Ala Gly Leu Lys Glu Ser Pro Leu
35 40 45

Gln Thr Pro Thr Glu Asp Gly Ser Glu Glu Pro Gly Ser Glu Thr Ser
50 55 60

Asp Ala Lys Ser Thr Pro Thr Ala Glu Asp Val Thr Ala Pro Leu Val
65 70 75 80

Asp Glu Gly Ala Pro Gly Lys Gln Ala Ala Ala Gln Pro His Thr Glu
85 90 95

Ile Pro Glu Gly Thr Thr Ala Glu Glu Ala Gly Ile Gly Asp Thr Pro
100 105 110

Ser Leu Glu Asp Glu Ala Ala Gly His Val Thr Gln Ala Arg Met Val
115 120 125

Ser Lys Ser Lys Asp Gly Thr Gly Ser Asp Asp Lys Lys Ala Lys Gly
130 135 140

Ala Asp Gly Lys Thr Lys Ile Ala Thr Pro Arg Gly Ala Ala Pro Pro
145 150 155 160

Gly Gln Lys Gly Gln Ala Asn Ala Thr Arg Ile Pro Ala Lys Thr Pro
165 170 175

Pro Ala Pro Lys Thr Pro Pro Ser Ser Gly Glu Pro Pro Lys Ser Gly
180 185 190

Asp Arg Ser Gly Tyr Ser Ser Pro Gly Ser Pro Gly Thr Pro Gly Ser
195 200 205

Arg Ser Arg Thr Pro Ser Leu Pro Thr Pro Pro Thr Arg Glu Pro Lys

```
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440


<210> SEQ ID NO 275
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: phosphorylated Thr
<220> FEATURE:
<221> NAME/KEY: MOD_RES
<222> LOCATION: (13)..(13)
<223> OTHER INFORMATION: phosphorylated Thr

<400> SEQUENCE: 275

Thr Pro Gly Ser Arg Ser Arg Xaa Pro Ser Leu Pro Xaa Pro Pro Thr
1               5                   10                  15

Arg Glu Pro Lys
            20


<210> SEQ ID NO 276
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<220> FEATURE:
<221> NAME/KEY: MOD_RES
<222> LOCATION: (9)..(9)
<223> OTHER INFORMATION: phosphorylated Thr
<220> FEATURE:
<221> NAME/KEY: MOD_RES
<222> LOCATION: (11)..(11)
<223> OTHER INFORMATION: phosphorylated Ser
<220> FEATURE:
<221> NAME/KEY: MOD_RES
<222> LOCATION: (14)..(14)
<223> OTHER INFORMATION: phosphorylated Thr

<400> SEQUENCE: 276

Gly Thr Pro Gly Ser Arg Ser Arg Xaa Pro Xaa Leu Pro Xaa Pro Pro
1 5 10 15

Thr Arg Glu

<210> SEQ ID NO 277
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:
<221> NAME/KEY: MOD_RES
<222> LOCATION: (18)..(18)
<223> OTHER INFORMATION: phosphorylated Ser
<220> FEATURE:
<221> NAME/KEY: MOD_RES
<222> LOCATION: (26)..(26)
<223> OTHER INFORMATION: phosphorylated Ser
<220> FEATURE:
<221> NAME/KEY: MOD_RES
<222> LOCATION: (31)..(31)
<223> OTHER INFORMATION: phosphorylated Ser

<400> SEQUENCE: 277

Arg Glu Asn Ala Lys Ala Lys Thr Asp His Gly Ala Glu Ile Val Tyr
1 5 10 15

Lys Xaa Pro Val Val Ser Gly Asp Thr Xaa Pro Arg His Leu Xaa Asn
20 25 30

Val Ser Ser Thr Gly
35

<210> SEQ ID NO 278
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 278

Pro Thr Arg Glu Pro Lys Lys Val
1 5

<210> SEQ ID NO 279
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 279

```
Ala Arg Met Val Ser Lys Ser
1               5


<210> SEQ ID NO 280
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Ser Pro Ser Ser Ala Lys Ser Arg Leu Gln Thr Ala Pro Val Pro Met
1               5                   10                  15

Pro Asp Leu Lys Asn Val Lys Ser
            20


<210> SEQ ID NO 281
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (18)..(18)
<223> OTHER INFORMATION: phosphorylated Ser

<400> SEQUENCE: 281

Asp His Gly Ala Glu Ile Val Tyr Lys Ser Pro Val Val Ser Gly Asp
1               5                   10                  15

Thr Xaa Pro Arg His Leu Ser Asn Val Ser Ser Thr Gly
            20                  25


<210> SEQ ID NO 282
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: phosphorylated Thr
<220> FEATURE:
<221> NAME/KEY: MOD_RES
<222> LOCATION: (9)..(9)
<223> OTHER INFORMATION: phosphorylated Thr

<400> SEQUENCE: 282

Cys Ser Arg Xaa Pro Ser Leu Pro Xaa Pro Pro Thr Arg Glu Pro Lys
1               5                   10                  15


<210> SEQ ID NO 283
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
```

```
<223> OTHER INFORMATION: phosphorylated Ser
<220> FEATURE:
<221> NAME/KEY: MOD_RES
<222> LOCATION: (6)..(6)
<223> OTHER INFORMATION: phosphorylated Ser
<220> FEATURE:
<221> NAME/KEY: MOD_RES
<222> LOCATION: (7)..(7)
<223> OTHER INFORMATION: phosphorylated Ser
<220> FEATURE:
<221> NAME/KEY: MOD_RES
<222> LOCATION: (10)..(10)
<223> OTHER INFORMATION: phosphorylated Ser
<220> FEATURE:
<221> NAME/KEY: MOD_RES
<222> LOCATION: (13)..(13)
<223> OTHER INFORMATION: phosphorylated Thr
<220> FEATURE:
<221> NAME/KEY: MOD_RES
<222> LOCATION: (16)..(16)
<223> OTHER INFORMATION: phosphorylated Ser
<220> FEATURE:
<221> NAME/KEY: MOD_RES
<222> LOCATION: (18)..(18)
<223> OTHER INFORMATION: phosphorylated Ser

<400> SEQUENCE: 283

Asp Arg Xaa Gly Tyr Xaa Xaa Pro Gly Xaa Pro Gly Xaa Pro Gly Xaa
1               5                   10                  15

Arg Xaa


<210> SEQ ID NO 284
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: phosphorylated Ser

<400> SEQUENCE: 284

Ser Gly Asp Arg Ser Gly Tyr Ser Xaa Pro Gly Ser Pro Gly Thr Pro
1               5                   10                  15

Gly Ser Arg Ser Arg Thr Pro Ser
            20


<210> SEQ ID NO 285
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: phosphorylated Ser

<400> SEQUENCE: 285

Ser Gly Asp Arg Ser Gly Tyr Ser Ser Pro Gly Xaa Pro Gly Thr Pro
1               5                   10                  15

Gly Ser Arg Ser Arg Thr Pro Ser
            20


<210> SEQ ID NO 286
```

-continued

<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (15)..(15)
<223> OTHER INFORMATION: phosphorylated Thr

<400> SEQUENCE: 286

```
Ser Gly Asp Arg Ser Gly Tyr Ser Ser Pro Gly Ser Pro Gly Xaa Pro
1               5                   10                  15

Gly Ser Arg Ser Arg Thr Pro Ser
            20
```

<210> SEQ ID NO 287
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (9)..(9)
<223> OTHER INFORMATION: phosphorylated Ser
<220> FEATURE:
<221> NAME/KEY: MOD_RES
<222> LOCATION: (12)..(12)
<223> OTHER INFORMATION: phosphorylated Ser
<220> FEATURE:
<221> NAME/KEY: MOD_RES
<222> LOCATION: (15)..(15)
<223> OTHER INFORMATION: phosphorylated Thr

<400> SEQUENCE: 287

```
Ser Gly Asp Arg Ser Gly Tyr Ser Xaa Pro Gly Xaa Pro Gly Xaa Pro
1               5                   10                  15

Gly Ser Arg Ser Arg Thr Pro Ser
            20
```

<210> SEQ ID NO 288
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (9)..(9)
<223> OTHER INFORMATION: phosphorylated Ser
<220> FEATURE:
<221> NAME/KEY: MOD_RES
<222> LOCATION: (12)..(12)
<223> OTHER INFORMATION: phosphorylated Ser

<400> SEQUENCE: 288

```
Ser Gly Asp Arg Ser Gly Tyr Ser Xaa Pro Gly Xaa Pro Gly Thr Pro
1               5                   10                  15

Gly Ser Arg Ser Arg Thr Pro Ser
            20
```

<210> SEQ ID NO 289
<211> LENGTH: 24

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: phosphorylated Ser
<220> FEATURE:
<221> NAME/KEY: MOD_RES
<222> LOCATION: (15)..(15)
<223> OTHER INFORMATION: phosphorylated Thr

<400> SEQUENCE: 289

Ser Gly Asp Arg Ser Gly Tyr Ser Ser Pro Gly Xaa Pro Gly Xaa Pro
1               5                   10                  15

Gly Ser Arg Ser Arg Thr Pro Ser
            20


<210> SEQ ID NO 290
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: phosphorylated Ser
<220> FEATURE:
<221> NAME/KEY: MOD_RES
<222> LOCATION: (15)..(15)
<223> OTHER INFORMATION: phosphorylated Thr

<400> SEQUENCE: 290

Ser Gly Asp Arg Ser Gly Tyr Ser Xaa Pro Gly Ser Pro Gly Xaa Pro
1               5                   10                  15

Gly Ser Arg Ser Arg Thr Pro Ser
            20


<210> SEQ ID NO 291
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: phosphorylated Thr

<400> SEQUENCE: 291

Gly Thr Pro Gly Ser Arg Ser Arg Xaa Pro Ser Leu Pro Thr Pro Pro
1               5                   10                  15

Thr Arg Glu


<210> SEQ ID NO 292
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<220> FEATURE:
<221> NAME/KEY: MOD_RES
<222> LOCATION: (11)..(11)
<223> OTHER INFORMATION: phosphorylated Ser

<400> SEQUENCE: 292

Gly Thr Pro Gly Ser Arg Ser Arg Thr Pro Xaa Leu Pro Thr Pro Pro
1 5 10 15

Thr Arg Glu

<210> SEQ ID NO 293
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (14)..(14)
<223> OTHER INFORMATION: phosphorylated Thr

<400> SEQUENCE: 293

Gly Thr Pro Gly Ser Arg Ser Arg Thr Pro Ser Leu Pro Xaa Pro Pro
1 5 10 15

Thr Arg Glu

<210> SEQ ID NO 294
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (9)..(9)
<223> OTHER INFORMATION: phosphorylated Thr
<220> FEATURE:
<221> NAME/KEY: MOD_RES
<222> LOCATION: (11)..(11)
<223> OTHER INFORMATION: phosphorylated Ser

<400> SEQUENCE: 294

Gly Thr Pro Gly Ser Arg Ser Arg Xaa Pro Xaa Leu Pro Thr Pro Pro
1 5 10 15

Thr Arg Glu

<210> SEQ ID NO 295
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (9)..(9)
<223> OTHER INFORMATION: phosphorylated Thr
<220> FEATURE:
<221> NAME/KEY: MOD_RES
<222> LOCATION: (14)..(14)
<223> OTHER INFORMATION: phosphorylated Thr

<400> SEQUENCE: 295

Gly Thr Pro Gly Ser Arg Ser Arg Xaa Pro Ser Leu Pro Xaa Pro Pro

```
1               5                   10                  15

Thr Arg Glu


<210> SEQ ID NO 296
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: phosphorylated Ser
<220> FEATURE:
<221> NAME/KEY: MOD_RES
<222> LOCATION: (14)..(14)
<223> OTHER INFORMATION: phosphorylated Thr

<400> SEQUENCE: 296

Gly Thr Pro Gly Ser Arg Ser Arg Thr Pro Xaa Leu Pro Xaa Pro Pro
1               5                   10                  15

Thr Arg Glu


<210> SEQ ID NO 297
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: phosphorylated Thr
<220> FEATURE:
<221> NAME/KEY: MOD_RES
<222> LOCATION: (11)..(11)
<223> OTHER INFORMATION: phosphorylated Ser
<220> FEATURE:
<221> NAME/KEY: MOD_RES
<222> LOCATION: (14)..(14)
<223> OTHER INFORMATION: phosphorylated Thr

<400> SEQUENCE: 297

Gly Thr Pro Gly Ser Arg Ser Arg Xaa Pro Xaa Leu Pro Xaa Pro Pro
1               5                   10                  15

Thr Arg Glu


<210> SEQ ID NO 298
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: phosphorylated Thr
<220> FEATURE:
<221> NAME/KEY: MOD_RES
<222> LOCATION: (4)..(4)
<223> OTHER INFORMATION: phosphorylated Thr
<220> FEATURE:
<221> NAME/KEY: MOD_RES
<222> LOCATION: (15)..(15)
<223> OTHER INFORMATION: phosphorylated Thr
```

-continued

<400> SEQUENCE: 298

```
Xaa Pro Pro Xaa Arg Glu Pro Lys Lys Val Ala Val Val Arg Xaa Pro
1               5                   10                  15

Pro Lys
```

<210> SEQ ID NO 299
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (7)..(7)
<223> OTHER INFORMATION: phosphorylated Thr

<400> SEQUENCE: 299

```
Lys Val Ala Val Val Arg Xaa Pro Pro Lys Ser Pro Ser Ser Ala Lys
1               5                   10                  15
```

<210> SEQ ID NO 300
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (11)..(11)
<223> OTHER INFORMATION: phosphorylated Ser

<400> SEQUENCE: 300

```
Lys Val Ala Val Val Arg Thr Pro Pro Lys Xaa Pro Ser Ser Ala Lys
1               5                   10                  15

Pro Ser
```

<210> SEQ ID NO 301
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (7)..(7)
<223> OTHER INFORMATION: phosphorylated Thr
<220> FEATURE:
<221> NAME/KEY: MOD_RES
<222> LOCATION: (11)..(11)
<223> OTHER INFORMATION: phosphorylated Ser

<400> SEQUENCE: 301

```
Lys Val Ala Val Val Arg Xaa Pro Pro Lys Xaa Pro Ser Ser Ala Lys
1               5                   10                  15

Pro Ser
```

TAU BINDING COMPOUNDS

RELATED APPLICATIONS

This International Patent Application is a U.S. national stage application of International Patent Application No. PCT/US2021/063551, filed on Dec. 15, 2021, which claims priority to U.S. Provisional Patent Application No. 63/126,024, filed on Dec. 16, 2020. The entire contents of each of the foregoing applications are hereby incorporated by reference in their entirety.

SEQUENCE LISTING

The instant application contains a Sequence Listing which has been filed electronically in ASCII format and is hereby incorporated by reference in its entirety. Said ASCII copy, created on Jun. 15, 2023, is named 135333-02203_SL.txt and is 151,493 bytes in size.

FIELD OF THE DISCLOSURE

The present disclosure presents tau binding compounds. In particular, the present disclosure provides antibodies which bind to tau (e.g., human tau), e.g., antibodies which bind to phospho-epitopes on human tau.

BACKGROUND

Tauopathies are a group of neurodegenerative diseases characterized by the dysfunction and/or aggregation of the microtubule associated protein tau. Tau is normally a very soluble protein known to associate with microtubules based on the extent of its phosphorylation. Tau is considered a critical component of intracellular trafficking processes, particularly in neuronal cells, given their unique and extended structure. Hyperphosphorylation of tau depresses its binding to microtubules and microtubule assembly activity. Further, hyperphosphorylation of tau renders it prone to misfolding and aggregation. In tauopathies, the tau becomes hyperphosphorylated, misfolds and aggregates as neurofibrillary tangles (NFT) of paired helical filaments (PHF), twisted ribbons or straight filaments. These NFT are largely considered indicative of impending neuronal cell death and thought to contribute to widespread neuronal cell loss, leading to a variety of behavioral and cognitive deficits.

The first genetically defined tauopathy was described when mutations in the tau gene were shown to lead to an autosomal dominantly inherited tauopathy known as frontotemporal dementia and parkinsonism linked to chromosome 17 (FTDP-17). This was the first causal evidence that changes in tau could lead to neurodegenerative changes in the brain. These molecules are considered to be more amyloidogenic, meaning they are more likely to become hyperphosphorylated and more likely to aggregate into NFT (Hutton, M. et al., 1998, Nature 393(6686):702-5).

Several approaches have been proposed for therapeutically interfering with progression of tau pathology and preventing the subsequent molecular and cellular consequences. Given that NFT are composed of hyperphosphorylated, misfolded and aggregated forms of tau, interference at each of these stages has yielded a set of avidly pursued targets. Introducing agents that limit phosphorylation, block misfolding or prevent aggregation have all generated promising results. Passive and active immunization with late stage anti-phospho-tau antibodies in mouse models have led to dramatic decreases in tau aggregation and improvements in cognitive parameters. It has also been suggested that introduction of anti-tau antibodies can prevent the trans-neuronal spread of tau pathology.

There remains a need for anti-tau antibodies for use in tauopathy treatment, diagnostics, and other applications. The present disclosure addresses this need with related compounds and methods described herein.

SUMMARY

Provided herein are isolated, e.g., recombinant, antibodies which bind to tau (e.g., human tau). In particular, provided herein are anti-tau antibodies which are not only structurally unique, but also exhibit different binding patterns to various phospho-epitopes in tau compared to phospho-epitopes recognized by anti-tau antibodies widely used to study tau pathology (e.g., PT3 and AT8), despite binding to similar/overlapping regions in tau. In addition to therapeutic applications, the anti-tau antibodies provided herein may also serve as diagnostic tools for the detection of unique phosphorylation states of tau.

In some embodiments, the present disclosure provides an antibody that includes: a heavy chain variable domain (VH) with a complementarity determining region (CDR)H1, CDRH2, and CDRH3 including an amino acid sequence according to any of those listed in Table 4, or a fragment thereof; and a light chain variable domain (VL) with a CDRL1, CDRL2, and CDRL3 including an amino acid sequence according to any of those listed in Table 1, or a fragment thereof. The antibody may include a set of variable domain CDR amino acid sequences, wherein the variable domain CDR amino acid sequence set is selected from any of those listed in Table 1. The antibody may include a pair of variable domain CDR amino acid sequence sets, wherein the variable domain CDR amino acid sequence set pair is selected from any those listed in Table 1. The VH may include a framework region (FR)H1, FRH2, FRH3, and FRH4 that include an amino acid sequence selected from any of those listed in Table 1, or a fragment thereof. The VL may include a FRL1, FRL2, FRL3, and FRL4 that include an amino acid sequence selected from any of those listed in Table 1 or a fragment thereof. The VH may include an amino acid sequence selected from any of those listed in Table 1 and/or may be encoded by a nucleic acid sequence selected from any of those listed in Table 1. The VL may include an amino acid sequence selected from any of those listed in Table 1 and/or may be encoded by a nucleic acid sequence selected from any of those listed in Table 1. The antibody may include a variable domain pair selected from any of those listed in Table 1. The antibody may include a format selected from a monoclonal antibody, a multispecific antibody, a chimeric antibody, an antibody mimetic, a single chain Fv (scFv) format, and an antibody fragment. The antibody may include an antibody class selected from IgA, IgD, IgE, IgG, and IgM. The antibody may include one or more non-human constant domain. The antibody may include one or more human constant domain. The one or more human constant domain may be selected from any of those listed in Table 5. The antibody may include a human IgG, wherein the human IgG includes an isotype selected from IgG1, IgG2, IgG3, or IgG4. The antibody may be a human antibody. The antibody may bind to a tau protein epitope. The tau protein epitope may include or may be included within an amino acid sequence selected from any of those listed in Table 4. The tau protein epitope may include a region formed by a complex of at least two tau proteins. The antibody may bind to enriched paired helical filament tau protein (ePHF) with a half maximal effective concentration (EC50) of from about 0.01 nM to about 100 nM as determined by direct enzyme-linked immunosorbent assay (ELISA). The antibody may not bind to non-pathological tau. The antibody may bind to pathological tau tangles. The antibody may inhibit tau aggregation. The antibody may include a conjugate. The conjugate may include a therapeutic agent. The conjugate may include a detectable label.

In some embodiments, the present disclosure provides a construct encoding an antibody according to any of those described above or herein.

In some embodiments, the present disclosure provides a method of treating a therapeutic indication in a subject, the method including administering to the subject an antibody according to any of those described above or herein. The therapeutic indication may include a neurological indication. The neurological indication may include one or more of neurodegenerative disease, Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), a prion disease, Creutzfeldt-Jakob disease (CJD), multiple system atrophy, tangle-only dementia, stroke, and progressive subcortical gliosis.

In some embodiments, the present disclosure provides a method of diagnosing a therapeutic indication in a subject, the method including the use of an antibody according to any of those described above or herein. The therapeutic indication may include a neurological indication. The neurological indication may include one or more of neurodegenerative disease, AD, FTDP-17, FTLD, FTD, CTE, PSP, Down's syndrome, Pick's disease, CBD, corticobasal syndrome, ALS, a prion disease, CJD, multiple system atrophy, tangle-only dementia, stroke, and progressive subcortical gliosis. The antibody may be used to detect pathological tau in a subject tissue. The subject tissue may include CNS tissue. The subject tissue may include a thin tissue section. The thin tissue section may include a cryopreserved tissue section.

Those skilled in the art will recognize or be able to ascertain using no more than routine experimentation, many equivalents to the specific embodiments of the invention described herein. Such equivalents are intended to be encompassed by the following enumerated embodiments.

ENUMERATED EMBODIMENTS

E1. An isolated, e.g., recombinant, antibody that binds to human tau (e.g., SEQ ID NO: 274), wherein the antibody comprises a heavy chain variable region (VH) comprising one, two, or three of a heavy chain complementary determining region 1 (HCDR1), a heavy chain complementary determining region 2 (HCDR2), and a heavy chain complementary determining region 3 (HCDR3), and/or a light chain variable region (VL) comprising one, two, or three of a light chain complementary determining region 1 (LCDR1), a light chain complementary determining region 2 (LCDR2), and a light chain complementary determining region 3 (LCDR3), e.g., CDR sequences according to the Chothia numbering system, wherein:

(i) the HCDR1, HCDR2, HCDR3, LCDR1, LCDR2, and LCDR3 comprise the amino acid sequences of SEQ ID NOs: 82, 97, 115, 127, 141, and 159, respectively;

(ii) the HCDR1, HCDR2, HCDR3, LCDR1, LCDR2, and LCDR3 comprise the amino acid sequences of SEQ ID NOs: 79, 94, 111, 127, 141, and 156, respectively;

(iii) the HCDR1, HCDR2, HCDR3, LCDR1, LCDR2, and LCDR3 comprise the amino acid sequences of SEQ ID NOs: 80, 95, 112, 129, 143, and 157, respectively;

(iv) the HCDR1, HCDR2, HCDR3, LCDR1, LCDR2, and LCDR3 comprise the amino acid sequences of SEQ ID NOs: 81, 94, 114, 127, 141, and 156, respectively;

(v) the HCDR1, HCDR2, HCDR3, LCDR1, LCDR2, and LCDR3 comprise the amino acid sequences of SEQ ID NOs: 82, 101, 119, 132, 149, and 164, respectively;

(vi) the HCDR1, HCDR2, HCDR3, LCDR1, LCDR2, and LCDR3 comprise the amino acid sequences of SEQ ID NOs: 77, 92, 109, 127, 141, and 154, respectively;

(vii) the HCDR1, HCDR2, HCDR3, LCDR1, LCDR2, and LCDR3 comprise the amino acid sequences of SEQ ID NOs: 78, 93, 110, 128, 142, and 155, respectively;

(viii) the HCDR1, HCDR2, HCDR3, LCDR1, LCDR2, and LCDR3 comprise the amino acid sequences of SEQ ID NOs: 78, 96, 113, 130, 144, and 158, respectively;

(xi) the HCDR1, HCDR2, HCDR3, LCDR1, LCDR2, and LCDR3 comprise the amino acid sequences of SEQ ID NOs: 83, 98, 116, 131, 145, and 160, respectively;

(x) the HCDR1, HCDR2, HCDR3, LCDR1, LCDR2, and LCDR3 comprise the amino acid sequences of SEQ ID NOs: 84, 99, 117, 132, 146, and 161, respectively;

(xi) the HCDR1, HCDR2, HCDR3, LCDR1, LCDR2, and LCDR3 comprise the amino acid sequences of SEQ ID NOs: 85, 100, 118, 133, 147, and 162, respectively;

(xii) the HCDR1, HCDR2, HCDR3, LCDR1, LCDR2, and LCDR3 comprise the amino acid sequences of SEQ ID NOs: 85, 100, 118, 134, 148, and 163, respectively;

(xiii) the HCDR1, HCDR2, HCDR3, LCDR1, LCDR2, and LCDR3 comprise the amino acid sequences of SEQ ID NOs: 86, 102, 120, 127, 141, and 156, respectively;

(xiv) the HCDR1, HCDR2, HCDR3, LCDR1, LCDR2, and LCDR3 comprise the amino acid sequences of SEQ ID NOs: 87, 103, 121, 132, 149, and 165, respectively;

(xv) the HCDR1, HCDR2, HCDR3, LCDR1, LCDR2, and LCDR3 comprise the amino acid sequences of SEQ ID NOs: 78, 104, 122, 135, 143, and 166, respectively;

(xvi) the HCDR1, HCDR2, HCDR3, LCDR1, LCDR2, and LCDR3 comprise the amino acid sequences of SEQ ID NOs: 78, 104, 122, 136, 150, and 167, respectively;

(xvii) the HCDR1, HCDR2, HCDR3, LCDR1, LCDR2, and LCDR3 comprise the amino acid sequences of SEQ ID NOs: 88, 105, 123, 137, 151, and 168, respectively;

(xviii) the HCDR1, HCDR2, HCDR3, LCDR1, LCDR2, and LCDR3 comprise the amino acid sequences of SEQ ID NOs: 89, 106, 124, 138, 152, and 169, respectively;

(xix) the HCDR1, HCDR2, HCDR3, LCDR1, LCDR2, and LCDR3 comprise the amino acid sequences of SEQ ID NOs: 90, 107 125, 139, 151, and 170, respectively;

(xx) the HCDR1, HCDR2, HCDR3, LCDR1, LCDR2, and LCDR3 comprise the amino acid sequences of SEQ ID NOs: 91, 108, 126, 140, 153, and 171, respectively;

(xxi) the HCDR1, HCDR2, HCDR3, LCDR1, LCDR2, and LCDR3 comprise the amino acid sequences of any of the HCDR and LCDR sequences provided in Table 1; or (xxii) a variant, e.g., functional variant, of the antibodies of any one of (i)-(xxi), wherein any one, two, three, four, five or all of the HCDR1, HCDR2, HCDR3, LCDR1, LCDR2, and/or LCDR3 comprises one, two, or at most three substitutions (e.g., conservative substitutions); or wherein any one, two, three, four, five or all of the HCDR1, HCDR2, HCDR3, LCDR1, LCDR2, and/or LCDR3 comprises one, two, or at most three different amino acids relative to any of the sequences in (i)-(xxi).

E2. The antibody of embodiment E1, wherein the antibody comprises the HCDR1, HCDR2, and HCDR3 sequences of any one of (i)-(xxii).

E3. The antibody of embodiment E1 or E2, wherein the antibody comprises the LCDR1, LCDR2, and LCDR3 sequences of any one of (i)-(xxii).

E4. The antibody of any one of embodiments E1-E3, wherein the antibody comprises the HCDR1, HCDR2, HCDR3, LCDR1, LCDR2, and LCDR3 sequences of any one of (i)-(xxii).

E4. An isolated, e.g., recombinant, antibody that binds to human tau (e.g., SEQ ID NO: 274), wherein the antibody comprises the heavy chain CDR1, CDR2, and CDR3, and/or light chain CDR1, CDR2, and CDR3 of an antibody comprising a heavy chain variable region (VH) and light chain variable region (VL) comprising: (i) SEQ ID NOs: 7 and 25, respectively; (ii) SEQ ID NOs: 3 and 21, respectively; (iii) SEQ ID NOs: 4 and 22, respectively; (iv) SEQ ID NOs: 6 and 24, respectively; (v) SEQ ID NOs: 11 and 30, respectively; (vi) SEQ ID NOs: 1 and 19, respectively; (vii) SEQ ID NOs: 2 and 20, respectively; (viii) SEQ ID NOs: 5 and 23, respectively; (ix) SEQ ID NOs: 8 and 26, respectively; (x) SEQ ID NOs: 9 and 27, respectively; (xi) SEQ ID NOs: 10 and 28, respectively; (xii) SEQ ID NOs: 10 and 29, respectively; (xiii) SEQ ID NOs: 12 and 31, respectively; (xiv) SEQ ID NOs: 13 and 32, respectively; (xv) SEQ ID NOs: 14 and 33, respectively; (xvi) SEQ ID NOs: 14 and 34, respectively; (xvii) SEQ ID NOs: 15 and 35, respectively; (xviii) SEQ ID NOs: 16 and 36, respectively; (xix) SEQ ID NOs: 17 and 37, respectively; or (xx) SEQ ID NOs: 18 and 38, respectively.

E5. The antibody of embodiment E4, wherein the CDR sequences are based on the Kabat numbering system, Chothia numbering system, or IMGT numbering system.

E6. The antibody of any one of the preceding embodiments, which comprises a VH comprising:

(i) the amino acid sequence of any VH provided in Table 1, or an amino acid sequence having at least 70%, 75%, 80%, 85%, 90%, 92%, 95%, 96%, 97%, 98%, or 99% sequence identity thereto;

(ii) an amino acid sequence comprising at least one, two or three modifications, but not more than 30, 20 or 10 modifications relative to the amino acid sequence of any VH provided in Table 1;

(iii) an amino acid sequence comprising at least one, two or three, but not more than 30, 20 or 10 different amino acids relative to any one of the amino acid sequences of any VH sequences provided in Table 1; or (iv) an amino acid sequence encoded by a nucleotide sequence of any VH provided in Table 1X, or a nucleotide sequence having at least 70%, 75%, 80%, 85%, 90%, 92%, 95%, 96%, 97%, 98%, or 99% sequence identity thereto.

E7. The antibody of any one of the preceding embodiments, which comprises a VH comprising:

(i) the amino acid sequence of any of SEQ ID NOs: 7, 3, 4, 6, and 11, or an amino acid sequence having at least 70%, 75%, 80%, 85%, 90%, 92%, 95%, 96%, 97%, 98%, or 99% sequence identity thereto;

(ii) an amino acid sequence comprising at least one, two or three modifications, but not more than 30, 20 or 10 modifications of the amino acid sequence of any of SEQ ID NOs: 7, 3, 4, 6, and 11;

(iii) an amino acid sequence comprising at least one, two or three, but not more than 30, 20 or 10 different amino acids relative to any one of the amino acid sequences of any of SEQ ID NOs: 7, 3, 4, 6, and 11; or (iv) an amino acid sequence encoded by a nucleotide sequence of any of SEQ ID NOs: 51, 55, 54, 52, 47, 39, 56, 41, 50, 49, 48, 46, 45, 44, 43, 42, 53, or 40, or a nucleotide sequence having at least 70%, 75%, 80%, 85%, 90%, 92%, 95%, 96%, 97%, 98%, or 99% sequence identity thereto.

E8. The antibody of any one of the preceding embodiments, which comprises a VL comprising:

(i) the amino acid sequence of any VL provided in Table 1, or an amino acid sequence having at least 70%, 75%, 80%, 85%, 90%, 92%, 95%, 96%, 97%, 98%, or 99% sequence identity thereto;

(ii) an amino acid sequence comprising at least one, two or three modifications, but not more than 30, 20 or 10 modifications relative to the amino acid sequence of any VL provided in Table 1;

(iii) an amino acid sequence comprising at least one, two or three, but not more than 30, 20 or 10 different amino acids relative to any one of the amino acid sequences of any VL sequences provided in Table 1; or (iv) an amino acid sequence encoded by a nucleotide sequence of any VL provided in Table 1, or a nucleotide sequence having at least 70%, 75%, 80%, 85%, 90%, 92%, 95%, 96%, 97%, 98%, or 99% sequence identity thereto.

E9. The antibody of any one of the preceding embodiments, which comprises a VL comprising:

(i) the amino acid sequence of any of SEQ ID NOs: 25, 21, 22, 24, and 30, or an amino acid sequence having at least 70%, 75%, 80%, 85%, 90%, 92%, 95%, 96%, 97%, 98%, or 99% sequence identity thereto;

(ii) an amino acid sequence comprising at least one, two or three modifications, but not more than 30, 20 or 10 modifications of the amino acid sequence of any of SEQ ID NOs: 25, 21, 22, 24, and 30;
(iii) an amino acid sequence comprising at least one, two or three, but not more than 30, 20 or 10 different amino acids relative to any one of the amino acid sequences of any of SEQ ID NOs: 25, 21, 22, 24, and 30; or
(iv) an amino acid sequence encoded by a nucleotide sequence of any of SEQ ID NOs: 67, 75, 74, 72, 66, 57, 76, 59, 70, 69, 68, 65, 64, 62, 63, 61, 60, 73, or 58, or a nucleotide sequence having at least 70%, 75%, 80%, 85%, 90%, 92%, 95%, 96%, 97%, 98%, or 99% sequence identity thereto.

E10. The antibody of any one of the preceding embodiments, comprising:
(i) a VH comprising:
(a) the amino acid sequence of any VH provided in Table 1, or an amino acid sequence having at least 70%, 75%, 80%, 85%, 90%, 92%, 95%, 96%, 97%, 98%, or 99% sequence identity thereto;
(b) an amino acid sequence comprising at least one, two or three modifications, but not more than 30, 20 or 10 modifications relative to the amino acid sequence of any VH provided in Table 1;
(c) an amino acid sequence comprising at least one, two or three, but not more than 30, 20 or 10 different amino acids relative to any one of the amino acid sequences of any VH sequences provided in Table 1; or
(d) an amino acid sequence encoded by a nucleotide sequence of any VH provided in Table 1, or a nucleotide sequence having at least 70%, 75%, 80%, 85%, 90%, 92%, 95%, 96%, 97%, 98%, or 99% sequence identity thereto; and
(ii) a VL comprising:
(a) the amino acid sequence of any VL provided in Table 1, or an amino acid sequence having at least 70%, 75%, 80%, 85%, 90%, 92%, 95%, 96%, 97%, 98%, or 99% sequence identity thereto;
(b) an amino acid sequence comprising at least one, two or three modifications, but not more than 30, 20 or 10 modifications relative to the amino acid sequence of any VL provided in Table 1;
(c) an amino acid sequence comprising at least one, two or three, but not more than 30, 20 or 10 different amino acids relative to any one of the amino acid sequences of any VL sequences provided in Table 1; or
(d) an amino acid sequence encoded by a nucleotide sequence of any VL provided in Table 1, or a nucleotide sequence having at least 70%, 75%, 80%, 85%, 90%, 92%, 95%, 96%, 97%, 98%, or 99% sequence identity thereto.

E11. The antibody of any one of the preceding embodiments, comprising the amino acid sequence of any VH of an antibody provided in Table 1, and the amino acid sequence of the VL of the antibody provided in Table 1.

E12. The antibody of any one of the preceding embodiments, comprising:
(i) a VH comprising the amino acid sequence of SEQ ID NO: 7; an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 7; or an amino acid sequence comprising at least one, two or three, but not more than 30, 20 or 10 modifications, e.g., substitutions (e.g., conservative substitutions) relative to SEQ ID NO: 7; and
(ii) a VL comprising the amino acid sequence of SEQ ID NO: 25, or an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 25; or an amino acid sequence comprising at least one, two or three, but not more than 30, 20 or 10 modifications, e.g., substitutions (e.g., conservative substitutions) relative to SEQ ID NO: 25.

E13. The antibody of any one of embodiments E1-E11, comprising:
(i) a VH comprising the amino acid sequence of SEQ ID NO: 3; an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 3; or an amino acid sequence comprising at least one, two or three, but not more than 30, 20 or 10 modifications, e.g., substitutions (e.g., conservative substitutions) relative to SEQ ID NO: 3; and
(ii) a VL comprising the amino acid sequence of SEQ ID NO: 21, or an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 21; or an amino acid sequence comprising at least one, two or three, but not more than 30, 20 or 10 modifications, e.g., substitutions (e.g., conservative substitutions) relative to SEQ ID NO: 21.

E14. The antibody of any one of embodiments E1-E11, comprising:
(i) a VH comprising the amino acid sequence of SEQ ID NO: 4; an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 4; or an amino acid sequence comprising at least one, two or three, but not more than 30, 20 or 10 modifications, e.g., substitutions (e.g., conservative substitutions) relative to SEQ ID NO: 4; and
(ii) a VL comprising the amino acid sequence of SEQ ID NO: 22, or an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 22; or an amino acid sequence comprising at least one, two or three, but not more than 30, 20 or 10 modifications, e.g., substitutions (e.g., conservative substitutions) relative to SEQ ID NO: 22.

E15. The antibody of any one of embodiments E1-E11, comprising:

(i) a VH comprising the amino acid sequence of SEQ ID NO: 6; an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 6; or an amino acid sequence comprising at least one, two or three, but not more than 30, 20 or 10 modifications, e.g., substitutions (e.g., conservative substitutions) relative to SEQ ID NO: 6; and (ii) a VL comprising the amino acid sequence of SEQ ID NO: 22, or an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 24; or an amino acid sequence comprising at least one, two or three, but not more than 30, 20 or 10 modifications, e.g., substitutions (e.g., conservative substitutions) relative to SEQ ID NO: 24.

E16. The antibody of any one of embodiments E1-E11, comprising:

(i) a VH comprising the amino acid sequence of SEQ ID NO: 11; an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 11; or an amino acid sequence comprising at least one, two or three, but not more than 30, 20 or 10 modifications, e.g., substitutions (e.g., conservative substitutions) relative to SEQ ID NO: 11; and (ii) a VL comprising the amino acid sequence of SEQ ID NO: 30, or an amino acid sequence having at least 70%, 75%, 80%, 85%, 90%, 92%, 95%, 96%, 97%, 98%, or 99% sequence identity thereto; an amino acid sequence comprising at least one, two or three, but not more than 30, 20 or 10 different amino acids relative to SEQ ID NO: 30; or an amino acid sequence comprising at least one, two or three, but not more than 30, 20 or 10 modifications, e.g., substitutions (e.g., conservative substitutions) relative to SEQ ID NO: 30.

E17. An isolated, e.g., recombinant, antibody that binds to human tau (e.g., SEQ ID NO: 274), wherein the antibody comprises a heavy chain variable region (VH) and/or a light chain variable region (VL) comprising: (i) SEQ ID NOs: 7 and/or 25, respectively; (ii) SEQ ID NOs: 3 and/or 21, respectively; (iii) SEQ ID NOs: 4 and/or 22, respectively; (iv) SEQ ID NOs: 6 and/or 24, respectively; (v) SEQ ID NOs: 11 and/or 30, respectively; (vi) SEQ ID NOs: 1 and/or 19, respectively; (vii) SEQ ID NOs: 2 and/or 20, respectively; (viii) SEQ ID NOs: 5 and/or 23, respectively; (ix) SEQ ID NOs: 8 and/or 26, respectively; (x) SEQ ID NOs: 9 and/or 27, respectively; (xi) SEQ ID NOs: 10 and/or 28, respectively; (xii) SEQ ID NOs: 10 and/or 29, respectively; (xiii) SEQ ID NOs: 12 and/or 31, respectively; (xiv) SEQ ID NOs: 13 and/or 32, respectively; (xv) SEQ ID NOs: 14 and/or 33, respectively; (xvi) SEQ ID NOs: 14 and/or 34, respectively; (xvii) SEQ ID NOs: 15 and/or 35, respectively; (xviii) SEQ ID NOs: 16 and/or 36, respectively; (xix) SEQ ID NOs: 17 and/or 37, respectively; (xx) SEQ ID NOs: 18 and/or 38, respectively; (xxi) a variant, e.g., functional variant, of the antibodies of any one of (i)-(xx), wherein the VH and/or VL has an amino acid sequence having at least 70%, 75%, 80%, 85%, 90%, 92%, 95%, 96%, 97%, 98%, or 99% sequence identity thereto; or (xxii) a variant, e.g., functional variant, of the antibodies of any one of (i)-(xx), wherein the VH and/or VL comprises at least one, two, or three modifications, but not more than 30, 20, or 10 modifications (e.g., amino acid substitutions, e.g., conservative substitutions) or wherein the VH and/or VL comprises at least one, two, or three, but not more than 30, 20, or 10 different amino acids.

E18. The antibody of any one of embodiments E1-E17, wherein the antibody comprises the VH and VL sequences of any one of (i)-(xxii) in embodiment E17.

E19. The antibody of any one of embodiments E1-E18, which binds to a tau protein at a half maximal effective concentration (EC50) of from about 0.001 nM to about 10 nM, or about 0.01 nM to about 2 nM, e.g., as assessed by direct enzyme-linked immunosorbent assay (ELISA).

E20. The antibody of any one of embodiments E1-E19, which binds to enriched paired helical filament tau protein (ePHF), e.g., at a half maximal effective concentration (EC50) of from about 0.001 nM to about 100 nM, or about 0.01 nM to about 20 nM e.g., as assessed by direct enzyme-linked immunosorbent assay (ELISA).

E21. The antibody of any one of embodiments E1-E20, which binds to iPHF with a dissociation constant ($K_D$) of about 0.1 to about 10 nM, or about 0.2-5 nM, e.g., as assessed by bio-layer interferometry.

E22. The antibody of any one of the preceding embodiments, wherein the antibody binds to a tau protein epitope comprising a region formed by a complex of at least two tau proteins.

E23. The antibody of any one of the preceding embodiments, wherein the antibody binds to all or a portion of amino acid residues of tau selected from: (a) 183-212, (b) 187-218, (c) 33-82, 159-182, 197-226, and 229-246; (d) 217-242, (e) 35-76 and 187-218, (f) 5-34, (g) 187-218, (h) 33-82, 159-188, and 191-230, (i) 35-62, 107-124, and 203-220, (j) 35-82, 159-188, and 197-224, and (k) 53-78, 329-348, or 381-408, wherein human tau is numbered according to SEQ ID NO: 274.

E24. An isolated, e.g., recombinant, antibody that binds to human tau (e.g., SEQ ID NO: 274), wherein the antibody binds to all or a portion of amino acid residues of tau selected from: (a) 183-212, (b) 187-218, (c) 33-82, 159-182, 197-226, and 229-246; (d) 217-242, (e) 35-76 and 187-218, (f) 5-34, (g) 187-218, (h) 33-82, 159-188, and 191-230, (i) 35-62, 107-124, and 203-220, (j) 35-82, 159-188, and 197-224, or (k) 53-78, 329-348, and 381-408, wherein human tau is numbered according to SEQ ID NO: 274.

E25. The antibody of embodiment E23 or E24, wherein one or more of the serines, threonines, and/or tyrosines in the stretch of amino acids selected from (a)-(k) are phosphorylated.

E26. The antibody of any one of embodiments E23-E25, wherein all of the serines, threonines, and/or tyrosines in the stretch of amino acids selected from (a)-(k) are phosphorylated.

E27. The antibody of any one of embodiments E24-E26, wherein the antibody comprises the HCDR1, HCDR2, HCDR3, LCDR1, LCDR2, and LCDR3 sequence of any one of (i)-(xxii) in embodiment E3.

E28. The antibody of any one of embodiments E24-E27, wherein the antibody comprises the VH and VL sequences of any one of (i)-(xxii) in embodiment E17.

E29. The antibody of any one of embodiments E1-E28, which binds to all or a portion of amino acids 195-215 of tau with a dissociation constant ($K_D$) of about 1 pM to about 50 pM, or about 1-25 pM, e.g., as assessed by bio-layer interferometry.

E30. The antibody of any one of embodiments E1-E28, which binds to all or a portion of amino acids 191-214 of tau phosphorylated at S199 with a dissociation constant ($K_D$) of about 0.1 nM to about 10 nM, or about 0.5-5 nM, e.g., as assessed by bio-layer interferometry.

E31. The antibody of any one of embodiments E1-E28, which binds to all or a portion of amino acids 217-234 of tau phosphorylated at T217, T220, and T231 with a dissociation constant ($K_D$) of about 0.1 nM to about 10 nM, or about 0.1-5 nM, e.g., as assessed by bio-layer interferometry.

E32. The antibody of any one of embodiments E1-E28, which binds to all or a portion of amino acids 225-240 of tau phosphorylated at T231 with a dissociation constant ($K_D$) of about 0.1 nM to about 25 nM, or about 0.1-15 nM, e.g., as assessed by bio-layer interferometry.

E33. An isolated, e.g., recombinant, antibody that binds to human tau phosphorylated at amino acid residue S404, or a peptide comprising or consisting of the amino acid sequence DHGAEIVYKSPVVSGDT(pS)PRHL-SNVSSTG (SEQ ID NO: 281), wherein p(S) corresponds to a phosphorylated serine residue.

E34. The antibody of embodiment E33, wherein the antibody comprises a heavy chain variable region (VH) comprising CDR1, CDR2, and CDR3 sequences comprising SEQ ID NOs: 89, 106, and 124, respectively, and a light chain variable region (VL) comprising CDR1, CDR2, and CDR3 sequences comprising SEQ ID NOs: 138, 152, and 169, respectively.

E35. The antibody of embodiment E33 or E34, wherein the antibody comprises VH and VL sequences comprising SEQ ID NOs: 16 and 36, respectively.

E36. An isolated, e.g., recombinant, antibody that binds to:

(a) human tau phosphorylated at amino acid residue S199, but not at amino acid residues S202 and T205, (b) human tau phosphorylated at amino acid residue S202, but not at amino acid residues S199 and T205, (c) human tau phosphorylated at amino acid residue T205, but not at amino acid residues S199 and S202, (d) human tau phosphorylated at a combination of amino acid residues S199 and T205, but not at amino acid residue S202 (e.g., wherein binding tau phosphorylated at a combination of S199 and T205 is at least 3-times stronger (e.g., at least 4-time stronger) than background (e.g., non-specific) level of binding, e.g., binding by hIgG1 isotype control), (e) human tau phosphorylated at a combination of amino acid residues S202 and T205, but not at amino acid residue S199, but not human tau phosphorylated at a combination of residues S199 and S202, but not T205, (f) human tau phosphorylated at a combination of amino acid residues (i) S202 and T205, but not S119, and (ii) S199 and T205, but not S202, at least 2 times (e.g., at least 3 times, at least 4 times, at least 5 times, 2-6 times, 2-5 times, 2-4 times, 2-3 times, 3-5 times or 4-5 times) more strongly than background (e.g., non-specific) level of binding, e.g., binding by hIgG1 isotype control).

(g) human tau phosphorylated at a combination of amino acid residues (i) S199 and S202, but not T205, (ii) S202 and T205, but not S199, (iii) S199 and T205, but not S202, and (iv) S199, S202, and T205 (e.g., wherein binding to phosphorylated tau is at least 1.6-times stronger (e.g., at least 1.7 times, at least 1.8 times, at least 1.9 times, at least 2 times, at least 3 times, 1.6-3 times, 1.6-2 times stronger) than background (e.g., non-specific) level of binding, e.g., binding by hIgG1 isotype control), (h) a peptide comprising or consisting of the amino acid sequence SGDRSGYS(pS)PGSPGTPGSRSRTPS (SEQ ID NO: 284), (i) a peptide comprising or consisting of the amino acid sequence SGDRSGYSSPG(pS)PGTPGSRSRTPS (SEQ ID NO: 285), (j) a peptide comprising or consisting of the amino acid sequence SGDRSGYSSPGSPG(pT)PGSRSRTPS (SEQ ID NO: 286), or (k) a peptide comprising or consisting of the amino acid sequence SGDRSGYS(pS)PGSPG(pT)PGSRSRTPS (SEQ ID NO: 290) (e.g., wherein binding to the peptide is at least 3 times stronger (e.g., at least 4 times stronger) than background (e.g., non-specific) level of binding, e.g., binding by hIgG1 isotype control), (l) a peptide comprising or consisting of the amino acid sequence SGDRSGYSSPG(pS)PG(pT)PGSRSRTPS (SEQ ID NO: 289), but not a peptide comprising or consisting of the amino acid sequence SGDRSGYS(pS)PG(pS)PGTPGSRSRTPS (SEQ ID NO: 288), (m) peptides comprising or consisting of the amino acid sequences SGDRSGYSSPG(pS)PG(pT)PGSRSRTPS (SEQ ID NO: 289) and SGDRSGYS(pS)PGSPG(pT)PGSRSRTPS (SEQ ID NO: 290), wherein binding to the latter peptide is at least 2 times (e.g., at least 3 times, at least 4 times, at least 5 times, 2-6 times, 2-5 times, 2-4 times, 2-3 times, 3-5 times or 4-5 times) more stronger than background (e.g., non-specific) level of binding, e.g., binding by hIgG1 isotype control), or (n) peptides comprising or consisting of the amino acid sequences SGDRSGYS(pS)PG(pS)PGTPGSRSRTPS (SEQ ID NO: 288), SGDRSGYSSPG(pS)PG(pT)PGSRSRTPS (SEQ ID NO: 289), SGDRSGYS(pS)PGSPG(pT)PGSRSRTPS (SEQ ID NO: 290), and SGDRSGYS(pS)PG(pS)PG(pT)PGSRSRTPS (SEQ ID NO: 287) (e.g., wherein binding to the peptides is at least 1.6 times stronger (e.g., at least 1.7 times, at least 1.8 times, at least 1.9 times, at least 2 times, at least 3 times, 1.6-4 times, 1.6-3 times stronger) than background (e.g., non-specific) level of binding, e.g., binding by hIgG1 isotype control), wherein p(S) and p(T) correspond to a phosphorylated serine and phosphorylated threonine, respectively, optionally wherein binding is assessed, e.g., using one point ELISA as described in Example 7, and optionally wherein human tau has the sequence set forth in SEQ ID NO: 274.

E37. The antibody of embodiment E36, wherein the antibody comprises:
(a) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively;
(b) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively;
(c) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively;
(d) a heavy chain variable region (VH) comprising CDR1, CDR2, and CDR3 sequences comprising SEQ ID NOs: 77, 92, and 109, respectively, and a light chain variable region (VL) comprising CDR1, CDR2, and CDR3 sequences comprising SEQ ID NOs: 127, 141, and 154, respectively; or
(e) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively.

E38. The antibody of embodiment E36 or E37, wherein the antibody comprises a VH and a VL, wherein the VH and the VL comprise the amino acid sequence of:
(a) SEQ ID NOs: 7 and 25, respectively,
(b) SEQ ID NOs: 8 and 21, respectively,
(c) SEQ ID NOs: 6 and 24, respectively,
(d) SEQ ID NOs: 1 and 19, respectively, or
(e) SEQ ID NOs: 12 and 31, respectively.

E39. An isolated, e.g., recombinant, antibody that binds to:
(a) human tau phosphorylated at amino acid residue S199, but not at amino acid residues S202 and T205, and wherein the antibody comprises a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively;
(b) human tau phosphorylated at amino acid residue S202, but not at amino acid residues S199 and T205, and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; or (iii) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;
(c) human tau phosphorylated at amino acid residue T205, but not at amino acid residues S199 and S202, and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; or (iii) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;
(d) human tau phosphorylated at a combination of amino acid residues S199 and T205, but not at amino acid residue S202 (e.g., wherein binding tau phosphorylated at a combination of S199 and T205 is at least 3-times stronger (e.g., at least 4-time stronger) than background (e.g., non-specific) level of binding, e.g., binding by hIgG1 isotype control), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (iii) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; or (iv) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;
(e) human tau phosphorylated at a combination of amino acid residues S202 and T205, but not at amino acid residue S199, but not human tau phosphorylated at a combination of residues S199 and S202, but not T205, and wherein the antibody comprises a heavy chain variable region (VH) comprising CDR1, CDR2, and CDR3 sequences comprising SEQ ID NOs: 77, 92, and 109, respectively, and a light chain variable region (VL) comprising CDR1, CDR2, and CDR3 sequences comprising SEQ ID NOs: 127, 141, and 154, respectively;

(f) human tau phosphorylated at a combination of amino acid residues (i) S202 and T205, but not S119, and (ii) S199 and T205, but not S202, at least 2 times (e.g., at least 3 times, at least 4 times, at least 5 times, 2-6 times, 2-5 times, 2-4 times, 2-3 times, 3-5 times or 4-5 times) more strongly than background (non-specific) level of binding, e.g., binding by hIgG1 isotype control), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (iii) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; or (iv) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;

(g) human tau phosphorylated at a combination of amino acid residues (i) S199 and S202, but not T205, (ii) S202 and T205, but not S199, (iii) S199 and T205, but not S202, and (iv) S199, S202, and T205 (e.g., wherein binding to phosphorylated tau is at least 1.6-times stronger (e.g., at least 1.7 times, at least 1.8 times, at least 1.9 times, at least 2 times, at least 3 times, 1.6-3 times, 1.6-2 times stronger) than background (non-specific) level of binding, e.g., binding by hIgG1 isotype control), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (iii) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; or (iv) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;

(h) a peptide comprising or consisting of the amino acid sequence SGDRSGYS(pS)PGSPGTPGSRSRTPS (SEQ ID NO: 284), and wherein the antibody comprises a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively (i) a peptide comprising or consisting of the amino acid sequence SGDRSGYSSPG(pS)PGTPGSRSRTPS (SEQ ID NO: 285), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; or (iii) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;

(j) a peptide comprising or consisting of the amino acid sequence SGDRSGYSSPGSPG(pT)PGSRSRTPS (SEQ ID NO: 286), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; or (iii) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;

(k) a peptide comprising or consisting of the amino acid sequence SGDRSGYS(pS)PGSPG(pT) PGSRSRTPS (SEQ ID NO: 290) (e.g., wherein binding to the peptide is at least 3 times stronger (e.g., at least 4 times stronger) than background (non-specific) level of binding, e.g., binding by hIgG1 isotype control), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH)

comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (iii) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; or (iv) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;

(l) a peptide comprising or consisting of the amino acid sequence SGDRSGYSSPG(pS)PG(pT)PGSRSRTPS (SEQ ID NO: 289), but not a peptide comprising or consisting of the amino acid sequence SGDRSGYS(pS)PG(pS)PGTPGSRSRTPS (SEQ ID NO: 288), and wherein the antibody comprises a heavy chain variable region (VH) comprising CDR1, CDR2, and CDR3 sequences comprising SEQ ID NOs: 77, 92, and 109, respectively, and a light chain variable region (VL) comprising CDR1, CDR2, and CDR3 sequences comprising SEQ ID NOs: 127, 141, and 154, respectively (m) peptides comprising or consisting of the amino acid sequences SGDRSGYSSPG(pS)PG(pT)PGSRSRTPS (SEQ ID NO: 289) and SGDRSGYS(pS)PGSPG(pT)PGSRSRTPS (SEQ ID NO: 290), wherein binding to the latter peptide is at least 2 times (e.g., at least 3 times, at least 4 times, at least 5 times, 2-6 times, 2-5 times, 2-4 times, 2-3 times, 3-5 times or 4-5 times) more stronger than background (non-specific) level of binding, e.g., binding by hIgG1 isotype control), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (iii) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; or (iv) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively; or (n) peptides comprising or consisting of the amino acid sequences SGDRSGYS(pS)PG(pS)PGTPGSRSRTPS (SEQ ID NO: 288), SGDRSGYSSPG(pS)PG(pT)PGSRSRTPS (SEQ ID NO: 289), SGDRSGYS(pS)PGSPG(pT)PGSRSRTPS (SEQ ID NO: 290), and SGDRSGYS(pS)PG(pS)PG(pT)PGSRSRTPS (SEQ ID NO: 287) (e.g., wherein binding to the peptides is at least 1.6 times stronger (e.g., at least 1.7 times, at least 1.8 times, at least 1.9 times, at least 2 times, at least 3 times, 1.6-4 times, 1.6-3 times stronger) than background (non-specific) level of binding, e.g., binding by hIgG1 isotype control), and wherein the antibody comprises (i) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (ii) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (iii) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; or (iv) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively;

wherein p(S) and p(T) correspond to a phosphorylated serine and phosphorylated threonine, respectively, optionally wherein binding is assessed, e.g., using one point ELISA as described in Example 7, and optionally wherein human tau has the sequence set forth in SEQ ID NO: 274.

E40. An isolated, e.g., recombinant, antibody that binds to:

(a) tau phosphorylated at T217, but not at T212 or T214, or (b) peptides comprising or consisting of the sequences GTPGSRSRTPSLP(pT)PPTRE (SEQ ID NO: 293) and GTPGSRSRTP(pS)LP(pT)PPTRE (SEQ ID NO: 296), but not peptides comprising or consisting of the sequences GTPGSRSR(pT)PSLPTPPTRE (SEQ ID NO: 291), GTPGSRSRTP(pS)LPTPPTRE (SEQ ID NO: 292), and GTPGSRSR(pT)P(pS)LPTPPTRE (SEQ ID NO: 294), wherein p(S) and p(T) correspond to a phosphorylated serine and phosphorylated threonine, respectively, optionally wherein binding of the antibody to tau or the peptide is at least 1.5 times stronger (e.g., at least 1.6 times, at least 1.7 times, at least 1.8 times, at least 1.9 times, at least 2 times, at least 3 times, at least 4 times, at least 5 times, at least 6 times, 1.5-4 times, 1.5-3, 4-6 times stronger) than background (non-specific) level of binding, e.g., binding by hIgG1 isotype control), optionally wherein binding of the antibody to tau or the peptide is assessed, e.g., using one point ELISA as described, e.g., in Example 8, and optionally wherein human tau has the sequence set forth in SEQ ID NO: 274.

E41. The antibody of embodiment E40, wherein the antibody comprises:
(a) a heavy chain variable region (VH) comprising CDR1, CDR2, and CDR3 sequences comprising SEQ ID NOs: 80, 95, and 112, respectively, and a light chain variable region (VL) comprising CDR1, CDR2, and CDR3 sequences comprising SEQ ID NOs: 129, 143, and 157, respectively;
(b) a heavy chain variable region (VH) comprising CDR1, CDR2, and CDR3 sequences comprising SEQ ID NOs: 78, 104, and 122, respectively, and a light chain variable region (VL) comprising CDR1, CDR2, and CDR3 sequences comprising SEQ ID NOs: 136, 150, and 167, respectively; or
(c) a heavy chain variable region (VH) comprising CDR1, CDR2, and CDR3 sequences comprising SEQ ID NOs: 90, 107, and 125, respectively, and a light chain variable region (VL) comprising CDR1, CDR2, and CDR3 sequences comprising SEQ ID NOs: 139, 151, and 170, respectively.

E42. The antibody of embodiment E40 or E41, wherein the antibody comprises a VH and a VL, wherein the VH and the VL comprise the amino acid sequence of:
(a) SEQ ID NOs: 4 and 22, respectively,
(b) SEQ ID NOs: 14 and 34, respectively, or
(c) SEQ ID NOs: 17 and 37, respectively.

E43. The antibody of any one of the preceding embodiments, wherein the antibody is an IgA, IgD, IgE, IgG, or IgM antibody.

E44. The antibody of embodiment E43, wherein the antibody is an IgG antibody.

E45. The antibody of any one of the preceding embodiments, wherein the IgG is an isotype selected from IgG1, IgG2, IgG3, and IgG4.

E46. The antibody of embodiment E45, wherein the antibody is an IgG1 antibody.

E47. The antibody of any of the preceding embodiments, wherein the antibody comprises a heavy chain constant region selected from human IgG1, human IgG2, human IgG3, human IgG4, murine IgG1, murine IgG2a, murine IgG2b, murine IgG2c, and murine IgG3; and/or a light chain constant region selected from the light chain constant regions of kappa or lambda.

E48. The antibody of embodiment E47, wherein the antibody comprises a heavy chain constant region of human IgG1.

E49. The antibody of any one of the preceding embodiments, wherein the antibody comprises:
(i) a heavy chain constant region (CH), e.g., a CH comprising an amino acid sequence of any of the heavy chain constant regions in Table 5, or a sequence having at least 80% (e.g., 85, 90, 95, 96, 97, 98, or 99%) sequence identity to the heavy chain constant region sequences in Table 5; an amino acid sequence comprising at least one, two or three modifications, but not more than 30, 20 or 10 modifications, relative to the amino acid sequence of the heavy chain constant region sequences in Table 5; or an amino acid sequence comprising at least one, two or three, but not more than 30, 20 or 10 different amino acids, relative to the amino acid sequence of the heavy chain constant region sequences in Table 5; and/or
(ii) a light chain constant region (CL), e.g., a CL comprising an amino acid sequence of any of the CL sequences in Table 5, or a sequence having at least 80% (e.g., 85, 90, 95, 96, 97, 98, or 99%) sequence identity to any of the CL sequences in Table 5; an amino acid sequence comprising at least one, two or three modifications, but not more than 30, 20 or 10 modifications, relative to the amino acid sequence of the light chain constant region sequences in Table 5; an amino acid sequence comprising at least one, two or three, but not more than 30, 20 or 10 different amino acids, relative to the amino acid sequence of the light chain constant region sequences in Table 5.

E50. The antibody of any one of the preceding embodiments, wherein the antibody molecule comprises an Fc region or variant, e.g., functional variant, thereof.

E51. The antibody of any one of the preceding embodiments, wherein the antibody molecule comprises an Fc region which has modified, e.g., increased or reduced affinity (e.g., ablated), affinity for an Fc receptor, e.g., as compared to a reference, wherein the reference is a wild-type Fc receptor.

E52. The antibody of any one of embodiments E1-E51, wherein the antibody molecule comprises an Fc region which comprises a mutation at one, two, or all of positions I253 (e.g., I235A), H310 (e.g., H310A), and/or H435 (e.g., H435A), numbered according to the EU index as in Kabat.

E53. The antibody of any one of the preceding embodiments, wherein the antibody is a full-length antibody, a bispecific antibody, an intrabody, a Fab, a F(ab')2, a Fv, a single chain Fv fragment (scFv), single domain antibody, or a camelid antibody.

E54. The antibody of any one of the preceding embodiments, wherein, in the antibody,
(i) the VH and VL are connected directly, e.g., without a linker; or
(ii) the VH and VL are connected via a linker.

E55. The antibody of any one of the preceding embodiments, wherein the antibody is a human, humanized, or chimeric antibody.

E56. The antibody of any one of the preceding embodiments, wherein the antibody comprises a signal sequence.

E57. The antibody of embodiment E56, wherein, in the antibody,
(i) the signal sequence is located 5' relative to the VH and/or the heavy chain; and/or
(ii) the signal sequence is located 5' relative to the VL and/or the light chain.

E58. The antibody of any one of the preceding embodiments, wherein the antibody molecule comprises a second antigen-binding region having a different binding specificity than the antigen-binding region that binds to tau.

E59. The antibody of any one of the preceding embodiments, wherein the antibody molecule is a multispecific antibody molecule comprising at least a first antigen-binding domain and a second antigen-binding domain, e.g., a bispecific antibody molecule.

E60. The antibody of any one of the preceding embodiments, wherein the antibody does not bind to non-pathological tau.

E61. The antibody of any one of the preceding embodiments, wherein the antibody binds to pathological tau tangles.

E62. The antibody of any one of the preceding embodiments, wherein the antibody inhibits tau aggregation.

E63. An isolated, e.g., recombinant, antibody that competes for binding to human tau with the antibody of any one of the preceding embodiments.

E64. An isolated, e.g., recombinant, antibody that binds to the same epitope, substantially the same epitope as, an epitope that overlaps with, or an epitope that substantially overlaps with, the epitope of the antibody of any one of the preceding embodiments.

E65. The antibody of any one of the preceding embodiments, wherein the antibody comprises a conjugate, e.g., a therapeutic agent or a detectable label.

E66. A composition (e.g., a pharmaceutical composition) comprising the antibody of any one of preceding embodiments and a carrier (e.g., a pharmaceutically-acceptable carrier).

E67. An isolated, e.g., recombinant, nucleic acid, or a combination of nucleic acids, encoding the antibody of any one of embodiments E1-E65.

E68. The nucleic acid, or combination of nucleic acids, of embodiment E67, comprising:
(a) the nucleotide sequence of any VH provided in Table 1, or a nucleic acid sequence having at least 70%, 75%, 80%, 85%, 90%, 92%, 95%, 96%, 97%, 98%, or 99% sequence identity thereto; and/or
(b) the nucleotide sequence of any VL provided in Table 1, or a nucleotide sequence having at least 70%, 75%, 80%, 85%, 90%, 92%, 95%, 96%, 97%, 98%, or 99% sequence identity thereto.

E69. The nucleic acid, or combination of nucleic acids, of any one of embodiments E67 or
E68, comprising:
(a) the nucleotide sequence of any one of SEQ ID NOs: 51, 55, 54, 52, 47, 39, 56, 41, 50, 49, 48, 46, 45, 44, 43, 42, 53, 40, or a nucleic acid sequence having at least 70%, 75%, 80%, 85%, 90%, 92%, 95%, 96%, 97%, 98%, or 99% sequence identity thereto; and/or
(b) the nucleotide sequence of any one of SEQ ID NOs: 67, 75, 74, 72, 66, 57, 76, 59, 70, 69, 68, 65, 64, 62, 63, 61, 60, 73, 58, or a nucleotide sequence having at least 70%, 75%, 80%, 85%, 90%, 92%, 95%, 96%, 97%, 98%, or 99% sequence identity thereto.

E70. The isolated nucleic acid sequence of any one of embodiments E67-E69, wherein the nucleic acid sequence encoding the heavy chain variable region and/or the light chain variable region is codon-optimized.

E71. An isolated, e.g., recombinant, antibody encoded by the nucleic acid of any one of embodiments E67-E70.

E72. A vector (e.g., an expression vector), or combination of vectors (e.g., combination of expression vectors), comprising the nucleic acid, or combination of nucleic acids, of any one of embodiments E67-E70.

E73. A host cell comprising the nucleic acid, or combination of nucleic acids, of any one of embodiments E67-E70, or the vector, or combination of vectors, of embodiment E62.

E74. The host cell of embodiment E73, wherein the host cell is a bacterial cell or a mammalian cell.

E75. A method of producing an antibody which binds to human tau, the method comprising culturing the host cell of embodiment E73 or E74, under conditions suitable for gene expression.

E76. A method of delivering to a subject an exogenous antibody that binds to human tau, the method comprising administering to the subject an effective amount of the antibody of any one of embodiments E1-E65, or the composition (e.g., a pharmaceutical composition) of embodiment E66.

E77. The method of embodiment E76, wherein the subject has, has been diagnosed with having, or is at risk of having a disease associated with expression of tau.

E78. The method of embodiment E76 or E77, wherein the subject has, has been diagnosed with having, or is at risk of having a neurological, e.g., neurodegenerative disorder.

E79. The method of any one of embodiments E76-E78, wherein the subject has, has been diagnosed with having, or is at risk of having a tauopathy.

E80. A method of treating a subject having or diagnosed with having a disease associated with expression of tau, the method comprising administering to the subject an effective amount of the antibody of any one of embodiments E1-E65, or the composition (e.g., a pharmaceutical composition) of embodiment E66.

E81. A method of treating a subject having or diagnosed with having a neurological, e.g., neurodegenerative disorder, the method comprising administering to the subject an effective amount of the antibody of any one of embodiments E1-E65, or the composition (e.g., a pharmaceutical composition) of embodiment E66.

E82. A method of treating a subject having or diagnosed with having a tauopathy, the method comprising administering to the subject an effective amount of the antibody of any one of embodiments E1-E65, or the composition (e.g., a pharmaceutical composition) of embodiment E66.

E83. The method of any one of embodiments E77-E82, wherein the disease associated with tau expression, the neurological disorder, or the tauopathy comprises Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), prion diseases, Creutzfeldt-Jakob disease (CJD), multiple system atrophy, tangle-only dementia, or progressive subcortical gliosis.

E84. The method of any one of embodiments E80-E83, wherein treating comprises prevention of progression of the disease or disorder in the subject.

E85. The method of any one of embodiments E76-E84, wherein the subject is human.

E86. The method of any one of embodiments E76-E85, wherein the antibody is administered intravenously.

E87. The method of any one of embodiments E76-E86, wherein administration of the antibody results in a decreased presence, level, and/or activity of tau protein.

E88. The method of any one of embodiments E76-E87, further comprising administration of an additional therapeutic agent and/or therapy suitable for treatment or prevention of a disorder associated with tau expression, a neurological, e.g., neurodegenerative, disorder.

E89. The method of embodiment E88, wherein the additional therapeutic agent and/or therapy comprises a cholinesterase inhibitor (e.g., donepezil, rivastigmine, and/or galantamine), an N-methyl D-aspartate (NMDA) antagonist (e.g., memantine), an antipsychotic drug, an anti-anxiety drug, an anticonvulsant, a dopamine agonist (e.g., pramipexole, ropinirole, rotigotine, and/or apomorphine), an MAO B inhibitor (e.g., selegiline, rasagiline, and/or safinamide), catechol O-methyltransferase (COMT) inhibitors (entacapone, opicapone, and/or tolcapone), anticholinergics (e.g., benztropine and/or trihexyphenidyl), amantadine, carbidopa-levodopa, deep brain simulation (DBS), or a combination thereof.

E90. A method of diagnosing a neurological disorder, a neurodegenerative disorder, a disease associated with tau expression or activity, or a tau-related disease (e.g., tauopathy) in a subject, the method comprising the use of the antibody of any one of embodiments E1-E65.

E91. A method of detecting tau, the method comprising contacting a sample (e.g., a biological sample such as human tissue, e.g., human CNS tissue) with the antibody of any one of embodiments E1-E65 and detecting the formation of a complex between the antibody and tau.

E92. The method of embodiment E91, wherein the tissue is a thin tissue section or cryopreserved tissue section.

E93. The antibody of any one of embodiments E1-E65, or composition of embodiment E56, for use in a method of treating a neurological disorder, a neurodegenerative disorder, a disease associated with tau expression or activity, or a tau-related disease (e.g., tauopathy).

E94. The antibody of any one of embodiments E1-E65, or composition of embodiment E56, for use in the manufacture of a medicament.

E95. The antibody of any one of embodiments E1-E65, or composition of embodiment E56, for use in the manufacture of a medicament for treating a neurological disorder, a neurodegenerative disorder, a disease associated with tau expression or activity, or a tau-related disease (e.g., tauopathy).

E96. Use of the antibody of any one of embodiments E1-E65, or composition of embodiment E66 in the manufacture of a medicament.

E97. Use of the antibody of any one of embodiments E1-E65, or composition of embodiment E66 in the manufacture of a medicament for treating a neurological disorder, a neurodegenerative disorder, a disease associated with tau expression or activity, or a tau-related disease (e.g., tauopathy).

ADDITIONAL EMBODIMENTS

1. An antibody comprising: (i) a heavy chain variable domain (VH), wherein the VH comprises: a complementarity determining region (CDR)H1 comprising an amino acid sequence selected from the group consisting of any of those listed in Table 1, or a fragment thereof; a CDRH2 comprising an amino acid sequence selected from the group consisting of any of those listed in Table 1, or a fragment thereof; and a CDRH3 comprising an amino acid sequence selected from the group consisting of any of those listed in Table 1, or a fragment thereof; and (ii) a light chain variable domain (VL), wherein the VL comprises: a CDRL1 comprising an amino acid sequence selected from the group consisting of any of those listed in Table 1, or a fragment thereof; a CDRL2 comprising an amino acid sequence selected from the group consisting of any of those listed in Table 1, or a fragment thereof; and a CDRL3 comprising an amino acid sequence selected from the group consisting of any of those listed in Table 1, or a fragment thereof.
2. The antibody of embodiment 1, wherein the antibody comprises a set of variable domain CDR amino acid sequences, wherein the variable domain CDR amino acid sequence set is selected from the group consisting of any of those listed in Table 1.
3. The antibody of embodiment 1 or 2, wherein the antibody comprises a pair of variable domain CDR amino acid sequence sets, wherein the variable domain CDR amino acid sequence set pair is selected from the group consisting of any those listed in Table 1.
4. The antibody of any one of embodiments 1-3, wherein: (i) the VH comprises: a framework region (FR)H1 comprising an amino acid sequence selected from the group consisting of any of those listed in Table 1, or a fragment thereof; a FRH2 comprising an amino acid sequence selected from the group consisting of any of those listed in Table 1, or a fragment thereof; a FRH3 comprising an amino acid sequence selected from the group consisting of any of those listed in Table 1, or a fragment thereof; and a FRH4 comprising an amino acid sequence selected from the group consisting of any of those listed in Table 1, or a fragment thereof; and (ii) the VL comprises: a FRL1 comprising an amino acid sequence selected from the group consisting of any of those listed in Table 1, or a fragment thereof; a FRL2 comprising an amino acid sequence selected from the group consisting of any of those listed in Table 1, or a fragment thereof; a FRL3 comprising an amino acid sequence selected from the group consisting of any of those listed in Table 1, or a fragment thereof; and a FRL4 comprising an amino acid sequence selected from the group consisting of any of those listed in Table 1, or a fragment thereof.
5. The antibody of any one of embodiments 1-4, wherein the VH comprises: an amino acid sequence selected from the group consisting of any of those listed in Table 1; and/or is encoded by a nucleic acid sequence selected from the group consisting of any of those listed in Table 1.
6. The antibody of any one of embodiments 1-5, wherein the VL comprises: an amino acid sequence selected from the group consisting of any of those listed in Table 1; and/or is encoded by a nucleic acid sequence selected from the group consisting of any of those listed in Table 1.
7. The antibody of any one of embodiments 1-6, wherein the antibody comprises a variable domain pair, the variable domain pair selected from the group consisting of any of those listed in Table 1.
8. The antibody of any one of embodiments 1-7, wherein the antibody comprises a format selected from the group consisting of a monoclonal antibody, a multispecific antibody, a chimeric antibody, an antibody mimetic, a single chain Fv (scFv) format, and an antibody fragment.
9. The antibody of any one of embodiments 1-7, wherein the antibody comprises an antibody class selected from the group consisting of IgA, IgD, IgE, IgG, and IgM.
10. The antibody of any one of embodiments 1-7, wherein the antibody comprises one or more non-human constant domain.
11. The antibody of any one of embodiments 1-7, wherein the antibody comprises one or more human constant domain.

12. The antibody of embodiment 11, wherein the one or more human constant domain is selected from the group consisting of any of those listed in Table 5.
13. The antibody of embodiment 12, wherein the antibody comprises a human IgG, wherein the human IgG comprises an isotype selected from the group consisting of IgG1, IgG2, IgG3, and IgG4.
14. The antibody of any one of embodiments 1-7, wherein the antibody comprises a human antibody.
15. The antibody of any one of embodiments 1-14, wherein the antibody binds to a tau protein epitope.
16. The antibody of embodiment 15, wherein the tau protein epitope comprises or is comprised within an amino acid sequence selected from the group consisting of any of those listed in Table 4.
17. The antibody of embodiment 15 or 16, wherein the tau protein epitope comprises a region formed by a complex of at least two tau proteins.
18. The antibody of any one of embodiments 15-17, wherein the antibody binds to enriched paired helical filament tau protein (ePHF) with a half maximal effective concentration (EC50) of from about 0.01 nM to about 100 nM as determined by direct enzyme-linked immunosorbent assay (ELISA).
19. The antibody of any one of embodiments 15-18, wherein the antibody does not bind to non-pathological tau.
20. The antibody of any one of embodiments 15-19, wherein the antibody binds to pathological tau tangles.
21. The antibody of any one of embodiments 15-20, wherein the antibody inhibits tau aggregation.
22. The antibody of any one of embodiments 1-21, wherein the antibody comprises a conjugate.
23. The antibody of embodiment 22, wherein the conjugate comprises a therapeutic agent.
24. The antibody of embodiment 22, wherein the conjugate comprises a detectable label.
25. A construct encoding the antibody of any one of embodiments 1-21.
26. A method of treating a therapeutic indication in a subject, the method comprising administering to the subject the antibody of any one of embodiments 1-24.
27. The method of embodiment 26, wherein the therapeutic indication comprises a neurological indication.
28. The method of embodiment 27, wherein the neurological indication comprises one or more of neurodegenerative disease, Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), a prion disease, Creutzfeldt-Jakob disease (CJD), multiple system atrophy, tangle-only dementia, stroke, and progressive subcortical gliosis.
29. A method of diagnosing a therapeutic indication in a subject, the method comprising the use of the antibody of any one of embodiments 1-24.
30. The method of embodiment 29, wherein the therapeutic indication comprises a neurological indication.
31. The method of embodiment 30, wherein the neurological indication comprises one or more of neurodegenerative disease, AD, FTDP-17, FTLD, FTD, CTE, PSP, Down's syndrome, Pick's disease, CBD, corticobasal syndrome, ALS, a prion disease, CJD, multiple system atrophy, tangle-only dementia, stroke, and progressive subcortical gliosis.
32. The method of any one of embodiments 29-31, wherein the antibody is used to detect pathological tau in a subject tissue.
33. The method of embodiment 32, wherein the subject tissue comprises CNS tissue.
34. The method of embodiment 32 or 33, wherein the subject tissue comprises a thin tissue section.
35. The method of embodiment 34, wherein the thin tissue section comprises a cryopreserved tissue section.

DETAILED DESCRIPTION

I. Compositions

Figure 1A:
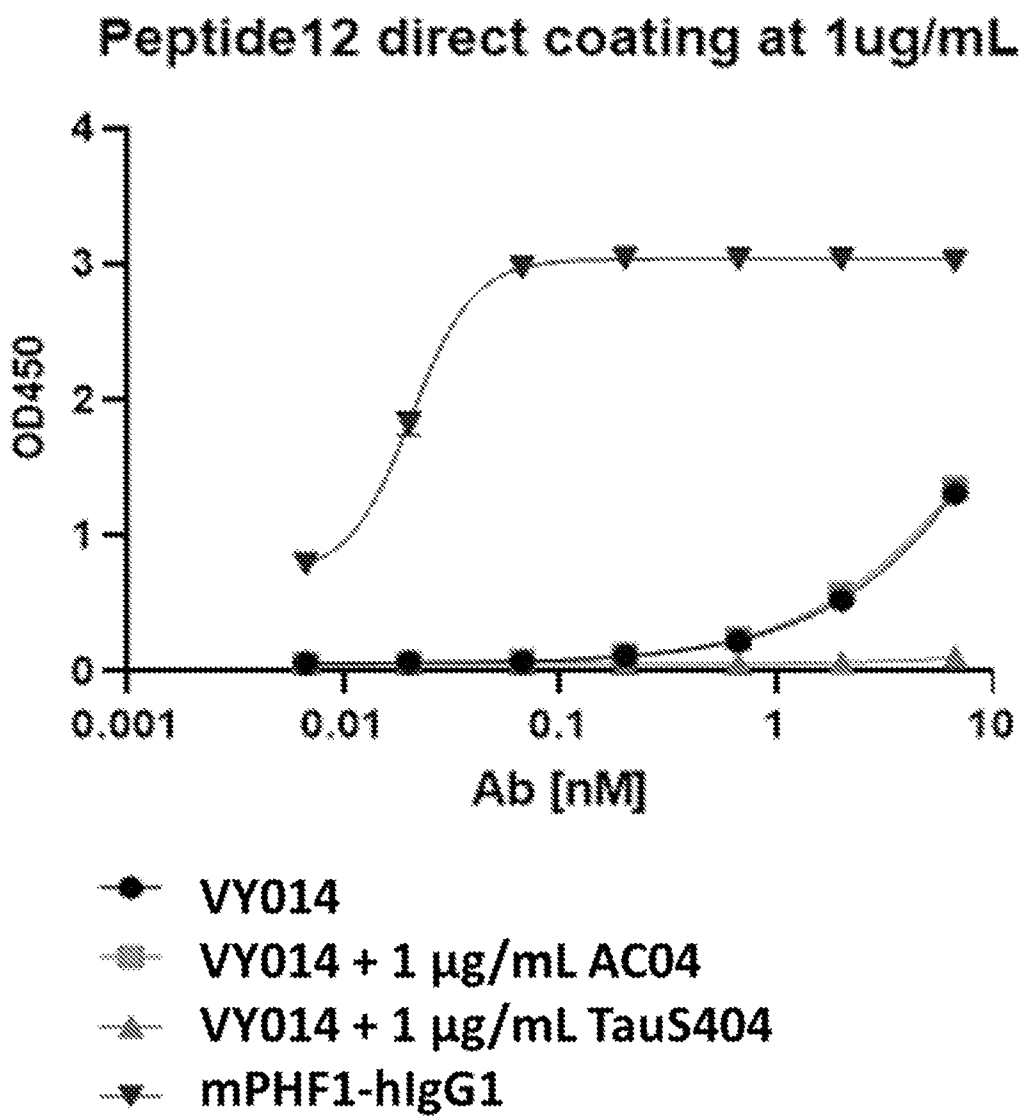
FIGS. 1A-1C show the results of competition ELISA assays for binding of the indicated antibodies (±competitors) to Peptide 12 (corresponding to SEQ ID NO: 277) (FIG. 1A), a TauS404 peptide (FIG. 1B), or the AC04 peptide (FIG. 1C).

In some embodiments, the present disclosure provides compositions that interact with human microtubule associated protein tau. Such compositions may be antibodies that bind tau protein epitopes, referred to herein as "anti-tau antibodies." Dysfunction and/or aggregation of tau is found in a class of neurodegenerative diseases referred to as tauopathies. Tau hyperphosphorylation leads to aggregation and depressed tau-dependent microtubule assembly. In tauopathies, the tau aggregates form paired helical filaments (PHF) found in neurofibrillary tangles (NFTs). These aggregates lead to neuronal loss and cognitive decline. Anti-tau antibodies of the present disclosure may be useful for treating and/or diagnosing tauopathies, as well as other applications described herein.

Antibodies

In some embodiments, compounds (e.g., anti-tau antibodies) and compositions of the present disclosure include antibodies or fragments thereof. As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), single chain Fv (scFv) formats, and antibody fragments (e.g., Fab, F(ab'), $F(ab')_2$, or Fv), so long as they exhibit a functional or biological activity. Antibodies are primarily amino-acid based molecules but may also include one or more modifications (including, but not limited to the addition of sugar moieties, fluorescent moieties, chemical tags). In some embodiments, the antibody is a full-length antibody.

Antibodies of the present disclosure may include, but are not limited to, polyclonal, monoclonal antibodies, multispecific antibodies, bispecific antibodies, trispecific antibodies, human antibodies, humanized antibodies, chimeric antibodies, single chain antibodies, diabodies, linear antibodies, Fab fragments, F(ab') fragments, $F(ab')_2$ fragments, Fv fragments, single-chain Fv fragment (scFv), fragments produced by a Fab expression library, variable domains, anti-idiotypic (anti-Id) antibodies (including, e.g., anti-Id antibodies to antibodies of the invention), intracellularly made antibodies (i.e., intrabodies), codon-optimized antibodies, tandem scFv antibodies, bispecific T-cell engagers, mAb2 antibodies, chimeric antigen receptors (CAR), tetravalent bispecific antibodies, biosynthetic antibodies, native antibodies, miniaturized antibodies, unibodies, maxibodies, intrabodies, camelid antibodies, and epitope-binding fragments of any of the above.

As used herein, the term "antibody fragment" refers to a portion of an intact antibody or fusion-protein thereof, in some cases including at least one antigen binding region. Examples of antibody fragments include Fab, Fab', $F(ab')_2$, Fv fragments, single-chain variable fragments (scFvs); diabodies; tri(a)bodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an $F(ab')_2$ fragment that has two antigen-binding sites and is still capable of cross-linking antigen. Antibodies of the present disclosure may include one or more of these fragments and may, for example, be generated through enzymatic digestion of whole antibodies or through recombinant expression.

"Native antibodies" are usually heterotetrameric glycoproteins of about 150,000 Daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 103 (12: 4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (V H) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains include hypervariable regions. As used herein, the term "hypervariable region" refers to a region within a variable domain that includes amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody that includes a structure that is complimentary to its target antigen or epitope. Other portions of the variable domain, not interacting with the antigen, are each referred to as a "framework region" (FR). The antigen-binding site (also known as the antigen combining site or paratope) includes the amino acid residues necessary to interact with a particular antigen. The exact residues making up the antigen-binding site may be determined by CDR analysis. As used herein, the term "CDR analysis" refers to any process used to determine which antibody variable domain residues make up the CDRs. CDR analysis may be conducted by co-crystallography with bound antigen. In some embodiments, CDR analysis may include computational assessments based on comparisons with other antibodies (Strohl, W. R. Therapeutic Antibody Engineering. Woodhead Publishing, Philadelphia PA. 2012. Ch. 3, p 47-54, the contents of which are herein incorporated by reference in their entirety). CDR analysis may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989), and Al-Lazikani, B. et al., 1997, J. Mol. Biol. 273(4):927-48, the contents of each of which are herein incorporated by reference in their entirety], Lefranc (Lefranc, M. P. et al., 2005, Immunome Res. 1:3), and Honegger (Honegger, A. and Pluckthun, A. 2001. J. Mol. Biol. 309(3):657-70, the contents of which are herein incorporated by reference in their entirety).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD (Kabat numbering scheme), Al-Lazikani et al., (1997) JMB 273,927-948 (Chothia numbering scheme). In some embodiments, the CDRs defined according the Chothia number scheme are also sometimes referred to as hypervariable loops.

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDR amino acid residues are numbered 26-35 (HCDR1), 50-65 (HCDR2), and 95-102 (HCDR3) in human VH and the CDR amino acid residues are numbered 24-34 (LCDR1), 50-56 (LCDR2), and 89-97 (LCDR3) in human VL.

VH and VL domains have three CDRs each. VL CDRs are referred to herein as CDRL1, CDRL2 and CDRL3, in order of occurrence when moving from N- to C-terminus along the variable domain polypeptide. VH CDRs are referred to herein as CDRH1, CDRH2 and CDRH3, in order of occurrence when moving from N- to C-terminus along the variable domain polypeptide. Each of the CDRs have favored canonical structures with the exception of the CDRH3, which includes amino acid sequences that may be highly variable in sequence and length between antibodies resulting in a variety of three-dimensional structures in antigen-binding domains (Nikoloudis, D. et al., 2014. PeerJ. 2: e456). In some cases, CDRH3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia PA. 2012. Ch. 3, p 47-54, the contents of which are herein incorporated by reference in their entirety).

VH and VL domains each have four framework regions (FRs) located before, after, and between CDR regions. VH framework regions are referred to herein as FRH1, FRH2, FRH3, and FRH4 and VL framework regions are referred to herein as FRL1, FRL2, FRL3, and FRL4. On VH domains, FRs and CDRs are typically in the order of FRH1-CDRH1-FRH2-CDRH2-FRH3-CDRH3-FRH4, from N-terminus to C-terminus. On VL domains, FRs and CDRs are typically in the order of FRL1-CDRL1-FRL2-CDRL2-FRL3-CDRL3-FRL4, from N-terminus to C-terminus.

As used herein, the term "Fv" refers to an antibody fragment that includes the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain [to form a single chain Fv (scFv)] or through the introduction of a disulfide bridge between heavy and light chain variable domains (Strohl, W. R. Therapeutic Antibody Engineering. Woodhead Publishing, Philadelphia PA. 2012. Ch. 3, p 46-4'7, the contents of which are herein incorporated by reference in their entirety).

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. In some embodiments, antibodies of the present disclosure are prepared as scFvFc antibodies. The term "scFvFc" refers to an antibody format which includes the fusion of one or more scFv with an antibody Fc domain.

The term "chimeric antibody" refers to an antibody with portions derived from two or more sources. Chimeric antibodies may include portions derived from different species. For example, chimeric antibodies may include antibodies with mouse variable domains and human constant domains. Further examples of chimeric antibodies and methods for producing them include any of those described in Morrison, S. L., *Transfectomas provide novel chimeric antibodies*. Science. 1985 Sep. 20; 229(4719):1202-7; Gillies, S. D. et al., *High-level expression of chimeric antibodies using adapted cDNA variable region cassettes*. J Immunol Methods. 1989 Dec. 20; 125 (1-2):191-202; and U.S. Pat. Nos. 5,807,715; 4,816,567; and 4,816,397, the contents of each of which are incorporated herein by reference in their entirety.

The term "diabodies" refers to small antibody fragments with two antigen-binding sites, which fragments include a heavy chain variable domain V H connected to a light chain variable domain V L in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "intrabody" refers to a form of antibody that is not secreted from a cell in which it is produced, but instead targets one or more intracellular protein(s). Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more constructs for intrabody-based therapy. In some cases, intrabodies of the invention may target one or more glycated intracellular proteins or may modulate the interaction between one or more glycated intracellular protein and an alternative protein.

The term "chimeric antigen receptor" or "CAR" as used herein, refers to artificial receptors that are engineered to be expressed on the surface of immune effector cells resulting in specific targeting of such immune effector cells to cells expressing entities that bind with high affinity to the artificial receptors. CARs may be designed to include one or more segments of an antibody, antibody variable domain and/or antibody CDR, such that when such CARs are expressed on immune effector cells, the immune effector cells bind and clear any cells that are recognized by the antibody portions of the CARs. In some cases, CARs are designed to specifically bind cancer cells, leading to immune-regulated clearance of the cancer cells.

The term "monoclonal antibody" as used herein refers to an antibody obtained from a population of substantially homogeneous cells (or clones), i.e., the individual antibodies making up the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

Antibodies of the present disclosure may be from any animal origin including mammals, birds, reptiles, and insects. Mammalian antibodies may be, for example, of human, murine (e.g., mouse or rat), donkey, sheep, rabbit, goat, guinea pig, camel, bovine, or horse origin.

In some embodiments, antibodies of the present disclosure may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure, sequence and/or function, but including some differences in their amino acid sequence, composition or structure as compared to another antibody or a native antibody.

Intrabody

In some embodiments, the antibody described herein is an intrabody. In some embodiments, an intrabody is a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. In some embodiments, methods described herein include intrabody-based therapies.

In some embodiments, the intrabody is a single chain variable fragment (scFv) expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. Exemplary intrabodies are described and reviewed in: (Marasco et al., 1993 Proc. Natl. Acad. Sci. USA, 90: 7889-7893; Chen et al., 1994, Hum. Gene Ther. 5:595-601; Chen et al., 1994, Proc. Natl. Acad. Sci. USA, 91: 5932-5936; Maciejewski et al., 1995, Nature Med., 1: 667-673; Marasco, 1995, Immunotech, 1: 1-19; Mhashilkar, et al., 1995, EMBO J. 14: 1542-51; Chen et al., 1996, Hum. Gene Therap., 7: 1515-1525; Marasco, Gene Ther. 4:11-15, 1997; Rondon and Marasco, 1997, Annu. Rev. Microbiol. 51:257-283; Cohen, et al., 1998, Oncogene 17:2445-56; Proba et al., 1998, J. Mol. Biol. 275:245-253; Cohen et al., 1998, Oncogene 17:2445-2456; Hassanzadeh, et al., 1998, FEBS Lett. 437:81-6; Richardson et al., 1998, Gene Ther. 5:635-44; Ohage and Steipe, 1999, J. Mol. Biol. 291:1119-1128; Ohage et al., 1999, J. Mol. Biol. 291:1129-1134; Wirtz and Steipe, 1999, Protein Sci. 8:2245-2250; Zhu et al., 1999, J. Immunol. Methods 231:207-222; Arafat et al., 2000, Cancer Gene Ther. 7:1250-6; der Maur et al., 2002, J. Biol. Chem. 277:45075-85; Mhashilkar et al., 2002, Gene Ther. 9:307-19; and Wheeler et al., 2003, FASEB J. 17: 1733-5; and references cited therein). In particular, a CCRS intrabody has been produced by Steinberger et al., 2000, Proc. Natl. Acad. Sci. USA 97:805-810). See generally Marasco, W A, 1998, "Intrabodies: Basic Research and Clinical Gene Therapy Applications" Springer: New York; and for a review of scFvs, see Pluckthun in "The Pharmacology of Monoclonal Antibodies," 1994, vol. 113, Rosenburg and Moore eds. Springer-Verlag, New York, pp. 269-315; all of which are hereby incorporated by reference in their entirety.

Sequences from donor antibodies may be used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form a single chain antibody comprising the variable domains of the heavy and light chains joined by a flexible linker polypeptide. Intrabodies typically lack disulfide bonds and are capable of modulating the expression or activity of target genes through their specific binding activity. Single chain antibodies can also be expressed as a single chain variable region fragment joined to the light chain constant region.

In some embodiments, an intrabody can be engineered into recombinant polynucleotide vectors to encode sub-cellular trafficking signals at its N or C terminus to allow expression at high concentrations in the sub-cellular compartments where a target protein is located. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

Intrabodies may be promising therapeutic agents for the treatment of misfolding diseases, including tauopathies, prion diseases, Alzheimer's, Parkinson's, and Huntington's, because of their virtually infinite ability to specifically recognize the different conformations of a protein, including pathological isoforms, and because they can be targeted to the potential sites of aggregation (both intra- and extracellular sites). These molecules can work as neutralizing agents against amyloidogenic proteins by preventing their aggregation, and/or as molecular shunters of intracellular traffic by rerouting the protein from its potential aggregation site (Cardinale, and Biocca, Curr. Mol. Med. 2008, 8:2-11).

Antibody Development

Antibodies according to the present disclosure may be developed using methods standard in the art. Two primary antibody preparation technologies are immunization and antibody display technology. In either case, desired antibodies are identified from a larger pool of candidates based on affinity for a specific target or epitope. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen.

Antigens

Antibodies may be developed (e.g., through immunization) or selected (e.g., from pool of candidates), for example, using any naturally occurring or synthetic antigen. As used herein, an "antigen" is an entity which induces or evokes an immune response in an organism and may also refer to an antibody binding partner. An immune response is characterized by the reaction of the cells, tissues and/or organs of an organism to the presence of a foreign entity. Such an immune response typically leads to the production by the organism of one or more antibodies against the foreign entity. In some embodiments, antigens include tau proteins. As used herein, the term "tau protein" refers to proteins or protein complexes that include microtubule-associated protein tau or peptide fragments thereof. Tau proteins may include enriched paired helical filament tau protein (ePHF), also referred to as "sarkosyl insoluble tau," or fragments thereof. Tau proteins may include one or more phosphorylated residues. Such phosphorylated residues may correspond to tau proteins associated with disease (also referred to herein as "pathological tau."

Immunization

In some embodiments, antibodies may be prepared by immunizing a host with an antigen of interest. Host animals (e.g., mice, rabbits, goats, or llamas) may be immunized with an antigenic protein to elicit lymphocytes that specifically bind to the antigen. Lymphocytes may be collected and fused with immortalized cell lines to generate hybridomas which can be cultured in a suitable culture medium to promote growth (e.g., see Kohler, G. et al., Continuous cultures of fused cells secreting antibody of predefined specificity. Nature. 1975 Aug. 7; 256(5517):495-7, the contents of which are herein incorporated by reference in their entirety). Alternatively, lymphocytes may be immunized in vitro.

In some embodiments, antibodies of the present disclosure may be prepared through immunization using mouse host animals. Such host animals may include transgenic mice. Transgenic mice may include those engineered to express human antibody sequences, in some cases, replacing mouse antibody sequences. Transgenic mice may express human variable domain sequences and/or constant domain sequences. In some embodiments, mouse host animals used for immunization may include any of the transgenic mice described in U.S. Pat. Nos. 7,435,871, 7,547,817, 9,346,873, 9,580,491, or 10,555,506, the content of each of which is herein incorporated by reference in its entirety.

Lymphocytes may be fused with immortalized cell lines using suitable fusing agents (e.g., polyethylene glycol) to form a hybridoma cell (e.g., see Goding, J. W., Monoclonal Antibodies: Principles and Practice. Academic Press. 1986; 59-1031, the contents of which are herein incorporated by reference in their entirety). Immortalized cell lines may be transformed mammalian cells, particularly myeloma cells of rodent, rabbit, bovine, or human origin. In some embodiments, rat or mouse myeloma cell lines are employed. Hybridoma cells may be cultured in suitable culture media, typically including one or more substances that inhibit the growth or survival of unfused cells. For example, parental cells lacking the enzyme hypoxanthine guanine phosphoribosyl transferase (HGPRT or HPRT) may be used and culture media for resulting hybridoma cells may be supplemented with hypoxanthine, aminopterin, and thymidine ("HAT medium") to prevent growth of HGPRT-deficient (unfused) cells.

Desirable properties for immortalized cell lines may include, but are not limited to, efficient fusing, supportive of high level antibody expression by selected antibody-producing cells, and sensitivity to unfused cell-inhibitory media (e.g., HAT media). In some embodiments, immortalized cell lines are murine myeloma lines. Such cell lines may be obtained, for example, from the Salk Institute Cell Distribution Center (San Diego, CA) or the American Type Culture Collection, (Manassas, VA). Human myeloma and mouse-human heteromyeloma cell lines may also be used for the production of human monoclonal antibodies (e.g., see Kozbor, D. et al., A human hybrid myeloma for production of human monoclonal antibodies. J Immunol. 1984 December; 133(6):3001-5 and Brodeur, B. et al., Monoclonal Antibody Production Techniques and Applications. Marcel Dekker, Inc., New York. 1987; 33:51-63, the contents of each of which are herein incorporated by reference in their entireties).

Hybridoma cell culture media may be assayed for the presence of monoclonal antibodies with desired binding specificity. Assays may include, but are not limited to, immunoprecipitation assay, in vitro binding assay, radioimmunoassay (RIA), surface plasmon resonance (SPR) assay, and/or enzyme-linked immunosorbent assay (ELISA). In some embodiments, binding specificity of monoclonal antibodies may be determined by Scatchard analysis (Munson, P. J. et al., Ligand: a versatile computerized approach for characterization of ligand-binding systems. Anal Biochem. 1980 Sep. 1; 107(1):220-39, the contents of which are herein incorporated by reference in their entirety).

Antibodies produced by cultured hybridomas may be analyzed to determine binding specificity for target antigens. Once antibodies with desirable characteristics are identified, corresponding hybridomas may be subcloned through limiting dilution procedures and grown by standard methods. Antibodies produced by hybridomas may be isolated and purified using standard immunoglobulin purification procedures such as, for example, protein A-Sepharose, hydroxyapatite chromatography, gel electrophoresis, dialysis, or affinity chromatography. Alternatively, hybridoma cells may be grown in vivo as ascites in a mammal. In some embodiments, antibodies may be isolated directly from serum of immunized hosts.

In some embodiments, recombinant versions of antibodies generated through immunization may be prepared. Such antibodies may be prepared using genomic antibody sequences from selected hybridomas. Hybridoma genomic antibody sequences may be obtained by extracting RNA molecules from antibody-producing hybridoma cells and producing cDNA by reverse transcriptase polymerase chain reaction (PCR). PCR may be used to amplify cDNA using primers specific for antibody heavy and light chains. PCR products may then be subcloned into plasmids for sequence analysis. Antibodies may be produced by insertion of resulting antibody sequences into expression vectors. Some recombinant antibodies may be prepared using synthetic nucleic acid constructs that encode amino acid sequences corresponding to amino acid sequences obtained from isolated hybridoma antibodies.

Antibody Display

In some embodiments, antibodies may be developed using antibody display technologies. "Display technology" refers to systems and methods for expressing amino acid-based candidate compounds in a format where they are linked with nucleic acids encoding them and are accessible to a target or ligand. Candidate compounds are expressed at the surface of a host capsid or cell in most systems, however, some host-free systems (e.g., ribosomal display) exist. Display technologies may be used to generate display "libraries," which include sets of candidate compound library members. Display libraries with antibodies (or variants or fragments thereof) as library members are referred to herein as "antibody display libraries." Antibodies may be designed, selected, or optimized by screening target antigens using antibody display libraries. Antibody display libraries may include millions to billions of members, each expressing unique antibody domains. Antibody fragments displayed may be scFv antibody fragments, which are fusion proteins of V H and V L antibody domains joined by a flexible linker. Display libraries may include antibody fragments with differing levels of diversity between variable domain framework regions and CDRs. Display library antibody fragment CDRs may include unique variable loop lengths and/or sequences. Antibody variable domains or CDRs obtained from display library selection may be directly incorporated into antibody sequences for recombinant antibody production or mutated and utilized for further optimization through in vitro affinity maturation.

Antibody display libraries may include antibody phage display libraries. Antibody phage display libraries utilize phage virus particles as hosts with millions to billions of members, each expressing unique antibody domains. Such libraries may provide richly diverse sources that may be used to select potentially hundreds of antibody fragments with diverse levels of affinity for one or more antigens of interest (McCafferty, et al., 1990. Nature. 348:552-4; Edwards, B. M. et al., 2003. JMB. 334: 103-18; Schofield, D. et al., 2007. Genome Biol. 8, R254 and Pershad, K. et al., 2010. Protein Engineering Design and Selection. 23:279-88; the contents of each of which are herein incorporated by reference in their entirety). Antibody fragments displayed may be scFv antibody fragments. Phage display library members may be expressed as fusion proteins, linked to viral coat proteins (e.g. the N-terminus of the viral pIII coat protein). V L chains may be expressed separately for assembly with V H chains in the periplasm prior to complex incorporation into viral coats. Precipitated library members may be sequenced from the bound phage to obtain cDNA encoding desired antibody domains.

In some embodiments, antibody display libraries may be generated using yeast surface display technology. Antibody yeast display libraries are made up of yeast cells with surface displayed antibodies or antibody fragments. Antibody yeast display libraries may include antibody variable domains expressed on the surface of *Saccharomyces cerevisiae* cells. Yeast display libraries may be developed by displaying antibody fragments of interest as fusion proteins with yeast surface proteins (e.g. Aga2p protein). Yeast cells displaying antibodies or antibody fragments with affinity for a specific target may be isolated according to standard methods. Such methods may include, but are not limited to, magnetic separation and flow cytometry.

Recombinant Synthesis

Antibodies of the present disclosure may be prepared using recombinant DNA technology and related processes. Constructs (e.g., DNA expression plasmids) encoding antibodies may be prepared and used to synthesize full antibodies or portions thereof. In some embodiments, DNA sequences encoding antibody variable domains of the present disclosure may be inserted into expression vectors (e.g., mammalian expression vectors) encoding other antibody domains and used to prepare antibodies with the inserted variable domains. DNA sequences encoding antibody variable domains may be inserted downstream of upstream expression vector regions with promoter/enhancer elements and/or encoding immunoglobulin signal sequences. DNA sequences encoding antibody variable domains may be inserted upstream of downstream expression vector regions encoding immunoglobulin constant domains. Encoded constant domains may be from any class (e.g., IgG, IgA, IgD, IgE, and IgM) or species (e.g., human, mouse, rabbit, rat, and non-human primate). In some embodiments, encoded constant domains encode human IgG (e.g., IgG1, IgG2a, IgG2b, IgG2c, IgG3, or IgG4) constant domains. In some embodiments, encoded constant domains encode mouse IgG (e.g., IgG1, IgG2a, IgG2b, or IgG3) constant domains.

Expression vectors encoding antibodies of the present disclosure may be used to transfect cells for antibody production. Such cells may be mammalian cells. Cell lines with stable transfection of antibody expression vectors may be prepared and used to establish stable cell lines. Cell lines producing antibodies may be expanded for expression of antibodies which may be isolated or purified from cell culture media.

Anti-Tau Antibody Sequences

Described herein are antibodies, e.g., recombinant antibodies, which are characterized by particular functional and structural features or properties. For example, the antibodies specifically bind human tau (e.g., human tau having the sequence set forth in SEQ ID NO: 274). Particular antibodies described herein are antibodies having the CDR and/or variable region (VH and/or VL) sequences of antibodies VY011, VY007, VY004, VY006, VY018, VY003, VY016, VY017, VY012, VY009, VY010, VY022, VY001, VY019, VY020, VY005, VY002, VY014, VY008, and VY013, as well as antibodies having at least 70%, 75%, 80%, 85%, 90%, 92%, 95%, 96%, 97%, 98%, or 99% sequence identity thereto, and antibodies having variable regions with at least one, two, or three modifications, but not more than 30, 20, or 10 modifications (e.g., 1-30, 1-20, 1-10, 1-5, 1-4, 1-3, 1-2, or 1 amino acid modification, such as amino acid substitutions (e.g., conservative substitutions)), relative to the VH and/or VL sequences of the VY antibodies listed above. The ability of variant antibodies to bind to tau (e.g., wild-type tau (e.g., SEQ ID NO: 274), ePHF, iPHF) can be determined using art-recognized binding assays, e.g., the binding assays described in the Examples. Table 1 summarizes the amino acid sequences and nucleotide sequences encoding the VY antibodies.

TABLE 1

Exemplary anti-tau antibodies

| Ab ID | SEQ ID | Description | Sequence |
|---|---|---|---|
| VY011 | 82 | HCDR1 | GGSISNYY |
| | 97 | HCDR2 | VYTSGSA |
| | 115 | HCDR3 | ARDRGLYY |
| | 175 | FR H1 | QVQLQESGPGLVKPSETLSLTCTVS |
| | 183 | FR H2 | WTWIRQPAGKGLEWIGR |
| | 197 | FR H3 | NYNPSLKSRVTMSVDTSKNQFSLTLSSVTAADTAVYYC |
| | 209 | FR H4 | WGQGTLVTVSS |
| | 127 | LCDR1 | QSLVHSDGNTY |
| | 141 | LCDR2 | KIS |
| | 159 | LCDR3 | MQATQFPLT |
| | 219 | FR L1 | DIVMTQTPLSSLVTLGQPASISCRSS |
| | 230 | FR L2 | LSWLQQRPGQPPRLLIY |
| | 250 | FR L3 | KRFFGVPDRFSGSGAGTDFTLKINRVEAEDVGIYYC |

TABLE 1-continued

Exemplary anti-tau antibodies

| Ab ID | SEQ ID | Description | Sequence |
|---|---|---|---|
| | 265 | FR L4 | FGGGTKVEIK |
| | 7 | VH | QVQLQESGPGLVKPSETLSLTCTVSGGSISNYYWTWIRQPAGKGLEW<br>IGRVYTSGSANYNPSLKSRVTMSVDTSKNQFSLTLSSVTAADTAVYY<br>CARDRGLYYWGQGTLVTVSS |
| | 25 | VL | DIVMTQTPLSSLVTLGQPASISCRSSQSLVHSDGNTYLSWLQQRPGQ<br>PPRLLIYKISKRFFGVPDRFSGSGAGTDFTLKINRVEAEDVGIYYCM<br>QATQFPLTFGGGTKVEIK |
| | 51 | VH(DNA) | CAGGTGCAGCTGCAGGAGTCGGGCCCAGGACTGGTGAAGCCTTCGGA<br>GACCCTGTCCCTCACCTGCACTGTCTCTGGTGGCTCCATCAGTAATT<br>ACTACTGGACCTGGATCCGGCAGCCCGCCGGGAAGGGACTGGAGTGG<br>ATTGGGCGTGTCTATACCAGTGGGAGCGCCAACTACAACCCCTCCCT<br>CAAGAGTCGAGTTACCATGTCAGTAGACACGTCCAAGAACCAGTTCT<br>CCCTGACGCTGAGCTCTGTGACCGCCGCGGACACGGCCGTGTATTAC<br>TGTGCGAGAGATAGAGGACTCTACTACTGGGGCCAGGGAACCCTGGT<br>CACCGTCTCCTCA |
| | 71 | VL(DNA) | GATATTGTGATGACCCAGACTCCACTCTCCTCACTTGTCACCCTTGG<br>ACAGCCGGCCTCCATCTCCTGCAGGTCTAGTCAAAGCCTCGTACACA<br>GTGATGGAAACACCTATTTGAGTTGGCTTCAGCAGAGGCCAGGCCAG<br>CCTCCAAGACTCCTAATTTATAAGATTTCTAAGCGGTTCTTTGGGGT<br>CCCAGACAGATTCAGTGGCAGTGGGGCAGGGACAGATTTCACACTGA<br>AAATCAACAGGGTGGAAGCTGAGGATGTCGGGATTTATTACTGCATG<br>CAAGCTACACAATTTCCGCTCACTTTCGGCGGAGGGACCAAGGTGGA<br>GATCAAA |
| VY007 | 79 | HCDR1 | RFTFSNYN |
| | 94 | HCDR2 | ISSSSSTI |
| | 111 | HCDR3 | ASLGRGY |
| | 173 | FR H1 | EVQLVESGGGLVQPGGSLRLSCAAS |
| | 182 | FR H2 | MNWVRQAPGKGLEWISY |
| | 194 | FR H3 | YYADSVKGRFTISRDNAKNSLSLQMNSLRDEDTAVYYC |
| | 209 | FR H4 | WGQGTLVTVSS |
| | 127 | LCDR1 | QSLVHSDGNTY |
| | 141 | LCDR2 | KIS |
| | 156 | LCDR3 | MQATQFPRT |
| | 215 | FR L1 | DIVMTQTPLSSPVTLGQPASISCRSS |
| | 230 | FR L2 | LSWLQQRPGQPPRLLIY |
| | 246 | FR L3 | NRFSGVPDRFSGSGAGTDFTLKISRVEAEDVGVYYC |
| | 264 | FR L4 | FGQGSKLEIK |
| | 3 | VH | EVQLVESGGGLVQPGGSLRLSCAASRFTFSNYNMNWVRQAPGKGLEW<br>ISYISSSSSTIYYADSVKGRFTISRDNAKNSLSLQMNSLRDEDTAVY<br>YCASLGRGYWGQGTLVTVSS |
| | 21 | VL | DIVMTQTPLSSPVTLGQPASISCRSSQSLVHSDGNTYLSWLQQRPGQ<br>PPRLLIYKISNRFSGVPDRFSGSGAGTDFTLKISRVEAEDVGVYYCM<br>QATQFPRTFGQGSKLEIK |
| | 55 | VH(DNA) | GAGGTGCAGCTGGTGGAGTCTGGGGGAGGCTTGGTACAGCCTGGGGG<br>GTCCCTGAGACTCTCCTGTGCAGCCTCTAGATTCACCTTCAGTAACT<br>ATAACATGAACTGGGTCCGCCAGGCTCCAGGGAAGGGGCTGGAGTGG<br>ATTTCATACATTAGTAGTAGTAGTAGTACCATATACTACGCAGACTC<br>TGTGAAGGGCCGATTCACCATCTCCAGAGACAATGCCAAGAACTCAC<br>TGTCTCTGCAAATGAACAGCCTGAGAGACGAGGACACGGCTGTGTAT<br>TACTGTGCGAGTCTGGGGAGGGGCTACTGGGGCCAGGGAACCCTGGT<br>CACCGTCTCCTCA |
| | 75 | VL(DNA) | GATATTGTGATGACCCAGACTCCACTCTCCTCACCTGTCACCCTTGG<br>ACAGCCGGCCTCCATCTCCTGCAGGTCTAGTCAAAGCCTCGTACACA<br>GTGATGGAAACACCTACTTGAGTTGGCTTCAGCAGAGGCCAGGCCAG<br>CCTCCAAGACTCCTAATTTATAAGATTTCTAACCGGTTCTCTGGGGT<br>CCCAGACAGATTCAGTGGCAGTGGGGCAGGGACAGATTTCACACTGA<br>AAATCAGCAGGGTGGAAGCTGAGGATGTCGGGGTTTATTATTGTATG<br>CAAGCTACTCAATTTCCTCGCACTTTTGGCCAGGGGTCCAAGCTGGA<br>GATCAAA |
| VY004 | 80 | HCDR1 | GFTFSDYS |
| | 95 | HCDR2 | IRSSSSII |
| | 112 | HCDR3 | ARRGHFDY |
| | 174 | FR H1 | EVQLVESGGGLVQAGGSLRLSCAAS |
| | 181 | FR H2 | MNWVRQAPGKGLEWVSY |
| | 195 | FR H3 | YYADSVKGRFTISRDNAKNSLHLQMNSLRDEDTAVYYC |
| | 209 | FR H4 | WGQGTLVTVSS |
| | 129 | LCDR1 | QSVSDY |
| | 143 | LCDR2 | DVS |
| | 157 | LCDR3 | QQRSNWPLT |
| | 217 | FR L1 | EIVLTQSPATLSLSPGERATLSCRAS |

TABLE 1-continued

Exemplary anti-tau antibodies

| Ab ID | SEQ ID | Description | Sequence |
|---|---|---|---|
| | 232 | FR L2 | LAWYQQKPGQAPRLFIY |
| | 247 | FR L3 | KRATGIPARFSGSGSGTDFTLTISSLEPEDFAVYYC |
| | 265 | FR L4 | FGGGTKVEIK |
| | 4 | VH | EVQLVESGGGLVQAGGSLRLSCAASGFTFSDYSMNWVRQAPGKGLEWVSYIRSSSSIIYYADSVKGRFTISRDNAKNSLHLQMNSLRDEDTAVYYCARRGHFDYWGQGTLVTVSS |
| | 22 | VL | EIVLTQSPATLSLSPGERATLSCRASQSVSDYLAWYQQKPGQAPRLFIYDVSKRATGIPARFSGSGSGTDFTLTISSLEPEDFAVYYCQQRSNWPLTFGGGTKVEIK |
| | 54 | VH(DNA) | GAGGTGCAGCTGGTGGAGTCTGGGGGAGGCTTGGTACAGGCTGGGGGGTCCCTGAGACTCTCCTGTGCAGCCTCTGGATTCACCTTCAGTGACTATAGCATGAACTGGGTCCGCCAGGCTCCAGGGAAGGGGCTGGAGTGGGTTTCATATATTAGGAGTAGTAGTAGTATCATATACTACGCAGACTCTGTGAAGGGCCGATTCACCATCTCCAGAGACAATGCCAAGAACTCACTGCATTTGCAAATGAACAGCCTGAGAGACGAGGACACGGCTGTGTATTACTGTGCGAGACGGGGTCACTTTGACTACTGGGGCCAGGGAACCCTGGTCACCGTCTCCTCA |
| | 74 | VL(DNA) | GAAATTGTGTTGACACAGTCTCCAGCCACCCTGTCTTTGTCTCCAGGGGAAAGAGCCACCCTCTCCTGCAGGGCCAGTCAGAGTGTTAGCGACTACTTAGCCTGGTACCAACAGAAACCTGGCCAGGCTCCCAGGCTCTTCATCTATGATGTATCCAAGAGGGCCACTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAGCGTAGCAACTGGCCGCTCACTTTCGGCGGAGGGACCAAGGTGGAGATCAAA |
| VY006 | 81 | HCDR1 | GFTFSSYT |
| | 94 | HCDR2 | ISSSSSTI |
| | 114 | HCDR3 | ASLGRGDC |
| | 173 | FR H1 | EVQLVESGGGLVQPGGSLRLSCAAS |
| | 181 | FR H2 | MNWVRQAPGKGLEWVSY |
| | 192 | FR H3 | YYADSVKGRFTISRDNAKNSLYLQMNSLRDEDTAVYYC |
| | 209 | FR H4 | WGQGTLVTVSS |
| | 127 | LCDR1 | QSLVHSDGNTY |
| | 141 | LCDR2 | KIS |
| | 156 | LCDR3 | MQATQFPRT |
| | 215 | FR L1 | DIVMTQTPLSSPVTLGQPASISCRSS |
| | 230 | FR L2 | LSWLQQRPGQPPRLLIY |
| | 249 | FR L3 | KRFSGVPDRFSGSGAGTDFTLKISRVEAEDVGVYYC |
| | 267 | FR L4 | FGQGTRLEIK |
| | 6 | VH | EVQLVESGGGLVQPGGSLRLSCAASGFTFSSYTMNWVRQAPGKGLEWVSYISSSSSTIYYADSVKGRFTISRDNAKNSLYLQMNSLRDEDTAVYYCASLGRGDCWGQGTLVTVSS |
| | 24 | VL | DIVMTQTPLSSPVTLGQPASISCRSSQSLVHSDGNTYLSWLQQRPGQPPRLLIYKISKRFSGVPDRFSGSGAGTDFTLKISRVEAEDVGVYYCMQATQFPRTFGQGTRLEIK |
| | 52 | VH(DNA) | GAGGTGCAGCTGGTGGAGTCTGGGGGAGGCTTGGTACAGCCTGGGGGGTCCCTGAGACTCTCCTGTGCAGCCTCTGGATTCACCTTCAGTAGTTATACCATGAACTGGGTCCGCCAGGCTCCAGGGAAGGGGCTGGAGTGGGTTTCATACATTAGTAGTAGTAGTAGTACCATATACTACGCAGACTCTGTGAAGGGCCGATTCACCATCTCCAGAGACAATGCCAAGAACTCACTGTATCTGCAAATGAACAGCCTGAGAGACGAGGACACGGCTGTGTATTACTGTGCGAGTCTGGGGAGAGGGGACTGCTGGGGCCAGGGAACCCTGGTCACCGTCTCCTCA |
| | 72 | VL(DNA) | GATATTGTGATGACCCAGACTCCACTCTCCTCACCTGTCACCCTTGGACAGCCGGCCTCCATCTCCTGCAGGTCTAGTCAAAGCCTCGTACACAGTGATGGAAACACCTACTTGAGTTGGCTTCAGCAGAGGCCAGGCCAGCCTCCAAGACTCCTAATTTATAAGATTTCTAAACGGTTCTCTGGGGTCCCAGACAGATTCAGTGGCAGTGGGGCAGGGACAGATTTCACACTGAAAATCAGCAGGGTGGAAGCTGAGGATGTCGGGGTTTATTACTGCATGCAAGCTACACAATTTCCTCGGACCTTCGGCCAAGGGACACGACTGGAGATTAAA |
| VY018 | 82 | HCDR1 | GGSISNYY |
| | 101 | HCDR2 | IYTSGDT |
| | 119 | HCDR3 | ARAGIVGTPGLGMDV |
| | 175 | FR H1 | QVQLQESGPGLVKPSETLSLTCTVS |
| | 187 | FR H2 | WSWIRQPAGKGLEWIGR |
| | 201 | FR H3 | YYNPSLQSRVTMSVDTSKNQFSLKLSAVTAADTAVYYC |
| | 211 | FR H4 | WGQGTTVTVSS |
| | 132 | LCDR1 | ALPKQY |
| | 149 | LCDR2 | KDS |
| | 164 | LCDR3 | QSADSSGTYRV |
| | 224 | FR L1 | SYELTQPPSVSVSPGQTARITCSGE |

TABLE 1-continued

| Exemplary anti-tau antibodies | | | |
|---|---|---|---|
| Ab ID | SEQ ID | Description | Sequence |
| | 238 | FR L2 | AYWYQQKPGQAPVLVIY |
| | 252 | FR L3 | ERPSGIPERFSGSSSGTTVILTISGVQAEDEADYYC |
| | 263 | FR L4 | FGGGTKLTVL |
| | 11 | VH | QVQLQESGPGLVKPSETLSLTCTVSGGSISNYYWSWIRQPAGKGLEW IGRIYTSGDTYYNPSLQSRVTMSVDTSKNQFSLKLSAVTAADTAVYY CARAGIVGTPGLGMDVWGQGTTVTVSS |
| | 30 | VL | SYELTQPPSVSVSPGQTARITCSGEALPKQYAYWYQQKPGQAPVLVI YKDSERPSGIPERFSGSSSGTTVTLTISGVQAEDEADYYCQSADSSG TYRVFGGGTKLTVL |
| | 47 | VH(DNA) | CAGGTGCAGCTGCAGGAGTCGGGCCCAGGACTGGTGAAGCCTTCGGA GACCCTGTCCCTCACCTGCACTGTCTCTGGTGGCTCCATCAGTAATT ACTACTGGAGTTGGATCCGGCAGCCCGCCGGGAAGGGTCTGGAGTGG ATTGGGCGTATCTATACCAGTGGGGACACCTACTACAACCCCTCCCT CCAGAGTCGAGTCACCATGTCAGTAGACACGTCCAAGAACCAGTTCT CCCTGAAGCTGAGCGCTGTGACCGCCGCGGACACGGCCGTCTATTAC TGTGCGAGAGCGGGTATAGTGGGAACTCCGGGACTCGGTATGGACGT CTGGGGCCAAGGGACCACGGTCACCGTCTCCTCA |
| | 66 | VL(DNA) | TCCTATGAGCTGACACAGCCACCCTCGGTGTCAGTGTCCCCAGGACA GACGGCCAGGATCACCTGCTCTGGAGAAGCATTGCCAAAGCAATATG CTTATTGGTACCAGCAGAAGCCAGGCCAGGCCCCTGTGCTGGTGATA TATAAAGACAGTGAGAGGCCCTCAGGGATCCCTGAGCGATTCTCTGG CTCCAGCTCAGGGACAACAGTCACGTTGACCATCAGTGGAGTCCAGG CAGAAGATGAGGCTGACTATTACTGTCAATCAGCAGACAGCAGTGGT ACTTATCGGGTGTTCGGCGGAGGGACCAAGCTGACCGTCCTA |
| VY003 | 77 | HCDR1 | GFTFSSYR |
| | 92 | HCDR2 | ISSSRSAI |
| | 109 | HCDR3 | ATLGIGY |
| | 172 | FR H1 | EVQMVESGGGLVQPGGSLTLSCAAS |
| | 181 | FR H2 | MNWVRQAPGKGLEWVSY |
| | 192 | FR H3 | YYADSVKGRFTISRDNAKNSLYLQMNSLRDEDTAVYYC |
| | 209 | FR H4 | WGQGTLVTVSS |
| | 127 | LCDR1 | QSLVHSDGNTY |
| | 141 | LCDR2 | KIS |
| | 154 | LCDR3 | MQVTQFPRT |
| | 215 | FR L1 | DIVMTQTPLSSPVTLGQPASISCRSS |
| | 230 | FR L2 | LSWLQQRPGQPPRLLIY |
| | 244 | FR L3 | NRFSGVPDRFSGSGAGTDFTLKITRVEAEDVGIYYC |
| | 262 | FR L4 | FGQGTKVEIR |
| | 1 | VH | EVQMVESGGGLVQPGGSLTLSCAASGFTFSSYRMNWVRQAPGKGLEW VSYISSSRSAIYYADSVKGRFTISRDNAKNSLYLQMNSLRDEDTAVY YCATLGIGYWGQGTLVTVSS |
| | 19 | VL | DIVMTQTPLSSPVTLGQPASISCRSSQSLVHSDGNTYLSWLQQRPGQ PPRLLIYKISNRFSGVPDRFSGSGAGTDFTLKITRVEAEDVGIYYCM QVTQFPRTFGQGTKVEIR |
| | 39 | VH(DNA) | GAGGTGCAGATGGTGGAGTCTGGGGGAGGCTTGGTACAGCCTGGGGG GTCCCTGACACTCTCCTGTGCAGCCTCTGGATTCACCTTCAGTAGCT ATAGAATGAACTGGGTCCGCCAGGCTCCAGGGAAGGGGCTGGAGTGG GTTTCATACATTAGCAGTAGTAGAAGTGCCATATACTACGCAGACTC TGTGAAGGGCCGATTCACCATCTCCAGAGACAATGCCAAGAACTCAC TGTATCTGCAAATGAACAGCCTGAGAGACGAGGACACGGCTGTGTAT TACTGTGCGACCCTGGGGATAGGCTACTGGGGCCAGGGAACCCTGGT CACCGTCTCCTCA |
| | 57 | VL(DNA) | GATATTGTGATGACCCAGACTCCACTCTCCTCACCTGTCACCCTTGG ACAGCCGGCCTCCATCTCCTGCAGGTCTAGTCAAAGCCTCGTACACA GTGATGGAAACACCTACTTGAGTTGGCTTCAGCAGAGGCCAGGCCAG CCTCCAAGACTCCTAATTTATAAGATTTCTAACCGGTTCTCTGGGGT CCCAGACAGATTCAGTGGCAGTGGGGCAGGGACAGATTTCACACTGA AAATCACCAGGGTGGAGGCTGAGGATGTCGGGATTTATTACTGCATG CAAGTTACACAATTTCCTCGGACGTTCGGCCAAGGGACCAAGGTGGA AATCAGA |
| VY016 | 78 | HCDR1 | GFTFSSYS |
| | 93 | HCDR2 | ISRSGSTI |
| | 110 | HCDR3 | ARGNWAY |
| | 173 | FR H1 | EVQLVESGGGLVQPGGSLRLSCAAS |
| | 181 | FR H2 | MNWVRQAPGKGLEWVSY |
| | 193 | FR H3 | YYADSVEGRFTISRDNAYNSLYLQMISLRDDDTAVYYC |
| | 210 | FR H4 | WGQGILVTVSS |
| | 128 | LCDR1 | SSNIGAGYD |
| | 142 | LCDR2 | GNS |

TABLE 1-continued

| Exemplary anti-tau antibodies | | | |
|---|---|---|---|
| Ab ID | SEQ ID | Description | Sequence |
| | 155 | LCDR3 | QSYDSSLSGSV |
| | 216 | FR L1 | QSVLTQPPSVSGAPGQRVTISCTGS |
| | 231 | FR L2 | VHWYQQLPGTAPKLLIY |
| | 245 | FR L3 | NRPSGVPDRFSGSKSGTSASLAITGLQAEDETDFYC |
| | 263 | FR L4 | FGGGTKLTVL |
| | 2 | VH | EVQLVESGGGLVQPGGSLRLSCAASGFTFSSYSMNWVRQAPGKGLEWVSYISRSGSTIYYADSVEGRFTISRDNAYNSLYLQMISLRDDDTAVYYCARGNWAYWGQGILVTVSS |
| | 20 | VL | QSVLTQPPSVSGAPGQRVTISCTGSSSNIGAGYDVHWYQQLPGTAPKLLIYGNSNRPSGVPDRFSGSKSGTSASLAITGLQAEDETDFYCQSYDSSLSGSVFGGGTKLTVL |
| | 56 | VH(DNA) | GAGGTGCAGCTGGTGGAGTCTGGGGGAGGCTTGGTACAGCCTGGGGGGTCCCTGAGACTCTCCTGTGCAGCCTCTGGATTCACCTTCAGTAGCTATAGCATGAACTGGGTCCGCCAGGCTCCAGGGAAGGGGCTGGAGTGGGTTTCATACATTAGTCGTAGTGGTAGTACCATATACTACGCAGACTCTGTGGAGGGCCGATTCACCATCTCCAGAGACAATGCCTACAACTCACTGTATCTGCAAATGATCAGCCTGAGAGACGATGACACGGCTGTGTATTACTGTGCGAGAGGGAACTGGGCCTACTGGGGCCAGGGAATCCTGGTCACCGTCTCCTCA |
| | 76 | VL(DNA) | CAGTCTGTGCTGACGCAGCCGCCCTCAGTGTCTGGGGCCCCAGGGCAGAGGGTCACCATCTCCTGCACTGGGAGCAGCTCCAACATCGGGGCAGGTTATGATGTACACTGGTACCAGCAGCTTCCAGGAACAGCCCCCAAACTCCTCATCTATGGTAACAGCAATCGGCCCTCAGGGGTCCCTGACCGATTCTCTGGCTCCAAGTCTGGCACCTCAGCCTCCCTGGCCATCACTGGGCTCCAGGCTGAGGATGAGACTGATTTTTACTGCCAGTCCTATGACAGCAGCCTGAGTGGTTCGGTTTTCGGCGGAGGGACCAAGCTGACCGTCCTG |
| VY017 | 78 | HCDR1 | GFTFSSYS |
| | 96 | HCDR2 | IRSSSSTI |
| | 113 | HCDR3 | ARRSIADY |
| | 173 | FR H1 | EVQLVESGGGLVQPGGSLRLSCAAS |
| | 181 | FR H2 | MNWVRQAPGKGLEWVSY |
| | 196 | FR H3 | YYADSVKGRFTISRDNAKKSLYLQMNSLRDEDTAVYYC |
| | 209 | FR H4 | WGQGTLVTVSS |
| | 130 | LCDR1 | QSVTSY |
| | 144 | LCDR2 | DAS |
| | 158 | LCDR3 | QQRSNWPYT |
| | 218 | FR L1 | EIVLTQSPATLSSSPGERATLSCRAS |
| | 233 | FR L2 | LNWYQQKPGQAPRLLIY |
| | 248 | FR L3 | NRATGIPARFSGSGSGTDFTLTISSLEPEDFALYYC |
| | 266 | FR L4 | FGQGTKLEIK |
| | 5 | VH | EVQLVESGGGLVQPGGSLRLSCAASGFTFSSYSMNWVRQAPGKGLEWVSYIRSSSSTIYYADSVKGRFTISRDNAKKSLYLQMNSLRDEDTAVYYCARRSIADYWGQGTLVTVSS |
| | 23 | VL | EIVLTQSPATLSSSPGERATLSCRASQSVTSYLNWYQQKPGQAPRLLIYDASNRATGIPARFSGSGSGTDFTLTISSLEPEDFALYYCQQRSNWPYTFGQGTKLEIK |
| | 41 | VH(DNA) | GAGGTGCAGTTGGTGGAGTCTGGGGGAGGCTTGGTACAGCCTGGGGGGTCCCTGAGACTCTCCTGTGCAGCCTCTGGATTCACCTTCAGTAGCTATAGCATGAACTGGGTCCGCCAGGCTCCAGGGAAGGGGCTGGAGTGGGTTTCATACATTAGGAGTAGTAGTAGTACCATATACTACGCAGACTCTGTGAAGGGCCGATTCACCATCTCCAGAGACAATGCCAAGAAATCATTGTATCTGCAAATGAATAGTCTGAGAGACGAGGACACGGCTGTGTATTACTGTGCGAGAAGGAGTATAGCTGACTACTGGGGCCAGGGAACCCTGGTCACCGTCTCCTCA |
| | 59 | VL(DNA) | GAAATTGTGTTGACACAGTCTCCAGCCACCCTGTCTTCGTCTCCAGGGGAAAGAGCCACCCTCTCCTGCAGGGCCAGTCAGAGTGTTACCAGCTACTTAAACTGGTACCAACAGAAACCTGGCCAGGCTCCCAGGCTCCTCATCTATGATGCATCCAACAGGGCCACTGGCATCCCAGCCAGGTTCAGTGGCAGTGGGTCTGGGACAGACTTCACTCTCACCATCAGCAGCCTCGAGCCTGAAGATTTTGCACTTTATTACTGTCAGCAGCGTAGCAACTGGCCGTACACTTTTGGCCAGGGGACCAAACTGGAGATCAAA |
| VY012 | 83 | HCDR1 | GFTYSSYA |
| | 98 | HCDR2 | ISGSSSIT |
| | 116 | HCDR3 | AKGGRYGYFQH |
| | 176 | FR H1 | EVQLLESGGGLVQPGGSLRLSCAAS |
| | 184 | FR H2 | MSWVRRAPGKGLEWISI |
| | 198 | FR H3 | YYADSMKGRFTISRDNSKNTLFLQMNSLRAEDTAVYYC |
| | 209 | FR H4 | WGQGTLVTVSS |
| | 131 | LCDR1 | NIGSKS |
| | 145 | LCDR2 | DDS |
| | 160 | LCDR3 | QVWDSSSDPVV |
| | 220 | FR L1 | SYVLTQPPSVSVAPGQTARITCGGN |
| | 234 | FR L2 | VHWYQQKPGQAPVLVVY |

TABLE 1-continued

| Exemplary anti-tau antibodies | | | |
|---|---|---|---|
| Ab ID | SEQ ID | Description | Sequence |
| | 251 | FR L3 | DRPSGIPERFSGSNSGNTATLTISRVEAGDEADYYC |
| | 268 | FR L4 | FGGGTMLTVL |
| | 8 | VH | EVQLLESGGGLVQPGGSLRLSCAASGFTYSSYAMSWVRRAPGKGLEW<br>ISIISGSSSITYYADSMKGRFTISRDNSKNTLFLQMNSLRAEDTAVY<br>YCAKGGRYGYFQHWGQGTLVTVSS |
| | 26 | VL | SYVLTQPPSVSVAPGQTARITCGGNNIGSKSVHWYQQKPGQAPVLVV<br>YDDSDRPSGIPERFSGSNSGNTATLTISRVEAGDEADYYCQVWDSSS<br>DPVVFGGGTMLTVL |
| | 50 | VH(DNA) | GAGGTGCAGCTGTTGGAGTCTGGGGGAGGCTTGGTACAGCCGGGGGG<br>GTCCCTGAGACTCTCCTGTGCAGCCTCGGGATTCACCTATAGCAGCT<br>ATGCCATGAGCTGGGTCCGCCGGGCTCCAGGGAAGGGGCTGGAGTGG<br>ATCTCAATTATTAGTGGTAGTAGTAGTATCACATACTACGCAGACTC<br>CATGAAGGGCCGGTTCACTATCTCTAGAGACAATTCCAAGAACACGC<br>TTTTTCTGCAAATGAATAGCCTGAGAGCCGAGGACACGGCCGTTTAT<br>TACTGTGCGAAGGGGGGGAGGTACGGGTACTTCCAACACTGGGGCCA<br>GGGCACCCTGGTCACCGTCTCCTCA |
| | 70 | VL(DNA) | TCCTATGTGCTGACTCAGCCACCCTCGGTGTCAGTGGCCCCAGGACA<br>GACGGCCAGGATTACCTGTGGGGGAAACAACATTGGAAGTAAAAGTG<br>TGCACTGGTACCAGCAGAAGCCAGGCCAGGCCCCTGTGCTGGTCGTC<br>TATGATGATAGCGACCGGCCCTCAGGGATCCCTGAGCGATTCTCTGG<br>CTCCAACTCTGGGAACACGGCCACCCTGACCATCAGCAGGGTCGAAG<br>CCGGGGATGAGGCCGACTATTACTGTCAGGTGTGGGATAGTAGTAGT<br>GATCCTGTGGTATTCGGCGGAGGGACCATGCTGACCGTCCTA |
| VY009 | 84 | HCDR1 | GFSLSTSEVG |
| | 99 | HCDR2 | IYWNDHK |
| | 117 | HCDR3 | ARRVTGEGFDP |
| | 177 | FR H1 | QITLKESGPTLVKPTQTLTLTCTLS |
| | 185 | FR H2 | VGWIRQPPGKALEWLAI |
| | 199 | FR H3 | RYSPSLKNRLTFTKDTSKNQVVLTMTNMDPVDTATYYC |
| | 209 | FR H4 | WGQGTLVTVSS |
| | 132 | LCDR1 | ALPKQY |
| | 146 | LCDR2 | KDT |
| | 161 | LCDR3 | QSADSSGSYV |
| | 221 | FR L1 | SYELTQPPSVSVSPGQTARITCSGD |
| | 235 | FR L2 | AYWYQQKPGQAPVLVIF |
| | 252 | FR L3 | ERPSGIPERFSGSSSGTTVILTISGVQAEDEADYYC |
| | 269 | FR L4 | FGTGTKVTVL |
| | 9 | VH | QITLKESGPTLVKPTQTLTLTCTLSGFSLSTSEVGVGWIRQPPGKAL<br>EWLAIIYWNDHKRYSPSLKNRLTFTKDTSKNQVVLTMTNMDPVDTAT<br>YYCARRVTGEGFDPWGQGTLVTVSS |
| | 27 | VL | SYELTQPPSVSVSPGQTARITCSGDALPKQYAYWYQQKPGQAPVLVI<br>FKDTERPSGIPERFSGSSSGTTVILTISGVQAEDEADYYCQSADSSG<br>SYVFGTGTKVTVL |
| | 49 | VH(DNA) | CAGATCACCTTAAAGGAGTCTGGTCCTACGCTGGTGAAACCCACACA<br>GACCCTCACGCTGACCTGCACCCTCTCTGGGTTCTCACTCAGCACTA<br>GTGAAGTGGGTGTGGGCTGGATCCGTCAGCCCCCAGGAAAGGCCCTG<br>GAGTGGCTTGCAATCATTTATTGGAATGATCATAAGCGCTACAGCCC<br>ATCTCTGAAGAACAGGCTCACCTTCACCAAGGACACCTCCAAAAACC<br>AGGTGGTCCTTACAATGACCAACATGGACCCTGTGGACACAGCCACA<br>TATTATTGTGCACGCAGAGTAACTGGGGAGGGGTTCGACCCCTGGGG<br>CCAGGGAACCCTGGTCACCGTCTCCTCA |
| | 69 | VL(DNA) | TCCTATGAGCTGACACAGCCACCCTCGGTGTCAGTGTCCCCAGGACA<br>GACGGCCAGGATCACCTGCTCTGGAGATGCATTGCCAAAGCAATATG<br>CTTATTGGTACCAGCAGAAGCCAGGCCAGGCCCCTGTGCTGGTGATA<br>TTTAAAGACACTGAGAGGCCCTCAGGGATCCCTGAGCGATTCTCTGG<br>CTCCAGCTCAGGGACAACAGTCACGITGACCATCAGTGGAGTCCAGG<br>CAGAAGATGAGGCTGACTATTACTGTCAATCAGCAGACAGCAGTGGT<br>TCTTATGTCTTCGGAACTGGGACCAAGGICACCGTCCTA |
| VY010 | 85 | HCDR1 | GFTFSTYS |
| | 100 | HCDR2 | ISSGSSYI |
| | 118 | HCDR3 | TVTTHFHH |
| | 178 | FR H1 | EVQLVESGGGLVKPGGSLRLSCAAS |
| | 186 | FR H2 | MNWVRQAPGKGLEWVSS |
| | 200 | FR H3 | YYADSVKGRFTISRDNAKNSLYLQMNSLRAEDTAVYYC |
| | 209 | FR H4 | WGQGTLVTVSS |
| | 133 | LCDR1 | QSLVYSDGNTY |
| | 147 | LCDR2 | KVS |
| | 162 | LCDR3 | MQGTHWPLT |
| | 222 | FR L1 | DVVMTQSPLSLPVTLGQPASISCRSS |
| | 236 | FR L2 | LNWFQQRPGQSPRRLIY |

TABLE 1-continued

| Exemplary anti-tau antibodies | | | |
|---|---|---|---|
| Ab ID | SEQ ID | Description | Sequence |
| | 253 | FR L3 | NRDSGVPDRFSGSGSGTDFTLKISRVEAEDVGVYYC |
| | 267 | FR L4 | FGQGTRLEIK |
| | 10 | VH | EVQLVESGGGLVKPGGSLRLSCAASGFTFSTYSMNWVRQAPGKGLEW<br>VSSISSGSSYIYYADSVKGRFTISRDNAKNSLYLQMNSLRAEDTAVY<br>YCTVTTHFHHWGQGTLVTVSS |
| | 28 | VL | DVVMTQSPLSLPVTLGQPASISCRSSQSLVYSDGNTYLNWFQQRPGQ<br>SPRRLIYKVSNRDSGVPDRFSGSGSGTDFTLKISRVEAEDVGVYYCM<br>QGTHWPLTFGQGTRLEIK |
| | 48 | VH (DNA) | GAGGTGCAGCTGGTGGAGTCTGGGGGAGGCCTGGTCAAGCCTGGGGG<br>GTCCCTGAGACTCTCCTGTGCAGCCTCTGGATTCACCTTCAGTACCT<br>ATAGCATGAACTGGGTCCGCCAGGCTCCAGGGAAGGGGCTGGAGTGG<br>GTCTCATCCATTAGTAGTGGTAGTAGTTACATATACTACGCAGACTC<br>AGTGAAGGGCCGATTCACCATCTCCAGAGACAACGCCAAGAACTCAC<br>TGTATCTGCAAATGAACAGCCTGAGAGCCGAGGACACGGCTGTGTAT<br>TACTGTACAGTAACTACACACTTCCACCACTGGGGCCAGGGCACCCT<br>GGTCACCGTCTCCTCA |
| | 67 | VL (DNA) | GATGTTGTGATGACTCAGTCTCCACTCTCCCTGCCCGTCACCCTTGG<br>ACAGCCGGCCTCCATCTCCTGCAGGTCTAGTCAAAGCCTCGTATACA<br>GTGATGGAAACACCTACTTGAATTGGTTTCAGCAGAGGCCAGGCCAA<br>TCTCCAAGGCGCCTAATTTATAAGGTTTCTAACCGGGACTCTGGGGT<br>CCCAGACAGATTCAGCGGCAGTGGGTCAGGCACTGATTTCACACTAA<br>AAATCAGCAGGGTGGAGGCTGAGGATGTTGGGGTTTATTACTGCATG<br>CAAGGTACACACTGGCCTCTCACCTTCGGCCAAGGGACACGACTGGA<br>GATTAAA |
| VY022 | 85 | HCDR1 | GFTFSTYS |
| | 100 | HCDR2 | ISSGSSYI |
| | 118 | HCDR3 | TVTTHFHH |
| | 178 | FR H1 | EVQLVESGGGLVKPGGSLRLSCAAS |
| | 186 | FR H2 | MNWVRQAPGKGLEWVSS |
| | 200 | FR H3 | YYADSVKGRFTISRDNAKNSLYLQMNSLRAEDTAVYYC |
| | 209 | FR H4 | WGQGTLVTVSS |
| | 134 | LCDR1 | SGINVGAYR |
| | 148 | LCDR2 | YKSDSDK |
| | 163 | LCDR3 | MIWHSSAWV |
| | 223 | FR L1 | QAVLTQPSSLSASPGASARLTCTLR |
| | 237 | FR L2 | LYWYQQKPGSPPQYLLR |
| | 254 | FR L3 | QQGSGVPSRFSGSKDASANAGILLISGLQSEDEADYYC |
| | 263 | FR L4 | FGGGTKLTVL |
| | 10 | VH | EVQLVESGGGLVKPGGSLRLSCAASGFTFSTYSMNWVRQAPGKGLEW<br>VSSISSGSSYIYYADSVKGRFTISRDNAKNSLYLQMNSLRAEDTAVY<br>YCTVTTHFHHWGQGTLVTVSS |
| | 29 | VL | QAVLTQPSSLSASPGASARLTCTLRSGINVGAYRLYWYQQKPGSPPQ<br>YLLRYKSDSDKQQGSGVPSRFSGSKDASANAGILLISGLQSEDEADY<br>YCMIWHSSAWVFGGGTKLTVL |
| | 48 | VH (DNA) | GAGGTGCAGCTGGTGGAGTCTGGGGGAGGCCTGGTCAAGCCTGGGGG<br>GTCCCTGAGACTCTCCTGTGCAGCCTCTGGATTCACCTTCAGTACCT<br>ATAGCATGAACTGGGTCCGCCAGGCTCCAGGGAAGGGGCTGGAGTGG<br>GTCTCATCCATTAGTAGTGGTAGTAGTTACATATACTACGCAGACTC<br>AGTGAAGGGCCGATTCACCATCTCCAGAGACAACGCCAAGAACTCAC<br>TGTATCTGCAAATGAACAGCCTGAGAGCCGAGGACACGGCTGTGTAT<br>TACTGTACAGTAACTACACACTTCCACCACTGGGGCCAGGGCACCCT<br>GGTCACCGTCTCCTCA |
| | 68 | VL (DNA) | CAGGCTGTGCTGACTCAGCCGTCTTCCCTCTCTGCATCTCCTGGAGC<br>ATCAGCCAGACTCACCTGCACCTTGCGCAGTGGCATCAATGTTGGTG<br>CCTACAGGCTATACTGGTACCAGCAGAAGCCAGGAAGTCCTCCCCAG<br>TATCTCCTGAGGTACAAATCAGACTCAGATAAGCAGCAGGGCTCTGG<br>AGTCCCCAGCCGCTTCTCTGGATCCAAAGATGCTTCGGCCAATGCAG<br>GGATTTTACTCATCTCTGGGCTCCAGTCTGAGGATGAGGCTGACTAT<br>TACTGTATGATTTGGCACAGCAGCGCTTGGGTGTTCGGCGGAGGGAC<br>CAAGCTGACCGTCCTA |
| VY001 | 86 | HCDR1 | GFTFSSYN |
| | 102 | HCDR2 | ISSSSNTI |
| | 120 | HCDR3 | ATLGRGY |
| | 173 | FR H1 | EVQLVESGGGLVQPGGSLRLSCAAS |
| | 182 | FR H2 | MNWVRQAPGKGLEWISY |
| | 202 | FR H3 | YYADSVKGRFTVSRDNAKNSLYLQMNSLRDEDTAVYYC |
| | 212 | FR H4 | WGQGTLVIASS |
| | 127 | LCDR1 | QSLVHSDGNTY |
| | 141 | LCDR2 | KIS |
| | 156 | LCDR3 | MQATQFPRT |
| | 225 | FR L1 | DVVMTQTPLSSPVTLGQPASISCRSS |
| | 230 | FR L2 | LSWLQQRPGQPPRLLIY |
| | 246 | FR L3 | NRFSGVPDRFSGSGAGTDFTLKISRVEAEDVGVYYC |
| | 266 | FR L4 | FGQGTKLEIK |

TABLE 1-continued

| Exemplary anti-tau antibodies | | | |
|---|---|---|---|
| Ab ID | SEQ ID | Description | Sequence |
| | 12 | VH | EVQLVESGGGLVQPGGSLRLSCAASGFTFSSYNMNWVRQAPGKGLEW<br>ISYISSSSNTIYYADSVKGRFTVSRDNAKNSLYLQMNSLRDEDTAVY<br>YCATLGRGYWGQGTLVIASS |
| | 31 | VL | DVVMTQTPLSSPVTLGQPASISCRSSQSLVHSDGNTYLSWLQQRPGQ<br>PPRLLIYKISNRFSGVPDRFSGSGAGTDFTLKISRVEAEDVGVYYCM<br>QATQFPRTFGQGTKLEIK |
| | 46 | VH(DNA) | GAGGTGCAACTGGTGGAGTCTGGGGGAGGCTTGGTACAGCCTGGGGG<br>GTCCCTGAGACTCTCCTGTGCAGCCTCTGGATTCACCTTCAGTAGCT<br>ATAACATGAACTGGGTTCGCCAGGCTCCAGGGAAGGGGCTGGAGTGG<br>ATTTCATACATTAGTAGTAGTAGTAATACCATATACTACGCAGACTC<br>TGTGAAGGGCCGATTCACCGTCTCCAGGGACAATGCCAAGAACTCAC<br>TGTATCTGCAAATGAACAGCCTGAGAGACGAGGACACGGCTGTGTAT<br>TACTGTGCGACTCTGGGGAGGGGCTACTGGGGCCAGGGAACCCTGGT<br>CATCGCCTCCTCA |
| | 65 | VL(DNA) | GATGTTGTGATGACCCAGACTCCACTCTCCTCACCTGTCACCCTTGG<br>ACAGCCGGCCTCCATCTCCTGCAGGTCTAGTCAAAGCCTCGTACACA<br>GTGATGGAAACACCTACTTGAGTTGGCTTCAGCAGAGGCCAGGCCAG<br>CCTCCAAGACTCCTAATTTATAAGATTTCTAACCGGTTCTCTGGGGT<br>CCCAGACAGATTCAGTGGCAGTGGGGCAGGGACAGATTTCACACTGA<br>AAATCAGCAGGGTGGAAGCTGAGGATGTCGGGGTTTATTACTGCATG<br>CAAGCTACACAATTTCCTCGCACTTTTGGCCAGGGGACCAAGCTGGA<br>GATCAAA |
| VY019 | 87 | HCDR1 | GGSISSYY |
| | 103 | HCDR2 | IDTSGST |
| | 121 | HCDR3 | ARGGDGYRY |
| | 175 | FR H1 | QVQLQESGPGLVKPSETLSLTCTVS |
| | 183 | FR H2 | WTWIRQPAGKGLEWIGR |
| | 203 | FR H3 | NYNPSLKSRVTMSIDTSKKQFSLKLSSVTAADTAVYYC |
| | 209 | FR H4 | WGQGTLVTVSS |
| | 132 | LCDR1 | ALPKQY |
| | 149 | LCDR2 | KDS |
| | 165 | LCDR3 | QSTDSSGSWV |
| | 221 | FR L1 | SYELTQPPSVSVSPGQTARITCSGD |
| | 239 | FR L2 | ACWYQQKPGQAPVLVIY |
| | 255 | FR L3 | ERPSGIPERFSGSSSGTTVTLTITGVQAEDEADYYC |
| | 263 | FR L4 | FGGGTKLTVL |
| | 13 | VH | QVQLQESGPGLVKPSETLSLTCTVSGGSISSYYWTWIRQPAGKGLEW<br>IGRIDTSGSTNYNPSLKSRVTMSIDTSKKQFSLKLSSVTAADTAVYY<br>CARGGDGYRYWGQGTLVTVSS |
| | 32 | VL | SYELTQPPSVSVSPGQTARITCSGDALPKQYACWYQQKPGQAPVLVI<br>YKDSERPSGIPERFSGSSSGTTVTLTITGVQAEDEADYYCQSTDSSG<br>SWVFGGGTKLTVL |
| | 45 | VH(DNA) | CAGGTGCAGCTGCAGGAGTCGGGCCCAGGACTGGTGAAGCCTTCGGA<br>GACCCTGTCCCTCACCTGCACTGTCTCTGGTGGCTCCATCAGTAGTT<br>ACTACTGGACCTGGATCCGGCAGCCCGCCGGGAAGGGACTGGAGTGG<br>ATTGGGCGTATCGATACCAGTGGGAGCACCAACTACAACCCCTCCCT<br>CAAGAGTCGAGTCACCATGTCAATAGACACGTCCAAGAAACAGTTCT<br>CCCTGAAGCTGAGCTCTGTGACCGCCGCGGACACGGCCGTGTATTAC<br>TGTGCGAGAGGGGGAGATGGCTACCGCTACTGGGGCCAGGGAACCCT<br>GGTCACCGTCTCCTCA |
| | 64 | VL(DNA) | TCCTATGAGCTGACACAGCCACCCTCGGTGTCAGTGTCCCCAGGACA<br>GACGGCCAGGATCACCTGCTCTGGAGATGCATTGCCAAAGCAATATG<br>CTTGTTGGTACCAGCAGAAGCCAGGCCAGGCCCCTGTGCTGGTGATA<br>TATAAAGACAGTGAGAGGCCCTCAGGGATCCCTGAGCGATTCTCTGG<br>CTCCAGCTCAGGGACAACAGTCACGTTGACCATCACTGGAGTCCAGG<br>CAGAAGATGAGGCTGACTATTACTGTCAATCCACAGACAGCAGTGGT<br>TCTTGGGTGTTCGGCGGAGGGACCAAGCTGACCGTCCTA |
| VY020 | 78 | HCDR1 | GFTFSSYS |
| | 104 | HCDR2 | ISSSNSTI |
| | 122 | HCDR3 | ARRSLGDY |
| | 173 | FR H1 | EVQLVESGGGLVQPGGSLRLSCAAS |
| | 182 | FR H2 | MNWVRQAPGKGLEWISY |
| | 204 | FR H3 | KYADSVKGRFTISRDNAKNSLYLQMNSLRDEDTAVYYC |
| | 213 | FR H4 | WGQGTLVIVSS |
| | 135 | LCDR1 | QSVSSY |
| | 143 | LCDR2 | DVS |
| | 166 | LCDR3 | QQRRNWPYT |
| | 217 | FR L1 | EIVLTQSPATLSLSPGERATLSCRAS |
| | 240 | FR L2 | LAWYLQKPGQAPRLLIY |
| | 256 | FR L3 | NRATGIPARFSGSGSGTDFTLTISRLEPEDFAVYYC |
| | 266 | FR L4 | FGQGTKLEIK |
| | 14 | VH | EVQLVESGGGLVQPGGSLRLSCAASGFTFSSYSMNWVRQAPGKGLEW<br>ISYISSSNSTIKYADSVKGRFTISRDNAKNSLYLQMNSLRDEDTAVY<br>YCARRSLGDYWGQGTLVIVSS |

TABLE 1-continued

| Exemplary anti-tau antibodies | | | |
|---|---|---|---|
| Ab ID | SEQ ID | Description | Sequence |
| | 33 | VL | EIVLTQSPATLSLSPGERATLSCRASQSVSSYLAWYLQKPGQAPRLLIYDVSNRATGIPARFSGSGSGTDFTLTISRLEPEDFAVYYCQQRRNWPYTFGQGTKLEIK |
| | 44 | VH(DNA) | GAGGTGCAGCTGGTGGAGTCTGGGGGAGGCTTGGTACAGCCTGGGGGGTCCCTGAGACTCTCCTGTGCAGCCTCTGGATTCACCTTCAGTAGCTATAGCATGAACTGGGTCCGCCAGGCTCCAGGGAAGGGGCTGGAGTGGATTTCATACATTAGTAGTAGTAATAGTACCATAAAGTACGCAGACTCTGTGAAGGGCCGATTCACCATCTCCAGAGACAATGCCAAGAACTCACTGTATCTGCAAATGAACAGCCTGAGAGACGAGGACACGGCTGTGTATTACTGTGCGAGAAGGAGTCTAGGTGACTACTGGGGCCAGGGAACCCTGGTCATCGTCTCCTCA |
| | 62 | VL(DNA) | GAAATTGTGTTGACACAGTCTCCAGCCACCCTGTCTTTGTCTCCAGGGGAAAGAGCCACCCTCTCCTGCAGGGCCAGTCAGAGTGTTAGCAGCTACTTAGCCTGGTACCTACAGAAACCTGGCCAGGCTCCCAGGCTCCTCATCTATGATGTGTCCAACAGGGCCACTGGCATCCCAGCCAGGTTCAGTGGCAGTGGGTCTGGGACAGACTTCACTCTCACCATCAGCAGACTAGAGCCTGAAGATTTTGCAGTTTATTACTGTCAGCAGCGTCGCAACTGGCCGTACACTTTTGGCCAGGGGACCAAGCTGGAGATCAAA |
| VY005 | 78 | HCDR1 | GFTFSSYS |
| | 104 | HCDR2 | ISSSNSTI |
| | 122 | HCDR3 | ARRSLGDY |
| | 173 | FR H1 | EVQLVESGGGLVQPGGSLRLSCAAS |
| | 182 | FR H2 | MNWVRQAPGKGLEWISY |
| | 204 | FR H3 | KYADSVKGRFTISRDNAKNSLYLQMNSLRDEDTAVYYC |
| | 213 | FR H4 | WGQGTLVIVSS |
| | 136 | LCDR1 | QGISCS |
| | 150 | LCDR2 | AAS |
| | 167 | LCDR3 | QQFNSYPFT |
| | 226 | FR L1 | DIQLTQSPSFLSASVGDRVTITCRAS |
| | 241 | FR L2 | LAWYQQKPGKAPKLLIY |
| | 257 | FR L3 | TLQSGVPSRFSGSGSGTEFTLTISSLQPEDFATYYC |
| | 270 | FR L4 | FGPGTKVDIK |
| | 14 | VH | EVQLVESGGGLVQPGGSLRLSCAASGFTFSSYSMNWVRQAPGKGLEWISYISSSNSTIKYADSVKGRFTISRDNAKNSLYLQMNSLRDEDTAVYYCARRSLGDYWGQGTLVIVSS |
| | 34 | VL | DIQLTQSPSFLSASVGDRVTITCRASQGISCSLAWYQQKPGKAPKLLIYAASTLQSGVPSRFSGSGSGTEFTLTISSLQPEDFATYYCQQFNSYPFTFGPGTKVDIK |
| | 44 | VH(DNA) | GAGGTGCAGCTGGTGGAGTCTGGGGGAGGCTTGGTACAGCCTGGGGGGTCCCTGAGACTCTCCTGTGCAGCCTCTGGATTCACCTTCAGTAGCTATAGCATGAACTGGGTCCGCCAGGCTCCAGGGAAGGGGCTGGAGTGGATTTCATACATTAGTAGTAGTAATAGTACCATAAAGTACGCAGACTCTGTGAAGGGCCGATTCACCATCTCCAGAGACAATGCCAAGAACTCACTGTATCTGCAAATGAACAGCCTGAGAGACGAGGACACGGCTGTGTATTACTGTGCGAGAAGGAGTCTAGGTGACTACTGGGGCCAGGGAACCCTGGTCATCGTCTCCTCA |
| | 63 | VL(DNA) | GACATCCAGTTGACCCAGTCTCCATCCTTCCTGTCTGCATCTGTAGGAGACAGAGTCACCATCACTTGCCGGGCCAGTCAGGGCATTAGCTGTTCTTTAGCCTGGTATCAGCAAAAACCAGGGAAAGCCCCTAAGCTCCTGATCTATGCTGCATCCACTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCAACAGTTTAATAGTTACCCATTCACTTTCGGCCCTGGGACCAAAGTGGATATCAAA |
| VY002 | 88 | HCDR1 | GFTFSNAW |
| | 105 | HCDR2 | IKSKTDGGTT |
| | 123 | HCDR3 | VTDYPKDV |
| | 178 | FR H1 | EVQLVESGGGLVKPGGSLRLSCAAS |
| | 188 | FR H2 | MSWVRQAPGKGLEWFGR |
| | 205 | FR H3 | DYAAPVKGRFTISRDDSKNTLYLQMNSLKTEDTAVYYC |
| | 211 | FR H4 | WGQGTTVTVSS |
| | 137 | LCDR1 | QSVLYSSKNKNY |
| | 151 | LCDR2 | WAS |
| | 168 | LCDR3 | QQYYSSPYT |
| | 227 | FR L1 | DIVMTQSPDSLAVSLGERATINCKSS |
| | 242 | FR L2 | LAWYQQKPGQPPKLLIY |
| | 258 | FR L3 | TRESGVPDRFSGSGSGTDFTLAISSLQAEDVAVYYC |
| | 266 | FR L4 | FGQGTKLEIK |
| | 15 | VH | EVQLVESGGGLVKPGGSLRLSCAASGFTFSNAWMSWVRQAPGKGLEWFGRIKSKTDGGTTDYAAPVKGRFTISRDDSKNTLYLQMNSLKTEDTAVYYCVTDYPKDVWGQGTTVTVSS |
| | 35 | VL | DIVMTQSPDSLAVSLGERATINCKSSQSVLYSSKNKNYLAWYQQKPGQPPKLLIYWASTRESGVPDRFSGSGSGTDFTLAISSLQAEDVAVYYCQQYYSSPYTFGQGTKLEIK |

TABLE 1-continued

| Exemplary anti-tau antibodies | | | |
|---|---|---|---|
| Ab ID | SEQ ID | Description | Sequence |
| | 43 | VH(DNA) | GAGGTGCAGCTGGTGGAGTCTGGGGGAGGCTTGGTAAAGCCTGGGGG GTCCCTTAGACTCTCCTGTGCAGCCTCTGGATTCACTTTCAGTAACG CCTGGATGAGCTGGGTCCGCCAGGCTCCAGGGAAGGGGCTGGAGTGG TTTGGCCGTATTAAAAGCAAAACTGATGGTGGGACAACAGACTACGC TGCACCCGTGAAAGGCAGATTCACCATCTCAAGAGATGACTCAAAAA ACACGCTGTATCTGCAAATGAACAGCCTGAAAACCGAGGACACAGCC GTGTATTACTGTGTCACAGATTACCCGAAGGACGTCTGGGGCCAAGG GACCACGGTCACCGTCTCCTCA |
| | 61 | VL(DNA) | GACATCGTGATGACCCAGTCTCCAGACTCCCTGGCTGTGTCTCTGGG CGAGAGGGCCACCATCAACTGCAAGTCCAGCCAGAGTGTTTTATACA GCTCCAAAAATAAGAACTACTTAGCTTGGTACCAGCAGAAACCAGGA CAGCCTCCTAAGCTGCTCATTTACTGGGCATCTACCCGGGAATCCGG GGTCCCTGACCGATTCAGTGGCAGCGGGTCTGGGACAGATTTCACTC TCGCCATCAGCAGCCTGCAGGCTGAAGATGTGGCAGTTTATTACTGT CAGCAATATTATAGTAGTCCGTACACTTTTGGCCAGGGGACCAAGCT GGAGATCAAA |
| VY014 | 89 | HCDR1 | GFTFNNYD |
| | 106 | HCDR2 | IGAAGDT |
| | 124 | HCDR3 | ARAGETLEGATIGYYYGMDV |
| | 173 | FR H1 | EVQLVESGGGLVQPGGSLRLSCAAS |
| | 189 | FR H2 | MHWVRQAAGKGLEWVST |
| | 206 | FR H3 | YYPGSVKGRFIISRENAKNSLYLQMNSLRAGDTAVYYC |
| | 211 | FR H4 | WGQGTTVTVSS |
| | 138 | LCDR1 | QSLLHSNGYNY |
| | 152 | LCDR2 | LGS |
| | 169 | LCDR3 | MQALQIPLT |
| | 228 | FR L1 | DILMTQSPLSLPVTPGEPASISCRSS |
| | 243 | FR L2 | LDWYLQKPGQSPQLLIY |
| | 259 | FR L3 | NRASGVPDRFSGSGSGTDFTLKFSRVEAEDVGLYYC |
| | 265 | FR L4 | FGGGTKVEIK |
| | 16 | VH | EVQLVESGGGLVQPGGSLRLSCAASGFTFNNYDMHWVRQAAGKGLEW VSTIGAAGDTYYPGSVKGRFIISRENAKNSLYLQMNSLRAGDTAVYY CARAGETLEGATIGYYYGMDVWGQGTTVTVSS |
| | 36 | VL | DILMTQSPLSLPVTPGEPASISCRSSQSLLHSNGYNYLDWYLQKPGQ SPQLLIYLGSNRASGVPDRFSGSGSGTDFTLKFSRVEAEDVGLYYCM QALQIPLIFGGGTKVEIK |
| | 42 | VH(DNA) | GAGGTGCAGCTGGTGGAGTCTGGGGGAGGCTTGGTACAGCCTGGGGG GTCCCTGAGACTCTCCTGTGCAGCCTCTGGATTCACCTTCAATAACT ACGACATGCACTGGGTCCGCCAAGCTGCAGGAAAAGGTCTGGAGTGG GTCTCAACTATTGGTGCTGCTGGTGACACATATTATCCAGGCTCCGT GAAGGGCCGATTCATCATCTCCAGAGAAAATGCCAAGAACTCCTTGT ATCTTCAAATGAACAGCCTGAGAGCCGGGGACACGGCTGTGTATTAC TGTGCAAGAGCCGGAGAGACCTTAGAGGGAGCTACTATCGGCTACTA CTACGGTATGGACGTCTGGGGCCAGGGGACCACGGTCACCGTCTCCT CA |
| | 60 | VL(DNA) | GATATTCTGATGACTCAGTCTCCACTCTCCCTGCCCGTCACCCCTGG AGAGCCGGCCTCCATCTCCTGCAGGTCTAGTCAGAGCCTCCTGCATA GTAATGGATACAACTATTTGGATTGGTACCTGCAGAAGCCAGGGCAG TCTCCACAGCTCCTGATCTATTTGGGTTCTAATCGGGCCTCCGGGGT CCCTGACAGGTTCAGTGGCAGTGGATCAGGCACAGATTTTACACTGA AATTCAGCAGAGTGGAGGCTGAGGATGTTGGACTTTATTACTGCATG CAAGCTCTACAAATTCCGCTCACTTTCGGCGGAGGGACCAAGGTGGA GATCAAA |
| VY008 | 90 | HCDR1 | GYTFTGYY |
| | 107 | HCDR2 | INPNSGGT |
| | 125 | HCDR3 | AGDAFDI |
| | 179 | FR H1 | QVQLVQSGAEVKKPGASVKVSCKAS |
| | 190 | FR H2 | MHWVRQAPGQGLEWMGW |
| | 207 | FR H3 | NYAQKFQGRVTMTRDTSISTAYMELSRLRSDDTAVYYC |
| | 214 | FR H4 | WGQGTMVTVSS |
| | 139 | LCDR1 | QSVLYSSNNKNY |
| | 151 | LCDR2 | WAS |
| | 170 | LCDR3 | QQYYSTPLT |
| | 227 | FR L1 | DIVMTQSPDSLAVSLGERATINCKSS |
| | 242 | FR L2 | LAWYQQKPGQPPKLLIY |
| | 260 | FR L3 | TRESGVPDRFSGSGSGTDFTLTISSLQAEDVAVYYC |
| | 265 | FR L4 | FGGGTKVEIK |
| | 17 | VH | QVQLVQSGAEVKKPGASVKVSCKASGYTFTGYYMHWVRQAPGQGLEW MGWINPNSGGTNYAQKFQGRVTMTRDTSISTAYMELSRLRSDDTAVY YCAGDAFDIWGQGTMVTVSS |
| | 37 | VL | DIVMTQSPDSLAVSLGERATINCKSSQSVLYSSNNKNYLAWYQQKPG QPPKLLIYWASTRESGVPDRFSGSGSGTDFTLTISSLQAEDVAVYYC QQYYSTPLTFGGGTKVEIK |

TABLE 1-continued

| Exemplary anti-tau antibodies | | | |
|---|---|---|---|
| Ab ID | SEQ ID | Description | Sequence |
| | 53 | VH (DNA) | CAGGTGCAGCTGGTGCAGTCTGGGGCTGAGGTGAAGAAGCCTGGGGC<br>CTCAGTGAAGGTCTCCTGCAAGGCTTCTGGATACACCTTCACCGGCT<br>ACTATATGCACTGGGTGCGACAGGCCCCTGGACAAGGGCTTGAGTGG<br>ATGGGATGGATCAACCCTAACAGTGGTGGCACAAACTATGCACAGAA<br>GTTTCAGGGCAGGGTCACCATGACCAGGGACACGTCCATCAGCACAG<br>CCTACATGGAGCTGAGCAGGCTGAGATCTGACGACACGGCCGTGTAT<br>TACTGTGCTGGGGATGCTTTTGATATCTGGGGCCAAGGGACAATGGT<br>CACCGTCTCTTCA |
| | 73 | VL (DNA) | GACATCGTGATGACCCAGTCTCCAGACTCCCTGGCTGTGTCTCTGGG<br>CGAGAGGGCCACCATCAACTGCAAGTCCAGCCAGAGTGTTTTATACA<br>GCTCCAACAATAAGAACTACTTAGCTTGGTACCAGCAGAAACCAGGA<br>CAGCCTCCTAAGCTGCTCATTTACTGGGCATCTACCCGGGAATCCGG<br>GGTCCCTGACCGATTCAGTGGCAGCGGGTCTGGGACAGATTTCACTC<br>TCACCATCAGCAGCCTGCAGGCTGAAGATGTGGCAGTTTATTACTGT<br>CAGCAATATTATAGTACTCCGCTCACTTTCGGCGGAGGGACCAAGGT<br>GGAGATCAAA |
| VY013 | 91 | HCDR1 | GFSLINARMA |
| | 108 | HCDR2 | IFSNDEK |
| | 126 | HCDR3 | ARIRGYSYNYGMDV |
| | 180 | FR H1 | QVTLKESGPVLVKPTETLTLTCTVS |
| | 191 | FR H2 | VSWIRQPPGKALEWLAH |
| | 208 | FR H3 | SYSTSLKSRLTISKDTSKSQVVLIMINMDPVDTATYYC |
| | 211 | FR H4 | WGQGTTVTVSS |
| | 140 | LCDR1 | QSLLHSNGYIY |
| | 153 | LCDR2 | VGS |
| | 171 | LCDR3 | MQTLQIPRT |
| | 229 | FR L1 | DIVMTQSPLSLPVIPGEPASISCRSS |
| | 243 | FR L2 | LDWYLQKPGQSPQLLIY |
| | 261 | FR L3 | NRASGVPDRFSGSGSGTDFKLKISRVEAEDVGVYYC |
| | 265 | FR L4 | FGGGTKVEIK |
| | 18 | VH | QVTLKESGPVLVKPTETLTLTCTVSGFSLINARMAVSWIRQPPGKAL<br>EWLAHIFSNDEKSYSTSLKSRLTISKDTSKSQVVLIMTNMDPVDTAT<br>YYCARIRGYSYNYGMDVWGQGTTVTVSS |
| | 38 | VL | DIVMTQSPLSLPVIPGEPASISCRSSQSLLHSNGYIYLDWYLQKPGQ<br>SPQLLIYVGSNRASGVPDRFSGSGSGTDFKLKISRVEAEDVGVYYCM<br>QTLQIPRTFGGGTKVEIK |
| | 40 | VH (DNA) | CAGGTCACCTTGAAGGAGTCTGGTCCTGTGCTGGTGAAACCCACAGA<br>GACCCTCACGCTGACCTGCACCGTCTCTGGGTTCTCACTCATCAATG<br>CTAGAATGGCTGTGAGCTGGATCCGTCAGCCCCCAGGGAAGGCCCTG<br>GAGTGGCTTGCACACATTTTTTCGAATGACGAAAAATCCTACAGCAC<br>ATCTCTGAAGAGCAGACTCACCATCTCCAAGGACACCTCCAAAAGCC<br>AGGTGGTCCTTATCATGACCAACATGGACCCTGTGGACACAGCCACA<br>TATTACTGTGCACGGATCCGTGGATACAGCTATAACTACGGTATGGA<br>CGTCTGGGGCCAAGGGACCACGGTCACCGTCTCCTCA |
| | 58 | VL (DNA) | GATATTGTGATGACTCAGTCTCCACTCTCCCTGCCCGTCATCCCTGG<br>AGAGCCGGCCTCCATCTCCTGCAGGTCTAGTCAGAGCCTCCTGCATA<br>GTAATGGATACATCTATTTGGATTGGTACCTGCAGAAGCCAGGGCAG<br>TCTCCACAGCTCCTGATCTATGTGGGTTCTAATCGGGCCTCCGGGGT<br>CCCTGACAGGTTCAGTGGCAGTGGATCAGGCACAGATTTCAAACTGA<br>AAATCAGCAGAGTGGAGGCTGAGGATGTTGGGGTTTATTACTGCATG<br>CAAACTCTACAAATTCCGCGCACTTTCGGCGGAGGGACCAAGGTGGA<br>GATCAAA |

Anti-tau antibodies of the present disclosure may include variable domain amino acid sequences according to any of those listed in Table 1. In some embodiments, anti-tau antibody variable domains include fragments or variants of variable domain amino acid sequences listed. For instance, in some embodiments, the anti-tau antibody may comprise a VH comprising an amino acid sequence selected from SEQ ID NO: 7, 3, 4, 6, 11, 1, 2, 5, 8, 9, 10, 12, 13, 14, 15, 16, 17, or 18, or an amino acid sequence at least 70%, 75%, 80%, 85%, 90%, 92%, 95%, 96%, 97%, 98%, or 99% sequence identity thereto, or an amino acid sequence having at least one, two, or three modifications, but not more than 30, 20, or 10 modifications (e.g., 1-30, 1-20, 1-10, 1-5, 1-4, 1-3, 1-2, or 1 amino acid modification, such as amino acid substitutions (e.g., conservative substitutions)) relative to the VH sequence. In some embodiments, the anti-tau antibody may comprise a VL comprising an amino acid sequence selected from SEQ ID NO: 25, 21, 22, 24, 30, 19, 20, 23, 26, 27, 28, 29, 31, 32, 33, 34, 35, 36, 37, or 38, or an amino acid sequence at least 70%, 75%, 80%, 85%, 90%, 92%, 95%, 96%, 97%, 98%, or 99% sequence identity thereto, or an amino acid sequence having at least one, two, or three modifications, but not more than 30, 20, or 10 modifications (e.g., 1-30, 1-20, 1-10, 1-5, 1-4, 1-3, 1-2, or 1 amino acid modification, such as amino acid substitutions (e.g., conservative substitutions)) relative to the VL sequence. In some embodiment, the anti-tau antibody may comprise a VH and a VL, wherein (a) the VH comprises an amino acid sequence selected from SEQ ID NO: 7, 3, 4, 6, 11, 1, 2, 5, 8, 9, 10, 12, 13, 14, 15, 16, 17, or 18, or an amino acid sequence at least 70%, 75%, 80%, 85%, 90%, 92%, 95%, 96%, 97%, 98%, or 99% sequence identity thereto, or an amino acid sequence having at least one, two, or three modifications, but not more than 30, 20, or 10 modifications (e.g., amino acid substitutions, such as conservative substitutions), relative to the VH sequence, and/or (b) the VL comprises an amino acid sequence selected from SEQ ID NO: 25, 21, 22, 24, 30, 19, 20, 23, 26, 27, 28, 29, 31, 32, 33, 34, 35, 36, 37, or 38, or an amino acid sequence at least 70%, 75%, 80%, 85%, 90%, 92%, 95%, 96%, 97%, 98%, or 99% sequence identity thereto, or an amino acid sequence having at least one, two, or three modifications, but not more than 30, 20, or 10 modifications (e.g., 1-30, 1-20, 1-10, 1-5, 1-4, 1-3, 1-2, or 1 amino acid modification, such as amino acid substitutions (e.g., conservative substitutions)), relative to the VL sequence.

Provided herein are isolated, e.g., recombinant, antibodies which bind to human tau (e.g., human tau having the sequence set forth in SEQ ID NO: 274), comprising a VH and/or VL sequence selected from: (i) SEQ ID NOs: 7 and/or 25, respectively; (ii) SEQ ID NOs: 3 and/or 21, respectively; (iii) SEQ ID NOs: 4 and/or 22, respectively; (iv) SEQ ID NOs: 6 and/or 24, respectively; (v) SEQ ID NOs: 11 and/or 30, respectively; (vi) SEQ ID NOs: 1 and/or 19, respectively; (vii) SEQ ID NOs: 2 and/or 20, respectively; (viii) SEQ ID NOs: 5 and/or 23, respectively; (ix) SEQ ID NOs: 8 and/or 26, respectively; (x) SEQ ID NOs: 9 and/or 27, respectively; (xi) SEQ ID NOs: 10 and/or 28, respectively; (xii) SEQ ID NOs: 10 and/or 29, respectively; (xiii) SEQ ID NOs: 12 and/or 31, respectively; (xiv) SEQ ID NOs: 13 and/or 32, respectively; (xv) SEQ ID NOs: 14 and/or 33, respectively; (xvi) SEQ ID NOs: 14 and/or 34, respectively; (xvii) SEQ ID NOs: 15 and/or 35, respectively; (xviii) SEQ ID NOs: 16 and/or 36, respectively; (xix) SEQ ID NOs: 17 and/or 37, respectively; or (xx) SEQ ID NOs: 18 and/or 38, respectively. In some embodiments, the antibodies comprise a VH and/or VL sequence having at least 70%, 75%, 80%, 85%, 90%, 92%, 95%, 96%, 97%, 98%, or 99% sequence identity to the sequences of any one of (i)-(xx). In some embodiments, the antibodies comprise a VH and/or VL sequence having at least one, two, or three modifications, but not more than 30, 20, or 10 modifications (e.g., 1-30, 1-20, 1-10, 1-5, 1-4, 1-3, 1-2, or 1 amino acid modification, such as amino acid substitutions (e.g., conservative substitutions)), relative to the VH and/or VL sequences of any one of (i)-(xx).

In some embodiments, the antibody which binds to human tau comprises VH and VL sequences selected from: (i) SEQ ID NOs: 7 and 25, respectively; (ii) SEQ ID NOs: 3 and 21, respectively; (iii) SEQ ID NOs: 4 and 22, respectively; (iv) SEQ ID NOs: 6 and 24, respectively; (v) SEQ ID NOs: 11 and 30, respectively; (vi) SEQ ID NOs: 1 and 19, respectively; (vii) SEQ ID NOs: 2 and 20, respectively; (viii) SEQ ID NOs: 5 and 23, respectively; (ix) SEQ ID NOs: 8 and 26, respectively; (x) SEQ ID NOs: 9 and 27, respectively; (xi) SEQ ID NOs: 10 and 28, respectively; (xii) SEQ ID NOs: 10 and 29, respectively; (xiii) SEQ ID NOs: 12 and 31, respectively; (xiv) SEQ ID NOs: 13 and 32, respectively; (xv) SEQ ID NOs: 14 and 33, respectively; (xvi) SEQ ID NOs: 14 and 34, respectively; (xvii) SEQ ID NOs: 15 and 35, respectively; (xviii) SEQ ID NOs: 16 and 36, respectively; (xix) SEQ ID NOs: 17 and 37, respectively; or (xx) SEQ ID NOs: 18 and 38, respectively. In some embodiments, the antibodies comprise a VH and VL sequences having at least 70%, 75%, 80%, 85%, 90%, 92%, 95%, 96%, 97%, 98%, or 99% sequence identity to the sequences of any one of (i)-(xx). In some embodiments, the antibodies comprise a VH and/or VL sequence having at least one, two, or three modifications, but not more than 30, 20, or 10 modifications (e.g., 1-30, 1-20, 1-10, 1-5, 1-4, 1-3, 1-2, or 1 amino acid modification, such as amino acid substitutions (e.g., conservative substitutions)), relative to the VH and VL sequences of any one of (i)-(xx).

Anti-tau antibody variable domains of the present disclosure may be encoded by nucleic acid sequences listed in Table 1. In some embodiments, nucleic acid sequences encoding anti-tau antibody variable domains of the present disclosure may include fragments or variants of the nucleic acid sequences listed. For instance, in some embodiments, the nucleic acid sequence encoding the VH may comprise a nucleotide sequence selected from SEQ ID NO: 51, 55, 54, 52, 47, 39, 56, 41, 50, 49, 48, 46, 45, 44, 43, 42, 53, or 40, or a nucleic acid sequence having at least 50%, 55%, 60%, 65%, 70%, 75%, 80%, 85%, 90%, 92%, 95%, 96%, 97%, 98%, or 99% sequence identity thereto. In some embodiments, the nucleic acid sequence encoding the VL may comprise a nucleotide sequence selected from SEQ ID NO: 67, 75, 74, 72, 66, 57, 76, 59, 70, 69, 68, 65, 64, 62, 63, 61, 60, 73, or 58, or a nucleic acid sequence having at least 50%, 55%, 60%, 65%, 70%, 75%, 80%, 85%, 90%, 92%, 95%, 96%, 97%, 98%, or 99% sequence identity thereto. In some embodiments, the nucleic acids described herein may encode an anti-tau antibody. In some embodiments, the anti-tau antibody may be encoded by a nucleic acid, or a combination of nucleic acids, comprising (a) a nucleotide sequence encoding a VH selected from SEQ ID NOs: 51, 55, 54, 52, 47, 39, 56, 41, 50, 49, 48, 46, 45, 44, 43, 42, 53, or 40, or a nucleic acid sequence having at least 50%, 55%, 60%, 65%, 70%, 75%, 80%, 85%, 90%, 92%, 95%, 96%, 97%, 98%, or 99% sequence identity thereto, and/or (b) a nucleotide sequence encoding a VL selected from SEQ ID NOs: 67, 75, 74, 72, 66, 57, 76, 59, 70, 69, 68, 65, 64, 62, 63, 61, 60, 73, or 58, or a nucleic acid sequence having at least 50%, 55%, 60%, 65%, 70%, 75%, 80%, 85%, 90%, 92%, 95%, 96%, 97%, 98%, or 99% sequence identity thereto. In some embodiments, the anti-tau antibody may be encoded by a nucleic acid, or a combination of nucleic acids, comprising a nucleotide sequence encoding a VH and a nucleotide sequence encoding a VL selected from: (i) SEQ ID NOs: 51 and 71, respectively, (ii) SEQ ID NOs: 55 and 75, respectively, (iii) SEQ ID NOs: 54 and 74, respectively, (iv) SEQ ID NOs: 52 and 72, respectively, (v) SEQ ID NOs: 47 and 66, respectively, (vi) SEQ ID NOs: 39 and 57, respectively, (vii) SEQ ID NOs: 56 and 76, respectively, (viii) SEQ ID NOs: 41 and 59, respectively, (ix) SEQ ID NOs: 50 and 70, respectively, (x) SEQ ID NOs: 49 and 69, respectively, (xi) SEQ ID NOs: 48 and 67, respectively, (xii) SEQ ID NOs: 48 and 68, respectively, (xiii) SEQ ID NOs: 46 and 65, respectively, (xiv) SEQ ID NOs: 45 and 64, respectively, (xv) SEQ ID NOs: 44 and 62, respectively, (xvi) SEQ ID NOs: 44 and 63, respectively, (xvii) SEQ ID NOs: 43 and 61, respectively, (xviii) SEQ ID NOs: 42 and 60, respectively, (ix) SEQ ID NOs: 53 and 73, respectively, or (xx) SEQ ID NOs: 40 and 58, respectively, In some embodiments, nucleic acid sequences encoding anti-tau antibody variable domains of the present disclosure include codon-optimized variants of the nucleic acid sequences listed.

In some embodiments, anti-tau antibodies of the present disclosure include one or more CDRs (e.g., 1, 2, 3, 4, 5, or all 6 CDRs), e.g., CDRs based on the Chothia numbering system, with amino acid sequences derived from one or more variable domain amino acid sequence provided in Table 1. In some embodiments, anti-tau antibodies of the present disclosure include one or more CDRs (e.g., 1, 2, 3, 4, 5, or all 6 CDRs) encoded by nucleic acid sequences derived from one or more variable domain nucleic acid sequences provided in Table 1. Anti-tau antibody CDRs may include one or more amino acid residues involved in antigen binding (e.g., as determined by co-crystallography with bound antigen). Anti-tau antibodies of the present disclosure may include CDRs identified through CDR analysis of variable domain sequences presented herein via co-crystallography with bound antigen; by computational assessments based on comparisons with other antibodies (e.g., see Strohl, W. R. Therapeutic Antibody Engineering. Woodhead Publishing, Philadelphia PA. 2012. Ch. 3, p 47-54); or art-recognized Kabat, Chothia, Al-Lazikani, Lefranc, IMGT, or Honegger numbering schemes, as described previously. In some embodiments, anti-tau antibody CDR amino acid sequences may include any of those presented in Table 1, or fragments thereof. In some embodiments, anti-tau antibodies of the present disclosure include CDRs that include amino acid sequence variants of those listed. Amino acid fragments or variants included in anti-tau antibody CDRs may include from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences.

The anti-tau antibodies described herein may comprise a VH comprising one, two, or three of a heavy chain complementary determining region 1 (HCDR1), a heavy chain complementary determining region 2 (HCDR2), and a heavy chain complementary determining region 3 (HCDR3), and/or a VL comprising one, two, or three of a light chain complementary determining region 1 (LCDR1), a light chain complementary determining region 2 (LCDR2), and a light chain complementary determining region 3 (LCDR3), e.g., CDRs based on the Chothia numbering system, of any one of VY011, VY007, VY004, VY006, VY018, VY003, VY016, VY017, VY012, VY009, VY010, VY022, VY001, VY019, VY020, VY005, VY002, VY014, VY008, and VY013.

In some embodiments, provided herein is a recombinant antibody that binds to human tau, wherein the antibody comprises the heavy chain CDR1, CDR2, and CDR3, and/or light chain CDR1, CDR2, and CDR3 of an antibody comprising a heavy chain variable region (VH) and light chain variable region (VL) comprising: (i) SEQ ID NOs: 7 and 25, respectively; (ii) SEQ ID NOs: 3 and 21, respectively; (iii) SEQ ID NOs: 4 and 22, respectively; (iv) SEQ ID NOs: 6 and 24, respectively; (v) SEQ ID NOs: 11 and 30, respectively; (vi) SEQ ID NOs: 1 and 19, respectively; (vii) SEQ ID NOs: 2 and 20, respectively; (viii) SEQ ID NOs: 5 and 23, respectively; (ix) SEQ ID NOs: 8 and 26, respectively; (x) SEQ ID NOs: 9 and 27, respectively; (xi) SEQ ID NOs: 10 and 28, respectively; (xii) SEQ ID NOs: 10 and 29, respectively; (xiii) SEQ ID NOs: 12 and 31, respectively; (xiv) SEQ ID NOs: 13 and 32, respectively; (xv) SEQ ID NOs: 14 and 33, respectively; (xvi) SEQ ID NOs: 14 and 34, respectively; (xvii) SEQ ID NOs: 15 and 35, respectively; (xviii) SEQ ID NOs: 16 and 36, respectively; (xix) SEQ ID NOs: 17 and 37, respectively; or (xx) SEQ ID NOs: 18 and 38, respectively. In some embodiments, the CDR sequences are based on the Kabat numbering system, Chothia numbering system, or IMGT numbering system.

In some embodiments, provided herein are isolated, e.g., recombinant, antibodies which bind to human tau, comprising: (a) one, two, or all three HCDRs selected from a HCDR1 comprising an amino acid sequence selected from SEQ ID NO: 77, 78, 79, 80, 81, 82, 83, 84, 85, 86, 87, 88, 89, 90, or 91, a HCDR2 comprising an amino acid sequence selected from SEQ ID NO: 92, 93, 94, 95, 96, 97, 98, 99, 100, 101, 102, 103, 104, 105, 106, 107, or 108, and a HCDR3 comprising an amino acid sequence selected from SEQ ID NO: 109, 110, 111, 112, 113, 114, 115, 116, 117, 118, 119, 120, 121, 122, 123, 124, 125, or 126, and/or (b) one, two, or all three LCDRs selected from a LCDR1 comprising an amino acid sequence selected from SEQ ID NO: 127, 128, 129, 130, 131, 132, 133, 134, 135, 136, 137, 138, 139, or 140, a LCDR1 comprising an amino acid sequence selected from SEQ ID NO: 141, 142, 143, 144, 145, 146, 147, 148, 149, 150, 151, 152, or 153, a LCDR1 comprising an amino acid sequence selected from SEQ ID NO: 154, 155, 156, 157, 158, 159, 160, 161, 162, 163, 164, 165, 166, 167, 168, 169, 170, or 171. In some embodiments, one or more (1, 2, 3, 4, 5, or all 6 CDRs) of the HCDR1, HCDR2, HCDR3, LCDR1, LCDR2, and LCDR3 has one, two, or at most three amino acid substitutions (e.g., conservative substitutions).

In some embodiments, the anti-tau antibodies described herein comprise a VH and a VL, wherein the VH comprises the HCDR1, HCDR2, and HCDR3 combinations described in Table 2. In some embodiments, the anti-tau antibodies described herein comprise a VH and a VL, wherein the VL comprises the LCDR1, LCDR2, and LCDR3 combinations described in Table 2. In some embodiments, one or more (1, 2, or all 3) of the HCDR1, HCDR2, and HCDR3, and/or one or more (1, 2, or all 3) of the LCDR1, LCDR2, and LCDR3 has one, two, or at most three amino acid substitutions (e.g., conservative substitutions).

TABLE 2

Variable domain CDR amino acid sequence sets

| ID# | Variable domain | CDR1 SEQ ID NO | CDR2 SEQ ID NO | CDR3 SEQ ID NO |
|---|---|---|---|---|
| VY003 | VH | 77 | 92 | 109 |
| VY016 | VH | 78 | 93 | 110 |
| VY007 | VH | 79 | 94 | 111 |
| VY004 | VH | 80 | 95 | 112 |
| VY017 | VH | 78 | 96 | 113 |
| VY006 | VH | 81 | 94 | 114 |
| VY011 | VH | 82 | 97 | 115 |
| VY012 | VH | 83 | 98 | 116 |
| VY009 | VH | 84 | 99 | 117 |
| VY010 | VH | 85 | 100 | 118 |
| VY022 | VH | 85 | 100 | 118 |
| VY018 | VH | 82 | 101 | 119 |
| VY001 | VH | 86 | 102 | 120 |
| VY019 | VH | 87 | 103 | 121 |
| VY020 | VH | 78 | 104 | 122 |
| VY005 | VH | 78 | 104 | 122 |
| VY002 | VH | 88 | 105 | 123 |
| VY014 | VH | 89 | 106 | 124 |
| VY008 | VH | 90 | 107 | 125 |
| VY013 | VH | 91 | 108 | 126 |
| VY003 | VL | 127 | 141 | 154 |
| VY016 | VL | 128 | 142 | 155 |
| VY007 | VL | 127 | 141 | 156 |
| VY004 | VL | 129 | 143 | 157 |
| VY017 | VL | 130 | 144 | 158 |
| VY006 | VL | 127 | 141 | 156 |
| VY011 | VL | 127 | 141 | 159 |
| VY012 | VL | 131 | 145 | 160 |
| VY009 | VL | 132 | 146 | 161 |
| VY010 | VL | 133 | 147 | 162 |
| VY022 | VL | 134 | 148 | 163 |
| VY018 | VL | 132 | 149 | 164 |
| VY001 | VL | 127 | 141 | 156 |
| VY019 | VL | 132 | 149 | 165 |

TABLE 2-continued

| Variable domain CDR amino acid sequence sets | | | | |
|---|---|---|---|---|
| ID# | Variable domain | CDR1 SEQ ID NO | CDR2 SEQ ID NO | CDR3 SEQ ID NO |
| VY020 | VL | 135 | 143 | 166 |
| VY005 | VL | 136 | 150 | 167 |
| VY002 | VL | 137 | 151 | 168 |
| VY014 | VL | 138 | 152 | 169 |
| VY008 | VL | 139 | 151 | 170 |
| VY013 | VL | 140 | 153 | 171 |

In some embodiments, anti-tau antibodies of the present disclosure include pairs of variable domain CDR amino acid sequence sets presented herein. In some embodiments, anti-tau antibodies of the present disclosure include variable domain CDR amino acid sequence set pairs presented in Table 3.

TABLE 3

| Variable domain CDR amino acid sequence set pairs | | | | | | |
|---|---|---|---|---|---|---|
| ID# | HCDR1 SEQ ID NO | HCDR2 SEQ ID NO | HCDR3 SEQ ID NO | LCDR1 SEQ ID NO | LCDR2 SEQ ID NO | LCDR3 SEQ ID NO |
| VY003 | 77 | 92 | 109 | 127 | 141 | 154 |
| VY016 | 78 | 93 | 110 | 128 | 142 | 155 |
| VY007 | 79 | 94 | 111 | 127 | 141 | 156 |
| VY004 | 80 | 95 | 112 | 129 | 143 | 157 |
| VY017 | 78 | 96 | 113 | 130 | 144 | 158 |
| VY006 | 81 | 94 | 114 | 127 | 141 | 156 |
| VY011 | 82 | 97 | 115 | 127 | 141 | 159 |
| VY012 | 83 | 98 | 116 | 131 | 145 | 160 |
| VY009 | 84 | 99 | 117 | 132 | 146 | 161 |
| VY010 | 85 | 100 | 118 | 133 | 147 | 162 |
| VY022 | 85 | 100 | 118 | 134 | 148 | 163 |
| VY018 | 82 | 101 | 119 | 132 | 149 | 164 |
| VY001 | 86 | 102 | 120 | 127 | 141 | 156 |
| VY019 | 87 | 103 | 121 | 132 | 149 | 165 |
| VY020 | 78 | 104 | 122 | 135 | 143 | 166 |
| VY005 | 78 | 104 | 122 | 136 | 150 | 167 |
| VY002 | 88 | 105 | 123 | 137 | 151 | 168 |
| VY014 | 89 | 106 | 124 | 138 | 152 | 169 |
| VY008 | 90 | 107 | 125 | 139 | 151 | 170 |
| VY013 | 91 | 108 | 126 | 140 | 153 | 171 |

Provided herein are isolated, e.g., recombinant, antibodies that bind to human tau, wherein the antibody comprises a VH comprising one, two, or all three of a heavy chain complementary determining region 1 (HCDR1), a heavy chain complementary determining region 2 (HCDR2), and a heavy chain complementary determining region 3 (HCDR3), and/or a VL comprising one, two, or all three of a light chain complementary determining region 1 (LCDR1), a light chain complementary determining region 2 (LCDR2), and a light chain complementary determining region 3 (LCDR3), wherein: (i) the HCDR1, HCDR2, HCDR3, LCDR1, LCDR2, and LCDR3 comprise the amino acid sequences of SEQ ID NOs: 82, 97, 115, 127, 141, and 159, respectively; (ii) the HCDR1, HCDR2, HCDR3, LCDR1, LCDR2, and LCDR3 comprise the amino acid sequences of SEQ ID NOs: 79, 94, 111, 127, 141, and 156, respectively; (iii) the HCDR1, HCDR2, HCDR3, LCDR1, LCDR2, and LCDR3 comprise the amino acid sequences of SEQ ID NOs: 80, 95, 112, 129, 143, and 157, respectively; (iv) the HCDR1, HCDR2, HCDR3, LCDR1, LCDR2, and LCDR3 comprise the amino acid sequences of SEQ ID NOs: 81, 94, 114, 127, 141, and 156, respectively; (v) the HCDR1, HCDR2, HCDR3, LCDR1, LCDR2, and LCDR3 comprise the amino acid sequences of SEQ ID NOs: 82, 101, 119, 132, 149, and 164, respectively; (vi) the HCDR1, HCDR2, HCDR3, LCDR1, LCDR2, and LCDR3 comprise the amino acid sequences of SEQ ID NOs: 77, 92, 109, 127, 141, and 154, respectively; (vii) the HCDR1, HCDR2, HCDR3, LCDR1, LCDR2, and LCDR3 comprise the amino acid sequences of SEQ ID NOs: 78, 93, 110, 128, 142, and 155, respectively; (viii) the HCDR1, HCDR2, HCDR3, LCDR1, LCDR2, and LCDR3 comprise the amino acid sequences of SEQ ID NOs: 78, 96, 113, 130, 144, and 158, respectively; (xi) the HCDR1, HCDR2, HCDR3, LCDR1, LCDR2, and LCDR3 comprise the amino acid sequences of SEQ ID NOs: 83, 98, 116, 131, 145, and 160, respectively; (x) the HCDR1, HCDR2, HCDR3, LCDR1, LCDR2, and LCDR3 comprise the amino acid sequences of SEQ ID NOs: 84, 99, 117, 132, 146, and 161, respectively; (xi) the HCDR1, HCDR2, HCDR3, LCDR1, LCDR2, and LCDR3 comprise the amino acid sequences of SEQ ID NOs: 85, 100, 118, 133, 147, and 162, respectively; (xii) the HCDR1, HCDR2, HCDR3, LCDR1, LCDR2, and LCDR3 comprise the amino acid sequences of SEQ ID NOs: 85, 100, 118, 134, 148, and 163, respectively; (xiii) the HCDR1, HCDR2, HCDR3, LCDR1, LCDR2, and LCDR3 comprise the amino acid sequences of SEQ ID NOs: 86, 102, 120, 127, 141, and 156, respectively; (xiv) the HCDR1, HCDR2, HCDR3, LCDR1, LCDR2, and LCDR3 comprise the amino acid sequences of SEQ ID NOs: 87, 103, 121, 132, 149, and 165, respectively; (xv) the HCDR1, HCDR2, HCDR3, LCDR1, LCDR2, and LCDR3 comprise the amino acid sequences of SEQ ID NOs: 78, 104, 122, 135, 143, and 166, respectively; (xvi) the HCDR1, HCDR2, HCDR3, LCDR1, LCDR2, and LCDR3 comprise the amino acid sequences of SEQ ID NOs: 78, 104, 122, 136, 150, and 167, respectively; (xvii) the HCDR1, HCDR2, HCDR3, LCDR1, LCDR2, and LCDR3 comprise the amino acid sequences of SEQ ID NOs: 88, 105, 123, 137, 151, and 168, respectively; (xviii) the HCDR1, HCDR2, HCDR3, LCDR1, LCDR2, and LCDR3 comprise the amino acid sequences of SEQ ID NOs: 89, 106, 124, 138, 152, and 169, respectively; (xix) the HCDR1, HCDR2, HCDR3, LCDR1, LCDR2, and LCDR3 comprise the amino acid sequences of SEQ ID NOs: 90, 107, 125, 139, 151, and 170, respectively; or (xx) the HCDR1, HCDR2, HCDR3, LCDR1, LCDR2, and LCDR3 comprise the amino acid sequences of SEQ ID NOs: 91, 108, 126, 140, 153, and 171, respectively.

In some embodiments, the antibody comprises the HCDR1, HCDR2, and HCDR3 sequences of any one of (i)-(xx). In some embodiments, the antibody comprises the LCDR1, LCDR2, and LCDR3 sequences of any one of (i)-(xx). In some embodiments, the antibody comprises the HCDR1, HCDR2, HCDR3, LCDR1, LCDR2, and LCDR3 sequences of any one of (i)-(xx).

In some embodiments, one or more (1, 2, 3, 4, 5, or all 6 CDRs) of the HCDR1, HCDR2, HCDR3, LCDR1, LCDR2, and LCDR3 of the antibodies of (i)-(xx) has one, two, or at most three amino acid substitutions (e.g., conservative substitutions).

In some embodiments, anti-tau antibodies of the present disclosure include one or more framework regions (FRs). FRs may include amino acid sequences derived from variable domain amino acid sequences provided in Table 1. FRs may be encoded by nucleic acid sequences derived from one or more variable domain nucleic acid sequences provided in Table 1. In some embodiments, anti-tau antibody FRs may include amino acid sequences according to any of those presented in Table 1, or fragments thereof. In some embodiments, anti-tau antibodies of the present disclosure include FRs that include amino acid sequence variants of those listed. Amino acid fragments or variants included in anti-tau antibody FRs may include from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the amino acid sequences listed. In some embodiments, the FRs have at least 50%, 55%, 60%, 65%, 70%, 75%, 80%, 85%, 90%, 92%, 95%, 96%, 97%, 98%, or 99% sequence identity to the FR sequences listed in Table 1, or have at least one, two, or three modifications, but not more than 30, 20, or 10 modifications (e.g., 1-30, 1-20, 1-10, 1-5, 1-4, 1-3, 1-2, or 1 amino acid modifications, such as amino acid substitutions (e.g., conservative substitutions)), relative to the FRs listed in Table 1.

Also provided herein are anti-tau antibodies which bind to tau protein antigens. Tau protein antigens may include human microtubule-associated protein tau, isoform 2 (SEQ ID NO: 274) or fragments thereof. Tau protein antigens may include ePHF or fragments thereof. Tau protein antigens may include one or more phosphorylated residues. Such phosphorylated residues may correspond to those found with pathological tau. In some embodiments tau protein antigens include any of those listed in Table 4. In the Table, phosphorylated residues associated with each antigen are denoted as (pS) for a phosphorylated serine and (pT) for phosphorylated threonine. In some embodiments, tau proteins may include variants (e.g., phosphorylated or unphosphorylated variants) or fragments of the sequences listed.

TABLE 4

Tau protein antigen sequences

| Antigen | Sequence | SEQ ID NO |
|---|---|---|
| human microtubule-associated protein tau, isoform 2 | MAEPRQEFEVMEDHAGTYGLGDRKDQGGYTMHQDQEGDTDAGLKESPLQ<br>TPTEDGSEEPGSETSDAKSTPTAEDVTAPLVDEGAPGKQAAAQPHTEIP<br>EGTTAEEAGIGDTPSLEDEAAGHVTQARMVSKSKDGTGSDDKKAKGADG<br>KTKIATPRGAAPPGQKGQANATRIPAKTPPAPKTPPSSGEPPKSGDRSG<br>YSSPGSPGTPGSRSRTPSLPTPPTREPKKVAVVRTPPKSPSSAKSRLQT<br>APVPMPDLKNVKSKIGSTENLKHQPGGGKVQIINKKLDLSNVQSKCGSK<br>DNIKHVPGGGSVQIVYKPVDLSKVTSKCGSLGNIHHKPGGGQVEVKSEK<br>LDFKDRVQSKIGSLDNITHVPGGGNKKIETHKLTFRENAKAKTDHGAEI<br>VYKSPVVSGDTSPRHLSNVSSTGSIDMVDSPQLATLADEVSASLAKQGL | 274 |
| PT3 epitope peptide (pT212/pT217) | TPGSRSR(PT)PSLP(pT)PPTREPK | 275 |
| Peptide 5 (tPeptide 5) (pT212/pS214/pT217) | GTPGSRSR(PT)P(pS)LP(pT)PPTRE | 276 |
| Peptide 12 (pS396/pS404/pS409) | RENAKAKTDHGAEIVYK(pS)PVVSGDT(pS)PRHL(pS)NVSSTG | 277 |
| Peptide 1 (AT120 epitope) | PTREPKKV | 278 |
| 6C5 epitope peptide | ARMVSKS | 279 |
| UCB D & PT76 epitope peptide | SPSSAKSRLQTAPVPMPDLKNVKS | 280 |
| Tau(pS404) | DHGAEIVYKSPVVSGDT(pS)PRHLSNVSSTG | 281 |
| AC04 peptide | CSR(pT)PSLP(PT)PPTREPK | 282 |
| PepScan 193-210 peptide | DR(pS)GY(pS)(pS)PG(pS)PG(pT)PG(pS)R(pS) | 283 |
| Tau191-214 phospho-peptide (pS199) | SGDRSGYS(pS)PGSPGTPGSRSRTPS | 284 |
| Tau191-214 phospho-peptide (pS202) | SGDRSGYSSPG(pS)PGTPGSRSRTPS | 285 |
| Tau191-214 phospho-peptide (pT205) | SGDRSGYSSPGSPG(pT)PGSRSRTPS | 286 |
| Tau191-214 phospho-peptide (pS199/pS202/pT205) | SGDRSGYSpSPG(pS)PG(pT)PGSRSRTPS | 287 |
| Tau191-214 phospho-peptide (pS199/pS202) | SGDRSGYS(pS)PG(pS)PGTPGSRSRTPS | 288 |
| Tau191-214 phospho-peptide (pS202/pT205) | SGDRSGYSSPG(pS)PG(pT)PGSRSRTPS | 289 |

TABLE 4-continued

| Tau protein antigen sequences | | |
|---|---|---|
| Antigen | Sequence | SEQ ID NO |
| Tau191-214 phospho-peptide (pS199/pT205) | SGDRSGYS(pS)PGSPG(pT)PGSRSRTPS | 290 |
| Tau204-222 phospho-peptide (pT212) | GTPGSRSR(pT)PSLPTPPTRE | 291 |
| Tau204-222 phospho-peptide (pS214) | GTPGSRSRTP(pS)LPTPPTRE | 292 |
| Tau204-222 phospho-peptide (pT217) | GTPGSRSRTPSLP(pT)PPTRE | 293 |
| Tau204-222 phospho-peptide (pT212/pS214) | GTPGSRSR(pT)P(pS)LPTPPTRE | 294 |
| Tau204-222 phospho-peptide (pT212/pT217) | GTPGSRSR(pT)PSLP(pT)PPTRE | 295 |
| Tau204-222 phospho-peptide (pS214/pT217) | GTPGSRSRTP(pS)LP(pT)PPTRE | 296 |
| Tau204-222 phospho-peptide (pT212/pS214/pT217) | GTPGSRSR(pT)P(pS)LP(pT)PPTRE | 297 |
| Tau217-234 phospho-peptide (pT217/pT220/pT231) | (pT)PP(pT)REPKKVAVVR(pT)PPK | 298 |
| Tau225-240 phospho-peptide (pT231) | KVAVVR(pT)PPKSPSSAK | 299 |
| Tau phospho-peptide (pS235) | KVAVVRTPPK(pS)PSSAKPS | 300 |
| Tau phospho-peptide (pT231/pS235) | KVAVVR(pT)PPK(pS)PSSAKPS | 301 |

In some embodiments, anti-tau antibodies of the present disclosure bind to tau protein epitopes on tau protein antigens described herein. Such tau protein epitopes may include or be included within a tau protein antigen amino acid sequence listed in Table 4. In some embodiments, anti-tau antibodies of the present disclosure bind to tau protein epitopes that include a region formed by a complex of at least two tau proteins.

In some embodiments, anti-tau antibodies of the present disclosure exhibit binding that overlaps with a region of tau recognized by art-recognized antibodies, such as AT8 and PT3, but exhibit binding patterns to phosphorylated tau that differs from the art-recognized antibodies.

Accordingly, in one aspect, provided herein is an isolated, e.g., recombinant, antibody that binds to human tau, wherein the antibody binds to all or a portion of amino acid residues of tau selected from: (a) 183-212, (b) 187-218, (c) 33-82, 159-182, 197-226, and 229-246; (d) 217-242, (e) 35-76 and 187-218, (f) 5-34, (g) 187-218, (h) 33-82, 159-188, and 191-230, (i) 35-62, 107-124, and 203-220, (j) 35-82, 159-188, and 197-224, or (k) 53-78, 329-348, and 381-408, wherein human tau is numbered according to SEQ ID NO: 274. In some embodiments, one or more of the serines, threonines, and/or tyrosines in the stretch of amino acids selected from (a)-(k) are phosphorylated. In some embodiments, all of the serines, threonines, and/or tyrosines in the stretch of amino acids selected from (a)-(k) are phosphorylated. In some embodiments, the antibody comprises the HCDR1, HCDR2, HCDR3, LCDR1, LCDR2, and LCDR3 sequences, or the VH and VL sequences, of an antibody listed in Table 1.

In some embodiments, the anti-tau antibody binds to all or a portion of amino acids 195-215 of human tau (e.g., phosphorylated at all serines, threonines, and/or tyrosines present in this stretch of amino acids) with a dissociation constant ($K_D$) of about 1 pM to about 50 pM, or about 1-25 pM, e.g., as assessed by bio-layer interferometry.

In some embodiments, the anti-tau antibody binds to all or a portion of amino acids 191-214 of human tau phosphorylated at S199 (e.g., phosphorylated only at S199 in this stretch of amino acids or throughout the entire tau protein) with a dissociation constant ($K_D$) of about 0.1 nM to about 10 nM, or about 0.5-5 nM, e.g., as assessed by bio-layer interferometry.

In some embodiments, the anti-tau antibody binds to all or a portion of amino acids 217-234 of human tau phosphorylated at T217, T220, and T231 (e.g., phosphorylated only at T217, T220, and T231 in this stretch of amino acids or throughout the entire tau protein) with a dissociation constant ($K_D$) of about 0.1 nM to about 10 nM, or about 0.1-5 nM, e.g., as assessed by bio-layer interferometry.

In some embodiments, the anti-tau antibody binds to all or a portion of amino acids 225-240 of tau phosphorylated at T231 (e.g., phosphorylated only at T231 in this stretch of amino acids or throughout the entire tau protein) with a dissociation constant ($K_D$) of about 0.1 nM to about 25 nM, or about 0.1-15 nM, e.g., as assessed by bio-layer interferometry.

In another aspect, provided herein is an isolated, e.g., recombinant, antibody that binds to human tau phosphorylated at amino acid residue S404, or a peptide comprising or consisting of the amino acid sequence DHGAEIVYKSPVVSGDT(pS)PRHLSNVSSTG (SEQ ID NO: 281), wherein p(S) corresponds to a phosphorylated serine residue. In some embodiments, the antibody comprises a heavy chain variable region (VH) comprising CDR1, CDR2, and CDR3 sequences comprising SEQ ID NOs: 89, 106, and 124, respectively, and a light chain variable region (VL) comprising CDR1, CDR2, and CDR3 sequences comprising SEQ ID NOs: 138, 152, and 169, respectively. In some embodiments, the antibody comprises VH and VL sequences comprising SEQ ID NOs: 16 and 36, respectively.

In another aspect, provided herein is an isolated, e.g., recombinant, antibody that binds to: (a) human tau phosphorylated at amino acid residue S199, but not at amino acid residues S202 and T205; (b) human tau phosphorylated at amino acid residue S202, but not at amino acid residues S199 and T205; (c) human tau phosphorylated at amino acid residue T205, but not at amino acid residues S199 and S202; (d) human tau phosphorylated at a combination of amino acid residues S199 and T205, but not at amino acid residue S202 (e.g., wherein binding tau phosphorylated at a combination of S199 and T205 is at least 3-times stronger (e.g., at least 4-time stronger) than background (e.g., non-specific) level of binding, e.g., binding by hIgG1 isotype control); (e) human tau phosphorylated at a combination of amino acid residues S202 and T205, but not at amino acid residue S199, but not human tau phosphorylated at a combination of residues S199 and S202, but not T205; (f) human tau phosphorylated at a combination of amino acid residues: (i) S202 and T205, but not S119, and (ii) S199 and T205, but not S202, at least 2 times (e.g., at least 3 times, at least 4 times, at least 5 times, 2-6 times, 2-5 times, 2-4 times, 2-3 times, 3-5 times or 4-5 times) more strongly than background (e.g., non-specific) level of binding, e.g., binding by hIgG1 isotype control); (g) human tau phosphorylated at a combination of amino acid residues: (i) S199 and S202, but not T205, (ii) S202 and T205, but not S199, (iii) S199 and T205, but not S202, and (iv) S199, S202, and T205 (e.g., wherein binding to phosphorylated tau is at least 1.6-times stronger (e.g., at least 1.7 times, at least 1.8 times, at least 1.9 times, at least 2 times, at least 3 times, 1.6-3 times, 1.6-2 times stronger) than background (e.g., non-specific) level of binding, e.g., binding by hIgG1 isotype control); (h) a peptide comprising or consisting of the amino acid sequence SGDRSGYS(pS)PGSPGTPGSRSRTPS (SEQ ID NO: 284); (i) a peptide comprising or consisting of the amino acid sequence SGDRSGYSSPG(pS)PGTPGSRSRTPS (SEQ ID NO: 285); (j) a peptide comprising or consisting of the amino acid sequence SGDRSGYSSPGSPG(pT)PGSRSRTPS (SEQ ID NO: 286); (k) a peptide comprising or consisting of the amino acid sequence SGDRSGYS(pS)PGSPG(pT)PGSRSRTPS (SEQ ID NO: 290) (e.g., wherein binding to the peptide is at least 3 times stronger (e.g., at least 4 times stronger) than background (e.g., non-specific) level of binding, e.g., binding by hIgG1 isotype control); (1) a peptide comprising or consisting of the amino acid sequence SGDRSGYSSPG(pS)PG(pT)PGSRSRTPS (SEQ ID NO: 289), but not a peptide comprising or consisting of the amino acid sequence SGDRSGYS(pS)PG(pS)PGTPGSRSRTPS (SEQ ID NO: 288); (m) peptides comprising or consisting of the amino acid sequences SGDRSGYSSPG(pS)PG(pT)PGSRSRTPS (SEQ ID NO: 289) and SGDRSGYS(pS)PGSPG(pT)PGSRSRTPS (SEQ ID NO: 290); wherein binding to the latter peptide is at least 2 times (e.g., at least 3 times, at least 4 times, at least 5 times, 2-6 times, 2-5 times, 2-4 times, 2-3 times, 3-5 times or 4-5 times) stronger than background (e.g., non-specific) level of binding, e.g., binding by hIgG1 isotype control); or (n) peptides comprising or consisting of the amino acid sequences SGDRSGYS(pS)PG(pS)PGTPGSRSRTPS (SEQ ID NO: 288), SGDRSGYSSPG(pS)PG(pT)PGSRSRTPS (SEQ ID NO: 289), SGDRSGYS(pS)PGSPG(pT)PGSRSRTPS (SEQ ID NO: 290), and SGDRSGYS(pS)PG(pS)PG(pT)PGSRSRTPS (SEQ ID NO: 287) (e.g., wherein binding to the peptides is at least 1.6 times stronger (e.g., at least 1.7 times, at least 1.8 times, at least 1.9 times, at least 2 times, at least 3 times, 1.6-4 times, 1.6-3 times stronger) than background (e.g., non-specific) level of binding, e.g., binding by hIgG1 isotype control); wherein p(S) and p(T) correspond to a phosphorylated serine and phosphorylated threonine, respectively, optionally wherein binding is assessed, e.g., using one point ELISA as described in Example 7. In some embodiments, the antibody comprises (a) a heavy chain variable region (VH) comprising CDR1, CDR2, and CDR3 sequences comprising SEQ ID NOs: 82, 97, and 115, respectively, and a light chain variable region (VL) comprising CDR1, CDR2, and CDR3 sequences comprising SEQ ID NOs: 127, 141, and 159, respectively; (b) a heavy chain variable region (VH) comprising CDR1, CDR2, and CDR3 sequences comprising SEQ ID NOs: 79, 94, and 111, respectively, and a light chain variable region (VL) comprising CDR1, CDR2, and CDR3 sequences comprising SEQ ID NOs: 127, 141, and 156, respectively; (c) a heavy chain variable region (VH) comprising CDR1, CDR2, and CDR3 sequences comprising SEQ ID NOs: 81, 94, and 114, respectively, and a light chain variable region (VL) comprising CDR1, CDR2, and CDR3 sequences comprising SEQ ID NOs: 127, 141, and 156, respectively; (d) a heavy chain variable region (VH) comprising CDR1, CDR2, and CDR3 sequences comprising SEQ ID NOs: 77, 92, and 109, respectively, and a light chain variable region (VL) comprising CDR1, CDR2, and CDR3 sequences comprising SEQ ID NOs: 127, 141, and 154, respectively; (e) a heavy chain variable region (VH) comprising CDR1, CDR2, and CDR3 sequences comprising SEQ ID NOs: 86, 102, and 120, respectively, and a light chain variable region (VL) comprising CDR1, CDR2, and CDR3 sequences comprising SEQ ID NOs: 127, 141, and 156, respectively; (f) VH and VL sequences comprising SEQ ID NOs: 7 and 25, respectively; (g) VH and VL sequences comprising SEQ ID NOs: 8 and 21, respectively; (h) VH and VL sequences comprising SEQ ID NOs: 6 and 24, respectively; (i) VH and VL sequences comprising SEQ ID NOs: 1 and 19, respectively; or (j) VH and VL sequences comprising SEQ ID NOs: 12 and 31, respectively.

In another aspect, provided herein is an isolated, e.g., recombinant, antibody that binds to: (a) tau phosphorylated at T217, but not at T212 or T214, or (b) peptides comprising or consisting of the sequences GTPGSRSRTPSLP(pT)PPTRE (SEQ ID NO: 293) and GTPGSRSRTP(pS)LP(pT)PPTRE (SEQ ID NO: 296), but not peptides comprising or consisting of the sequences GTPGSRSR(pT)PSLPTPPTRE (SEQ ID NO: 291), GTPGSRSRTP(pS)LPTPPTRE (SEQ ID NO: 292), and GTPGSRSR(pT)P(pS)LPTPPTRE (SEQ ID NO: 294), wherein p(S) and p(T) correspond to a phosphorylated serine and phosphorylated threonine, respectively, optionally wherein binding of the antibody to tau or the peptide is at least 1.5 times stronger (e.g., at least 1.6 times, at least 1.7 times, at least 1.8 times, at least 1.9 times, at least 2 times, at least 3 times, at least 4 times, at least 5 times, at least 6 times, 1.5-4 times, 1.5-3, 4-6 times stronger) than background (non-specific) level of binding, e.g., binding by hIgG1 isotype control), and optionally wherein binding of the antibody to tau or the peptide is assessed, e.g., using one point ELISA as described, e.g., in Example 8. In some embodiments, the antibody comprises: (a) a heavy chain variable region (VH) comprising CDR1, CDR2, and CDR3 sequences comprising SEQ ID NOs: 80, 95, and 112, respectively, and a light chain variable region (VL) comprising CDR1, CDR2, and CDR3 sequences comprising SEQ ID NOs: 129, 143, and 157, respectively; (b) a heavy chain variable region (VH) comprising CDR1, CDR2, and CDR3 sequences comprising SEQ ID NOs: 78, 104, and 122, respectively, and a light chain variable region (VL) comprising CDR1, CDR2, and CDR3 sequences comprising SEQ ID NOs: 136, 150, and 167, respectively; (c) a heavy chain variable region (VH) comprising CDR1, CDR2, and CDR3 sequences comprising SEQ ID NOs: 90, 107, and 125, respectively, and a light chain variable region (VL) comprising CDR1, CDR2, and CDR3 sequences comprising SEQ ID NOs: 139, 151, and 170, respectively; (d) VH and VL sequences comprising SEQ ID NOs: 4 and 22, respectively; (e) VH and VL sequences comprising SEQ ID NOs: 14 and 24, respectively; or (f) VH and VL sequences comprising SEQ ID NOs: 17 and 37, respectively.

Specific binding to the aforementioned recited phosphorylated residues or peptides can be determined by comparison with the background level of binding of the assay (e.g., one point ELISA) or level of binding by a negative control, such as an isotype control antibody (e.g., a human IgG1 isotype control antibody), for example, as described in the Examples.

In some embodiments, provided herein are anti-tau antibodies which compete for binding to human tau, or human tau peptides, with any of the anti-tau antibodies described herein.

Also provided herein are anti-tau antibodies which exhibit similar epitope binding features, such as the ability to bind to phospho-epitopes on human tau, as the anti-tau antibodies described herein. Accordingly, in some embodiments, provided herein hare antibodies which bind to the same epitope (e.g., phospho-epitope), substantially the same epitope as, an epitope that overlaps with, or an epitope that substantially overlaps with, the epitope recognized by an anti-tau antibody described herein. In some embodiments, the antibodies described herein bind to a discontinuous epitope, such as a conformational epitope.

Exemplary methods for determining whether an antibody binds to the same epitope (or substantially the same epitope, an epitope that overlaps with, or an epitope that substantially overlaps with) on human tau with the antibodies described herein include, e.g., epitope mapping methods such as x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. Computational combinatorial methods for epitope mapping can also be used. Methods may also rely on the ability of an antibody of interest to affinity isolate specific short peptides (either in native three dimensional form or in denatured form) from combinatorial phage display peptide libraries. Epitope mapping can also be performed using MS-based protein footprinting (e.g., HDX-MS, FPOP). Overlapping phospho-peptide scanning, as described in the Examples, can also be used for epitope mapping.

Anti-tau antibodies according to the present disclosure may be prepared using any of the antibody sequences (e.g., variable domain amino acid sequences, variable domain amino acid sequence pairs, CDR amino acid sequences, variable domain CDR amino acid sequence sets, variable domain CDR amino acid sequence set pairs, and/or framework region amino acid sequences) presented herein, any may be prepared, for example, as monoclonal antibodies, multispecific antibodies, chimeric antibodies, antibody mimetic s, scFvs, or antibody fragments. In some embodiments, anti-tau antibodies using any of the antibody sequences presented herein may be prepared as IgA, IgD, IgE, IgG, or IgM antibodies. When prepared as mouse IgG antibodies, anti-tau antibodies may be prepared as IgG1, IgG2a, IgG2b, or IgG3 isotypes. When prepared as human IgG antibodies, anti-tau antibodies may be prepared as IgG1, IgG2, IgG3, or IgG4 isotypes. Anti-tau antibodies prepared as human or humanized antibodies may include one or more human constant domains. Human constant domains included in anti-tau antibodies of the present disclosure may include, but are not limited to, any of those listed in Table 5.

In some embodiments, the anti-tau antibodies comprise: (i) a heavy chain constant region (CH), e.g., a CH comprising an amino acid sequence of a human CH, such as the CH of human IgG1, IgG2, IgG3, or IgG4 (e.g., a CH described in Table 5) or a murine CH, or a sequence having at least 80% (e.g., 85, 90, 95, 96, 97, 98, or 99%) sequence identity thereto, or an amino acid sequence having at least one, two or three modifications, but not more than 30, 20 or 10 modifications (e.g., 1-30, 1-20, 1-10, 1-5, 1-4, 1-3, 1-2, or 1 amino acid modification, such as a substitution (e.g., a conservative substitution)), relative to the constant region sequence (e.g., a CH described in Table 5); and/or (ii) a light chain constant region (CL), e.g., a CL comprising an amino acid sequence of a human CL, such as the CL of a human lambda or kappa light chain (e.g., a CL described in Table 5) or a murine CL, or a sequence having at least 80% (e.g., 85, 90, 95, 96, 97, 98, or 99%) sequence identity thereto, or an amino acid sequence having at least one, two or three modifications, but not more than 30, 20 or 10 modifications (e.g., 1-30, 1-20, 1-10, 1-5, 1-4, 1-3, 1-2, or 1 amino acid modification, such as a substitution (e.g., a conservative substitution)), relative to the constant region sequence (e.g., a CH described in Table 5).

In some embodiments, the heavy chain constant region sequence (e.g., human heavy chain constant region sequence) has a C-terminal lysine (K), a C-terminal glycine (G), or a C-terminal glycine and lysine (GK). In some embodiments, the heavy chain constant region sequence (e.g., human heavy chain constant region sequence) lacks the C-terminal lysine (K), C-terminal glycine (G), or C-terminal glycine and lysine (GK).

In some embodiments, anti-tau antibodies of the present disclosure include constant domains that include amino acid sequence variants and/or fragments of those listed in Table 5. Amino acid fragments or variants included in anti-tau antibody constant domains may include from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the amino acid sequences listed in Table 5. In some embodiments, the constant domains have at least 50%, 55%, 60%, 65%, 70%, 75%, 80%, 85%, 90%, 92%, 95%, 96%, 97%, 98%, or 99% sequence identity, or at least one, two, or three modifications, but not more than 30, 20, or 10 modifications (e.g., amino acid substitutions, such as conservative substitutions), relative to the amino acid sequences listed in Table 5.

A VH domain, or one or more CDRs thereof, described herein can be linked to a constant domain to form a heavy chain, e.g., a full length heavy chain. Similarly, a VL domain, or one or more CDRs thereof, described herein can be linked to a constant domain to form a light chain, e.g., a full length light chain. A full length heavy chain (with the exception of the C-terminal lysine (K), with the exception of the C-terminal glycine (G), or with the exception of the C-terminal glycine and lysine (GK), which may be absent) and full length light chain may combine to form a full length antibody.

TABLE 5

Constant domains

| Constant domain | Sequence | SEQ ID NO |
|---|---|---|
| Human IgG1 heavy chain constant region (1) | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLT<br>VDKSRWQQGNVFSCSVMHEALHNHYTQKSLSLSPG | 271 |
| Human IgG1 heavy chain constant region (2) | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKRV<br>EPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLI<br>VDKSRWQQGNVFSCSVMHEALHNHYTQKSLSLSPG | 302 |
| Human IgG2 heavy chain constant region | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLFPPKPKDTLMISRTPEVTCVVVDVSH<br>EDPEVQFNWYVDGVEVHNAKTKPREEQFNSTFRVVSVLTVVHQDWLNGK<br>EYKCKVSNKGLPAPIEKTISKTKGQPREPQVYTLPPSREEMTKNQVSLT<br>CLVKGFYPSDISVEWESNGQPENNYKTTPPMLDSDGSFFLYSKLIVDKS<br>RWQQGNVFSCSVMHEALHNHYTQKSLSLSPGK | 303 |
| Human IgG3 heavy chain constant region | ASTKGPSVFPLAPCSRSTSGGTAALGCLVKDYFPEPVTVSWNSGALTSG<br>VHTFPAVLQSSGLYSLSSVVTVPSSSLGTQTYTCNVNHKPSNTKVDKRV<br>ELKTPLGDTTHTCPRCPEPKSCDTPPPCPRCPEPKSCDTPPPCPRCPEP<br>KSCDTPPPCPRCPAPELLGGPSVFLFPPKPKDTLMISRTPEVTCVVVDV<br>SHEDPEVQFKWYVDGVEVHNAKTKPREEQYNSTFRVVSVLTVLHQDWLN<br>GKEYKCKVSNKALPAPIEKTISKTKGQPREPQVYTLPPSREEMTKNQVS<br>LTCLVKGFYPSDIAVEWESSGQPENNYNTTPPMLDSDGSFFLYSKLTVD<br>KSRWQQGNIFSCSVMHEALHNRFTQKSLSLSPGK | 304 |
| Human IgG4 heavy chain constant region | ASTKGPSVFPLAPCSRSTSESTAALGCLVKDYFPEPVTVSWNSGALTSG<br>VHTFPAVLQSSGLYSLSSVVTVPSSSLGTKTYTCNVDHKPSNTKVDKRV<br>ESKYGPPCPSCPAPEFLGGPSVFLFPPKPKDTLMISRTPEVTCVVVDVS<br>QEDPEVQFNWYVDGVEVHNAKTKPREEQFNSTYRVVSVLTVLHQDWLNG<br>KEYKCKVSNKGLPSSIEKTISKAKGQPREPQVYTLPPSQEEMTKNQVSL<br>TCLVKGFYPSDIAVEWESNGQPENNYKTTPPVLDSDGSFFLYSRLTVDK<br>SRWQEGNVFSCSVMHEALHNHYTQKSLSLSLGK | 305 |
| Human IgG1 lambda light chain constant region (subclass 1) | GQPKANPTVTLFPPSSEELQANKATLVCLISDFYPGAVTVAWKADGSPV<br>KAGVETTKPSKQSNNKYAASSYLSLTPEQWKSHRSYSCQVTHEGSTVEK<br>TVAPTECS | 306 |
| Human IgG1 lambda light chain constant region (subclass 2) | GQPKAAPSVTLFPPSSEELQANKATLVCLISDFYPGAVTVAWKADSSPV<br>KAGVETTTPSKQSNNKYAASSYLSLTPEQWKSHRSYSCQVTHEGSTVEK<br>TVAPTECS | 272 |
| Human IgG1 lambda light chain constant region (subclass 3) | GQPKAAPSVTLFPPSSEELQANKATLVCLISDFYPGAVTVAWKADSSPV<br>KAGVETTTPSKQSNNKYAASSYLSLTPEQWKSHKSYSCQVTHEGSTVEK<br>TVAPTECS | 307 |

TABLE 5-continued

Constant domains

| Constant domain | Sequence | SEQ ID NO |
|---|---|---|
| Human IgG1 lambda light chain constant region (subclass 6) | GQPKAAPSVTLFPPSSEELQANKATLVCLISDFYPGAVKVAWKADGSPV<br>NTGVETTTPSKQSNNKYAASSYLSLTPEQWKSHRSYSCQVTHEGSTVEK<br>TVAPAECS | 308 |
| Human IgG1 lambda light chain constant region (subclass 7) | GQPKAAPSVTLFPPSSEELQANKATLVCLVSDFNPGAVTVAWKADGSPV<br>KVGVETTKPSKQSNNKYAASSYLSLTPEQWKSHRSYSCRVTHEGSTVEK<br>TVAPAECS | 309 |
| Human IgG1 kappa light chain constant region | RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGEC | 273 |
| Murine mIgG1 heavy chain constant region (secreted form) | AKTTPPSVYPLAPGSAAQTNSMVTLGCLVKGYFPEPVTVTWNSGSLSSG<br>VHTFPAVLQSDLYTLSSSVTVPSSPRPSETVTCNVAHPASSTKVDKKIV<br>PRDCGCKPCICTVPEVSSVFIFPPKPKDVLTITLTPKVTCVVVDISKDD<br>PEVQFSWFVDDVEVHTAQTQPREEQFNSTFRSVSELPIMHQDWLNGKEF<br>KCRVNSAAFPAPIEKTISKTKGRPKAPQVYTIPPPKEQMAKDKVSLTCM<br>ITDFFPEDITVEWQWNGQPAENYKNTQPIMNTNGSYFVYSKLNVQKSNW<br>EAGNTFTCSVLHEGLHNHHTEKSLSHSPGK | 310 |
| Murine mIgG1 heavy chain constant region (membrane-bound form) | AKTTPPSVYPLAPGSAAQTNSMVTLGCLVKGYFPEPVTVTWNSGSLSSG<br>VHTFPAVLQSDLYTLSSSVTVPSSPRPSETVTCNVAHPASSTKVDKKIV<br>PRDCGCKPCICTVPEVSSVFIFPPKPKDVLTITLTPKVTCVVVDISKDD<br>PEVQFSWFVDDVEVHTAQTQPREEQFNSTFRSVSELPIMHQDWLNGKEF<br>KCRVNSAAFPAPIEKTISKTKGRPKAPQVYTIPPPKEQMAKDKVSLTCM<br>ITDFFPEDITVEWQWNGQPAENYKNTQPIMNTNGSYFVYSKLNVQKSNW<br>EAGNTFTCSVLHEGLHNHHTEKSLSHSPGLQLD*ETC*AEAQDGELDGLWT<br>TITIFISLFLLSVCYSAAVTLFKVKWIFSSVVELKQTLVPEYKNMIGQA<br>P | 311 |
| Murine mIgG2a heavy chain constant region | AKTTAPSVYPLAPVCGDTTGSSVTLGCLVKGYFPEPVTLTWNSGSLSSG<br>VHTFPAVLQSDLYTLSSSVTVISSTWPSQSITCNVAHPASSTKVDKKIE<br>PRGPTIKPCPPCKCPAPNLLGGPSVFIFPPKIKDVLMISLSPIVTCVVV<br>DVSEDDPDVQISWFVNNVEVHTAQTQTHREDYNSTLRVVSALPIQHQDW<br>MSGKEFKCKVNNKDLPAPIERTISKPKGSVRAPQVYVLPPPEEEMTKKQ<br>VTLTCMVTDEMPEDIYVEWTNNGKTELNYKNTEPVLDSDGSYFMYSKLR<br>VEKKNWVERNSYSCSVVHEGLHNHHTTKSFSRTPGK | 312 |
| Murine mIgG2a heavy chain constant region (secreted form) | AKTTAPSVYPLVPVCGGTTGSSVTLGCLVKGYFPEPVTLTWNSGSLSSG<br>VHTFPALLQSGLYTLSSSVTVTSNTWPSQTITCNVAHPASSTKVDKKIE<br>PRVPITQNPCPPHQRVPPCAAPDLLGGPSVFIFPPKIKDVLMISLSPMV<br>TCVVVDVSEDDPDVQISWFVNNVEVHTAQTQTHREDYNSTLRVVSALPI<br>QHQDWMSGKEFKCKVNNRALPSPIEKTISKPRGPVRAPQVYVLPPPAEE<br>MTKKEFSLTCMITGFLPAEIAVDWTSNGRTEQNYKNTATVLDSDGSYFM<br>YSKLRVQKSTWERGSLFACSVVHEVLHNHLTTKTISRSLGK | 313 |
| Murine mIgG2b heavy chain constant region (secreted form) | KTTPPSVYPLAPGCGDTTGSSVILGCLVKGYFPESVTVTWNSGSLSSSV<br>HTFPALLQSGLYTMSSSVTVPSSTWPSQTVTCSVAHPASSTTVDKKLEP<br>SGPISTINPCPPCKECHKCPAPNLEGGPSVFIFPPNIKDVLMISLTPKV<br>TCVVVDVSEDDPDVQISWFVNNVEVHTAQTQTHREDYNSTIRVVSTLPI<br>QHQDWMSGKEFKCKVNNKDLPSPIERTISKIKGLVRAPQVYILPPPAEQ<br>LSRKDVSLTCLVVGFNPGDISVEWTSNGHTEENYKDTAPVLDSDGSYFI<br>YSKLNMKTSKWEKTDSFSCNVRHEGLKNYYLKKTISRSPGLDLDDICAE<br>AKDGELDGLWTTITIFISLFLLSVCYSASVTLFKVKWIFSSVVELKQKI<br>SPDYRNMIGQGA | 314 |
| Murine mIgG2b heavy chain constant region | KTTAPSVYPLAPVCGGTTGSSVTLGCLVKGYFPEPVTLTWNSGSLSSGV<br>HTFPALLQSGLYTLSSSVTVTSNTWPSQTITCNVAHPASSTKVDKKIEP<br>RVPITQNPCPPLKECPPCAAPDLLGGPSVFIFPPKIKDVLMISLSPMVT<br>CVVVDVSEDDPDVQISWFVNNVEVHTAQTQTHREDYNSTLRVVSALPIQ<br>HQDWMSGKEFKCKVNNRALPSPIEKTISKPRGPVRAPQVYVLPPPAEEM<br>TKKEFSLTCMITGFLPAEIAVDWTSNGRTEQNYKNTATVLDSDGSYFMY<br>SKLRVQKSTWERGSLFACSVVHEGLHNHLTTKTISRSLGLDLDDVCTEA<br>QDGELDGLWTTITIFISLFLLSVCYSASVTLFKVKWIFSSVVELKQKIS<br>PDYRNMIGQGA | 315 |

TABLE 5-continued

| Constant domains | | |
|---|---|---|
| Constant domain | Sequence | SEQ ID NO |
| Murine mIgG3 heavy chain constant region (secreted form) | TTTAPSVYPLVPGCSDTSGSSVTLGCLVKGYFPEPVTVKWNYGALSSGV RTVSSVLQSGFYSLSSLVTVPSSTWPSQTVICNVAHPASKTELIKRIEP RIPKPSTPPGSSCPPGNILGGPSVFIFPPKPKDALMISLTPKVTCVVVD VSEDDPDVHVSWFVDNKEVHTAWTQPREAQYNSTFRVVSALPIQHQDWM RGKEFKCKVNNKALPAPIERTISKPKGRAQTPQVYTIPPPREQMSKKKV SLTCLVTNFFSEAISVEWERNGELEQDYKNTPPILDSDGTYFLYSKLTV DTDSWLQGEIFTCSVVHEALHNHHTQKNLSRSPELELN*ETC*AEAQDGEL DGLWTTITIFISLFLLSVCYSASVTLFKVKWIFSSVVQVKQTAIPDYRN MIGQGA | 316 |
| Murine kappa light chain constant region | ADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIV KSFNRNEC | 317 |
| Murine lambda light chain constant region (subclass 1) | QPKSSPSVTLFPPSSEELETNKATLVCTITDFYPGVVTVDWKVDGTPVT QGMETTQPSKQSNNKYMASSYLTLTARAWERHSSYSCQVTHEGHTVEKS LSRADCS | 318 |
| Murine lambda light chain constant region (subclass 2) | QPKSTPTLTVFPPSSEELKENKATLVCLISNFSPSGVTVAWKANGTPIT QGVDTSNPTKEGNKFMASSFLHLTSDQWRSHNSFTCQVTHEGDTVEKSL SPAECL | 319 |
| Murine lambda light chain constant region (subclass 3) | QPKSTPTLTMFPPSPEELQENKATLVCLISNFSPSGVTVAWKANGTPIT QGVDTSNPTKEDNKYMASSFLHLTSDQWRSHNSFTCQVTHEGDTVEKSL SPAECL | 320 |

In some embodiments, the anti-tau antibodies may comprise an Fc region or variant, e.g., functional variant, thereof.

In some embodiments, the antibody comprises an Fc region which has modified, e.g., increased or reduced affinity (e.g., ablated), affinity for an Fc receptor, e.g., as compared to a reference, wherein the reference is a wild-type Fc receptor.

In some embodiments, the antibody comprises an Fc region which comprises a mutation at one, two, or all of positions 1253 (e.g., I235A), H310 (e.g., H310A), and/or H435 (e.g., H435A), numbered according to the EU index as in Kabat.

Antibody Characterization

In some embodiments, antibodies of the present disclosure may be identified, selected, or excluded based on different characteristics. Such characteristics may include, but are not limited to, physical and functional characteristics. Physical characteristics may include features of antibody structures [e.g., amino acid sequence or residues; secondary, tertiary, or quaternary protein structure; post-translational modifications (e.g., glycosylations); chemical bonds, and stability]. Functional characteristics may include, but are not limited to, antibody affinity (i.e., for specific epitopes and/or antigens) and antibody activity (e.g., antibody ability to activate or inhibit a target, process, or pathway).

Antibody Binding and Affinity

In some embodiments, antibodies of the present disclosure may be identified, selected, or excluded based on binding and/or level of affinity for specific epitopes and/or antigens. Antibody binding and/or affinity level may be assessed with different antigen formats. In some embodiments, antibody affinity for different antigen formats may be tested in vitro (e.g., by ELISA). Anti-tau antibody in vitro testing may be carried out using brain samples or fractions. Such samples or fractions may be obtained from subjects with AD (e.g., human AD patients). In some embodiments, brain samples or fractions may be obtained from non-human subjects. Such non-human subjects may include non-human animals used in AD disease model studies (e.g., mice, rats, and primates). In some embodiments, brain samples or fractions used for antibody affinity testing may be derived from TG4510/P301S mouse strains. Antibody affinity may be compared against control samples lacking the particular antigen for which affinity is being analyzed. In some embodiments, control samples used for anti-tau antibody testing may include brain samples or fractions from non-diseased human subjects. In some embodiments, brain samples or fractions from wild type and/or Tau knockout mouse strains may be used as control samples.

In vitro affinity testing may be carried out (e.g., by ELISA) using recombinant or isolated protein antigens. For example, recombinant or isolated ePHF may be used for anti-tau antibody affinity testing. In some embodiments, anti-tau antibodies of the present disclosure may exhibit a half maximal effective concentration (EC50) of from about 0.01 nM to about 100 nM for binding to ePHF when assessed by ELISA. In some embodiments, the exhibited EC50 may be less than about 50 nM, less than about 20 nM, less than about 10 nM, or less than about 1 nM. In some embodiments, anti-tau antibodies of the present disclosure may exhibit an EC50 of from about 0.01 nM to about 100 nM for binding to any of the antigens listed in Table 4, or an epitope that includes or is included within any of the antigens (including, but not limited to conformational epitopes), when assessed by ELISA. In some embodiments, the exhibited EC50 may be less than about 50 nM, less than about 20 nM, less than about 10 nM, or less than about 1 nM.

In some embodiments, anti-tau antibodies of the present disclosure bind to pathological tau, but do not bind to non-pathological tau. Such antibodies may be referred to herein as being "selective" for pathological forms of tau. In some embodiments, anti-tau antibodies of the present disclosure bind to tau tangles.

In some embodiments, antibody affinity analysis may be used to identify, select, or exclude polyspecific antibodies.

As used herein, the term "polyspecific antibody" refers to an antibody with affinity for more than one epitope or antigen. In some embodiments, polyspecific antibodies may be identified, selected, or excluded based on relative affinity for each epitope or antigen recognized. For example, a polyspecific antibody may be selected for use or further development based on higher affinity for one epitope or antigen over a second epitope or antigen for which the polyspecific antibody demonstrates affinity.

In some embodiments, anti-tau antibodies may be tested for competition with other anti-tau antibodies. Such testing may be carried out to provide information on the specific epitope recognized by an antibody and may yield information related to level of epitope affinity in comparison to the competing antibody. In some embodiments, anti-tau antibodies used in antibody binding and/or affinity analysis may include anti-tau antibody PT3, as described in U.S. Pat. No. 9,371,376; anti-tau antibody C10.2, as described in U.S. Pat. No. 10,196,439 (referred to as antibody "C10-2," therein); anti-tau antibody IPN002, as described in U.S. Pat. No. 10,040,847; anti-tau antibody AT8 (ThermoFisher, Waltham, MA); anti-tau antibody AT100 (ThermoFisher, Waltham, MA); anti-tau antibody AT120 as described in U.S. Pat. No. 5,843,779; or anti-tau antibody PT76, as described in Vandermeeren, M. et al., J Alzheimers Dis. 2018; 65(1):265-281.

Antibody Activity

In some embodiments, antibodies of the present disclosure may be identified, selected, or excluded based on their ability to promote or reduce a certain activity. Antibody activity may be assessed using analytical assays. Such assays may be selected or designed to detect, screen, measure, and/or rank antibodies based on such antibody activity.

Anti-tau antibodies may be characterized by ability to inhibit tau aggregation. Inhibition may be based on physical disruption of tau aggregation or may be based on anti-tau antibody-dependent depletion (immunodepletion) of tau protein. Characterization based on tau aggregation inhibition may be assessed using one or more assays of tau aggregation. In some embodiments, anti-tau antibodies may be characterized by tau seeding assay. Tau seeding assays typically involve in vitro initiation of tau aggregation and assessment of aggregation inhibition by candidate compounds being tested. Tau seeding assays may be carried out using tau aggregation biosensor cells. Tau aggregation biosensor cells yield a detectable signal (e.g., a fluorescent signal) in response to tau aggregation. Tau aggregation biosensor cells may be cultured with recombinant or isolated tau or with samples from high tau brain tissues or fluids (to promote tau aggregation) and treated with or without candidate compounds to assess tau aggregation inhibition. In some embodiments, anti-tau antibodies may be used to deplete tau from media prior to incubation with biosensor cells. Aggregation levels with depleted media may be compared to aggregation levels with non-depleted media to assess anti-tau antibody inhibitory function. Tau aggregation biosensor cells may include, but are not limited to, tau RD Biosensor cells. In some embodiments, neurons expressing human tau may be used.

In some embodiments, anti-tau antibodies of the present disclosure may inhibit tau aggregation with a half maximal inhibitory concentration (IC50) of from about 1 nM to about 30 nM as determined by immunodepletion assay (e.g., using tau RD Biosensor cells).

Antibody Structure and Variations

Antibodies of the present disclosure may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. Polypeptides smaller than about 50 amino acids may be referred to using the term "peptide." Peptides may be at least about 2, 3, 4, or at least 5 amino acid residues long. Polypeptides of the present disclosure may include gene products, naturally occurring polypeptides, synthetic polypeptides, homologs, orthologs, paralogs, fragments, or other equivalents, variants, and analogs of the foregoing. Polypeptides may be single molecules or may be multi-molecular complexes such as dimers, trimers, or tetramers. Polypeptides may also include single chain or multichain polypeptides, which may be associated or linked. Polypeptides may include amino acid polymers in which one or more amino acid residues are artificial chemical analogues of corresponding naturally occurring amino acids.

The term "polypeptide variant" refers to molecules which differ in their amino acid sequence from a native or reference sequence. Amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphorylated threonine and/or phosphorylated serine. Alternatively, variant mimics may result in deactivation or in an inactivated product containing the mimic, e.g., phenylalanine may act as an inactivating substitution for tyrosine; or alanine may act as an inactivating substitution for serine.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least 70%, at least 75%, at least 80%, at least 85%, at least 90%, at least 95%, at least 96%, at least 97%, at least 98%, at least 99%, at least 99.5% at least 99.8%, or at least 99.9% sequence identity as compared to a native sequence.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

The present disclosure contemplates variants and derivatives of antibodies presented herein. These include substitutional, insertional, deletion and covalent variants and derivatives. For example, sequence tags or amino acids, such as one or more lysines, may be added to antibody peptide sequences (e.g., at the N-terminal or C-terminal ends). Sequence tags may be used for peptide purification or localization. Lysines may be used to increase peptide solubility or to allow for biotinylation. Alternatively, amino acid residues located at the carboxy and amino terminal regions of the amino acid sequence of a peptide or polypeptide may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

The term "functional variant" refers to a polypeptide variant or a polynucleotide variant that has at least one activity of the reference sequence.

"Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting polypeptides that have been modified with an organic proteinaceous or non-proteinaceous derivatizing agent, and post-translational modifications. Covalent modifications are traditionally introduced by reacting targeted amino acid residues of a polypeptide with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of antibodies for immunoaffinity purification.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in polypeptides used in accordance with the present disclosure.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W. H. Freeman & Co., San Francisco, pp. 79-86 (1983)).

Covalent derivatives specifically include fusion molecules in which polypeptides are covalently bonded to non-proteinaceous polymers. Non-proteinaceous polymers may include hydrophilic synthetic polymers, i.e., polymers not otherwise found in nature. However, polymers which exist in nature and are produced by recombinant or in vitro methods are useful, as are polymers which are isolated from nature. Hydrophilic polyvinyl polymers may include polyvinylalcohol and/or polyvinylpyrrolidone. Particularly useful are polyvinylalkylene ethers such a polyethylene glycol and polypropylene glycol. Polypeptides may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337, the contents of each of which are herein incorporated by reference in their entirety.

"Features" when referring to polypeptides are defined as distinct amino acid sequence-based components of a molecule. Polypeptide features may include surface manifestations, local conformational shape, folds, loops, half-loops, domains, half-domains, sites, termini or any combination thereof.

As used herein when referring to polypeptides the term "surface manifestation" refers to an amino acid-based component of a polypeptide appearing on an outermost surface.

As used herein when referring to polypeptides the term "local conformational shape" means an amino acid-based structural manifestation of a polypeptide which is located within a definable space of the polypeptide.

As used herein when referring to polypeptides the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to polypeptide conformation means a bend which alters the direction of the backbone of a peptide or polypeptide and may involve one, two, three or more amino acid residues.

As used herein when referring to polypeptides the term "loop" refers to a structural feature of a peptide or polypeptide which reverses the direction of the backbone of a peptide or polypeptide and includes four or more amino acid residues. Oliva et al. have identified at least 5 classes of polypeptide loops (J. Mol Biol 266 (4): 814-830; 1997, the contents of which are herein incorporated by reference in their entirety).

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to include an odd number of amino acids, a half-loop of the odd-numbered loop will include the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+1-0.5 being 3 or 4).

As used herein when referring to polypeptides the term "domain" refers to a motif of a polypeptide having one or more identifiable structural or functional characteristics or properties (e.g., binding capacity), serving as a site for protein-protein interactions.

As used herein when referring to polypeptides the term "half-domain" means portion of an identified domain having at least half the number of amino acid resides as the domain from which it is derived. It is understood that domains may not always contain an even number of amino acid residues. Therefore, in those cases where a domain contains or is identified to include an odd number of amino acids, a half-domain of the odd-numbered domain will include the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+1-0.5 being 3 or 4). It is also understood that sub-domains may be identified within domains or half-domains, these subdomains possessing less than all of the structural or functional properties identified in the domains or half domains from which they were derived. It is also understood that the amino acids of any of the domain types herein need not be contiguous along the backbone of the polypeptide (i.e., nonadjacent amino acids may fold structurally to produce a domain, half-domain or subdomain).

As used herein when referring to polypeptides, the term "site" is synonymous with "amino acid residue" and "amino acid side chain." A site represents a position on a polypeptide that may be modified, manipulated, altered, derivatized or varied within the polypeptide.

As used herein the terms "termini or terminus" when referring to polypeptides refers to an extremity of a peptide or polypeptide. Such extremity is not limited only to the first or final site of the peptide or polypeptide but may include additional amino acids in the terminal regions. Polypeptide based molecules of the present disclosure may be characterized as having both an N-terminus (terminated by an amino acid with a free amino group) and a C-terminus (terminated by an amino acid with a free carboxyl group). Proteins of the present disclosure are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Antibody Modification

Antibodies may be modified to obtain variants with one or more altered properties. Such properties may include or relate to antibody structure, function, affinity, specificity, protein folding, stability, manufacturing, expression, and/or immunogenicity (i.e., immune reactions in subjects being treated with such antibodies). In some embodiments, antibody fragments or variants may be used to modify another antibody or may be incorporated into a synthetic antibody.

Antibody modification may include amino acid sequence modifications. Such modifications may include, but are not limited to, amino acid deletions, additions, and/or substitutions. Modifications may be informed by amino acid sequence analysis. Such analysis may include alignment of amino acid sequences between different antibodies or antibody variants. Two or more antibodies may be compared to identify residues or regions suitable for modification. Compared antibodies may include those binding to the same epitope. Compared antibodies may bind to different epitopes (separate or overlapping) of the same protein or target (e.g., to identify residues or regions conferring specificity to specific epitopes). Comparisons may include light and/or heavy chain sequence variation analysis, CDR sequence variation analysis, germline sequence analysis, and/or framework sequence analysis. Information obtained from such analysis may be used to identify amino acid residues, segments of amino acids, amino acid side chains, CDR lengths, and/or other features or properties that are conserved or variable among antibodies binding to the same or different epitopes.

Functional Modifications

In some embodiments, antibodies of the present disclosure be modified to optimize one or more functional properties (e.g., antibody affinity or activity). Non-limiting examples of antibody functional properties include epitope or antigen affinity, ability to mobilize or immobilize targets, and ability to activate or inhibit a target, process, or pathway. In some embodiments, functional properties include or relate to ability to modulate protein-protein interactions, protein aggregation, enzyme activity, receptor-ligand interactions, cellular signaling pathways, proteolytic cascades, and/or biological or physiological responses.

Antibody modifications may optimize antibodies by modulating epitope affinity. Such modifications may be carried out by affinity maturation. Affinity maturation technology is used to identify sequences encoding CDRs with highest affinity for target antigens. In some embodiments, antibody display technologies (e.g., phage or yeast) may be used. Such methods may include mutating nucleotide sequences encoding parental antibodies being optimized. Nucleotide sequences may be mutated randomly as a whole or to vary expression at specific amino acid residues to create millions to billions of variants. Sites or residues may be selected for mutation based on sequences or amino acid frequencies observed in natural human antibody repertoires. Variants may be subjected to repeated rounds of affinity screening [e.g., using display library screening technologies, surface plasmon resonance technologies, fluorescence-associated cell sorting (FACS) analysis, enzyme-linked immunosorbent assay (ELISA), etc.] for target antigen binding. Repeated rounds of selection, mutation, and expression may be carried out to identify antibody fragment sequences with highest affinity for target antigens. Such sequences may be directly incorporated into antibody sequences for production. In some cases, the goal of affinity maturation is to increase antibody affinity by at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100 fold, at least 500-fold, at least 1,000-fold, or more than 1,000-fold as compared to the affinity of an original or starting antibody. In cases where affinity is less than desired, the process may be repeated.

In some embodiments, antibody affinity may be assessed with different antigen formats. In some embodiments, antibody affinity for different antigen formats may be tested in vitro (e.g., by ELISA). In vitro testing may be carried out using brain samples or fractions. Such samples or fractions may be obtained from subjects with AD (e.g., human AD patients). In some embodiments, brain samples or fractions may be obtained from non-human subjects. Such non-human subjects may include non-human animals used in AD disease model studies (e.g., mice, rats, and primates). In some embodiments, brain samples or fractions used for antibody affinity testing may be derived from TG4510/P301S mouse strains. Antibody affinity may be compared against control samples lacking the particular antigen for which affinity is being analyzed. In some embodiments, control samples may include brain samples or fraction from non-diseased human subjects. In some embodiments, brain samples or fractions from wild type and/or Tau knockout mouse strains may be used as control samples. In vitro affinity testing may be carried out (e.g., by ELISA) using recombinant or isolated protein antigens. In some embodiments, recombinant or isolated ePHF is used for antibody affinity testing. In some embodiments, antigens listed in Table 4 may be used.

In some embodiments, antibody affinity analysis may be used to modulate antibody polyspecificity (e.g., to reduce or enhance antibody polyspecificity). Such modulation may include modulating relative affinity for two or more epitopes or antigens. For example, antibodies may be optimized for higher affinity for one epitope or antigen over a second epitope or antigen.

Antibodies may be modified to optimize antibody functional properties. Such functional properties may be assessed or engineered based on analytical assay results relating to one or more antibody functional properties. Assays may be used to screen multiple antibodies to identify or rank antibodies based on functional criteria. Anti-tau antibodies may be modified to optimize tau aggregation inhibition. Such inhibition may be based on physical disruption of tau aggregation or may be based on the ability of anti-tau antibodies to deplete tau protein from assay samples. Optimization based on tau aggregation inhibition may be assessed using one or more assays of tau aggregation (e.g., by tau seeding assay).

Production Modifications

In some embodiments, modifications may be made to optimize antibody production. Such modifications may include or relate to one or more of protein folding, stability, expression, and/or immunogenicity. Modifications may be carried out to address one or more antibody features negatively impacting production. Such features may include, but are not limited to, unpaired cysteines or irregular disulfides; glycosylation sites (e.g., N-linked NXS/T sites); acid cleavage sites, amino acid oxidation sites, conformity with mouse germline sequences; asparagine deamidation sites; aspartate isomerization sites; N-terminal pyroglutamate formation sites; and aggregation-prone amino acid sequence regions (e.g., within CDR sequences).

Methods of Production

In some embodiments, antibodies of the present disclosure may be prepared using recombinant DNA technology (e.g., see U.S. Pat. No. 4,816,567, which is hereby incorporated by reference in its entirety). Antibody-encoding DNA may be isolated and sequenced using conventional procedures (e.g., by using oligonucleotide probes that are capable of binding specifically to genes encoding the heavy and light chains of murine antibodies). In some embodiments, hybridoma cells may be used as a preferred source of DNA. Once isolated, the DNA can be placed into expression vectors, which are then transfected into host cells. Host cells may include, but are not limited to HEK293 cells, HEK293T cells, simian COS cells, Chinese hamster ovary (CHO) cells, and myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide.

Methods for producing the anti-tau antibodies described herein include, for example, expressing the heavy chain and the light chains of the antibody in a cell line comprising the nucleic acid sequences or vector(s) (e.g., expression vector(s)) expressing the heavy chain and light chains. Host cells comprising these nucleic acid sequences (e.g., the nucleic acid sequences described herein, such as in Table 1) are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region (e.g., a constant region listed in Table 5) or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3), e.g., a heavy chain constant region described in Table 5. The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region, as discussed supra. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL, e.g., a light chain constant region described in Table 5. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, as discussed supra.

To express the antibodies described herein, nucleic acids encoding partial or full-length light and heavy chains, or a combination of nucleic acids encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the V H segment is operatively linked to the C H segment(s) within the vector and the V L segment is operatively linked to the C L segment within the vector.

Additionally, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

For expression of the light and heavy chains, the expression vector (e.g., when nucleic acids encoding the light and heavy chains are present in one vector), or combination of expression vectors (e.g., when the nucleic acid encoding the light chain is present in one vector, and the nucleic acid encoding the heavy chain is present in a separate vector), is transfected into a host cell by standard techniques. The various forms of the term "transfection" are intended to encompass a wide variety of techniques commonly used for the introduction of exogenous DNA into a prokaryotic (bacterial host cell) or eukaryotic host cell, e.g., electroporation, calcium-phosphate precipitation, DEAE-dextran transfection and the like.

Exemplary mammalian cells for expressing the recombinant antibodies described herein include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibody Humanization

In some embodiments, anti-tau antibodies of the present disclosure may be prepared as humanized antibodies. "Humanized" antibodies are chimeric antibodies that contain minimal sequences (e.g., variable domains or CDRs) derived from non-human immunoglobulins (e.g., murine immunoglobulins). Humanized antibodies may be prepared from human (recipient) immunoglobulins in which residues from the hypervariable regions are replaced by hypervariable region residues from one or more non-human "donor" antibodies (e.g., mouse, rat, rabbit, or nonhuman primate). Donor antibodies may be selected based on desired specificity, affinity, and/or capacity. Humanized antibodies may include one or more back-mutation that includes the reversion of one or more amino acids back to amino acids found in a donor antibody. Conversely, residues from donor antibodies included in humanized antibodies may be mutated to match residues present in human recipient antibodies. Back-mutations may be introduced to reduce human immune response to the humanized antibodies. In some embodiments, back-mutations are introduced to avoid issues with antibody manufacturing (e.g., protein aggregation or post-translational modification).

For construction of expression plasmids encoding fully humanized antibodies with human constant regions, DNA sequences encoding antibody variable regions may be inserted into expression vectors (e.g., mammalian expression vectors) between an upstream promoter/enhancer and immunoglobulin signal sequence and a downstream immunoglobulin constant region gene. DNA samples may then be transfected into mammalian cells for antibody production. Constant domains from any class of human antibody may be used. There are five major classes of intact human antibodies: IgA, IgD, IgE, IgG, and IgM, and several of these may be further divided into subclasses (isotypes), e.g., IgG1, IgG2a, IgG2b, IgG2c, IgG3, IgG4, IgA, and IgA2.

Cell lines with stable transfection of DNA encoding humanized antibodies may be prepared and used to establish stable cell lines. Cell lines producing humanized antibodies may be expanded for expression of humanized antibodies that may be harvested and purified from cell culture media.

In some embodiments, humanized antibodies of the present disclosure may have cross-reactivity with non-human species. Species cross-reactivity may allow antibodies to be used in different animals for various purposes. For example, cross-reactive antibodies may be used in pre-clinical animal studies to provide information about antibody efficacy and/or toxicity. Non-human species may include, but are not limited to, mouse, rat, rabbit, dog, pig, goat, sheep, and nonhuman primates (e.g., Cynomolgus monkeys).

Antibody Conjugates

In some embodiments, antibodies of the present disclosure may be or be prepared as antibody conjugates. As used herein, the term "conjugate" refers to any agent, cargo, or chemical moiety that is attached to a recipient entity or the process of attaching such an agent, cargo, or chemical moiety. As used herein, the term "antibody conjugate" refers to any antibody with an attached agent, cargo, or chemical moiety. Conjugates utilized to prepare antibody conjugates may include therapeutic agents. Such therapeutic agents may include drugs. Antibody conjugates that include a conjugated drug are referred to herein as "antibody drug conjugates." Antibody drug conjugates may be used to direct conjugated drugs to specific targets based on the affinity of associated antibodies for proteins or epitopes associated with such targets. Such antibody drug conjugates may be used to localize biological activity associated with such conjugated drugs to targeted cells, tissues, organs, or other targeted entities. In some embodiments, conjugates utilized to prepare antibody conjugates include detectable labels. Antibodies may be conjugated with detectable labels for purposes of detection. Such detectable labels may include, but are not limited to, radioisotopes, fluorophores, chromophores, chemiluminescent compounds, enzymes, enzyme co-factors, dyes, metal ions, ligands, biotin, avidin, streptavidin, haptens, quantum dots, or any other detectable labels known in the art or described herein.

Conjugates may be attached to antibodies directly or via a linker. Direct attachment may be by covalent bonding or by non-covalent association (e.g., ionic bonds, hydrostatic bonds, hydrophobic bonds, hydrogen bonds, hybridization, etc.). Linkers used for conjugate attachment may include any chemical structure capable of connecting an antibody to a conjugate. In some embodiments, linkers include polymeric molecules (e.g., nucleic acids, polypeptides, polyethylene glycols, carbohydrates, lipids, or combinations thereof). Antibody conjugate linkers may be cleavable (e.g., through contact with an enzyme, change in pH, or change in temperature).

II. Formulation and Delivery

Pharmaceutical Compositions

Compounds disclosed herein may be prepared as pharmaceutical compositions. As used herein the term "pharmaceutical composition" refers to compositions including at least one active ingredient and, most often, a pharmaceutically acceptable excipient.

Relative amounts of the active ingredient (e.g. an antibody), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may include between 0.1% and 99% (w/w) of the active ingredient. By way of example, the composition may include between 0.1% and 100%, e.g., between 0.5 and 50%, between 1-30%, between 5-80%, at least 80% (w/w) active ingredient.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients, or subjects.

Formulations

Compounds of the present disclosure can be formulated using one or more excipients to: (1) increase stability; (2) increase cell permeability; (3) permit the sustained or delayed release (e.g., from a sustained release formulation); and/or (4) alter the biodistribution (e.g., target an antibody to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present disclosure can include, without limitation, liposomes, lipid nanoparticles, polymers, lipoplexes, core-shell nanoparticles, peptides, proteins, transfected cells (e.g., for transplantation into a subject) and combinations thereof.

Pharmaceutical compositions described herein may be prepared by methods known or hereafter developed in the art of pharmacology. Such preparatory methods may include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition including a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of active ingredient (e.g. antibody), pharmaceutically acceptable excipients, and/or any additional ingredients in pharmaceutical compositions in accordance with the present disclosure may vary, depending upon the identity, size, and/or condition of subjects being treated and further depending upon route of administration. For example, compositions may include between 0.1% and 99% (w/w) of active ingredient. By way of example, compositions may include between 0.1% and 100%, e.g., between 0.5 and 50%, between 1-30%, between 5-80%, or at least 80% (w/w) active ingredient.

According to the present disclosure, compounds may be formulated for CNS delivery. Agents that cross the brain blood barrier may be used. For example, some cell penetrating peptides that can target molecules to the brain blood barrier endothelium may be used for formulation (e.g., Mathupala, *Expert Opin Ther Pat.,* 2009, 19, 137-140; the content of which is incorporated herein by reference in its entirety).

Excipients and Diluents

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by the United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparation are known in the art (see Remington: The Science and Practice of Pharmacy, 21st Edition, A. R. Gennaro, Lippincott, Williams & Wilkins, Baltimore, M D, 2006; incorporated herein by reference in its entirety). The use of conventional excipient media may be contemplated within the scope of the present disclosure, except insofar as any conventional excipient media may be incompatible with certain substances or their derivatives, such as by producing any undesirable biological effects or otherwise interacting in a deleterious manner with any other component(s) of pharmaceutical compositions of the present disclosure.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Inactive Ingredients

In some embodiments, formulations of the present disclosure may include at least one inactive ingredient. As used herein, the term "inactive ingredient" refers to an agent that does not contribute to the activity of a pharmaceutical composition. In some embodiments, all, none or some of the inactive ingredients which may be used in formulations of the present disclosure may be approved by the US Food and Drug Administration (FDA).

Formulations disclosed herein may include cations or anions. Formulations may include $Zn^{2+}$, $Ca^{2+}$, $Cu^{2+}$, $Mn^{2+}$, $Mg^{+}$, or combinations thereof. As a non-limiting example, formulations may include polymers and complexes with metal cations (See e.g., U.S. Pat. Nos. 6,265,389 and 6,555,525, each of which is herein incorporated by reference in its entirety).

III. Administration and Dosing

Administration

Compounds and compositions of the present disclosure may be administered by any delivery route which results in a therapeutically effective outcome. These include, but are not limited to, enteral (into the intestine), gastroenteral, epidural (into the dura mater), oral (by way of the mouth), transdermal, intracerebral (into the cerebrum), intracerebroventricular (into the cerebral ventricles), epicutaneous (application onto the skin), intradermal (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraparenchymal (into the substance of a tissue, e.g., brain tissue), intraperitoneal (infusion or injection into the peritoneum), intravesical infusion, intravitreal (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna *magna* cerebellomedularis), intracorneal (within the cornea), dental intracoronal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis, and spinal.

In some embodiments, compositions may be administered in a way which allows them to cross the blood-brain barrier, vascular barrier, or other epithelial barrier. Compounds and compositions of the present disclosure may be administered in any suitable form, including, but not limited to, as a liquid solution, as a suspension, or as a solid form suitable for liquid solution or suspension in a liquid solution.

In some embodiments, delivery to a subject may be via a single route administration. In some embodiments, delivery to a subject may be via multi-site route of administration. Administration may include a bolus infusion. Administration may include sustained delivery over a period of minutes, hours, or days. Administration by infusion may include an infusion rate that may be changed depending on the subject, distribution, formulation, or other delivery parameter. Administration may be by more than one route of administration. As non-limiting examples, combination administrations may include intrathecal and intracerebroventricular administration, or intravenous and intraparenchymal administration.

Intravenous Administration

Compounds and compositions of the present disclosure may be administered to a subject by systemic administration. Systemic administration may include intravenous administration. Systemic administration may include intraarterial administration.

Compounds and compositions of the present disclosure may be administered to a subject by intravenous administration. Intravenous administration may be achieved by subcutaneous delivery. Intravenous administration may be achieved by a tail vein injection (e.g., in a mouse model). Intravenous administration may be achieved by retro-orbital injection.

Administration to the CNS

Compounds and compositions of the present disclosure may be administered to a subject by direct injection into the brain. As a non-limiting example, the brain delivery may be by intrahippocampal administration. Administration may be by intraparenchymal administration. In one embodiment, the intraparenchymal administration is to tissue of the central nervous system. Administration may be by intracranial delivery (See, e.g., U.S. Pat. No. 8,119,611; the content of which is incorporated herein by reference in its entirety). Administration may be by injection into the CSF pathway. Non-limiting examples of delivery to the CSF pathway include intrathecal and intracerebroventricular administration. Administration to the brain may be by systemic delivery. As a non-limiting example, the systemic delivery may be by intravascular administration. As a non-limiting example, the systemic or intravascular administration may be intravenous. Administration may be by intraocular delivery route. A non-limiting example of intraocular administration includes an intravitreal injection.

Dose and Regimen

The present disclosure provides methods of administering compounds and compositions in accordance with the disclosure to a subject in need thereof. Administration may be in any amount and by any route of administration effective for preventing, treating, managing, or diagnosing diseases, disorders, and/or conditions. The exact amount required may vary from subject to subject, depending on species, age, general condition of the subject, severity of disease, particular composition, mode of administration, mode of activity, and the like. Subjects may be, but are not limited to, humans, mammals, or animals. Compositions may be formulated in unit dosage form for ease of administration and uniformity of dosage. It will be understood, however, that the total daily usage of compositions of the present disclosure may be decided by an attending physician within the scope of sound medical judgment. Specific therapeutically effective, prophylactically effective, or appropriate diagnostic dose levels for any particular individual may vary depending upon a variety of factors including the disorder being treated and severity of the disorder; the activity of specific payloads employed; specific compositions employed; age, body weight, general health, sex, and diet of patients; time of administration, route of administration, and rate of excretion of compounds and compositions employed; duration of treatment; drugs used in combination or coincidental with compounds and compositions employed; and like factors well known in the medical arts.

In certain embodiments, compounds and compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect.

In certain embodiments, the desired dosage may be delivered using multiple administrations (e.g., two, three, four, or more than four administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

Compounds and compositions of the present disclosure may be administered as a "pulse dose" or as a "continuous flow." As used herein, a "pulse dose" is a series of single unit doses of any therapeutic agent administered with a set frequency over a period of time. As used herein, a "continuous flow" is a dose of therapeutic agent administered continuously for a period of time in a single route/single point of contact, i.e., continuous administration event. A total daily dose, an amount given or prescribed in a 24-hour period, may be administered by any of these methods, or as a combination of these methods, or by any other methods suitable for pharmaceutical administration.

Combinations

Compounds and compositions of the present disclosure may be used in combination with one or more other therapeutic, prophylactic, research or diagnostic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, research, or diagnostic compositions in combination with agents that may improve their bioavailability, reduce and/or modify their metabolism, inhibit their excretion, and/or modify their distribution within the body.

IV. Methods and Uses of the Compositions

In some embodiments, the present disclosure provides methods related to using and evaluating compounds and compositions for therapeutic and diagnostic applications.

Therapeutic Applications

In some embodiments, methods of the present disclosure include methods of treating therapeutic indications using compounds and/or compositions disclosed herein. As used herein, the term "therapeutic indication" refers to any symptom, condition, disorder, or disease that may be alleviated, stabilized, improved, cured, or otherwise addressed by some form of treatment or other therapeutic intervention. In some embodiments, methods of the present disclosure include treating therapeutic indications by administering antibodies disclosed herein. In some embodiments, the therapeutic indication is a neurological, e.g., neurodegenerative disorder, a disease associated with tau expression or activity, and/or a tau-related disease (e.g., a tauopathy).

As used herein the terms "treat," "treatment," and the like, refer to relief from or alleviation of pathological processes. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

By "lower" or "reduce" in the context of a disease marker or symptom is meant a significant decrease in such a level, often statistically significant. The decrease may be, for example, at least 10%, at least 20%, at least 30%, at least 40% or more, and is preferably down to a level accepted as within the range of normal for an individual without such a disorder.

By "increase" or "raise" in the context of a disease marker or symptom is meant a significant rise in such level, often statistically significant. The increase may be, for example, at least 10%, at least 20%, at least 30%, at least 40% or more, and is preferably up to a level accepted as within the range of normal for an individual without such disorder.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a compound or composition described herein, "effective against" a disease or disorder indicates that administration in a clinically appropriate manner results in a beneficial effect for at least a fraction of patients, such as an improvement of symptoms, a cure, a reduction in disease load, reduction in protein aggregation, reduction in neurofibrillary tangles, reduction in neurodegeneration, extension of life, improvement in quality of life, or other effect generally recognized as positive by medical doctors familiar with treating the particular type of disease or disorder.

A treatment or preventive effect is evident when there is a significant improvement, often statistically significant, in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more may be indicative of effective treatment. Efficacy for a given compound or composition may also be judged using an experimental animal model for the given disease as known in the art. When using an experimental animal model, efficacy of treatment is evidenced when a statistically significant modulation in a marker or symptom is observed.

Compounds of the present disclosure and additional therapeutic agents and/or therapies can be administered in combination. Such combinations may be in the same composition, or the additional therapeutic agents can be administered as part of a separate composition or by another method described herein. In some embodiments, the additional therapeutic agent and/or therapy is a therapeutic agent and/or therapy that is suitable for treating or preventing a neurological, e.g., neurodegenerative disorder, a disease associated with tau expression or activity, and/or a tau-related disease (e.g., a tauopathy). In some embodiments, the additional therapeutic agent and/or therapy is a cholinesterase inhibitor (e.g., donepezil, rivastigmine, and/or galantamine), an N-methyl D-aspartate (NMDA) antagonist (e.g., memantine), an antipsychotic drug, an anti-anxiety drug, an anticonvulsant, a dopamine agonist (e.g., pramipexole, ropinirole, rotigotine, and/or apomorphine), an MAO B inhibitor (e.g., selegiline, rasagiline, and/or safinamide), catechol O-methyltransferase (COMT) inhibitors (entacapone, opicapone, and/or tolcapone), anticholinergics (e.g., benztropine and/or trihexyphenidyl), amantadine, carbidopa-levodopa, deep brain simulation (DBS), or a combination thereof.

In some embodiments, therapeutic indications that may be addressed by methods of the present disclosure include neurological indications. As used herein, a "neurological indication" refers to any therapeutic indication relating to the central nervous system (CNS). Methods of treating neurological indications according to the present disclosure may include administering compounds (e.g., antibodies) and/or compositions described herein. Neurological indications may include neurological diseases and/or disorders involving irregular expression or aggregation of tau. Such indications may include, but are not limited to neurodegenerative disease, Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), a prion disease, Creutzfeldt-Jakob disease (CJD), multiple system atrophy, tangle-only dementia, stroke, and progressive subcortical gliosis.

In some embodiments, methods of treating neurological diseases and/or disorders in a subject in need thereof may include one or more of the steps of: (1) deriving, generating, and/or selecting an anti-tau antibody or fragment or composition thereof; and (2) administering the anti-tau antibody or fragment or composition thereof to the subject. Administration to the subject may slow, stop, or reverse disease progression. As a non-limiting example, disease progression may be measured by cognitive tests such as, but not limited to, the Mini-Mental State Exam (MMSE) or other similar diagnostic tool(s), known to those skilled in the art. As another non-limiting example, disease progression may be measured by change in the pathological features of the brain, CSF or other tissues of the subject, such as, but not limited to a decrease in levels of tau (either soluble or insoluble). In some embodiments, levels of insoluble hyperphosphorylated tau are decreased. In some embodiments, levels of soluble tau are decreased. In some embodiments, both soluble and insoluble tau are decreased. In some embodiments, levels of insoluble hyperphosphorylated tau are increased. In some embodiments, levels of soluble tau are increased. In some embodiments, both insoluble and soluble tau levels are increased. In some embodiments, neurofibrillary tangles are decreased in size, number, density, or combination thereof. In another embodiment, neurofibrillary tangles are increased in size, number, density or combination thereof.

Neurodegeneration

Neurodegenerative disease refers to a group of conditions characterized by progressive loss of neuronal structure and function, ultimately leading to neuronal cell death. Neurons are the building blocks of the nervous system(s) and are generally not able to reproduce and/or be replaced, and therefore neuron damage and/or death is especially devastating. Other, non-degenerating diseases that lead to neuronal cell loss, such as stroke, have similarly debilitating outcomes. Targeting molecules that contribute to deteriorating cell structure or function may prove beneficial generally for treatment of neurological indications, including neurodegenerative disease and stroke.

Certain molecules are believed to have inhibitory effects on neurite outgrowth, contributing to the limited ability of the central nervous system to repair damage. Such molecules include, but are not limited to, myelin associated proteins, such as, but not limited to, RGM (Repulsive guidance molecule), NOGO (Neurite outgrowth inhibitor), NOGO receptor, MAG (myelin associated glycoprotein), and MAI (myelin associated inhibitor). In some embodiments, anti-tau antibodies of the present disclosure may be utilized to target the aforementioned antigens (e.g., neurite outgrowth inhibitors).

Many neurodegenerative diseases are associated with aggregation of misfolded proteins, including, but not limited to, alpha synuclein, tau (as in tauopathies), amyloid (3, prion proteins, TDP-43, and huntingtin (see, e.g. De Genst et al., 2014, Biochim Biophys Acta; 1844(11):1907-1919, and Yu et al., 2013, Neurotherapeutics; 10(3): 459-472, references therein, all of which are herein incorporated by reference in their entirety). The aggregation results from disease-specific conversion of soluble proteins to an insoluble, highly ordered fibrillary deposit. This conversion is thought to prevent the proper disposal or degradation of misfolded proteins, thereby leading to further aggregation. Conditions associated with alpha synuclein misfolding and aggregation are referred to as "synucleinopathies." In some embodiments, anti-tau antibodies of the present disclosure may be utilized to target misfolded or aggregated proteins.

Alzheimer's Disease

Alzheimer Disease (AD) is a debilitating neurodegenerative disease currently afflicting more than 35 million people worldwide, with that number expected to double in coming decades. Symptomatic treatments have been available for many years but these treatments do not address the underlying pathophysiology. Recent clinical trials using these and other treatments have largely failed and, to date, no known cure has been identified.

The AD brain is characterized by the presence of two forms of pathological aggregates, the extracellular plaques composed of (3-amyloid (A(3) and the intracellular neurofibrillary tangles (NFT) comprised of hyperphosphorylated microtubule associated protein tau. Based on early genetic findings, (3-amyloid alterations were thought to initiate disease, with changes in tau considered downstream. Thus, most clinical trials have been AP-centric. Although no mutations of the tau gene have been linked to AD, such alterations have been shown to result in a family of dementias known as tauopathies, demonstrating that changes in tau can contribute to neurodegenerative processes. Tau is normally a very soluble protein known to associate with microtubules based on the extent of its phosphorylation. Hyperphosphorylation of tau depresses its binding to microtubules and microtubule assembly activity. In tauopathies, the tau becomes hyperphosphorylated, misfolds and aggregates as NFT of paired helical filaments (PHF), twisted ribbons or straight filaments. In AD, NFT pathology, rather than plaque pathology, correlates more closely with neuropathological markers such as neuronal loss, synaptic deficits, severity of disease and cognitive decline. NFT pathology marches through the brain in a stereotyped manner and animal studies suggest a trans-cellular propagation mechanism along neuronal connections.

Several approaches have been proposed for therapeutically interfering with progression of tau pathology and preventing the subsequent molecular and cellular consequences. Given that NFT are composed of a hyperphosphorylated, misfolded and aggregated form of tau, interference at each of these stages has yielded the most avidly pursued set of targets. Introducing agents that limit phosphorylation, block misfolding or prevent aggregation have all generated promising results. Passive and active immunization with late stage anti-phospho-tau antibodies in mouse models have led to dramatic decreases in tau aggregation and improvements in cognitive parameters. It has also been suggested that introduction of anti-tau antibodies can prevent the trans-neuronal spread of tau pathology.

In some embodiments, anti-tau antibodies of the present disclosure may be used according to methods presented herein to treat subjects suffering from AD and other tauopathies. In some cases, methods of the present disclosure may be used to treat subjects suspected of developing AD or other tauopathies.

Frontotemporal Dementia and Parkinsonism Linked to Chromosome 17 (FTDP-17)

Although Alzheimer's disease is, in part, characterized by the presence of tau pathology, no known mutations in the tau gene have been causally linked to the disease. Mutations in the tau gene have been shown to lead to an autosomal dominantly inherited tauopathy known as frontotemporal dementia and parkinsonism linked to chromosome 17 (FTDP-17) and demonstrate that alterations in tau can lead to neurodegenerative changes in the brain. Mutations in the tau gene that lead to FTDP-17 are thought to influence splicing patterns, thereby leading to an elevated proportion of tau with four microtubule binding domains (rather than three). These molecules are considered to be more amyloidogenic, meaning they are more likely to become hyperphosphorylated and more likely to aggregate into NFT (Hutton, M. et al., 1998, Nature 393(6686):702-5, the contents of which are herein incorporated by reference in their entirety). Although physically and behaviorally, FTDP-17 patients can appear quite similar to Alzheimer's disease patients, at autopsy FTDP-17 brains lack the prominent AP plaque pathology of an AD brain (Gotz, J. et al., 2012, British Journal of Pharmacology 165(5):1246-59, the contents of which are herein incorporated by reference in their entirety). Therapeutically targeting the aggregates of tau protein may ameliorate and prevent degenerative changes in the brain and potentially lead to improved cognitive ability.

As of today, there is no treatment to prevent, slow the progression, or cure FTDP-17. Medication may be prescribed to reduce aggressive, agitated or dangerous behavior. There remains a need for therapy affecting the underlying pathophysiology, such as antibody therapies targeting tau protein.

In some embodiments, anti-tau antibodies of the present disclosure may be used to treat subjects suffering from FTDP-17. In some cases, methods of the present disclosure may be used to treat subjects suspected of developing FTDP-17.

Chronic Traumatic Encephalopathy

Unlike the genetically linked tauopathies, chronic traumatic encephalopathy is a degenerative tauopathy linked to repeated head injuries. The disease was first described in boxers whom behaved "punch drunk" and has since been identified primarily in athletes that play American football, ice hockey, wrestling and other contact sports. The brains of those suffering from CTE are characterized by distinctive patterns of brain atrophy accompanied by accumulation of hyperphosphorylated species of aggregated tau in NFT. In CTE, pathological changes in tau are accompanied by a number of other pathobiological processes, such as inflammation (Daneshvar, D. H. et al., 2015 Mol Cell Neurosci 66 (Pt B): 81-90, the contents of which are herein incorporated by reference in their entirety). Targeting the tau aggregates may provide reprieve from the progression of the disease and may allow cognitive improvement.

As of today, there is no medical therapy to treat or cure CTE. The condition is only diagnosed after death, due to lack of in vivo techniques to identify CTE specific biomarkers. There remains a need for therapy affecting the underlying pathophysiology, such as antibody therapies targeting tau protein.

In some embodiments, anti-tau antibodies of the present disclosure may be used to treat subjects suffering from CTE. In some cases, methods of the present disclosure may be used to treat subjects suspected of developing CTE.

Prion Diseases

Prion diseases, also known as transmissible spongiform encephalopathies (TSEs), are a group of rare progressive conditions affecting the nervous system. The related conditions are rare and are typically caused by mutations in the PRNP gene which enables production of the prion protein. Gene mutations lead to an abnormally structured prion protein. Alternatively, the abnormal prion may be acquired by exposure from an outside source, e.g. by consumption of beef products containing the abnormal prion protein. Abnormal prions are misfolded, causing the brain tissue to degenerate rapidly. Prion diseases include, but are not limited to, Creutzfeldt-Jakob disease (CJD), Gerstmann-Sträussler-Scheinker syndrome (GSS), fatal insomnia (FFI), variably protease-sensitive prionopathy (VPSPr), and kuru. Prion diseases are rare. Approximately 350 cases of prion diseases are diagnosed in the US annually.

CJD is a degenerative brain disorder characterized by problems with muscular coordination, personality changes including mental impairment, impaired vision, involuntary muscle jerks, weakness and eventually coma. The most common categories of CJD are sporadic, hereditary due to a genetic mutation, and acquired. Sporadic CJD is the most common form affecting people with no known risk factors for the disease. The acquired form of CJD is transmitted by exposure of the brain and nervous system tissue to the prion. As an example, variant CJD (vCDJ) is linked to a bovine spongiform encephalopathy (BSE), also known as a 'mad cow' disease. CJD is fatal and patients typically die within one year of diagnosis.

Prion diseases are associated with an infectious agent consisting of an alternative conformational isoform of the prion protein, PrPSc. PrPSc replication is considered to occur through an induction of the infectious prion in the normal prion protein (PrPC). The replication occurs without a nucleic acid.

As of today, there is no therapy to manage or cure CJD, or other prion diseases. Typically, treatment is aimed at alleviating symptoms and increasing comfort of the patient, e.g. with pain relievers. There remains a need for therapy affecting the underlying pathophysiology.

In some embodiments, anti-tau antibodies of the present disclosure may be used to treat subjects suffering from a prion disease. In some cases, methods of the present disclosure may be used to treat subjects suspected of developing a prion disease.

Diagnostic Applications

In some embodiments, compounds (e.g., antibodies) and compositions of the present disclosure may be used as diagnostics. Anti-tau antibodies may be used to identify, label, or stain cells, tissues, organs, etc. expressing tau proteins. Anti-tau antibodies may be used to identify tau proteins present in tissue sections (e.g., histological tissue sections), including tissue known or suspected of having tau protein aggregates. Such antibodies may in some cases be used to identify subjects with neurological diseases and/or disorders. Tissue sections may be from CNS tissue.

In some embodiments, diagnostic methods of the present disclosure may include the analysis of one or more cells or tissues using immunohistochemical techniques. Such methods may include the use of one or more of any of the anti-tau antibodies described herein. Immunohistochemical methods may include staining tissue sections to determine the presence and/or level of one or more tau proteins or other markers. Tissue sections may be derived from subject CNS tissue (e.g., patient CNS, animal CNS, and CNS from animal models of disease). Tissue sections may come from formalin-fixed or unfixed fresh frozen tissues. In some cases, tissue sections come from formalin fixed paraffin-embedded (FFPE) tissues. Anti-tau antibodies described herein may be used as primary antibodies. Primary antibodies are used to contact tissue sections directly and bind to target epitopes. Primary antibodies may be directly conjugated with a detectable label or may be detected through the use of a detection agent such as a secondary antibody. In some embodiments, primary antibodies or detection agents include an enzyme that can be used to react with a substrate to generate a visible product (e.g., precipitate). Such enzymes may include, but are not limited to horse radish peroxidase, alkaline phosphatase, beta-galactosidase, and catalase.

Anti-tau antibodies described herein may be used according to immunohistochemical methods of the present disclosure to detect tau proteins in tissues or cells. In some cases, these antibodies are used to detect and/or determine the level of tau proteins in tissues. Levels of anti-tau antibodies used in immunohistochemical staining techniques may be varied to increase visible staining or to decrease background levels of staining. In some embodiments, antibody concentrations of from about 0.01 μg/ml to about 50 μg/ml are used. For example, antibody concentrations of from about 0.01 μg/ml to about 1 μg/ml, from about 0.05 μg/ml to about 5 μg/ml, from about 0.1 μg/ml to about 3 μg/ml, from about 1 μg/ml to about 10 μg/ml, from about 2 μg/ml to about 20 μg/ml, from about 3 μg/ml to about 25 μg/ml, from about 4 μg/ml to about 30 μg/ml, or from about 5 μg/ml to about 50 μg/ml may be used.

Levels and/or identities of tau proteins may be determined according to any methods known in the art for identifying proteins and/or quantitating protein levels. In some embodiments, such methods may include, but are not limited to mass spectrometry, array analysis (e.g., antibody array or protein array), Western blotting, flow cytometry, immunoprecipitation, surface plasmon resonance analysis, and ELISA. Tau proteins may in some cases be immunoprecipitated from samples prior to analysis. Such immunoprecipitation may be carried out using anti-tau antibodies disclosed herein. In some embodiments, tau proteins are immunoprecipitated from biological samples using anti-tau antibodies and then identified and/or quantitated using mass spectrometry.

In some embodiments, a method for detecting tau (e.g., human tau) using the antibodies described herein comprises: (a) contacting a sample (e.g., a biological sample such as a tissue section) with an anti-tau antibody described herein for a time sufficient to allow specific binding of the anti-tau antibody to tau in the sample, and (b) contacting the sample with a detection reagent, e.g., an antibody, that specifically binds to the anti-tau antibody, such as to the Fc region of the anti-tau antibody, to thereby detect tau bound by the anti-tau antibody.

Also provided are methods of detecting the presence of tau (e.g., human tau) in a sample, or measuring the amount of tau, comprising contacting a sample (e.g., biological sample such as a tissue sample) with an anti-tau antibody described herein under conditions that allow for formation of a complex between the antibody and tau, and detecting the formation of a complex. In some embodiments, the method may also include contacting the sample with a control antibody (e.g., an isotype control antibody) in parallel, wherein the difference in complex formation between the anti-tau antibody and sample and control antibody and sample is indicative of the presence of tau in the sample. In some embodiments, the anti-tau antibodies described herein can be used to purify tau (e.g., the various phospho-tau species recognized by the anti-tau antibodies described herein) via immunoaffinity purification.

In some embodiments, treatments are informed by diagnostic information generated using anti-tau antibodies. Accordingly, the present disclosure provides methods of treating neurological diseases and/or disorders that include obtaining a sample from a subject, diagnosing one or more neurological diseases and/or disorders using an anti-tau antibody, and administering a treatment selected based on the diagnosis. Such treatments may include treatment with anti-tau antibodies. Anti-tau antibodies administered according to such methods may include any of those described herein.

In some embodiments, the present disclosure provides methods of detecting and/or quantifying tau proteins in samples through the use of capture and detection antibodies. As used herein, a "capture antibody" is an antibody that binds an analyte in a way that it may be isolated or detected. Capture antibodies may be associated with surfaces or other carriers (e.g., beads). Detection antibodies are antibodies that facilitate observation of the presence or absence of an analyte. According to some methods of detecting and/or quantifying tau proteins, both capture antibodies and detection antibodies bind to tau proteins. Capture and detection antibodies may bind to different epitopes or regions of tau proteins to avoid competition for binding. In some embodiments, detection antibodies may be conjugated with a detectable label for direct detection. In some embodiments, binding of detection antibodies may be assessed using a secondary antibody that binds to a constant domain of the detection antibody or to a detectable label of the detection antibody. Capture, detection, and/or secondary antibodies may be derived from different species. This may prevent secondary antibodies from binding to both capture and detection antibodies.

V. Kits and Devices

Kits

In some embodiments, compounds and composition of the present disclosure may be included in a kit. Such compounds and compositions may include anti-tau antibodies disclosed herein. In a non-limiting example, kits may include reagents for generating anti-tau antibodies, including tau protein antigens. Kits may include additional reagents and/or instructions for use, e.g., for creating or synthesizing anti-tau antibodies. Kits may include one or more buffers. Kits may include additional components, for example, solid supports or substrates for antibody or antigen attachment.

In some embodiments, the present disclosure includes kits for screening, monitoring, and/or diagnosis of a subject that include one or more anti-tau antibodies. Such kits may be used alone or in combination with one or more other methods of screening, monitoring, and/or diagnosis. Kits may include one or more of a buffer, a biological standard, a secondary antibody, a detection reagent, and a composition for sample pre-treatment (e.g., for antigen retrieval, blocking, etc.).

Kit components may be packaged. In some embodiments, kit components are packaged in aqueous media or in lyophilized form. Packaging may include one or more vial, test tube, flask, bottle, syringe or other container into which a component may be placed and/or suitably aliquoted. Where there are multiple kit components (labeling reagent and label may be packaged together), kits may include second, third or other additional containers into which additional components may be separately placed.

When kit components are provided in one and/or more liquid solutions, liquid solutions may be aqueous. Liquid solutions may be provided sterile. Kit components may be provided as dried powder(s). Dried powder components may be provided for reconstitution by kit users, e.g., by addition of suitable solvent. Solvents may also be provided in kits in one or more separate containers. In some embodiments, labeling dyes are provided in dried powder format.

Kits may include instructions for employing kit components as well other reagents not included in the kit. Instructions may include variations that can be implemented.

Devices

Any of the compounds and compositions described herein may be combined with, coated onto, or embedded in, or delivered by a device. Devices may include, but are not limited to, implants, stents, bone replacements, artificial joints, valves, pacemakers, or other implantable therapeutic devices.

VI. Definitions

At various places in the present specification, substituents of compounds of the present disclosure are disclosed in groups or in ranges. It is specifically intended that the present disclosure include each and every individual sub combination of the members of such groups and ranges.

About. As used herein, the term "about" means+/−10% of the recited value.

Activity: As used herein, the term "activity" refers to the condition in which things are happening or being done. Compositions may have activity and this activity may involve one or more biological events.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more entities, means that the entities are physically associated or connected with one another, either directly or via a linker, to form a structure that is sufficiently stable so that the entities remain physically associated, e.g., under working conditions, e.g., under physiological conditions. An "association" need not be through covalent chemical bonding and may include other forms of association or bonding sufficiently stable such that the "associated" entities remain physically associated, e.g., ionic bonding, hydrostatic bonding, hydrophobic bonding, hydrogen bonding, or hybridization-based connectivity.

Bifunctional: As used herein, the term "bifunctional" refers to any substance, molecule or moiety which is capable of or maintains at least two functions. The functions may affect the same outcome or a different outcome. The structure that produces the function may be the same or different.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active.

Chimeric antigen receptor (CAR): As used herein, the term "chimeric antigen receptor" or "CAR" refers to an artificial chimeric protein comprising at least one antigen specific targeting region (ASTR), a transmembrane domain and an intracellular signaling domain, wherein the antigen specific targeting region comprises a full-length antibody or a fragment thereof. As a non-limiting example, the ASTR of a CAR may be any of the antibodies presented herein or fragments thereof. Any molecule that is capable of binding a target antigen with high affinity can be used in the ASTR of a CAR. The CAR may optionally have an extracellular spacer domain and/or a co-stimulatory domain. A CAR may also be used to generate a cytotoxic cell carrying the CAR.

Compound: Compounds of the present disclosure include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Comprehensive Positional Evolution (CPE™): As used herein, the term "comprehensive positional evolution" refers to an antibody evolution technology that allows for mapping of the effects of amino acid changes at every position along an antibody variable domain's sequence. This comprehensive mutagenesis technology can be used to enhance one or more antibody properties or characteristics.

Comprehensive Protein Synthesis (CPS™): As used herein, the term "comprehensive protein synthesis" refers to a combinatorial protein synthesis technology that can be used to optimize antibody properties or characteristics by combining the best properties into a new, high-performance antibody.

Conditionally active: As used herein, the term "conditionally active" refers to a mutant or variant of a wild-type polypeptide, wherein the mutant or variant is more or less active at physiological conditions than the parent polypeptide. Further, the conditionally active polypeptide may have increased or decreased activity at aberrant conditions as compared to the parent polypeptide. A conditionally active polypeptide may be reversibly or irreversibly inactivated at normal physiological conditions or aberrant conditions.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of providing a compound, substance, entity, moiety, cargo, or payload to a subject or destination.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance and the like. Detectable labels include, but are not limited to, radioisotopes, fluorophores, chemiluminescent compounds, chromophores, enzymes, enzyme co-factors, dyes, metal ions, ligands, biotin, avidin, streptavidin, haptens, quantum dots, and the like. Detectable labels may be located at any position in or on an entity with which they are conjugated or otherwise attached, incorporated, or associated. For example, when conjugated or otherwise attached, incorporated, or associated with a peptide or protein, detectable labels may be on, within, or between amino acids or may be attached or associated with the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Dosing regimen: As used herein, a "dosing regimen" is a schedule of administration or physician determined regimen of treatment, prophylaxis, or palliative care.

Engineered: As used herein, embodiments are "engineered" when they are designed to have a feature or property, whether structural or chemical, that varies from a starting compound, material or molecule (e.g., from a wild type or native molecule).

Effective Amount. As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment of a therapeutic indication as compared to the response obtained without administration of the agent.

Epitope: As used herein, an "epitope" refers to a surface or region on one or more entities that is capable of interacting with an antibody or other binding biomolecule. For example, a protein epitope may contain one or more amino acids and/or post-translational modifications (e.g., phosphorylated residues) which interact with an antibody. In some embodiments, an epitope may be a "conformational epitope," which refers to an epitope involving a specific three-dimensional arrangement of the entity(ies) having or forming the epitope. For example, conformational epitopes of proteins may include combinations of amino acids and/or post-translational modifications from folded, non-linear stretches of amino acid chains.

EvoMap™: As used herein, an EvoMap™ refers to a map of a polypeptide, wherein detailed informatics are presented about the effects of single amino acid mutations within the length of the polypeptide and their influence on the properties and characteristics of that polypeptide.

Expression: As used herein, "expression" of a gene, nucleic acid, or protein refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" refers to a material or mixture prepared according to a formula. Formulations may include a compound (e.g., an antibody) or substance combined with a carrier or excipient.

Fragment: A "fragment," as used herein, refers to a portion. For example, fragments of proteins may include polypeptides obtained by digesting full-length protein isolated from cultured cells.

Functional: As used herein, a "functional" biological molecule is a biological molecule in a form in which it exhibits a property and/or activity by which it is characterized. For example, a "functional" antibody may include an antibody that binds a specific target or that activates or inhibits a specific biological process.

Half maximal effective concentration: As used herein, the term "half maximal effective concentration" or "EC50" refers to the concentration of a substance necessary to increase a given reaction, activity or process by half. For example, when measuring binding of an antibody in a sample to a target using a binding assay (e.g., an ELISA assay), the EC50 is the concentration of antibody in the sample needed to yield 50% of the maximum binding that can be observed with that assay. Similarly, the term "half maximal inhibitory concentration" or "IC50" refers to a concentration necessary to reduce a given reaction or process by half. For example, the IC50 for an antibody capable of inhibiting a biological process is the concentration of antibody necessary in a sample to reduce the biological process by 50%. EC50 and IC50 values may be differ under specific time constraints and/or conditions.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Heterologous Region: As used herein the term "heterologous region" refers to a region which would not be considered a homologous region.

Homologous Region: As used herein the term "homologous region" refers to a region which is similar in position, structure, evolution origin, character, form or function.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H. and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that a substance is substantially separated from the environment in which it was formed or detected. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein "linker" refers to a molecule or group of molecules which connects two molecules. In some embodiments, linkers may be cleavable (e.g., through contact with an enzyme, change in pH, or change in temperature).

Modified: As used herein "modified" refers to a changed state or structure of a molecule. Molecules may be modified in many ways including chemically, structurally, and functionally.

Naturally occurring: As used herein, "naturally occurring" or "wild-type" means existing in nature without artificial aid, or involvement of the hand of man.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, primate, rabbit, reindeer, sheep, water buffalo, and yak.

Off-target. As used herein, "off-target" refers to unintended activity or binding to an entity other than an expected target.

Operably linked. As used herein, the phrase "operably linked" refers to a functional connection between two or more molecules, constructs, transcripts, entities, moieties or the like.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients or pharmaceutically acceptable carrier: The phrase "pharmaceutically acceptable excipient" or "pharmaceutically acceptable carrier," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspension or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* $17^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Pharmaceutically acceptable solvate: The term "pharmaceutically acceptable solvate," as used herein, means a compound wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest. As used herein, the terms "proteins of interest" or "desired proteins" include those provided herein and fragments, mutants, variants, and alterations thereof.

Purified. As used herein, "purify," "purified," "purification" means to make substantially pure or clear from unwanted components, material defilement, admixture or imperfection. "Purified" refers to the state of being pure. "Purification" refers to the process of making pure.

Region: As used herein, the term "region" refers to a zone or general area. In some embodiments, when referring to a polypeptide or protein, a region may include a linear sequence of amino acids along the polypeptide or protein or may include a three-dimensional area, an epitope, or a cluster of epitopes. When referring to a polynucleotide, a region may include a linear sequence of nucleic acids along the polynucleotide or may include a three-dimensional area, secondary structure, or tertiary structure. Regions may include terminal regions. As used herein, the term "terminal region" refers to a region located at the end or "terminus" of a given entity. When referring to polypeptides, terminal regions may include N- and/or C-termini. N-terminus refers to the end of a polypeptide with a free amino acid amino group. C-terminus refers to the end of a polypeptide with a free amino acid carboxyl group. N- and/or C-terminal regions may refer to a single terminal functional group, single amino acid, or multiple amino acids located at either terminus. When referring to polynucleotides, terminal regions may include 5' and 3' termini. The 5' terminus refers to the end of a polynucleotide that includes a free nucleic acid phosphate group. The 3' terminus refers to the end of a polynucleotide that includes a free nucleic acid hydroxyl group. Polynucleotide terminal regions may refer to a single terminal functional group, single nucleotide, or multiple nucleotides located at a terminus.

RNA and DNA: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. RNA and DNA can be single-stranded (i.e., ssRNA or ssDNA, respectively) or multi-stranded (e.g., double stranded, i.e., dsRNA and dsDNA, respectively). The term "messenger RNA" or "mRNA," as used herein, refers to a single stranded RNA that encodes an amino acid sequence of one or more polypeptide chains.

Sample: As used herein, the term "sample" refers to a portion or subset of larger entity. A sample from a biological organism or material is referred to herein as a "biological sample" and may include, but is not limited to, tissues, cells, and body fluids (e.g., blood, mucus, lymphatic fluid, synovial fluid, cerebrospinal fluid, saliva, amniotic fluid, amniotic cord blood, urine, vaginal fluid, and semen). Samples may further include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, and organs. Samples may further include a medium, such as a nutrient broth or gel, which may contain cellular components, such as proteins or nucleic acid molecules.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Split dose: As used herein, a "split dose" is the division of single unit dose or total daily dose into two or more doses.

Stable: As used herein "stable" refers to a state of an entity that is sufficiently robust to survive a certain degree of perturbation. For example, a stable compound or protein may remain intact during isolation to a useful degree of purity from a reaction mixture.

Stabilized: As used herein, the term "stabilize" or "stabilized" means to make or become stable.

Subject: As used herein, the term "subject" refers to any organism to which a compound, composition, method, kit, or device according to the present disclosure may be administered or applied, e.g., for experimental, diagnostic, prophylactic, and/or therapeutic purposes. Subjects can include animals (e.g., mammals such as mice, rats, rabbits, non-human primates, and humans) and plants. A subject receiving, requiring, eligible for, or seeking medical treatment is referred to herein as a "patient."

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, neurodegenerative disease) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity or disfunction of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to release of a compound or agent over a specific period of time, typically at a relatively controlled or consistent rate.

Synthetic: The term "synthetic" means produced, prepared, and/or manufactured by the hand of man. Synthetic polynucleotides, polypeptides, or other molecules of the present disclosure may be prepared using chemical or enzymatic processes.

Target. As used herein, the term "target" refers to an entity of interest or attention, which may include a subject, an organ, a tissue, a cell, a protein, a nucleic acid, biomolecule, or a group, complex, or portion of any of the foregoing. In some embodiments, a target may be a protein or epitope thereof for which an antibody has affinity or for which an antibody is desired, designed, or developed to have affinity for. As used herein, the term "target" may also be used to refer to an activity of an agent that is directed to a particular object. For example, an antibody that has affinity for a specific protein "X" may be said to target protein X or may be referred to as an antibody targeting protein X or referred to as a protein X-targeting antibody. Similarly, an object that is the subject of an agent's activity may be referred to as a "targeted" object. For example, where an antibody has affinity for a specific protein "X," protein X may be referred to as being targeted by the antibody.

Therapeutic Agent: The term "therapeutic agent" refers to any agent that, when administered to a subject, has a therapeutic, diagnostic, and/or prophylactic effect and/or elicits a desired biological and/or pharmacological effect. Therapeutic agents capable of producing a biological effect in living organisms are referred to herein as "drugs."

Therapeutically effective amount: As used herein, the term "therapeutically effective amount" means an amount of an agent (e.g., antibody or other therapeutic agent) to be delivered to a subject suffering from or susceptible to an infection, disease, disorder, and/or condition, that when delivered or administered in that amount is sufficient to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" neurodegenerative disease in a subject may refer to inhibiting neurodegeneration; promoting the health of neuronal cells; reversing, preventing, or reducing the formation of plaques or tangles in the brain; and/or reversing, preventing, or reducing memory loss or loss of other neurological functions or activities of the subject. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may refer to the wild type or native form of a biomolecule. Molecules may undergo a series of modifications whereby each modified molecule may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly.

VII. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation.

Section and table headings are not intended to be limiting.

EXAMPLES

Example 1. Antigen Preparation

Antigen preparation was carried out to support generation and characterization of anti-human tau antibodies. Enriched paired helical filament (ePHF; sarkosyl insoluble tau) including human microtubule-associated protein tau, isoform 2 (SEQ ID NO: 274) was prepared along with several tau protein antigens with different phosphorylated residues corresponding to pathological tau. Related sequences are presented in Table 6. Phosphorylated residues are underlined in the Table.

TABLE 6

Tau protein antigens

| Antigen | Sequence | SEQ ID NO |
|---|---|---|
| human microtubule-associated protein tau, isoform 2 | MAEPRQEFEVMEDHAGTYGLGDRKDQGGYTMHQDQEGDTDAG<br>LKESPLQTPTEDGSEEPGSETSDAKSTPTAEDVTAPLVDEGAPGKQ<br>AAAQPHTEIPEGTTAEEAGIGDTPSLEDEAAGHVTQARMVSKSKD<br>GTGSDDKKAKGADGKTKIATPRGAAPPGQKGQANATRIPAKTPP<br>APKTPPSSGEPPKSGDRSGYSSPGSPGTPGSRSRTPSLPTPPTREPKK<br>VAVVRTPPKSPSSAKSRLQTAPVPMPDLKNVKSKIGSTENLKHQP<br>GGGKVQIINKKLDLSNVQSKCGSKDNIKHVPGGGSVQIVYKPVDL<br>SKVTSKCGSLGNIHHKPGGGQVEVKSEKLDFKDRVQSKIGSLDNIT<br>HVPGGGNKKIETHKLTFRENAKAKTDHGAEIVYKSPVVSGDTSPR<br>HLSNVSSTGSIDMVDSPQLATLADEVSASLAKQGL | 274 |
| PT3 epitope peptide (pT212/pT217) | TPGSRSRTPSLPTPPTREPK | 275 |
| Peptide 5 (pT212/pS214/pT217) | GTPGSRSRTPSLPTPPTRE | 276 |
| Peptide 12 (pS396/pS404/pS409) | RENAKAKTDHGAEIVYKSPVVSGDTSPRHLSNVSSTG | 277 |
| Peptide 1 (AT120 epitope) | PTREPKKV | 278 |

Tau protein antigens were conjugated with keyhole limpet hemocyanin (KLH) for immunization. For ePHF antigen preparation, ePHF was isolated from fractions of AD or non-AD frontal cortical tissue. Cortical tissue fractions were prepared according to methods described by Greenberg and Davies (1990) with minor modification (Liu et al., J Neuroscience, 2016, the contents of which are herein incorporated by reference in their entirety). Briefly, brain tissue was homogenized with cold homogenization buffer (10 mM Tris/1 mM EDTA/0.8 M NaCl/10% sucrose, pH 7.4) with protease inhibitor (Roche Molecular Systems, Inc., Branchburg, NJ) and phosphatase inhibitors cocktail (ThermoFisher, Waltham, MA, catalog #78437) or 1 mM NaF/1 mM $Na_3VO_4$ in a Teflon glass homogenizer. Brain homogenate was then centrifuged at 27,000×g for 30 min at 4° C. The resulting supernatant was subjected to extraction with 1% (w/v) N-lauroylsarcosine in the presence of 1% (v/v) 2-mercaptoethanol at 37° C. for 2.5 h followed by centrifugation at 108,000×g for 30 min at room temperature. The pellet recovered from this centrifugation was quickly rinsed one time with 0.5 mL of PBS/tube. The rinsed PBS was discarded. Another 0.5 mL of PBS was added to each tube to dissolve PHF. PHF from 6 tubes were pooled and the pooled PHF solution was sonicated. The resulting solution was concentrated to ~5× and further sonicated. PHF samples were then analyzed by HT7 western for qualitative and PT3 ELISA quantitative assessment. PHF samples were then stored at −80° C.

Example 2. Immunization

Transgenic mice developed to express antibodies with human variable domains were used for immunization with ePHF (prepared as described in Example 1). Sera from immunized mice were screened by enzyme-linked immunosorbent assay (ELISA) for the presence of antibodies binding to tau protein antigens. Immunized mice with sera testing positive for antigen-specific antibodies were used to prepare hybridoma cells. Supernatants from hybridoma cell culture medium were screened by direct ELISA to identify cells producing antigen-specific antibodies. Hybridoma clones producing antibodies with positive antigen binding were selected for subcloning and antibody sequence analysis.

Variable domain amino acid sequences for selected clones included those presented in Table 1, with each ID #corresponding to an antibody expressed by a selected hybridoma clone. Complementarity determining region (CDR) analysis was carried out to identify heavy chain CDRH1, CDRH2, and CDRH3 sequences and light chain CDRL1, CDRL2, and CDRL3 sequences. CDR amino acid sequences identified include those presented in Table 1.

Example 3. Tau Binding

A set of recombinant human IgG1 antibodies were prepared with clone-specific variable domain pairs selected from those presented in Table 1 and human IgG1 constant domains. These candidate antibodies were analyzed for binding to ePHF and specificity for ePHF over wild type tau by direct ELISA.

For direct ePHF and wildtype tau ELISA, plates were first coated with ePHF or wild type tau. Antigen solutions were prepared in PBS and 50 μL were pipetted into each well. Plates were covered and incubated for one hour at 37° C. or overnight at 4° C. Plates were then washed and blocked by addition of 150 μl of blocking buffer to each well and incubated one hour at room temperature. Plates were then washed before addition of serially diluted candidate antibody samples prepared in blocking buffer. Detection of candidate antibody binding was carried out by washing plates and adding a solution of enzyme-labeled secondary antibody in blocking buffer to each well. Secondary antibody binding was detected by addition of substrate and spectrophotometric analysis of resulting reaction product. Half maximal effective concentration (EC50) for antibody binding to ePHF and wild type tau are presented in Table 7.

TABLE 7

| ELISA results | | |
|---|---|---|
| ID# | ePHF EC50 (nM) | Wild type Tau EC50 (nM) |
| VY001 | 0.02 | No binding |
| VY002 | 0.03 | No binding |
| VY003 | 0.06 | No binding |
| VY004 | 0.07 | No binding |
| VY005 | 0.07 | No binding |
| VY006 | 0.11 | No binding |
| VY007 | 0.18 | No binding |
| VY008 | 0.27 | No binding |
| VY009 | 1.74 | No binding |
| VY010 | 8.99 | No binding |
| VY011 | 0.03 | No binding |
| VY012 | 0.04 | 0.01 |
| VY013 | 0.06 | 0.98 |
| VY014 | 6.23 | 0.04 |
| VY016 | No binding | No binding |
| VY017 | No binding | No binding |
| VY018 | No binding | No binding |
| VY019 | No binding | No binding |
| VY020 | No binding | No binding |

Example 4. Epitope Affinity Analysis

Anti-human tau antibodies were assessed for affinity for iPHF by Octet (ForteBio, Menlo Park, CA) analysis. A set of recombinant human IgG1 antibodies were prepared with clone-specific variable domain pairs selected from those presented in Table 1 and human IgG1 constant domains. Candidate antibodies were immobilized on biosensor tips (ForteBio) in kinetic buffer (ForteBio). Biosensor tips were then washed before introduction of a solution of iPHF in kinetic buffer for analysis of association and dissociation with candidate antibodies. Affinity measurements ($K_D$) were obtained using Data Analysis HT version 11.1 and corrected for background and high-frequency noise. Results are presented in Table 8.

TABLE 8

| Affinity analysis results | |
|---|---|
| ID# | iPHF $K_D$ (nM) |
| VY007 | 0.6 |
| VY005 | 1.0 |
| VY002 | 1.0 |
| VY009 | 1.1 |
| VY006 | 1.5 |
| VY010 | 1.5 |
| VY011 | 2.0 |
| VY008 | 2.3 |
| VY020 | 2.6 |
| VY013 | 2.9 |
| VY018 | 3.0 |
| VY004 | 3.7 |
| VY017 | 3.7 |
| VY003 | 4.6 |
| VY012 | 5.1 |
| VY014 | 5.3 |
| VY001 | 7.7 |

The antibodies shown in Table 8 all demonstrated $K_D$ values less than 10 nM, with antibodies VY002, VY005, and VY007 demonstrating $K_D$ values less than or equal to 1 nM.

Example 5. Epitope Binning by Peptide Antigen

Anti-human tau antibodies were subjected to PHF tau epitope binning analysis by sandwich ELISA. A set of recombinant human IgG1 antibodies were prepared with clone-specific variable domain pairs selected from those presented in Table 1 and human IgG1 constant domains. Anti-tau antibodies AT120 (directed to peptide 1), PT3 (directed to peptide 5), and C10.2 (directed to peptide 12) were used as capture antibodies in the assay. Capture antibodies were diluted in PBS at a concentration of 1 μg/ml and 50 μl of the solution was used to coat each assay plate well. Plates were covered and incubated overnight at 4° C. Plates were then washed and blocked by addition of 150 μl of blocking buffer to each well and incubated one hour at room temperature. Plates were again washed before coating with ePHF or wild type tau in blocking buffer followed by incubation for 1 hour at room temperature. Plates were then washed before addition of serially diluted candidate antibody samples prepared in blocking buffer. Detection of candidate antibody binding was carried out by washing plates and adding a solution of enzyme-labeled secondary antibody in blocking buffer to each well. Secondary antibody binding was detected by addition of substrate and spectrophotometric analysis of resulting reaction product. Epitope “bins” were determined for each candidate antibody tested based on observed competition (epitope blocking) by each anti-tau capture antibody tested. Results are shown in Table 9.

TABLE 9

| Epitope binning results | |
|---|---|
| ID# | Epitope bin |
| VY017 | AT120 |
| VY013 | C10.2 |
| VY004 | PT3 |
| VY005 | PT3 |
| VY014 | C10.2 |
| VY002 | PT3 |
| VY008 | PT3 |

Multiple antibodies competed for epitope binding with PT3, with one antibody competing for AT120, and two antibodies competing for epitope binding with C10.2.

Figure 1B:
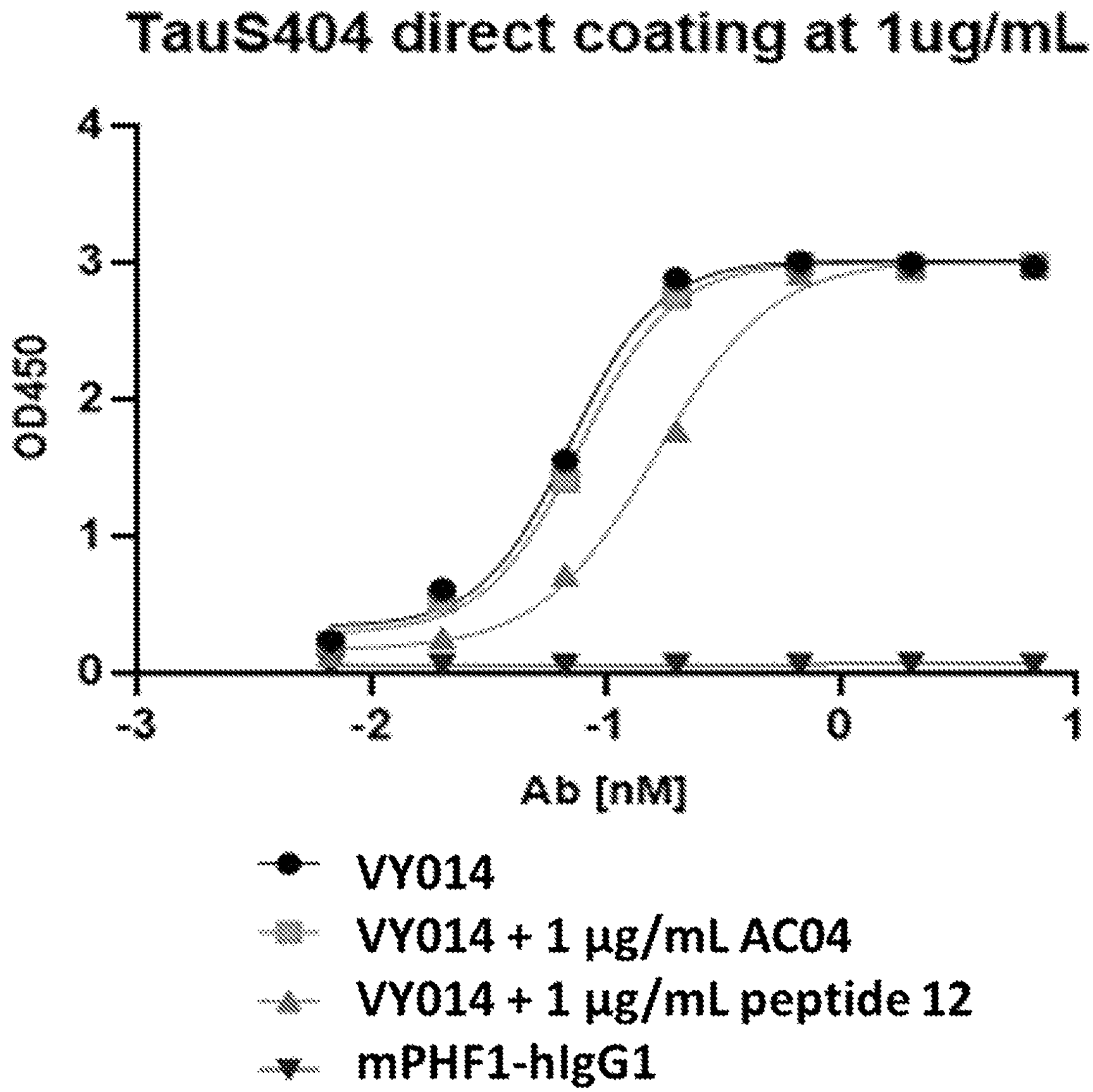
Figure 1C:
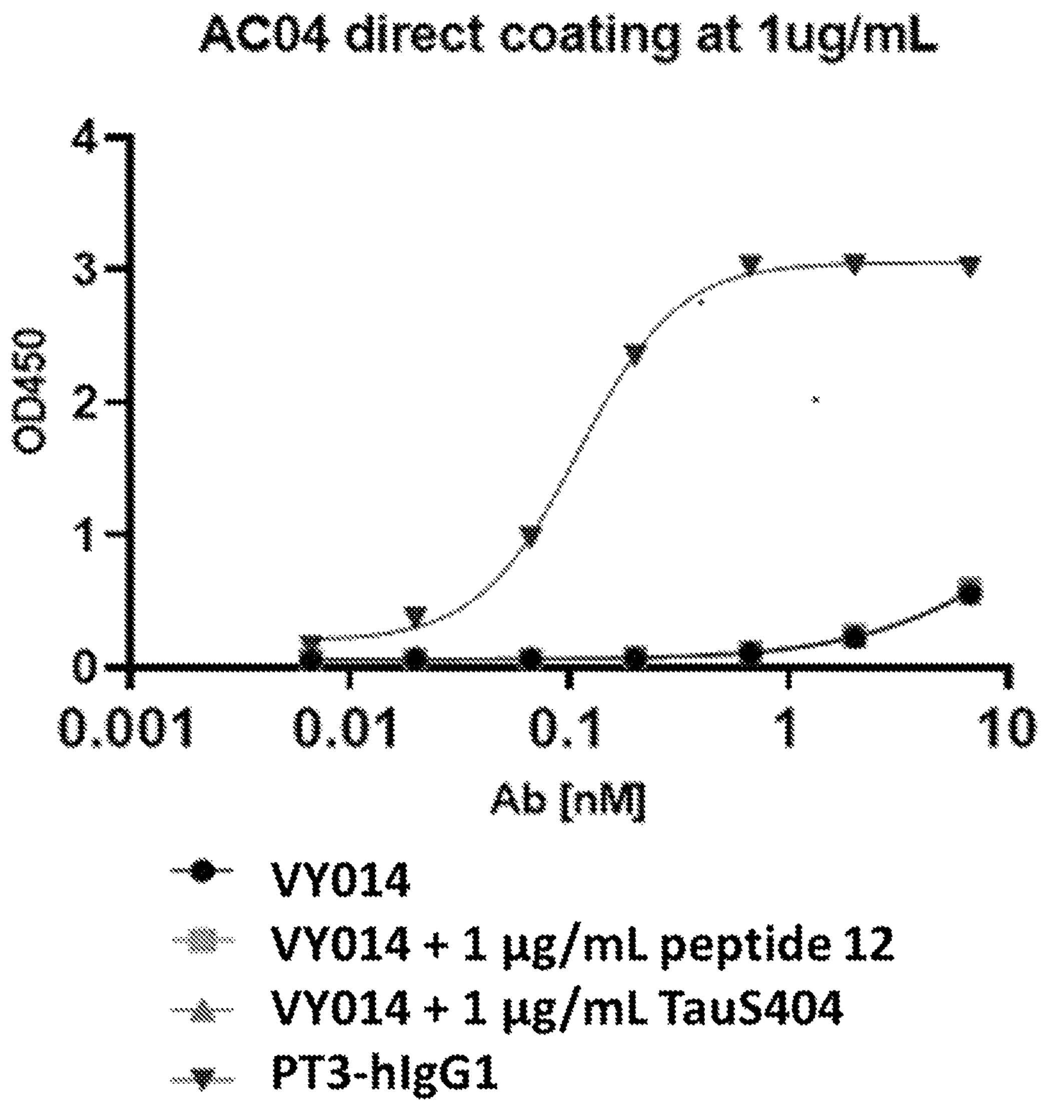

Additional competition assays were performed to further characterize the binding specificity of VY014. Specifically, the binding of VY014 to a Tau(pS404) peptide with only S404 phosphorylated (DHGAEIVYK-SPVVSGDTpSPRHLSNVSSTG; SEQ ID NO: 281) was tested. As shown in FIG. 1A, competitive ELISA using peptide-12 (bound by C10.2/PHF1) from Table 6 (SEQ ID NO: 277) showed that the Tau(pS404) peptide competitively inhibited the binding of VY014 to peptide-12. While PHF-1 showed binding to the C-terminus of tau (peptide 12) (FIG. 1A), it did not bind to the Tau(pS404) peptide (FIG. 1B). Finally, the AC04 peptide (recognized by antibody PT3 (FIG. 1C) and corresponding to the dual phosphorylated peptide: CSRpTPSLPpTPPTREPK; SEQ ID NO: 282) did not inhibit VY014 binding to TauS404 (FIG. 1B). These results suggest that VY014 binds to tau phosphorylated at 5404 and exhibits a distinct binding pattern to phosphorylated tau species compared to PHF-1.

Example 6. Epitope Binning of Anti-Human Tau Antibodies by PepScan Overlapping Phosphorylated Peptide Library Epitope binning of 15 additional anti-Tau antibodies (i.e., VY003, VY007, VY004, VY006, VY011, VY012, VY009, VY018, VY001, VY019, VY020, VY005, VY002, VY008, and VY013) was performed using a PepScan overlapping phospho-peptide library strategy.

Briefly, the PepScan library used included 212 phosphorylated overlapping 18-mer peptides, with each fragment containing at least one phosphorylated site (with the exception of 5 fragments). Tau has 45 serines, 35 threonines, and 5 tyrosines, for a total of 85 possible sites.

In a control run, PT3, PHF1, and C10.2 antibodies were tested for binding to the PepScan library and found to bind to their expected epitopes. Specifically, PT3 bound to amino acids 201-228, PHF1 to amino acids 13-34 and 377-408, and C10.2 to amino acids 39-56, 205-222, and 383-402.

Table 10 summarizes the epitopes recognized by the tested antibodies using the PepScan library.

TABLE 10

Epitope mapping

| Antibody | Peptide epitopes (amino acid residues) |
|---|---|
| PT3 | 201-228 |
| PHF1 | 13-34; 377-408 |
| C10.2 | 39-56, 205-222, 383-402 |
| MC1 | 1-22 |
| IPN002 | 2-24 |
| AT8 | 187-218 |
| AT180 | 215-238 |
| VY003 | 35-62, 53-76, 187-218 |
| VY007 | 187-218 |
| VY006 | 187-218 |
| VY004 | 33-64; 53-82, 159-178, 165-182, 197-214, 201-226, 229-246 |
| VY011 | 183-201; 187-212 |
| VY012 | 5-34 |
| VY009 | 217-242 |
| VY018 | 217-242 |
| VY001 | 187-218 |
| VY019 | 217-242 |
| VY020 | 187-218 |
| VY005 | 33-64, 53-82, 159-178, 165-188, 191-230 |
| VY002 | 35-62, 107-124, 203-220 |
| VY008 | 35-64, 53-82, 159-188, 197-214, 201-224 |
| VY013 | 53-78, 329-348, 381-408 |

*amino acid residues are in relation to human tau having the sequence of SEQ ID NO: 274 from Table 10.

Similar to MC1 and IPN002, VY012 exhibited strong binding to the N-terminal region of Tau.

Figure 2:
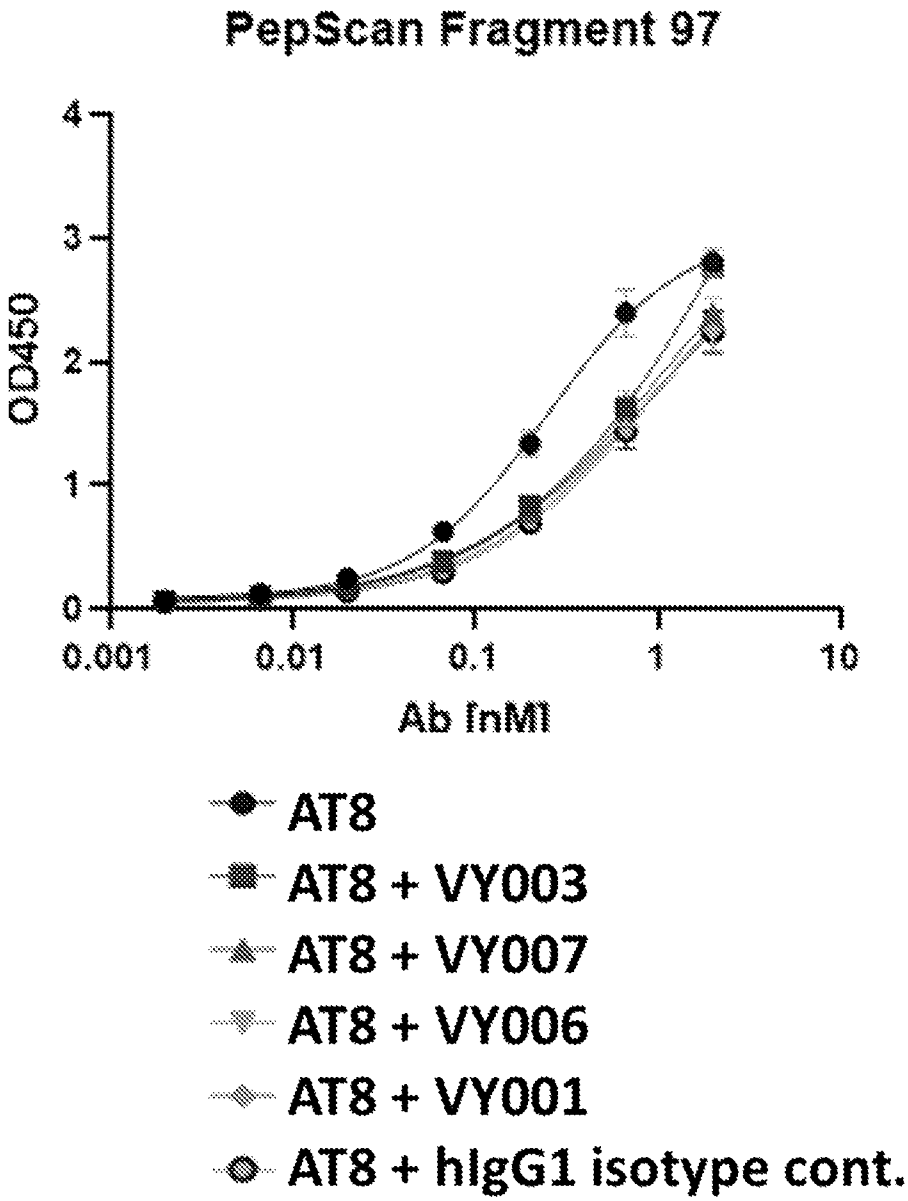
FIG. 2 shows the results of a competition ELISA assay for binding of AT8 in the presence or absence of VY003, VY007, VY006, VY001, or an isotype antibody control to PepScan Fragment 97 (corresponding to SEQ ID NO: 283).

VY003, VY007, VY006, VY011, VY001, and VY020 exhibited binding to a peptide region similar to the AT8 antibody. However, competitive ELISA using the phosphopeptide spanning amino acids 193-210 (DRpSGYpSpSPGpSPGpTPGpSRpS; SEQ ID NO: 283) did not demonstrate competition between AT8 and VY003, VY007, VY006, and VY001 (FIG. 2), suggesting that these antibodies may have a different binding specificity to the 193-210 region compared to AT8.

VY009 and VY018 exhibited binding to a peptide region containing pT231 (Tau217-242).

VY004, VY005, and VY008 showed strong binding to the proline-rich domain, similar to PT3 (Tau201-228), while VY002 showed very weak binding to PepScan overlapping phosphorylated peptides (Tau203-220). VY004, VY005, VY002, and VY008 also showed strong binding to other regions of tau, especially the N-terminal region (Tau33-64 and Tau53-82).

VY013 showed strong binding to the C-terminal region of tau (Tau381-408), as well as the N-terminal region (Tau53-78).

Example 7. Fine Epitope Mapping of AT8 Bin Antibodies

This Example describes the further characterization of the binding specificity of antibodies tentatively categorized as belonging to the AT8 bin (i.e., VY003, VY007, VY006, VY011, VY001, and VY020).

As an initial experiment, the ability of the antibodies to bind to the AT8 peptide (amino acids 195-215 of tau) was tested by bio-layer interferometry (BLI; Octet assay). Briefly, phospho-peptides were immobilized on streptavidin biosensor tips and the binding ability of each antibody was assessed using an eight-point concentration gradient.

As shown in Table 11, VY003, VY007, VY006, VY011, and VY001 showed strong binding to the AT8 peptide, whereas VY020 showed no binding to the peptide.

TABLE 11

Affinity of AT8 bin antibodies for AT8 peptide by BLI

| Antibody | KD (pM) |
|---|---|
| AT8 (positive control) | 309 |
| hIgG1 isotype control | no binding |
| VY003 | 12.4 |
| VY007 | 18.2 |
| VY006 | 3.82 |
| VY011 | 8.9 |
| VY001 | 4.35 |
| VY020 | no binding |

To further assess the binding characteristics of VY003, VY007, VY006, VY011, and VY001, the ability of these antibodies to bind to different phosphorylated species of the AT8 peptide were tested by one point ELISA using a high resolution sub-phospho-peptide library.

Briefly, peptides were generated that showed all possible combinations of phosphorylation patterns within known epitopes containing multiple possible phosphorylation sites. One-point ELISA was used to determine differential binding based on the individual phosphorylation patterns of each peptide. OD values (450 nm) were collected (as shown in Table 13), where a stronger positive signal is shown as a higher OD value, which is indicative of increased binding.

Table 12 lists the Tau191-214 phospho-peptides used in the binding assay, and Table 13 summarizes the specific binding patterns of the antibodies to the phospho-peptides.

TABLE 12

Tau191-214 phospho-peptides used in binding assay

| SEQ ID | Description | Sequence |
|---|---|---|
| 284 | pS199 | SGDRSGYS(pS)PGSPGTPGSRSRTPS |
| 285 | pS202 | SGDRSGYSSPG(pS)PGTPGSRSRTPS |
| 286 | pT205 | SGDRSGYSSPGSPG(pT)PGSRSRTPS |
| 287 | pS199-pS202-pT205 | SGDRSGYS(pS)PG(pS)PG(pT)PGSRSRTPS |
| 288 | pS199-pS202 | SGDRSGYS(pS)PG(pS)PGTPGSRSRTPS |
| 289 | pS202-pT205 | SGDRSGYSSPG(pS)PG(pT)PGSRSRTPS |
| 290 | pS199-pT205 | SGDRSGYS(pS)PGSPG(pT)PGSRSRTPS |

TABLE 13

| Binding assay for AT8 bin antibodies (OD values*) | | | | | | | | | |
|---|---|---|---|---|---|---|---|---|---|
| SCBio-4PEG-Peptide (Tau191-214) | VY003 | VY007 | VY006 | VY011 | VY001 | AT8 Mab | pS199 Rab | pS202 Rab | hIgG1 iso-type cont |
| pS199-old | 0.062 | 0.057 | 0.063 | 0.544 | 0.059 | 0.056 | 3.168 | | 0.060 |
| pS199 | 0.065 | 0.057 | 0.054 | 0.103 | 0.059 | 0.056 | 3.207 | | 0.058 |
| pS202 | 0.065 | 1.142 | 0.345 | 0.060 | 2.996 | 0.058 | | 3.203 | 0.055 |
| pT205 | 0.060 | 2.023 | 0.365 | 0.060 | 3.117 | 0.065 | | 0.208 | 0.054 |
| pS199-pS202-pT205 | 3.083 | 3.082 | 3.124 | 1.691 | 3.152 | 3.069 | | 1.085 | 0.245 |
| pS199-pS202 | 0.082 | 0.544 | 0.435 | 1.222 | 1.906 | 2.389 | | 3.203 | 0.062 |
| pS202-pT205 | 3.064 | 3.063 | 3.087 | 0.402 | 3.149 | 2.940 | | 0.740 | 0.249 |
| pS199-pT205 | 0.119 | 3.134 | 3.124 | 0.518 | 3.163 | 0.139 | 3.162 | | 0.090 |

*values are readings at OD450 nm

As shown in Table 13, many of the antibodies showed a distinct binding pattern compared to AT8 for Tau191-214 phospho-peptide species. AT8 did not bind to any of the singly phosphorylated peptides, exhibited binding to all doubly phosphorylated peptides, albeit weakly to the pS199/pT205 peptide, and bound strongly to the triple phosphorylated peptide (pS199/pS202/pT205).

VY003, VY007, VY006, VY011, and VY001 all exhibited binding to the triple phosphorylated peptide (pS199/pS202/pT205). VY003 exhibited binding when the peptide was doubly phosphorylated at pS202/pT205. VY007 exhibited binding to the peptide when S202 and T205 were singly phosphorylated, and to all doubly phosphorylated peptides, although binding was weaker for the peptide doubly phosphorylated at pS199/pS202 compared to the other two doubly phosphorylated peptides (pS202/pT205 and pS199/pT205). VY006 exhibited binding to the peptide when 5202 and T205 were singly phosphorylated; however, no binding was observed with when only pS199 was phosphorylated, and strongest binding was observed when the peptide was doubly phosphorylated at pS202/pT205 and pS199/pT205. This suggests that VY006 likely binds strongly to pT205 and an additional epitope, such as pS199 and/or pS202. Both VY007 and VY006 showed strongest binding when T205 and at least one other site on the peptide were phosphorylated. VY001 exhibited binding to the peptide when 5202 and T205 were singly phosphorylated, and all three doubly phosphorylated peptides.

VY011 exhibited binding to the peptide when S199 was singly phosphorylated, as well as when the peptide was doubly phosphorylated at pS199/pT205, pS202/pT205, and pS199/pS202. VY011 showed strongest binding to the peptide when all three sites (pS199/pS202/pT205) were phosphorylated. Notably, VY011 was the only antibody which exhibited binding to the peptide when S199 was singly phosphorylated. As shown in Table 14, VY011 exhibited nanomolar binding to the pS199 peptide, whereas neither VY020 nor AT8 exhibited binding to the peptide, as assessed by BLI.

TABLE 14

| Specificity of VY011 for pS199 by BLI | |
|---|---|
| Antibody | KD (nM) |
| pS199 Ab (positive control) | 0.004 |
| hIgG1 isotype control | no binding |
| AT8 | no binding |
| VY011 | 1.049 |
| VY020 | no binding |
| VY003 | no binding |
| VY006 | no binding |
| VY007 | no binding |
| VY001 | no binding |

In addition, neither VY011 nor VY020 were found to bind to the AT270 peptide (pT181; Tau172-186) by one point ELISA.

These results collectively suggest that the VY003, VY007, VY006, VY011, and VY001 antibodies exhibit a distinct pattern of binding to phosphorylated tau species compared to AT8, and that VY011 uniquely binds to the tau peptide singly phosphorylated at S199. Distinct binding patterns of these four antibodies were also observed relative to each other.

Example 8. Fine Epitope Mapping of PT3 Bin Antibodies

This Example describes the further characterization of the binding specificity of antibodies tentatively categorized as belonging to the PT3 bin (i.e., VY004, VY005, VY002, and VY008).

To assess the binding characteristics of VY004, VY005, VY002, and VY008, the ability of these antibodies to bind to different phosphorylated species of the Tau204-222 peptide was tested by one point ELISA using a high resolution sub-phospho-peptide library, in the manner described in Example 7. OD values (450 nm) were collected (as shown in Tables 16 and 18), where a stronger positive signal is shown as a higher OD value, which is indicative of increased binding.

Table 15 lists the Tau204-222 phospho-peptides used in the binding assay, and Table 16 summarizes the specific binding patterns of the antibodies to the phospho-peptides.

TABLE 15

| SEQ ID | Description | Sequence |
|---|---|---|
| Tau204-222 phospho-peptides | | |
| 291 | pT212 | GTPGSRSR(pT)PSLPTPPTRE |
| 292 | pS214 | GTPGSRSRTP(pS)LPTPPTRE |
| 293 | pT217 | GTPGSRSRTPSLP(pT)PPTRE |
| 294 | pT212/pS214 | GTPGSRSR(pT)P(pS)LPTPPTRE |
| 295 | pT212/pT217 | GTPGSRSR(pT)PSLP(pT)PPTRE |
| 296 | pS214/pT217 | GTPGSRSRTP(pS)LP(pT)PPTRE |
| 297 | pT212/pS214/pT217 | GTPGSRSR(pT)P(pS)LP(pT)PPTRE |

TABLE 16

| SCBiot-(dPEG4)-peptide (Tau204-222) | VY004 | VY005 | VY002 | VY008 | hIgG1 isotype cont. | PT3-hIgG1 | AT100 |
|---|---|---|---|---|---|---|---|
| Binding assay for PT3 bin antibodies (OD values at 450 nm) | | | | | | | |
| pT212 | 0.082 | 0.087 | 0.055 | 0.112 | 0.060 | 3.162 | 0.069 |
| pS214 | 0.069 | 0.092 | 0.058 | 0.143 | 0.061 | 3.142 | 0.065 |
| pT217 | 0.287 | 2.967 | 0.068 | 3.134 | 0.083 | 3.132 | 0.068 |
| pT212, pS214, pT217 | 0.795 | 0.789 | 0.060 | 2.418 | 0.053 | 3.166 | 0.187 |
| pT212, pS214 | 0.067 | 0.111 | 0.055 | 0.186 | 0.059 | 3.142 | 0.071 |
| pS214, pT217 | 0.207 | 2.468 | 0.062 | 2.825 | 0.059 | 3.131 | 0.067 |
| pT212, pT217 | 2.623 | 2.593 | 0.060 | 3.123 | 0.057 | 3.158 | 0.069 |

As shown in Table 16, VY004, VY005, VY002, and VY008 showed distinct binding patterns compared to PT3 for Tau204-222 phospho-peptide species. PT3 exhibited binding to all single, double, and triple phosphorylated peptides tested.

VY004 exhibited binding when the peptide was singly phosphorylated at T217, when doubly phosphorylated at pS214/pT217 and pT212/pT217 (albeit substantially more weakly for pS214/pT217), and when triply phosphorylated (pT212/pS214/pT217). VY005 and VY008 showed similar binding patterns, with both binding when the peptide was singly phosphorylated at T217, doubly phosphorylated at pS214/pT217 and pT212/pT217, and when triply phosphorylated (pT212/pS214/pT217). VY002 did not bind to any of the phosphorylated peptides in this experiment.

Further testing was done with additional peptides spanning the PT3 epitope having a different length than the Tau204-222 phosho-peptides described above. Table 17 lists the peptides used in this experiment.

TABLE 17

| Peptide | Specificity | Sequence | SEQ ID NO: |
|---|---|---|---|
| Additional PT3 peptides | | | |
| AC04 | pT212, pT217 | CSR(pT)PSLP(pT)PPTREPK | 282 |
| wtTau C2 | AT120 | 219-227 | — |
| tPeptide | pT212, | GTPGSRSR(pT)P(pS)LP(pT)PPTRE | 276 |

TABLE 17-continued

| Peptide | Specificity | Sequence | SEQ ID NO: |
|---|---|---|---|
| Additional PT3 peptides | | | |
| 5 (204-222) | pS214, pT217 | | |

As expected, PT3 exhibited binding to all 3 peptides (Table 18). Consistent with the results described above, VY004, VY005, and VY008 all showed binding to the doubly phosphorylated (pT212/pT217) AC04 peptide. VY004, VY005, and VY008 also showed binding to tpeptide5 (pT212/pS214/pT217), although the binding was weak for VY004 and VY005.

TABLE 18

| Peptides | VY004 | VY005 | VY008 | PT3-hIgG1 | IPN002-hIgG1 | hIgG1 isotype control |
|---|---|---|---|---|---|---|
| Binding assay for PT3 bin antibodies (OD values at 450 nm) | | | | | | |
| AC04 | 2.850 | 2.825 | 2.963 | 2.802 | 0.211 | 0.147 |
| wtTau C2 | 0.169 | 0.153 | 0.125 | 1.202 | 0.161 | 0.124 |
| tPeptide5 | 0.382 | 0.288 | 2.872 | 2.806 | 0.281 | 0.141 |

These results collectively suggest that the VY004, VY005, and VY008 exhibit a distinct pattern of binding to phosphorylated tau species compared to PT3. Additionally, VY005 and VY008 appear to require phosphorylation of T217 for binding.

Example 9. Fine Epitope Mapping of AT180 Bin Antibodies

This Example describes the further characterization of the binding specificity of antibodies tentatively categorized as belonging to the AT180 bin (i.e., VY009, VY018, and VY019).

Screening of the overlapping phospho-peptide library identified all three antibodies as binding to a similar region as AT180, as demonstrated by their binding to the phospho-peptide (pT)PP(pT)REPKKVAVVR(pT)PPK (Tau217-234; SEQ ID NO: 298) (Table 19), as assessed by BLI.

TABLE 19

| Binding affinity of AT180 bin antibodies for Tau217-234 phospho-peptide | |
|---|---|
| Antibody | KD (nM) |
| AT180 | 0.005 |
| VY009 | 0.31 |
| VY018 | 4.08 |
| VY019 | 3.7 |

Next, the ability of the three antibodies to bind to an AT180 peptide singly phosphorylated at T231 was tested (Tau225-240: KVAVVR(pT)PPKSPSSAK; SEQ ID NO: 299). As shown in Table 20, all three antibodies exhibited binding to the pT231 peptide in the nanomolar/subnanomolar range, as assessed by BLI.

TABLE 20

| Binding affinity of AT180 bin antibodies for pT231 phospho-peptide | |
|---|---|
| Antibody | KD (nM) |
| AT180 | 0.006 |
| hIgG1 isotype control | no binding |
| pT231 mAb | 1.950 |
| VY009 | 0.439 |
| VY018 | 3.649 |
| VY019 | 11.539 |

Finally, the ability of the three antibodies to bind to an AT180 peptide having different combinations of phosphorylated residues were tested using ELISA. The phosphopeptides used in the experiment are shown in Table 21.

TABLE 21

| AT180 phospho-peptides | | |
|---|---|---|
| SEQ ID | Description | Sequence |
| 299 | pT231 | KVAVVR(pT)PPKSPSSAK |
| 300 | pS235 | KVAVVRTPPK(pS)PSSAKPS |
| 301 | pT231/pS235 | KVAVVR(pT)PPK(pS)PSSAKPS |

Figure 3:
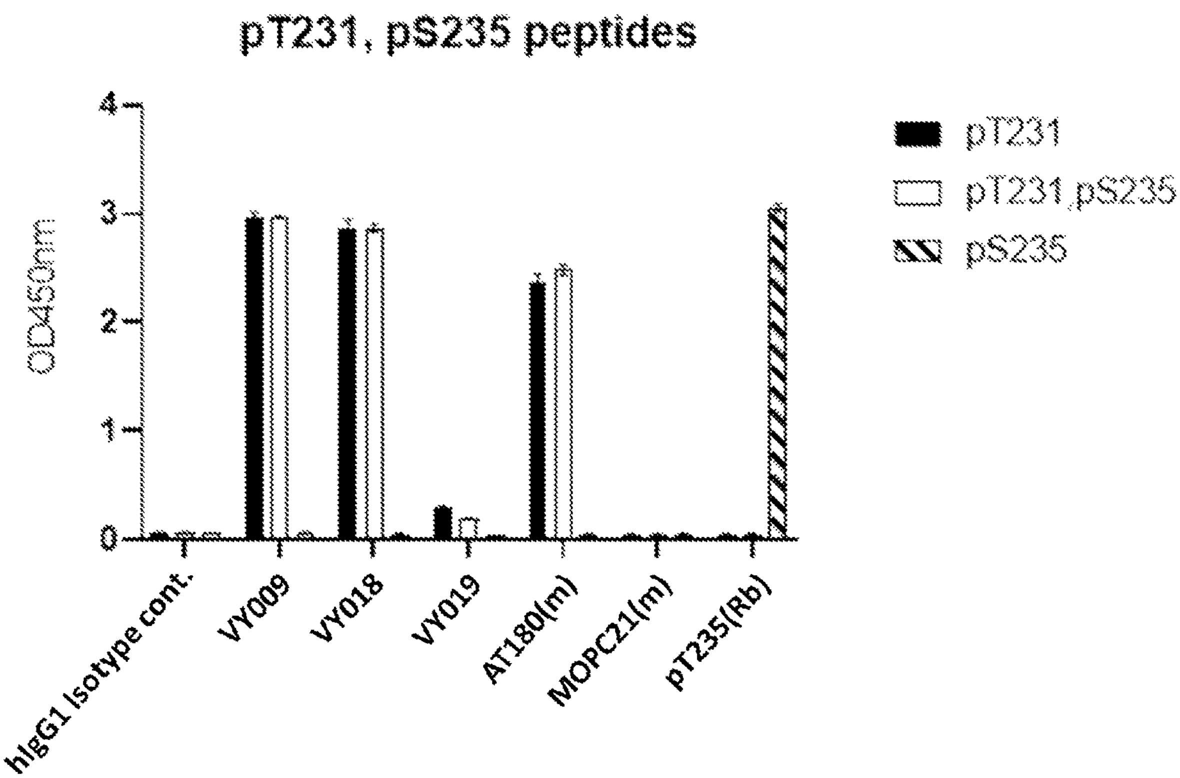
FIG. 3 shows the results of a one point ELISA assay for binding of the indicated antibodies to Tau peptides having the following phosphorylated residues: pT231 (left bar), pS235 (right bar), or pT231/pS235 (middle bar).

As shown in FIG. 3, while VY009, VY018, and AT180 (and to a small extent VY019) exhibited binding to the pT231 phospho-peptide and pT231/pS235 phospho-peptide, none of the antibodies exhibited binding to the pS235 phospho-peptide.

We claim:

1. An antibody that binds to tau comprising a heavy chain variable region (VH) comprising a heavy chain complementarity determining region 1 (HC CDR1), an HC CDR2, and an HC CDR3; and a light chain variable region (VL) comprising a light chain complementarity determining region 1 (LC CDR1), LC CDR2, and an LC CDR3, wherein:

(i) the HC CDR1 comprises the amino acid sequence of SEQ ID NO: 82, the HC CDR2 comprises the amino acid sequence of SEQ ID NO: 97, the HC CDR3 comprises the amino acid sequence of SEQ ID NO: 115, the LC CDR1 comprises the amino acid sequence of SEQ ID NO: 127, the LC CDR2 comprises the amino acid sequence of SEQ ID NO: 141, and the LC CDR3 comprises the amino acid sequence of SEQ ID NO: 159;

(ii) the HC CDR1 comprises the amino acid sequence of SEQ ID NO: 79, the HC CDR2 comprises the amino acid sequence of SEQ ID NO: 94, the HC CDR3 comprises the amino acid sequence of SEQ ID NO: 111, the LC CDR1 comprises the amino acid sequence of SEQ ID NO: 127, the LC CDR2 comprises the amino acid sequence of SEQ ID NO: 141, and the LC CDR3 comprises the amino acid sequence of SEQ ID NO: 156;

(iii) the HC CDR1 comprises the amino acid sequence of SEQ ID NO: 80, the HC CDR2 comprises the amino acid sequence of SEQ ID NO: 95, the HC CDR3 comprises the amino acid sequence of SEQ ID NO: 112, the LC CDR1 comprises the amino acid sequence of SEQ ID NO: 129, the LC CDR2 comprises the amino acid sequence of SEQ ID NO: 143, and the LC CDR3 comprises the amino acid sequence of SEQ ID NO: 157;

(iv) the HC CDR1 comprises the amino acid sequence of SEQ ID NO: 81, the HC CDR2 comprises the amino acid sequence of SEQ ID NO: 94, the HC CDR3 comprises the amino acid sequence of SEQ ID NO: 114, the LC CDR1 comprises the amino acid sequence of SEQ ID NO: 127, the LC CDR2 comprises the amino acid sequence of SEQ ID NO: 141, and the LC CDR3 comprises the amino acid sequences of SEQ ID NO: 156;

(v) the HC CDR1 comprises the amino acid sequence of SEQ ID NO: 88, the HC CDR2 comprises the amino acid sequence of SEQ ID NO: 105, the HC CDR3 comprises the amino acid sequence of SEQ ID NO: 123, the LC CDR1 comprises the amino acid sequence of SEQ ID NO: 137, the LC CDR2 comprises the amino acid sequence of SEQ ID NO: 151, and the LC CDR3 comprises the amino acid sequence of SEQ ID NO: 168;

(vi) the HC CDR1 comprises the amino acid sequence of SEQ ID NO: 82, the HC CDR2 comprises the amino acid sequence of SEQ ID NO: 101, the HC CDR3 comprises the amino acid sequence of SEQ ID NO: 119, the LC CDR1 comprises the amino acid sequence of SEQ ID NO: 132, the LC CDR2 comprises the amino acid sequence of SEQ ID NO: 149, and the LC CDR3 comprises the amino acid sequence of SEQ ID NO: 164;

(vii) the HC CDR1 comprises the amino acid sequence of SEQ ID NO: 86, the HC CDR2 comprises the amino acid sequence of SEQ ID NO: 102, the HC CDR3 comprises the amino acid sequence of SEQ ID NO: 120, the LC CDR1 comprises the amino acid sequence of SEQ ID NO: 127, the LC CDR2 comprises the amino acid sequence of SEQ ID NO: 141, and the LC CDR3 comprises the amino acid sequence of SEQ ID NO: 156;

(viii) the HC CDR1 comprises the amino acid sequence of SEQ ID NO: 77, the HC CDR2 comprises the amino acid sequence of SEQ ID NO: 92, the HC CDR3 comprises the amino acid sequence of SEQ ID NO: 109, the LC CDR1 comprises the amino acid sequence of SEQ ID NO: 127, the LC CDR2 comprises the amino acid sequence of SEQ ID NO: 141, and the LC CDR3 comprises the amino acid sequence of SEQ ID NO: 154;

(ix) the HC CDR1 comprises the amino acid sequence of SEQ ID NO: 78, the HC CDR2 comprises the amino acid sequence of SEQ ID NO: 93, the HC CDR3 comprises the amino acid sequence of SEQ ID NO: 110, the LC CDR1 comprises the amino acid sequence of SEQ ID NO: 128, the LC CDR2 comprises the amino acid sequence of SEQ ID NO: 142, and LC CDR3 comprises the amino acid sequence of SEQ ID NO: 155;

(x) the HC CDR1 comprises the amino acid sequence of SEQ ID NO: 78, the HC CDR2 comprises the amino acid sequence of SEQ ID NO: 96, the HC CDR3 comprises the amino acid sequence of SEQ ID NO: 113, the LC CDR1 comprises the amino acid sequence of SEQ ID NO:

130, the LC CDR2 comprises the amino acid sequence of SEQ ID NO: 144, and the LC CDR3 comprises the amino acid sequence of SEQ ID NO: 158;

(xi) the HC CDR1 comprises the amino acid sequence of SEQ ID NO: 83, the HC CDR2 comprises the amino acid sequence of SEQ ID NO: 98, the HC CDR3 comprises the amino acid sequence of SEQ ID NO: 116, the LC CDR1 comprises the amino acid sequence of SEQ ID NO: 131, the LC CDR2 comprises the amino acid sequence of SEQ ID NO: 145, and the LC CDR3 comprises the amino acid sequences of SEQ ID NO: 160;

(xii) the HC CDR1 comprises the amino acid sequence of SEQ ID NO: 84, the HC CDR2 comprises the amino acid sequence of SEQ ID NO: 99, the HC CDR3 comprises the amino acid sequence of SEQ ID NO: 117, the LC CDR1 comprises the amino acid sequence of SEQ ID NO: 132, the LC CDR2 comprises the amino acid sequence of SEQ ID NO: 146, and the LC CDR3 comprises the amino acid sequence of SEQ ID NO: 161;

(xiii) the HC CDR1 comprises the amino acid sequence of SEQ ID NO: 85, the HC CDR2 comprises the amino acid sequence of SEQ ID NO: 100, the HC CDR3 comprises the amino acid sequence of SEQ ID NO: 118, the LC CDR1 comprises the amino acid sequence of SEQ ID NO: 133, the LC CDR2 comprises the amino acid sequence of SEQ ID NO: 147, and the LC CDR3 comprises the amino acid sequence of SEQ ID NO: 162;

(xiv) the HC CDR1 comprises the amino acid sequence of SEQ ID NO: 85, the HC CDR2 comprises the amino acid sequence of SEQ ID NO: 100, the HC CDR3 comprises the amino acid sequence of SEQ ID NO: 118, the LC CDR1 comprises the amino acid sequence of SEQ ID NO: 134, the LC CDR2 comprises the amino acid sequence of SEQ ID NO: 148, and the LC CDR3 comprises the amino acid sequence of SEQ ID NO: 163;

(xv) the HC CDR1 comprises the amino acid sequence of SEQ ID NO: 87, the HC CDR2 comprises the amino acid sequence of SEQ ID NO: 103, the HC CDR3 comprises the amino acid sequence of SEQ ID NO: 121, the LC CDR1 comprises the amino acid sequence of SEQ ID NO: 132, the LC CDR2 comprises the amino acid sequence of SEQ ID NO: 149, and the LC CDR3 comprises the amino acid sequence of SEQ ID NO: 165;

(xvi) the HC CDR1 comprises the amino acid sequence of SEQ ID NO: 78, the HC CDR2 comprises the amino acid sequence of SEQ ID NO: 104, the HC CDR3 comprises the amino acid sequence of SEQ ID NO: 122, the LC CDR1 comprises the amino acid sequence of SEQ ID NO: 135, the LC CDR2 comprises the amino acid sequence of SEQ ID NO: 143, and the LC CDR3 comprises the amino acid sequence of SEQ ID NO: 166;

(xvii) the HC CDR1 comprises the amino acid sequence of SEQ ID NO: 78, the HC CDR2 comprises the amino acid sequence of SEQ ID NO: 104, the HC CDR3 comprises the amino acid sequence of SEQ ID NO: 122, the LC CDR1 comprises the amino acid sequence of SEQ ID NO: 136, the LC CDR2 comprises the amino acid sequence of SEQ ID NO: 150, and the LC CDR3 comprises the amino acid sequence of SEQ ID NO: 167;

(xviii) the HC CDR1 comprises the amino acid sequence of SEQ ID NO: 89, the HC CDR2 comprises the amino acid sequence of SEQ ID NO: 106, the HC CDR3 comprises the amino acid sequence of SEQ ID NO: 124, the LC CDR1 comprises the amino acid sequence of SEQ ID NO: 138, the LC CDR2 comprises the amino acid sequence of SEQ ID NO: 152, and the LC CDR3 comprises the amino acid sequence of SEQ ID NO: 169;

(xix) the HC CDR1 comprises the amino acid sequence of SEQ ID NO: 90, the HC CDR2 comprises the amino acid sequence of SEQ ID NO: 107, the HC CDR3 comprises the amino acid sequence of SEQ ID NO: 125, the LC CDR1 comprises the amino acid sequence of SEQ ID NO: 139, the LC CDR2 comprises the amino acid sequence of SEQ ID NO: 151, and the LC CDR3 comprises the amino acid sequence of SEQ ID NO: 170; or (xx) the HC CDR1 comprises the amino acid sequence of SEQ ID NO: 91, the HC CDR2 comprises the amino acid sequence of SEQ ID NO: 108, the HC CDR3 comprises the amino acid sequence of SEQ ID NO: 126, the LC CDR1 comprises the amino acid sequence of SEQ ID NO: 140, the LC CDR2 comprises the amino acid sequence of SEQ ID NO: 153, and the LC CDR3 comprises the amino acid sequence of SEQ ID NO: 171.

2. The antibody of claim 1, wherein the VH comprises the amino acid sequence of any one of SEQ ID NOs: 1-18; an amino acid sequence at least 90% identical to any one of SEQ ID NOs: 1-18; or an amino acid sequence having at least one, two, or three modifications, but not more than 30, 20, or 10 modifications of the amino acid sequence of any one of SEQ ID NOs: 1-18.

3. The antibody of claim 1, wherein the VL comprises the amino acid sequence of any one of SEQ ID NOs: 19-38; an amino acid sequence at least 90% identical to any one of SEQ ID NOs: 19-38; or an amino acid sequence having at least one, two, or three modifications, but not more than 30, 20, or 10 modifications of the amino acid sequence of any one of SEQ ID NOs: 19-38.

4. The antibody of claim 1, wherein (i) the VH comprises an amino acid sequence at least 90% identical to SEQ ID NO: 11; and the VL comprises an amino acid sequence at least 90% identical to SEQ ID NO: 30;

(ii) the VH comprises an amino acid sequence at least 90% identical to SEQ ID NO: 12; and the VL comprises an amino acid sequence at least 90% identical to SEQ ID NO: 31;

(iii) the VH comprises an amino acid sequence at least 90% identical to SEQ ID NO: 7; and the VL comprises an amino acid sequence at least 90% identical to SEQ ID NO: 25;

(iv) the VH comprises an amino acid sequence at least 90% identical to SEQ ID NO: 3; and the VL comprises an amino acid sequence at least 90% identical to SEQ ID NO: 21;

(v) the VH comprises an amino acid sequence at least 90% identical to SEQ ID NO: 4; and the VL comprises an amino acid sequence at least 90% identical to SEQ ID NO: 22;

(vi) the VH comprises an amino acid sequence at least 90% identical to SEQ ID NO: 6; and the VL comprises an amino acid sequence at least 90% identical to SEQ ID NO: 24; or (vii) the VH comprises an amino acid sequence at least 90% identical to SEQ ID NO: 15; and the VL comprises an amino acid sequence at least 90% identical to SEQ ID NO: 35.

5. The antibody of claim 1, wherein (i) the VH comprises an amino acid sequence at least 95% identical to the amino acid sequence of SEQ ID NO: 11; and the VL comprises an amino acid sequence at least 95% identical to the amino acid sequence of SEQ ID NO: 30;

(ii) the VH comprises an amino acid sequence at least 95% identical to the amino acid sequence of SEQ ID NO: 12; and the VL comprises an amino acid sequence at least 95% identical to the amino acid sequence of SEQ ID NO: 31;

(iii) the VH comprises an amino acid sequence at least 95% identical to the amino acid sequence of SEQ ID NO: 7; and the VL comprises an amino acid sequence at least 95% identical to the amino acid sequence of SEQ ID NO: 25;

(iv) the VH comprises an amino acid sequence at least 95% identical to the amino acid sequence of SEQ ID NO: 3; and the VL comprises an amino acid sequence at least 95% identical to the amino acid sequence of SEQ ID NO: 21;

(v) the VH comprises an amino acid sequence at least 95% identical to the amino acid sequence of SEQ ID NO: 4; and the VL comprises an amino acid sequence at least 95% identical to the amino acid sequence of SEQ ID NO: 22;

(vi) the VH comprises an amino acid sequence at least 95% identical to the amino acid sequence of SEQ ID NO: 6; and the VL comprises an amino acid sequence at least 95% identical to the amino acid sequence of SEQ ID NO: 24; or (vii) the VH comprises an amino acid sequence at least 95% identical to the amino acid sequence of SEQ ID NO: 15; and the VL comprises an amino acid sequence at least 95% identical to the amino acid sequence of SEQ ID NO: 35.

6. The antibody of claim 1, wherein (i) the VH comprises the amino acid sequence of SEQ ID NO: 11; and the VL comprises the amino acid sequence of SEQ ID NO: 30;

(ii) the VH comprises the amino acid sequence of SEQ ID NO: 12; and the VL comprises the amino acid sequence of SEQ ID NO: 31;

(iii) the VH comprises the amino acid sequence of SEQ ID NO: 7; and the VL comprises the amino acid sequence of SEQ ID NO: 25;

(iv) the VH comprises the amino acid sequence of SEQ ID NO: 3; and the VL comprises the amino acid sequence of SEQ ID NO: 21;

(v) the VH comprises the amino acid sequence of SEQ ID NO: 4; and the VL comprises the amino acid sequence of SEQ ID NO: 22;

(vi) the VH comprises the amino acid sequence of SEQ ID NO: 6; and the VL comprises the amino acid sequence of SEQ ID NO: 24; or (vii) the VH comprises the amino acid sequence of SEQ ID NO: 15; and the VL comprises the amino acid sequence of SEQ ID NO: 35.

7. The antibody of claim 1, which is a full length antibody, an intrabody, a bispecific antibody, an Fab, an F(ab') 2, an Fv, or a single chain Fv fragment (scFv).

8. The antibody of claim 1, comprising a heavy chain constant region selected from IgG1, IgG2, IgG3, or IgG4; and/or a light chain constant region of kappa or lambda.

9. The antibody of claim 1, which:

(a) does not bind to non-pathological tau;

(b) binds to pathological tau tangles;

(c) binds a tau protein which comprises at one or more phosphorylated residues; and/or (d) inhibits tau aggregation.

10. An antibody that binds to tau comprising a heavy chain variable region (VH) comprising a heavy chain complementarity determining region 1 (HC CDR1) comprising the amino acid sequence of SEQ ID NO: 82, an HC CDR2 comprising the amino acid sequence of SEQ ID NO: 101, and an HC CDR3 comprising the amino acid sequence of SEQ ID NO: 119; and a light chain variable region (VL) comprising a light chain complementarity determining region 1 (LC CDR1) comprising the amino acid sequence of SEQ ID NO: 132, an LC CDR2 comprising the amino acid sequence of SEQ ID NO: 149, and an LC CDR3 comprises the amino acid sequence of SEQ ID NO: 164.

11. The antibody of claim 10, wherein the VH comprises an amino acid sequence at least 90% identical to SEQ ID NO: 11; and the VL comprises an amino acid sequence at least 90% identical to SEQ ID NO: 30.

12. The antibody of claim 10, wherein the VH comprises an amino acid sequence at least 95% identical to SEQ ID NO: 11; and the VL comprises an amino acid sequence at least 95% identical to SEQ ID NO: 30.

13. The antibody of claim 10, wherein the VH comprises the amino acid sequence of SEQ ID NO: 11; and the VL comprises the amino acid sequence of SEQ ID NO: 30.

14. A pharmaceutical composition comprising the antibody of claim 1, and a pharmaceutically acceptable excipient.

15. A pharmaceutical composition comprising the antibody of claim 10, and a pharmaceutically acceptable excipient.

16. A pharmaceutical composition comprising the antibody of claim 12, and a pharmaceutically acceptable excipient.

17. A pharmaceutical composition comprising the antibody of claim 13, and a pharmaceutically acceptable excipient.

* * * * *